(12) United States Patent
Atkinson et al.

(10) Patent No.: US 10,370,356 B2
(45) Date of Patent: Aug. 6, 2019

(54) PYRIDINONE DICARBOXAMIDE FOR USE AS BROMODOMAIN INHIBITORS

(71) Applicant: GlaxoSmithKline Intellectual Property (No. 2) Limited, Brentford, Middlesex (GB)

(72) Inventors: Stephen John Atkinson, Stevenage (GB); Emmanuel Hubert Demont, Stevenage (GB); Lee Andrew Harrison, Stevenage (GB); Thomas George Christopher Hayhow, Stevenage (GB); David House, Stevenage (GB); Matthew J. Lindon, Stevenage (GB); Alexander G. Preston, Stevenage (GB); Jonathan Thomas Seal, Stevenage (GB); Ian David Wall, Stevenage (GB); Robert J. Watson, Stevenage (GB); James Michael Woolven, Stevenage (GB)

(73) Assignee: GlaxoSmithKline Intellectual Property (No. 2) Limited, Brentford, Middlesex (GB)

( * ) Notice: Subject to any disclaimer, the term of this patent is extended or adjusted under 35 U.S.C. 154(b) by 0 days.

(21) Appl. No.: 15/762,229

(22) PCT Filed: Sep. 20, 2016

(86) PCT No.: PCT/EP2016/072216
§ 371 (c)(1),
(2) Date: Mar. 22, 2018

(87) PCT Pub. No.: WO2017/050714
PCT Pub. Date: Mar. 30, 2017

(65) Prior Publication Data
US 2018/0282301 A1 Oct. 4, 2018

Related U.S. Application Data

(60) Provisional application No. 62/221,649, filed on Sep. 22, 2015.

(51) Int. Cl.
| | |
|---|---|
| *C07D 401/12* | (2006.01) |
| *C07D 401/14* | (2006.01) |
| *C07D 405/12* | (2006.01) |
| *C07D 409/12* | (2006.01) |
| *A61K 31/4427* | (2006.01) |
| *A61K 31/443* | (2006.01) |
| *A61K 31/4433* | (2006.01) |
| *A61K 31/4436* | (2006.01) |
| *A61K 31/4545* | (2006.01) |
| *A61K 31/496* | (2006.01) |
| *A61K 31/5377* | (2006.01) |
| *A61K 31/541* | (2006.01) |

(52) U.S. Cl.
CPC .......... *C07D 401/12* (2013.01); *A61K 31/443* (2013.01); *A61K 31/4427* (2013.01); *A61K 31/4433* (2013.01); *A61K 31/4436* (2013.01); *A61K 31/4545* (2013.01); *A61K 31/496* (2013.01); *A61K 31/5377* (2013.01); *A61K 31/541* (2013.01); *C07D 401/14* (2013.01); *C07D 405/12* (2013.01); *C07D 409/12* (2013.01)

(58) Field of Classification Search
CPC .............. A61K 31/4427; A61K 31/443; A61K 31/4433; A61K 31/4436; A61K 31/4545; A61K 31/496; A61K 31/5377; A61K 31/541; C07D 401/12; C07D 401/14; C07D 405/12; C07D 409/12
See application file for complete search history.

(56) References Cited

U.S. PATENT DOCUMENTS

2012/0208814 A1    8/2012  Demont et al.
2014/0179648 A1*   6/2014  Liu et al. ............. A61K 31/501
                                                    514/171

FOREIGN PATENT DOCUMENTS

EP    1 357 111 A1   10/2003
EP    1 433 788 A1    6/2004
(Continued)

OTHER PUBLICATIONS

Dittmer et al., "Models for the Pyridine Nucleotide Coenzymes. Synthesis and Properties of Bridged Dinicotinamide Derivatives[1-3]", *J. Org. Chem.*, vol. 38, No. 16, pp. 2873-2882 (1973).

(Continued)

*Primary Examiner* — Erich A Leeser
(74) *Attorney, Agent, or Firm* — Jane F. Djung; Duke M. Fitch; Edward R. Gimmi

(57) ABSTRACT

The present invention relates to compounds of formula (I) and salts thereof, pharmaceutical compositions containing such compounds and to their use in therapy

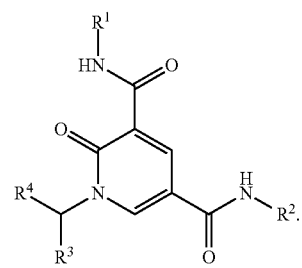

20 Claims, No Drawings

(56) References Cited

FOREIGN PATENT DOCUMENTS

| EP | 1 477 186 A1 | 11/2004 |
|---|---|---|
| WO | WO 2004/033446 A1 | 4/2004 |
| WO | WO 2014/074675 A1 | 5/2014 |
| WO | WO 2014/096965 A2 | 6/2014 |
| WO | WO 2015/015318 A2 | 2/2015 |
| WO | WO 2017/037116 A1 | 3/2017 |
| WO | WO 2017/060180 A1 | 4/2017 |
| WO | WO 2017/174621 A1 | 10/2017 |
| WO | WO 2017/202742 A1 | 11/2017 |

OTHER PUBLICATIONS

Gallenkamp et al., "Bromodomains and Their Pharmacological Inhibitors", *ChemMedChem*, vol. 9, No. 3, pp. 438-464 (2014).

Garnier et al., "BET bromodomain inhibitors: a patent review", *Expert Opinion on Therapeutic Patents*, vol. 24, No. 2, pp. 185-199 (2014).

International Search Report for International application No. PCT/EP2016/070519, dated Oct. 20, 2016, 4 pages.

International Search Report for International application No. PCT/EP2016/072216, International filing date: Sep. 20, 2016, 3 pages.

International Search Report for International application No. PCT/EP2016/073532, dated Nov. 30, 2016, 5 pages.

International Search Report for International application No. PCT/EP2017/058050, dated May 24, 2017, 5 pages.

International Search Report for International application No. PCT/EP2017/062208, dated Jul. 6, 2017, 5 pages.

International Search Report for International application No. PCT/EP2018/054730, dated May 4, 2018, 5 pages.

International Search Report for International application No. PCT/EP2018/054733, dated Jun. 11, 2018, 5 pages.

Non-Final Office Action for U.S. Appl. No. 15/766,222, USPTO, dated Oct. 4, 2018, 9 pages.

Notice of Allowance for U.S. Appl. No. 15/766,222, USPTO, dated Jan. 17, 2019, 6 pages.

Restriction Requirement for U.S. Appl. No. 15/757,199, USPTO, dated Feb. 11, 2019, 9 pages.

\* cited by examiner

PYRIDINONE DICARBOXAMIDE FOR USE AS BROMODOMAIN INHIBITORS

This application is a § 371 of International Application No. PCT/EP2016/072216, filed Sep. 20, 2016, which claims the benefit of U.S. Provisional Application No. 62/221,649, filed Sep. 22, 2015, which are incorporated herein in their entireties.

FIELD OF THE INVENTION

The present invention is directed to certain compounds which are bromodomain inhibitors, processes for their preparation, pharmaceutical compositions comprising the compounds and the use of the compounds or the compositions in the treatment of various diseases or conditions. Compounds which are bromodomain inhibitors may be useful in the treatment of various diseases and conditions, for example acute or chronic autoimmune and/or inflammatory conditions, viral infections and cancer.

BACKGROUND TO THE INVENTION

The genomes of eukaryotic organisms are highly organised within the nucleus of the cell. The long strands of duplex DNA are wrapped around an octomer of histone proteins (most usually comprising two copies of histones H2A, H2B, H3 and H4) to form a nucleosome. This basic unit is then further compressed by the aggregation and folding of nucleosomes to form a highly condensed chromatin structure. A range of different states of condensation are possible, and the tightness of this structure varies during the cell cycle, being most compact during the process of cell division. Chromatin structure plays a critical role in regulating gene transcription, which cannot occur efficiently from highly condensed chromatin. The chromatin structure is controlled by a series of post translational modifications to histone proteins, notably histones H3 and H4, and most commonly within the histone tails which extend beyond the core nucleosome structure. These modifications include acetylation, methylation, phosphorylation, ubiquitinylation, SUMOylation. These epigenetic marks are written and erased by specific enzymes, which place the tags on specific residues within the histone tail, thereby forming an epigenetic code, which is then interpreted by the cell to allow gene specific regulation of chromatin structure and thereby transcription.

Histone acetylation is most usually associated with the activation of gene transcription, as the modification loosens the interaction of the DNA and the histone octomer by changing the electrostatics. In addition to this physical change, specific proteins recognise and bind to acetylated lysine residues within histones to read the epigenetic code. Bromodomains are small (~110 amino acid) distinct domains within proteins that bind to acetylated lysine resides commonly but not exclusively in the context of histones. There is a family of around 50 proteins known to contain bromodomains, and they have a range of functions within the cell.

The BET family of bromodomain containing proteins comprises 4 proteins (BRD2, BRD3, BRD4 and BRDT) which contain tandem bromodomains capable of binding to two acetylated lysine residues in close proximity, increasing the specificity of the interaction. Numbering from the N-terminal end of each BET protein the tandem bromodomains are typically labelled Binding Domain 1 (BD1) and Binding Domain 2 (BD2) (Chung et al, *J Med. Chem.*, 2011, 54, 3827-3838).

Chan et al. report that BET bromodomain inhibition suppresses transcriptional responses to cytokine-Jak-STAT signalling in a gene-specific manner in human monocytes, which suggests that BET inhibition reduces inflammation partially through suppression of cytokine activity. (Chan et al., *Eur. J. Immunol.*, 2015, 45: 287-297).

Klein et al. report that the bromodomain protein inhibitor I-BET151 suppresses expression of inflammatory genes and matrix degrading enzymes in rheumatoid arthritis synovial fibroblasts, which suggests a therapeutic potential in the targeting of epigenetic reader proteins in rheumatoid arthritis. (Klein et al., *Ann. Rheum. Dis.*, 2014, 0:1-8).

Park-Min et al. report that I-BET151 that targets bromo and extra-terminal (BET) proteins that 'read' chromatin states by binding to acetylated histones, strongly suppresses osteoclastogenesis. (Park-Min et al. *Nature Communications*, 2014, 5, 5418).

Funabashi et al describe 1,2,3,4-tetrahydroquinolines and conduct a configuration and conformation analysis (Funabashi et al, *Bulletin of the Chemical Society of Japan*, 1969, 42, 2885-2894).

WO2014/140076 discloses 2,3-disubstituted 1-acyl-4-amino-1,2,3,4-tetrahydroquinoline derivatives and their use as bromodomain inhibitors.

SUMMARY OF THE INVENTION

The present invention relates to a compound of formula (I)

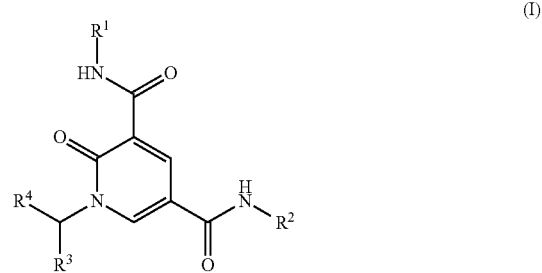

(I)

or a salt thereof
wherein
$R^1$ is $C_{1-3}$alkyl or cyclopropyl;
$R^2$ is —$(CH_2)_n$—$C_{4-10}$heterocyclyl or —$(CH_2)_p$O—$C_{4-10}$heterocyclyl wherein each $C_{4-10}$heterocyclyl is optionally substituted by one or two substituents independently selected from halo, $C_{1-4}$alkyl, $C_{3-4}$cycloalkyl, —$CH_2CF_3$, —$CH_2CHF_2$, —$CH_2CH_2F$, —$OR^5$, —$OCH_2CH_2OR^5$, —$CH_2OR^5$, —$CH_2CH_2OR^5$, —$NR^6R^7$, —$CH_2NR^6R^7$, —$CH_2CH_2NR^6R^7$, —$NHCH_2CH_2OR^5$, —$NHCO_2C(CH_3)_3$, oxo, —$CO_2H$, —$SO_2C_{1-3}$alkyl, —$CO_2C(CH_3)_3$ and —$C(O)R^5$;
$R^3$ is a) phenyl (which may be unsubstituted or substituted by one, two or three $R^8$ groups which may be the same or different); b) a $C_{5-6}$heteroaryl group (which may be unsubstituted or substituted by $C_{1-3}$alkyl, $C_{1-3}$alkoxy or halo); c) a $C_{9-11}$heteroaryl group (which may be unsubstituted or substituted by one, two or three groups independently selected from —$C_{1-3}$alkylR$^9$, —$OCH_3$, —$OC_{2-3}$alkylR$^9$, halo, oxo and cyano); or d) —$(CH_2)_m$-phenyl;

R$^4$ is —H, C$_{1-4}$alkyl, cyclopropyl, —CH$_2$OR$^{10}$ or —CH$_2$CH$_2$OR$^{10}$;

R$^5$ is —H or C$_{1-3}$alkyl;

R$^6$ and R$^7$ are each independently selected from —H, C$_{1-3}$alkyl, COC$_{1-3}$alkyl and CO$_2$C$_{1-4}$alkyl; or R$^6$ and R$^7$ may join together with the nitrogen to which they are attached, to form a C$_{4-7}$heterocyclyl optionally containing a further heteroatom selected from nitrogen, oxygen and sulphur and optionally substituted by one or two substituents independently selected from C$_{1-3}$alkyl, —OH and fluoro;

R$^8$ is —NR$^{11}$R$^{12}$, halo, —CN, —CH$_2$CN, —CO$_2$R$^1$, —C(O)C$_{1-3}$alkyl, —OH, —OCHF$_2$, —OCF$_3$, —O—C$_{2-6}$alkylR$^9$, —OCH$_3$, —CH$_2$CH$_2$NR$^{11}$R$^{12}$, —C$_{1-6}$alkylR$^9$, —OC$_6$heterocyclyl, —OCH$_2$C$_6$heterocyclyl, —CH$_2$C$_6$heterocyclyl, —CH$_2$CH$_2$C$_6$heterocyclyl, —CO$_2$CH$_3$, —NHC(O)R$^{10}$, —SO$_2$R$^{10}$ or —SOR$^{10}$;

R$^9$ is —H, —OR$^{10}$ or —NR$^{11}$R$^{12}$;

R$^{10}$ is —H or C$_{1-3}$alkyl;

R$^{11}$ and R$^{12}$ are each independently selected from —H and C$_{1-3}$alkyl; or R$^{11}$ and R$^{12}$ may join together with the nitrogen to which they are attached, to form a C$_{4-7}$heterocyclyl optionally containing a further heteroatom selected from nitrogen, oxygen and sulphur and optionally substituted by one or two substituents independently selected from C$_{1-3}$alkyl, —OH and fluoro;

n is an integer selected from 0, 1, 2, 3 and 4;

m is an integer selected from 1 and 2; and p is an integer selected from 2 and 3.

Certain compounds of the invention have been shown to be bromodomain inhibitors, in particular BD2 selective and may be useful in the treatment of various diseases or conditions, for example acute or chronic auto-immune and/or inflammatory conditions, for example rheumatoid arthritis. Accordingly, the invention is further directed to pharmaceutical compositions comprising a compound of formula (I), or a pharmaceutically acceptable salt thereof. The invention is still further directed to methods of treatment of diseases or conditions associated therewith using a compound of formula (I) or a pharmaceutically acceptable salt thereof, or a pharmaceutical composition comprising a compound of formula (I) or a pharmaceutically acceptable salt thereof. The invention is yet further directed towards processes for the preparation of the compounds of the invention.

DETAILED DESCRIPTION OF THE INVENTION

Compounds of formula (I) and salts thereof are referred to herein as "compounds of the invention".

"BD2" refers to Binding Domain 2 of any of the BET family of proteins BRD2, BRD3, BRD4 or BRDT.

"Alkyl" refers to a saturated hydrocarbon chain having the specified number of carbon atoms. For example, the term "C$_{1-6}$alkyl" as used herein refers to a straight or branched alkyl group having from 1 to 6 carbon atoms, for example 1 to 3 carbon atoms. For example the term "C$_{0-3}$alkyl" refers to a straight or branched alkyl group having from 0 (i.e. is absent) to 3 carbon atoms, for example 0 to 2 carbon atoms. Representative branched alkyl groups have one, two or three branches. "Alkyl" includes, but is not limited to, methyl, ethyl, n-propyl, n-butyl, iso-butyl, iso-propyl, t-butyl, pentyl and hexyl.

"Cycloalkyl" refers to a saturated hydrocarbon ring or a saturated spiro-linked bicyclic hydrocarbon ring, having the specified number of member atoms in the ring. For example, the term "C$_{3-4}$cycloalkyl" as used herein refers to a cycloalkyl group having from 3 to 4 member atoms, for example 3 member atoms. Examples of C$_{3-4}$cycloalkyl groups include, but are not limited to, cyclopropyl and cyclobutyl.

"Enantiomeric excess" (ee) is the excess of one enantiomer over the other expressed as a percentage. In a racemic modification, since both enantiomers are present in equal amounts, the enantiomeric excess is zero (0% ee). However, if one enantiomer were enriched such that it constitutes 95% of the product, then the enantiomeric excess would be 90% ee (the amount of the enriched enantiomer, 95%, minus the amount of the other enantiomer, 5%).

"Enantiomerically enriched" refers to products whose enantiomeric excess (ee) is greater than zero. For example, "enantiomerically enriched" refers to products whose enantiomeric excess is greater than 50% ee, greater than 75% ee, and greater than 90% ee.

"Enantiomerically pure" as used herein refers to products whose enantiomeric excess is 99% or greater.

"Half-life" (or "half-lives") refers to the time required for half of a quantity of a substance to be converted to another chemically distinct species in vitro or in vivo.

"Halo" refers to a halogen radical, for example, fluoro, chloro, bromo, or iodo.

"Heteroaryl" refers to a cyclic or bicyclic group having the specified number of member atoms wherein at least a portion of the group is aromatic. The point of attachment to the rest of the molecule may be by any suitable carbon or nitrogen atom. For example, the term "C$_{5-6}$heteroaryl" as used herein refers to a heteroaryl group having 5 or 6 member atoms, including 1 or 2 heteroatoms independently selected from nitrogen, sulphur and oxygen. Examples of "C$_{5-6}$ membered heteroaryl" groups include, but are not limited to, thiophenyl, pyrazolyl and pyridinyl. The term "C$_{9-11}$heteroaryl" as used herein refers to a bicyclic structure having 9, 10 or 11 member atoms, including 1 or 2 heteroatoms independently selected from nitrogen and oxygen. Examples of "C$_{9-11}$heteroaryl" groups include, but are not limited to, 2,3-dihydrobenzo[b][1,4]dioxinyl, 1H-benzo[d]imidazolyl, benzoimidazolyl, benzazepinyl, 2,3,4,5-tetrahydro-1H-benzo[d]azepinyl, quinoxalinyl, quinolinyl, indazolyl, indolyl, 1,2,3,4-tetrahydroquinolinyl, 1,2,3,4-tetrahydroisoquinolinyl, indolinyl, benzofuranyl, isoquinolinyl and 2,3-dihydrobenzofuranyl.

"Heteroatom" refers to a nitrogen, sulfur or oxygen atom, for example a nitrogen atom or an oxygen atom.

"Heterocyclyl" refers to an aliphatic cyclic group having the specified number of member atoms. The point of attachment may be by any suitable carbon or nitrogen atom. For example the term "C$_{4-10}$heterocyclyl" as used herein refers to a heterocyclyl having 4, 5, 6, 7, 8, 9 or 10 member atoms including one heteroatom selected from nitrogen, oxygen and sulphur and optionally containing a further heteroatom selected from nitrogen and oxygen. Examples of "C$_{4-10}$heterocyclyl" groups include, but are not limited to, oxetanyl, azetidinyl, pyrrolidinyl, tetrahydrofuranyl, pyrazolidinyl, imidiazolidinyl, thiazolidinyl, tetrahydrothiophenyl, morpholinyl, piperidinyl, piperazinyl, homopiperazinyl, tetrahydro-2H-pyranyl, tetrahydro-2H-thiopyranyl, thiomorpholinyl, 2-oxabicyclo[4.2.0]octanyl, 3-azabicyclo[3.1.0]hexanyl, (1R,5S)-3-azabicyclo[3.1.0]hexanyl, 3-oxabicyclo[3.1.0]hexanyl, (1R,5S)-3-oxabicyclo[3.1.0]hexanyl, 3-thiabicyclo[3.1.0]hexanyl and (1R,5S)-3-thiabicyclo[3.1.0]hexanyl. Examples of "C$_{4-7}$heterocyclyl" groups include, but are not limited to azetidinyl, pyrrolidinyl, piperidinyl, piperazinyl, morpholinyl and azepanyl. Examples of "C$_6$heterocyclyl" groups include, but are not limited to, piperidinyl, piperazinyl and morpholinyl. A further example of a "C₆heterocyclyl" group is 1,3-dioxanyl.

"Member atoms" refers to the atom or atoms that form a chain or ring. Where more than one member atom is present in a chain and within a ring, each member atom is covalently bound to an adjacent member atom in the chain or ring. Atoms that make up a substituent group on a chain or ring are not member atoms in the chain or ring.

"Substituted" in reference to a group indicates that a hydrogen atom attached to a member atom within a group is replaced. It should be understood that the term "substituted" includes the implicit provision that such substitution be in accordance with the permitted valence of the substituted atom and the substituent and that the substitution results in a stable compound (i.e. one that does not spontaneously undergo transformation such as rearrangement, cyclisation, or elimination). In certain embodiments, a single atom may be substituted with more than one substituent as long as such substitution is in accordance with the permitted valence of the atom. Suitable substituents are defined herein for each substituted or optionally substituted group.

"Pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

"Pharmaceutically acceptable excipient" refers to a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of formula (I) or a pharmaceutically acceptable salt thereof when administered to a patient and interactions which would result in pharmaceutical compositions that are not pharmaceutically acceptable are avoided. In addition, each excipient must of course be pharmaceutically acceptable e.g. of sufficiently high purity.

"rac" refers to the racemic mixture of the compounds of formula (I). For example, "rac-(2S,3R,4R)" means a racemic mixture of the (2S,3R,4R) enantiomer and the (2R,3S,4S) enantiomer.

"Treatment" of a particular disease or condition includes the prevention or prophylaxis of such a disease or condition.

Throughout the description and the claims which follow, unless the context requires otherwise, the word "comprise", and variations such as "comprises" and "comprising", will be understood to imply the inclusion of a stated integer or step or group of integers but not to the exclusion of any other integer or step or group of integers or steps.

The compounds of the invention may exist in solid or liquid form. In the solid state, the compounds of the invention may exist in crystalline or non-crystalline form, or as a mixture thereof. For compounds of the invention that are in crystalline form, the skilled artisan will appreciate that pharmaceutically acceptable solvates may be formed wherein solvent molecules are incorporated into the crystalline lattice during crystallization. Solvates may involve non-aqueous solvents such as ethanol, iso-propyl alcohol, -dimethylsulfoxide (DMSO), acetic acid, ethanolamine, and ethyl acetate, or they may involve water as the solvent that is incorporated into the crystalline lattice. Solvates wherein water is the solvent that is incorporated into the crystalline lattice are typically referred to as "hydrates". Hydrates include stoichiometric hydrates as well as compositions containing variable amounts of water.

It will be further appreciated that certain compounds of the invention that exist in crystalline form, including the various solvates thereof, may exhibit polymorphism (i.e. the capacity to occur in different crystalline structures). These different crystalline forms are typically known as "polymorphs". Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. It will be appreciated that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions. Polymorphic forms of compounds of formula (I) may be characterized and differentiated using a number of conventional analytical techniques, including, but not limited to, X-ray powder diffraction (XRPD) patterns, infrared (IR) spectra, Raman spectra, differential scanning calorimetry (DSC), thermogravimetric analysis (TGA) and solid state nuclear magnetic resonance (SSNMR).

The compounds of formula (I) may contain one or more asymmetric centres (also referred to as a chiral centres) and may, therefore, exist as individual enantiomers, diastereoisomers, or other stereoisomeric forms, or as mixtures thereof. Chiral centres, such as chiral carbon atoms, may also be present in a substituent such as an alkyl group. Where the stereochemistry of a chiral centre present in formula (I), or in any chemical structure illustrated herein, is not specified, the structure is intended to encompass any stereoisomer and all mixtures thereof. Thus, compounds according to formula (I) containing one or more chiral centres may be used as racemic modifications including racemic mixtures and racemates, enantiomerically-enriched mixtures, or as enantiomerically-pure individual stereoisomers. Accordingly, the present invention encompasses all isomers of the compounds of formula (I) whether as individual isomers isolated such as to be substantially free of the other isomer (i.e. pure) or as mixtures (i.e. racemates and racemic mixtures). An individual isomer isolated such as to be substantially free of the other isomer (i.e. pure) may be isolated such that less than 10%, particularly less than about 1%, for example less than about 0.1% of the other isomer is present.

Racemic compounds with a single stereocentre are denoted with either no stereochemistry (single bond) or have the annotation (+/−) or rac. Racemic compounds with two or more stereocentres where relative stereochemistry is known are denoted cis or trans as drawn in the structure. Resolved single enantiomers with unknown absolute stereochemistry but known relative stereochemistry are referred to with (R* or S*) with the appropriate relative stereochemistry depicted.

Where diastereoisomers are represented and only the relative stereochemistry is referred to, the bold or hashed solid bond symbols (━/┉) are used. Where the absolute stereochemistry is known and the compound is a single enantiomer, the bold or hashed wedges symbols (▬/┉) are used as appropriate.

Individual stereoisomers of a compound of formula (I) which contain one or more asymmetric centres may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. It will be appreciated that where the desired stereoisomer is converted into another chemical entity by one of the separation procedures described above, a further step is required to liberate the desired form. Alternatively, specific stereoisomers may be synthesised by asymmetric synthesis using optically active reagents, substrates, catalysts or solvents, or by converting one enantiomer to the other by asymmetric transformation.

It will be appreciated that, for compounds of formula (I) tautomers may be observed. Any comment relating to the biological activity of a tautomer should be taken to include both tautomers.

It is to be understood that the references herein to compounds of formula (I) and salts thereof covers the compounds of formula (I) as free bases, or as salts thereof, for example as pharmaceutically acceptable salts thereof. Thus, in one embodiment, the invention is directed to compounds of formula (I) as the free base. In another embodiment, the invention is directed to compounds of formula (I) and salts thereof. In a further embodiment, the invention is directed to compounds of formula (I) and pharmaceutically acceptable salts thereof.

Because of their potential use in medicine, salts of the compounds of formula (I) are desirably pharmaceutically acceptable. Suitable pharmaceutically acceptable salts can include acid addition salts or base addition salts. For a review of suitable pharmaceutically acceptable salts see Berge et al., *J. Pharm. Sci.*, 66:1-19, (1977). Typically, a pharmaceutically acceptable salt may be readily prepared by using a desired acid or base as appropriate. The resultant salt may precipitate from solution and be collected by filtration or may be recovered by evaporation of the solvent.

A pharmaceutically acceptable acid addition salt can be formed by reaction of a compound of formula (I) with a suitable inorganic or organic acid (such as hydrobromic, hydrochloric, sulphuric, nitric, phosphoric, succinic, maleic, acetic, propionic, fumaric, citric, tartaric, lactic, benzoic, salicylic, aspartic, p-toluenesulphonic, benzenesulphonic, methanesulphonic, ethanesulphonic, naphthalenesulphonic such as 2-naphthalenesulphonic, or hexanoic acid), optionally in a suitable solvent such as an organic solvent, to give the salt which is usually isolated for example by crystallisation and filtration or by evaporation followed by trituration. A pharmaceutically acceptable acid addition salt of a compound of formula (I) can comprise or be for example a hydrobromide, hydrochloride, sulfate, nitrate, phosphate, succinate, maleate, acetate, propionate, fumarate, citrate, tartrate, lactate, benzoate, salicylate, glutamate, aspartate, p-toluenesulphonate, benzenesulphonate, methanesulphonate, ethanesulphonate, naphthalenesulphonate (e.g. 2-naphthalenesulphonate) or hexanoate salt.

Other non-pharmaceutically acceptable salts, e.g. formates, oxalates or trifluoroacetates, may be used, for example in the isolation of the compounds of formula (I), and are included within the scope of this invention.

The invention includes within its scope all possible stoichiometric and non-stoichiometric forms of the salts of the compounds of formula (I).

It will be appreciated from the foregoing that the invention includes solvates, isomers and polymorphic forms of the compounds of formula (I) and salts thereof.

In a first aspect there are provided compounds of formula (I):

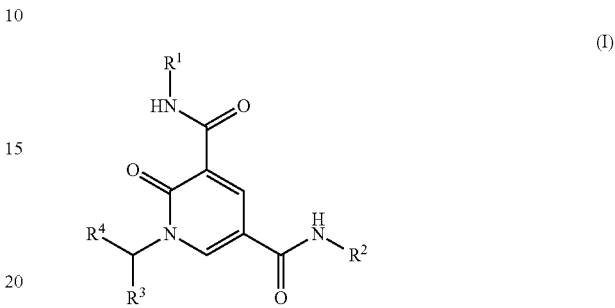

or a salt thereof
wherein
$R^1$ is $C_{1-3}$alkyl or cyclopropyl;
$R^2$ is —$(CH_2)_n$—$C_{4-10}$heterocyclyl or —$(CH_2)_pO$—$C_{4-10}$heterocyclyl wherein each $C_{4-10}$heterocyclyl is optionally substituted by one or two substituents independently selected from halo, $C_{1-4}$alkyl, $C_{3-4}$cycloalkyl, —$CH_2CF_3$, —$CH_2CHF_2$, —$CH_2CH_2F$, —$OR^5$, —$OCH_2CH_2OR^5$, —$CH_2OR^5$, —$CH_2CH_2OR^5$, —$NR^6R^7$, —$CH_2NR^6R^7$, —$CH_2CH_2NR^6R^7$, —$NHCH_2CH_2OR^5$, —$NHCO_2C(CH_3)_3$, oxo, —$CO_2H$, —$SO_2C_{1-3}$alkyl, —$CO_2C(CH_3)_3$ and —$C(O)R^5$;
$R^3$ is a) phenyl (which may be unsubstituted or substituted by one, two or three $R^8$ groups which may be the same or different); b) a $C_{5-6}$heteroaryl group (which may be unsubstituted or substituted by $C_{1-3}$alkyl, $C_{1-3}$alkoxy or halo); c) a $C_{9-11}$heteroaryl group (which may be unsubstituted or substituted by one, two or three groups independently selected from —$C_{1-3}$alkyl$R^9$, —$OCH_3$, —$OC_{2-3}$alkyl$R^9$, halo, oxo and cyano); or d) —$(CH_2)_m$-phenyl;
$R^4$ is —H, $C_{1-4}$alkyl, cyclopropyl, —$CH_2OR^{10}$ or —$CH_2CH_2OR^{10}$;
$R^5$ is —H or $C_{1-3}$alkyl;
$R^6$ and $R^7$ are each independently selected from —H, $C_{1-3}$alkyl, $COC_{1-4}$alkyl and $CO_2C_{1-4}$alkyl; or $R^6$ and $R^7$ may join together with the nitrogen to which they are attached, to form a $C_{4-7}$heterocyclyl optionally containing a further heteroatom selected from nitrogen, oxygen and sulphur and optionally substituted by one or two substituents independently selected from $C_{1-3}$alkyl, —OH and fluoro;
$R^8$ is —$NR^{11}R^{12}$, halo, —CN, —$CH_2CN$, —$CO_2R^{10}$, —$C(O)C_{1-3}$alkyl, —OH, —$OCHF_2$, —$OCF_3$, —O—$C_{2-6}$alkyl$R^9$, —$OCH_3$, —$CH_2CH_2NR^{11}R^{12}$, —$C_{1-6}$alkyl$R^9$, —$OC_6$heterocyclyl, —$OCH_2C_6$heterocyclyl, —$CH_2C_6$heterocyclyl, —$CH_2CH_2C_6$heterocyclyl, —$CO_2CH_3$, —$NHC(O)R^{10}$, —$SO_2R^{10}$ or —$SOR^{10}$;
$R^9$ is —H, —$OR^{10}$ or —$NR^{11}R^{12}$;
$R^{10}$ is —H or $C_{1-3}$alkyl;
$R^{11}$ and $R^{12}$ are each independently selected from —H and $C_{1-3}$alkyl; or $R^{11}$ and $R^{12}$ may join together with the nitrogen to which they are attached, to form a $C_{4-7}$heterocyclyl optionally containing a further heteroatom selected from nitrogen, oxygen and sulphur and optionally substituted by one or two substituents independently selected from $C_{1-3}$alkyl, —OH and fluoro;

n is an integer selected from 0, 1, 2, 3 and 4;
m is an integer selected from 1 and 2; and
p is an integer selected from 2 and 3.

In one embodiment there are provided compounds of formula (I) wherein
$R^1$ is $C_{1-3}$alkyl or cyclopropyl;
$R^2$ is —$(CH_2)_n$—$C_{4-10}$heterocyclyl or —$(CH_2)_p$O—$C_{4-10}$heterocyclyl wherein each $C_{4-10}$heterocyclyl is optionally substituted by one or two substituents independently selected from halo, $C_{1-4}$alkyl, $C_{3-4}$cycloalkyl, —$CH_2CF_3$, —$CH_2CHF_2$, —$CH_2CH_2F$, —$OR^5$, —$OCH_2CH_2OR^5$, —$CH_2OR^5$, —$CH_2CH_2OR^5$, —$NR^6R^7$, —$CH_2NR^6R^7$, —$CH_2CH_2NR^6R^7$, —$NHCH_2CH_2OR^5$, —$NHCO_2C(CH_3)_3$, oxo, —$CO_2H$, —$CO_2C(CH_3)_3$ and —$C(O)R^5$;
$R^3$ is a) phenyl (which may be unsubstituted or substituted by one, two or three $R^8$ groups which may be the same or different); b) a $C_{5-6}$heteroaryl group (which may be unsubstituted or substituted by $C_{1-3}$alkyl, $C_{1-3}$alkoxy or halo); c) a $C_{9-11}$heteroaryl group (which may be unsubstituted or substituted by one, two or three groups independently selected from —$C_{1-3}$alkyl$R^9$, —$OCH_3$, —$OC_{2-3}$alkyl$R^9$, halo, oxo and cyano); or d) —$(CH_2)_m$-phenyl;
$R^4$ is —H, $C_{1-4}$alkyl, cyclopropyl, —$CH_2OR^{10}$ or —$CH_2CH_2OR^{10}$;
$R^5$ is —H or $C_{1-3}$alkyl;
$R^6$ and $R^7$ are each independently selected from —H and $C_{1-3}$alkyl; or $R^6$ and $R^7$ may join together with the nitrogen to which they are attached, to form a $C_{4-7}$heterocyclyl optionally containing a further heteroatom selected from nitrogen, oxygen and sulphur and optionally substituted by one or two substituents independently selected from $C_{1-3}$alkyl, —OH and fluoro;
$R^8$ is —$NR^{11}R^{12}$, halo, oxo, —CN, —$CH_2CN$, —$CO_2R^{10}$, —$C(O)C_{1-3}$alkyl, —OH, —$OCHF_2$, —$OCF_3$, —O—$C_{2-6}$alkyl$R^9$, —$OCH_3$, —$CH_2CH_2NR^{11}R^{12}$, —$C_{1-6}$alkyl$R^9$, —$OC_6$heterocyclyl, —$OCH_2C_6$heterocyclyl, —$CH_2C_6$heterocyclyl, —$CH_2CH_2C_6$heterocyclyl, —$CO_2CH_3$, —$NHC(O)R^{10}$, —$SO_2R^{10}$ or —$SOR^{10}$;
$R^9$ is —H, —$OR^{10}$ or —$NR^{11}R^{12}$;
$R^{10}$ is —H or $C_{1-3}$alkyl;
$R^{11}$ and $R^{12}$ are each independently selected from —H and $C_{1-3}$alkyl; or $R^{11}$ and $R^{12}$ may join together with the nitrogen to which they are attached, to form a $C_{4-7}$heterocyclyl optionally containing a further heteroatom selected from nitrogen, oxygen and sulphur and optionally substituted by one or two substituents independently selected from $C_{1-3}$alkyl, —OH and fluoro;
n is an integer selected from 0, 1, 2, 3 and 4;
m is an integer selected from 1 and 2; and
p is an integer selected from 2 and 3.

In one embodiment there are provided compounds of formula (Ia):

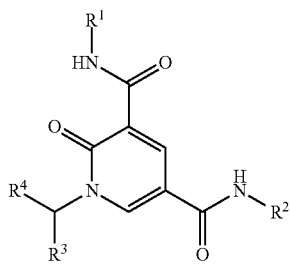

(Ia)

or a salt thereof wherein:
$R^1$ is methyl or cyclopropyl;
$R^2$ is —$(CH_2)_n$—$C_{4-10}$heterocyclyl wherein $C_{4-10}$heterocyclyl is optionally substituted by one or two substituents independently selected from halo, methyl, ethyl, —$CH_2CF_3$, —$CH_2CHF_2$, —$CH_2CH_2F$, —OH, —$CH_2CH_2OH$, oxo, —$CO_2C(CH_3)_3$ and —$C(O)CH_3$;
$R^3$ is a) phenyl (which may be unsubstituted or substituted by one or two $R^8$ groups, which may be the same or different); or c) an unsubstituted $C_{9-11}$heteroaryl group;
$R^4$ is —H or methyl;
$R^8$ is methyl, fluoro, —$OCH_3$ or —$OCH_2CH_2OH$; and
n is an integer selected from 0, 1, 2 and 3;

In one embodiment $R^1$ is methyl, ethyl or cyclopropyl. In another embodiment $R^1$ is methyl.

In one embodiment $R^2$ is —$(CH_2)_n$—$C_{4-10}$heterocyclyl and $C_{4-10}$heterocyclyl is selected from tetrahydro-2H-pyranyl, piperidinyl, azetidinyl, tetrahydrofuranyl, pyrrolidinyl, piperazinyl, morpholinyl, tetrahydro-2H-thiopyranyl, tetrahydrothiophenyl, thiomorpholinyl and 2-oxabicyclo[4.2.0]octanyl, optionally substituted by one or two substituents independently selected from halo, $C_{1-4}$alkyl, —$CH_2CF_3$, —$CH_2CHF_2$, —$CH_2CH_2F$, —$OR^5$, —$OCH_2CH_2OR^5$, —$CH_2CH_2OR^5$, —$NR^6R^7$, —$NHCH_2CH_2OR^5$, —$NHCO_2C(CH_3)_3$, oxo, —$CO_2H$, —$CO_2C(CH_3)_3$ and —$C(O)R^5$. In another embodiment $R^2$ is —$(CH_2)_n$—$C_{4-10}$heterocyclyl and $C_{4-10}$heterocyclyl is piperidinyl or morpholinyl, optionally substituted by one or two substituents independently selected from halo, $C_{1-4}$alkyl, —$CH_2CF_3$, —$CH_2CHF_2$, —$CH_2CH_2F$, —$OR^5$, —$OCH_2CH_2OR^5$, —$CH_2CH_2OR^5$, —$NR^6R^7$, —$NHCH_2CH_2OR^5$, —$NHCO_2C(CH_3)_3$, oxo, —$CO_2H$, —$CO_2C(CH_3)_3$ and —$C(O)R^5$. In another embodiment $R^2$ is —$(CH_2)_n$—$C_{4-10}$heterocyclyl and $C_{4-10}$heterocyclyl is piperidinyl or morpholinyl optionally substituted by one or two substituents independently selected from fluoro, methyl, —$CH_2CF_3$, —$CH_2CHF_2$, —$CH_2CH_2F$, —OH, —$CH_2CH_2OH$, —$CO_2C(CH_3)_3$—$C(O)CH_3$, and —$C(O)CH_3$. In another embodiment $R^2$ is —$(CH_2)_n$—$C_{4-10}$heterocyclyl and $C_{4-10}$heterocyclyl is unsubstituted piperidinyl. In another embodiment $R^2$ is —$(CH_2)_n$—$C_{4-10}$heterocyclyl and $C_{4-10}$heterocyclyl is unsubstituted morpholinyl. In another embodiment $R^2$ is —$(CH_2)_n$—$C_{4-10}$heterocyclyl wherein the $C_{4-10}$heterocyclyl is selected from:

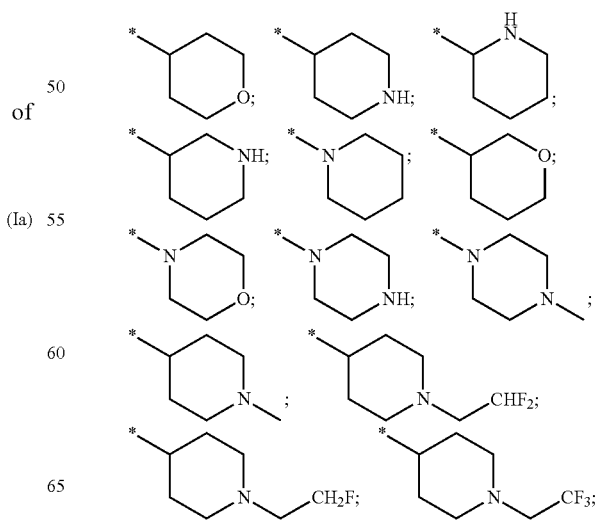

-continued

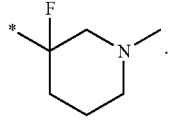

wherein * denotes the point of attachment.

In a further embodiment $R^2$ is —$(CH_2)_n$—$C_{4-10}$ heterocyclyl wherein the $C_{4-10}$heterocyclyl is selected from:

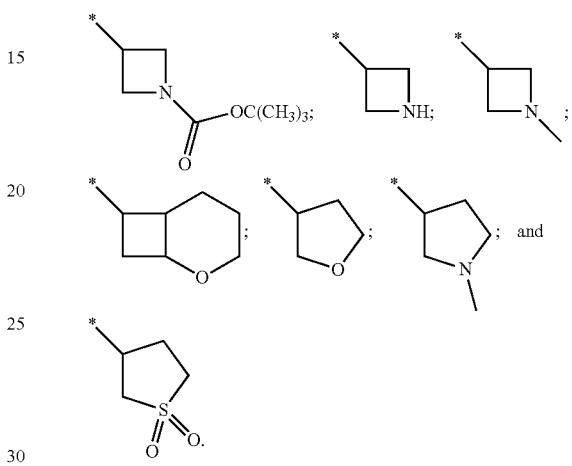

wherein * denotes the point of attachment.

In one embodiment n is 2 or 3. In another embodiment n is 3.

In one embodiment R is —$(CH_2)_p$O—$C_{4-10}$heterocyclyl and $C_{4-10}$heterocyclyl is azetidinyl, pyrrolidinyl or piperidinyl optionally substituted by methyl.

In one embodiment $R^2$ is —$(CH_2)_n$—$C_4$-10heterocyclyl wherein n is 0 and the $C_{4-10}$heterocyclyl is 3-oxabicyclo[3.1.0]hexanyl or is 3-azabicyclo[3.1.0]hexanyl optionally substituted by —$CO_2C(CH_3)_3$ or —C(O)Me.

In one embodiment $R^2$ is —$(CH_2)_n$—$C_{4-10}$heterocyclyl in wherein the $C_{4-10}$heterocyclyl is 1,3 dioxanyl optionally substituted by —$NR^6R^7$.

In one embodiment p is 2.

In one embodiment $R^3$ is phenyl or indolyl wherein each are optionally substituted by one or two $R^8$ groups selected from methyl, fluoro, oxo, —$OCH_3$, —$OCH_2CH_2OH$, —$OCH_2OH$, —$CH_2CH_2OH$, —$CH_2CH_2N(CH_3)_2$, —$OCH_2N(CH_3)_2$, —$OCH_2C_6$heterocyclyl, —$CH_2CH_2C_6$heterocyclyl and —$OC_6$heterocyclyl. In another embodiment $R^3$ is phenyl or indolyl wherein each are optionally substituted by one or two substituents independently selected from methyl, fluoro, oxo, —$OCH_3$, —$OCH_2CH_2OH$, —$OCH_2OH$, —$CH_2CH_2OH$, —$CH_2CH_2N(CH_3)_2$, —$OCH_2N(CH_3)_2$, —$OCH_2$morpholinyl, —$CH_2CH_2$morpholinyl and -Opiperidinyl. In another embodiment $R^3$ is phenyl optionally substituted by one or two $R^8$ groups independently selected from halo, O—$C_{1-6}$alkyl$R^9$ and —$C_{1-6}$alkyl$R^9$. In another embodiment $R^3$ is phenyl optionally substituted by one or two $R^8$ groups independently selected from fluoro, —$OCH_3$, —$OCH_2CH_2OH$ and methyl. In another embodiment $R^3$ is unsubstituted indolyl.

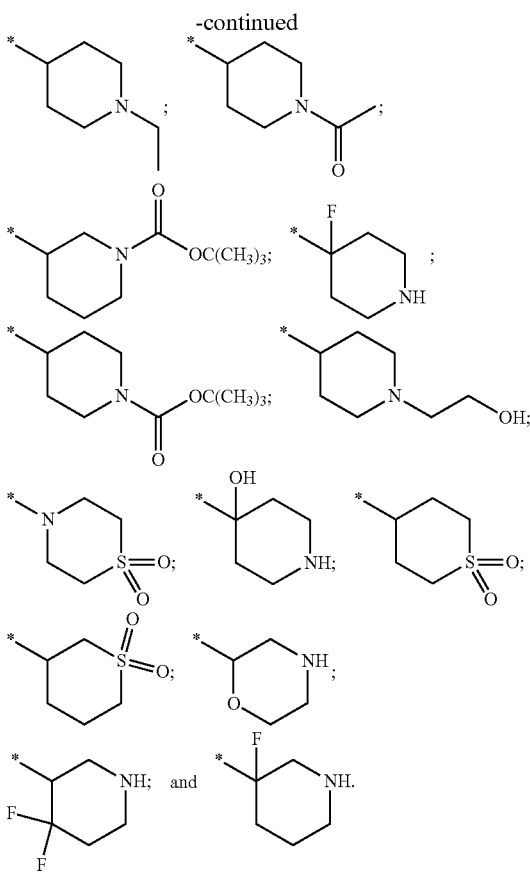

wherein * denotes the point of attachment.

It will be appreciated that when the point of attachment is via a nitrogen atom of the $C_{4-10}$heterocyclyl then n is 2, 3 or 4.

In another embodiment $R^2$ is —$(CH_2)_n$—$C_{4-10}$heterocyclyl wherein the $C_{4-10}$heterocyclyl is selected from:

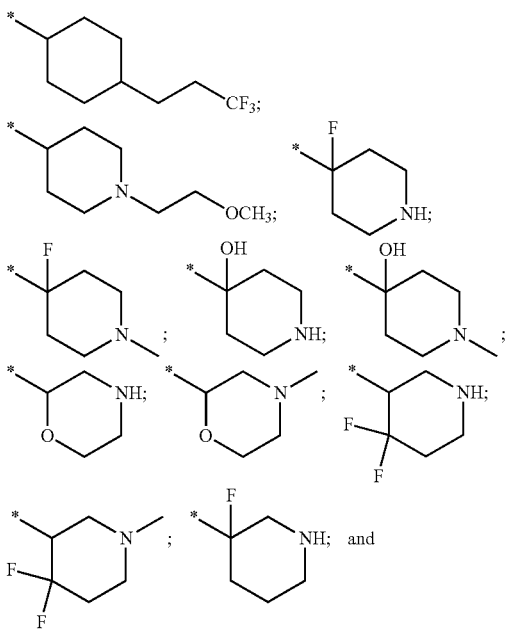

In another embodiment R³ is selected from

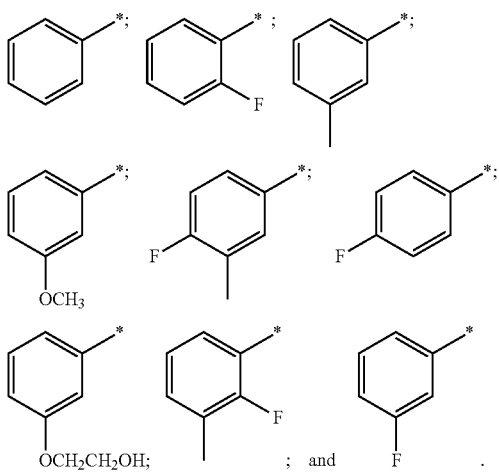

wherein * denotes the point of attachment to the alkyl residue.

In another embodiment R³ is selected from

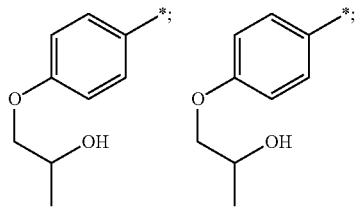

wherein * denotes the point of attachment to the alkyl residue.

In another embodiment R³ is

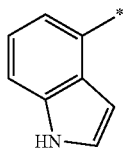

wherein * denotes the point of attachment to the alkyl residue.

In another embodiment R³ is selected from

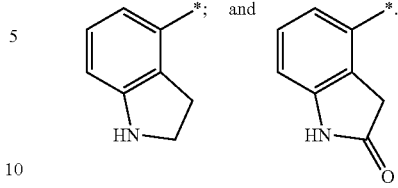

wherein * denotes the point of attachment to the alkyl residue.

In another embodiment R³ is selected from

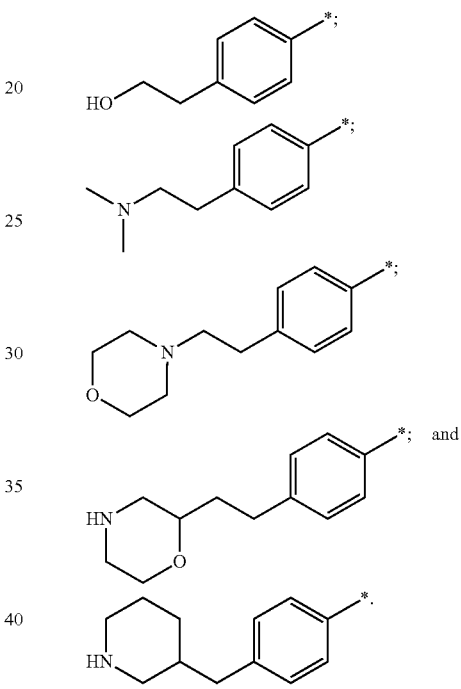

wherein * denotes the point of attachment to the alkyl residue.

In one embodiment m is 2.

In one embodiment p is 1. In another embodiment p is 2.

In one embodiment $R^5$ and $R^{10}$ are each independently selected from —H and methyl.

In one embodiment $R^4$ is H. In another embodiment $R^4$ is methyl.

In one embodiment $R^6$ and $R^7$ are each independently selected from —H and methyl.

In another embodiment $R^6$ and $R^7$ join together with the nitrogen atom to which they are attached, to form a $C_{4-7}$heterocyclyl selected from azetidinyl, pyrrolidinyl, piperidinyl, piperazinyl, morpholinyl and azepanyl optionally substituted by one or two substituents independently selected from $C_{1-3}$alkyl, —OH and fluorine.

In one embodiment $R^9$ is —H. In another embodiment $R^9$ is —OR$^{10}$ or —NR$^{11}$R$^{12}$.

In one embodiment $R^{11}$ and $R^{12}$ are each independently selected from —H and methyl.

In another embodiment $R^{11}$ and $R^{12}$ join together with the nitrogen atom to which they are attached, to form a $C_{4-7}$heterocyclyl selected from azetidinyl, pyrrolidinyl, piperidinyl, piperazinyl, morpholinyl and azepanyl optionally substituted by one or two substituents independently selected from $C_{1-3}$alkyl, —OH and fluorine.

It is to be understood that the present invention covers all combinations of substituent groups described hereinabove.

Compounds of the invention include the compounds of Examples 1 to 91 and salts thereof.

In one embodiment there is provided compounds of Examples 1-61 and salts thereof.

In one embodiment the compound of formula (I) is
1-benzyl-$N^3$-methyl-2-oxo-$N^5$-(2-(tetrahydro-2H-pyran-4-yl)ethyl)-1,2-dihydropyridine-3,5-dicarboxamide;
1-benzyl-$N^3$-methyl-2-oxo-$N^5$-(2-(piperidin-4-yl)ethyl)-1,2-dihydropyridine-3,5-dicarboxamide;
1-benzyl-$N^3$-methyl-$N^5$-(2-(1-methylpiperidin-4-yl)ethyl)-2-oxo-1,2-dihydropyridine-3,5-dicarboxamide;
tert-butyl 3-(1-benzyl-5-(methylcarbamoyl)-6-oxo-1,6-dihydropyridine-3-carboxamido)azetidine-1-carboxylate;
tert-butyl 4-(3-(1-benzyl-5-(methylcarbamoyl)-6-oxo-1,6-dihydropyridine-3-carboxamido)propyl)piperidine-1-carboxylate;
1-benzyl-$N^3$-methyl-2-oxo-$N^5$-(3-(piperidin-4-yl)propyl)-1,2-dihydropyridine-3,5-dicarboxamide;
1-benzyl-$N^3$-methyl-$N^5$-(3-(1-methylpiperidin-4-yl)propyl)-2-oxo-1,2-dihydropyridine-3,5-dicarboxamide;
$N^5$-(3-(1-acetylpiperidin-4-yl)propyl)-1-benzyl-$N^3$-methyl-2-oxo-1,2-dihydropyridine-3,5-dicarboxamide;
1-benzyl-$N^3$-methyl-2-oxo-$N^5$-(2-(tetrahydrofuran-3-yl)ethyl)-1,2-dihydropyridine-3,5-dicarboxamide;
1-benzyl-$N^3$-methyl-2-oxo-$N^5$-(3-(1-(2,2,2-trifluoroethyl)piperidin-4-yl)propyl)-1,2-dihydropyridine-3,5-dicarboxamide;
1-benzyl-$N^5$-(3-(1-ethylpiperidin-4-yl)propyl)-$N^3$-methyl-2-oxo-1,2-dihydropyridine-3,5-dicarboxamide;
1-benzyl-$N^3$-methyl-2-oxo-N5-(3-(piperazin-1-yl)propyl)-1,2-dihydropyridine-3,5-dicarboxamide;
1-benzyl-$N^5$-(2-(1,1-dioxidotetrahydro-2H-thiopyran-4-yl)ethyl)-$N^3$-methyl-2-oxo-1,2-dihydropyridine-3,5-dicarboxamide;
1-(2-fluorobenzyl)-$N^3$-methyl-2-oxo-$N^5$-(3-(piperidin-4-yl)propyl)-1,2-dihydropyridine-3,5-dicarboxamide;
$N^3$-methyl-1-(3-methylbenzyl)-2-oxo-$N^5$-(3-(piperidin-4-yl)propyl)-1,2-dihydropyridine-3,5-dicarboxamide;
$N^3$-methyl-1-(3-methylbenzyl)-2-oxo-$N^5$-(2-(piperidin-4-yl)ethyl)-1,2-dihydropyridine-3,5-dicarboxamide;
(R)—$N^3$-methyl-2-oxo-1-(1-phenylethyl)-$N^5$-(3-(piperidin-4-yl)propyl)-1,2-dihydropyridine-3,5-dicarboxamide;
(R)—$N^3$-methyl-2-oxo-1-(1-phenylethyl)-$N^5$-(2-(piperidin-4-yl)ethyl)-1,2-dihydropyridine-3,5-dicarboxamide;
1-(3-methoxybenzyl)-$N^3$-methyl-2-oxo-$N^5$-(3-(piperidin-4-yl)propyl)-1,2-dihydropyridine-3,5-dicarboxamide;
1-(3-methoxybenzyl)-$N^3$-methyl-2-oxo-$N^5$-(2-(piperidin-4-yl)ethyl)-1,2-dihydropyridine-3,5-dicarboxamide;
1-(4-fluoro-3-methylbenzyl)-$N^3$-methyl-2-oxo-$N^5$-(3-(piperidin-4-yl)propyl)-1,2-dihydropyridine-3,5-dicarboxamide;
1-(4-fluorobenzyl)-$N^3$-methyl-2-oxo-$N^5$-(3-(piperidin-4-yl)propyl)-1,2-dihydropyridine-3,5-dicarboxamide;
1-(3-(2-hydroxyethoxy)benzyl)-$N^3$-methyl-2-oxo-N5-(3-(piperidin-4-yl)propyl)-1,2-dihydropyridine-3,5-dicarboxamide;
1-(3-(2-hydroxyethoxy)benzyl)-$N^3$-methyl-2-oxo-N-(2-(piperidin-4-yl)ethyl)-1,2-dihydropyridine-3,5-dicarboxamide;
1-benzyl-$N^5$-(3-(1-(2-hydroxyethyl)piperidin-4-yl)propyl)-$N^3$-methyl-2-oxo-1,2-dihydropyridine-3,5-dicarboxamide;
1-(2-fluoro-3-methylbenzyl)-$N^3$-methyl-2-oxo-$N^5$-(3-(piperidin-4-yl)propyl)-1,2-dihydropyridine-3,5-dicarboxamide;
1-(2-fluoro-3-methylbenzyl)-$N^3$-methyl-2-oxo-$N^5$-(2-(piperidin-4-yl)ethyl)-1,2-dihydropyridine-3,5-dicarboxamide;
1-benzyl-$N^5$-(3-(1-(2,2-difluoroethyl)piperidin-4-yl)propyl)-$N^3$-methyl-2-oxo-1,2-dihydropyridine-3,5-dicarboxamide;
1-benzyl-$N^5$-(3-(1-(2-fluoroethyl)piperidin-4-yl)propyl)-$N^3$-methyl-2-oxo-1,2-dihydropyridine-3,5-dicarboxamide;
1-((1H-indol-4-yl)methyl)-$N^3$-methyl-2-oxo-$N^5$-(3-(piperidin-4-yl)propyl)-1,2-dihydropyridine-3,5-dicarboxamide;
1-benzyl-$N^3$-methyl-2-oxo-$N^5$-(2-(tetrahydro-2H-pyran-3-yl)ethyl)-1,2-dihydropyridine-3,5-dicarboxamide;
tert-butyl 4-(2-(1-benzyl-5-(methylcarbamoyl)-6-oxo-1,6-dihydropyridine-3-carboxamido)ethyl)piperidine-1-carboxylate;
$N^5$-(azetidin-3-yl)-1-benzyl-$N^3$-methyl-2-oxo-1,2-dihydropyridine-3,5-dicarboxamide;
1-benzyl-$N^3$-methyl-$N^5$-(1-methylazetidin-3-yl)-2-oxo-1,2-dihydropyridine-3,5-dicarboxamide;
1-benzyl-$N^5$-(2-oxabicyclo[4.2.0]octan-7-yl)-$N^3$-methyl-2-oxo-1,2-dihydropyridine-3,5-dicarboxamide;
1-benzyl-$N^3$-methyl-$N^5$-(2-(1-methylpyrrolidin-3-yl)ethyl)-2-oxo-1,2-dihydropyridine-3,5-dicarboxamide;
1-benzyl-$N^3$-methyl-$N^5$-(3-morpholinopropyl)-2-oxo-1,2-dihydropyridine-3,5-dicarboxamide;
tert-butyl 3-(2-(1-benzyl-5-(methylcarbamoyl)-6-oxo-1,6-dihydropyridine-3-carboxamido)ethyl)piperidine-1-carboxylate;
1-benzyl-$N^3$-methyl-2-oxo-$N^5$-(2-(piperidin-3-yl)ethyl)-1,2-dihydropyridine-3,5-dicarboxamide;
1-benzyl-$N^3$-methyl-2-oxo-$N^5$-(2-(piperidin-2-yl)ethyl)-1,2-dihydropyridine-3,5-dicarboxamide;
1-benzyl-$N^3$-methyl-2-oxo-$N^5$-(tetrahydro-2H-pyran-4-yl)-1,2-dihydropyridine-3,5-dicarboxamide;
1-benzyl-$N^5$-(1,1-dioxidotetrahydro-2H-thiopyran-3-yl)-$N^3$-methyl-2-oxo-1,2-dihydropyridine-3,5-dicarboxamide;
1-benzyl-$N^5$-(1,1-dioxidotetrahydrothiophen-3-yl)-$N^3$-methyl-2-oxo-1,2-dihydropyridine-3,5-dicarboxamide;
1-benzyl-$N^5$-(1,1-dioxidotetrahydro-2H-thiopyran-4-yl)-$N^3$-methyl-2-oxo-1,2-dihydropyridine-3,5-dicarboxamide;
1-benzyl-$N^3$-methyl-2-oxo-$N^5$-(3-(piperidin-1-yl)propyl)-1,2-dihydropyridine-3,5-dicarboxamide;
(R)-1-benzyl-$N^3$-methyl-2-oxo-$N^5$-((tetrahydro-2H-pyran-3-yl)methyl)-1,2-dihydropyridine-3,5-dicarboxamide;
(S)-1-benzyl-$N^3$-methyl-2-oxo-$N^5$-((tetrahydro-2H-pyran-3-yl)methyl)-1,2-dihydropyridine-3,5-dicarboxamide;
1-benzyl-$N^5$-((1,1-dioxidotetrahydrothiophen-3-yl)methyl)-$N^3$-methyl-2-oxo-1,2-dihydropyridine-3,5-dicarboxamide;
1-benzyl-$N^3$-methyl-2-oxo-$N^5$-((tetrahydro-2H-pyran-4-yl)methyl)-1,2-dihydropyridine-3,5-dicarboxamide;
1-benzyl-$N^3$-methyl-2-oxo-$N^5$-(tetrahydro-2H-pyran-3-yl)-1,2-dihydropyridine-3,5-dicarboxamide;
1-benzyl-$N^3$-methyl-$N^5$-(3-(4-methylpiperazin-1-yl)propyl)-2-oxo-1,2-dihydropyridine-3,5-dicarboxamide;
1-benzyl-$N^5$-(3-(1,1-dioxidothiomorpholino)propyl)-$N^3$-methyl-2-oxo-1,2-dihydropyridine-3,5-dicarboxamide;
1-benzyl-$N^5$-((1,1-dioxidotetrahydro-2H-thiopyran-4-yl)methyl)-$N^3$-methyl-2-oxo-1,2-dihydropyridine-3,5-dicarboxamide;

N³-methyl-1-(3-methylbenzyl)-2-oxo-N⁵-(3-(piperidin-4-yl)propyl)-1,2-dihydropyridine-3,5-dicarboxamide;
(R)—N³-methyl-2-oxo-1-(1-phenylethyl)-N⁵-(3-(piperidin-4-yl)propyl)-1,2-dihydropyridine-3,5-dicarboxamide;
1-((1H-indol-4-yl)methyl)-N³-methyl-2-oxo-N⁵-(2-(piperidin-4-yl)ethyl)-1,2-dihydropyridine-3,5-dicarboxamide;
1-benzyl-N⁵-(3-(4-hydroxypiperidin-4-yl)propyl)-N³-methyl-2-oxo-1,2-dihydropyridine-3,5-dicarboxamide;
1-(3-fluorobenzyl)-N³-methyl-2-oxo-N⁵-(3-(piperidin-4-yl)propyl)-1,2-dihydropyridine-3,5-dicarboxamide;
tert-butyl 3-(3-(1-benzyl-5-(methylcarbamoyl)-6-oxo-1,6-dihydropyridine-3-carboxamido)propyl)piperidine-1-carboxylate;
1-benzyl-N³-methyl-2-oxo-N⁵-(3-(piperidin-3-yl)propyl)-1,2-dihydropyridine-3,5-dicarboxamide;
1-benzyl-N⁵-(3-(4-fluoropiperidin-4-yl)propyl)-N³-methyl-2-oxo-1,2-dihydropyridine-3,5-dicarboxamide;
1-((1H-indol-4-yl)methyl)-N³-methyl-2-oxo-N-(3-(piperidin-4-yl)propyl)-1,2-dihydropyridine-3,5-dicarboxamide;
1-benzyl-N⁵-(3-(4-fluoropiperidin-4-yl)propyl)-N³-methyl-2-oxo-1,2-dihydropyridine-3,5-dicarboxamide;
1-benzyl-N³-methyl-N⁵-(2-(4-methylmorpholin-2-yl)ethyl)-2-oxo-1,2-dihydropyridine-3,5-dicarboxamide;
N⁵-(2-(4-acetylmorpholin-2-yl)ethyl)-1-benzyl-N³-methyl-2-oxo-1,2-dihydropyridine-3,5-dicarboxamide;
1-benzyl-N³-methyl-N⁵-(2-(morpholin-2-yl)ethyl)-2-oxo-1,2-dihydropyridine-3,5-dicarboxamide;
1-benzyl-N³-methyl-2-oxo-N⁵-(2-(pyrrolidin-3-yloxy)ethyl)-1,2-dihydropyridine-3,5-dicarboxamide;
1-benzyl-N³-methyl-2-oxo-N⁵-(2-(piperidin-3-yloxy)ethyl)-1,2-dihydropyridine-3,5-dicarboxamide;
1-benzyl-N⁵-((1R,5S,6r)-3-oxabicyclo[3.1.0]hexan-6-yl)-N³-methyl-2-oxo-1,2-dihydropyridine-3,5-dicarboxamide;
1-benzyl-N³-methyl-N⁵-(3-(1-methylpiperidin-3-yl)propyl)-2-oxo-1,2-dihydropyridine-3,5-dicarboxamide;
1-benzyl-N³-methyl-N⁵-(3-(1-methylpiperidin-3-yl)propyl)-2-oxo-1,2-dihydropyridine-3,5-dicarboxamide;
N⁵-((1R,5S,6r)-3-oxabicyclo[3.1.0]hexan-6-yl)-1-(3-methoxybenzyl)-N³-methyl-2-oxo-1,2-dihydropyridine-3,5-dicarboxamide;
1-benzyl-N³-methyl-N⁵-(3-(morpholin-2-yl)-2-oxo-1,2-dihydropyridine-3,5-dicarboxamide;
1-((1H-indol-4-yl)methyl)-N⁵-(3-(1-acetylpiperidin-4-yl)propyl)-N³-methyl-2-oxo-1,2-dihydropyridine-3,5-dicarboxamide;
(1R,5S,6s)-tert-butyl 6-(1-benzyl-5-(methylcarbamoyl)-6-oxo-1,6-dihydropyridine-3-carboxamido)-3-azabicyclo[3.1.0]hexane-3-carboxylate;
1-benzyl-N⁵-((1R,5S,6s)-3-azabicyclo[3.1.0]hexan-6-yl)-N³-methyl-2-oxo-1,2-dihydropyridine-3,5-dicarboxamide;
1-benzyl-N³-methyl-N⁵-(3-(morpholin-2-yl)propyl)-2-oxo-1,2-dihydropyridine-3,5-dicarboxamide;
1-benzyl-N³-ethyl-2-oxo-N⁵-(3-(piperidin-4-yl)propyl)-1,2-dihydropyridine-3,5-dicarboxamide;
(1R,5S,6s)-tert-butyl 6-(1-((1H-indol-4-yl)methyl)-5-(methylcarbamoyl)-6-oxo-1,6-dihydropyridine-3-carboxamido)-3-azabicyclo[3.1.0]hexane-3-carboxylate;
1-((1H-indol-4-yl)methyl)-N⁵-((1R,5S,6s)-3-azabicyclo[3.1.0]hexan-6-yl)-N³-methyl-2-oxo-1,2-dihydropyridine-3,5-dicarboxamide;
1-((1H-indol-4-yl)methyl)-N⁵-((1R,5S,6s)-3-acetyl-3-azabicyclo[3.1.0]hexan-6-yl)-N³-methyl-2-oxo-1,2-dihydropyridine-3,5-dicarboxamide;
(R)-1-benzyl-N³-ethyl-N⁵-(3-(3-fluoropiperidin-3-yl)propyl)-2-oxo-1,2-dihydropyridine-3,5-dicarboxamide;
(R)-1-benzyl-N³-ethyl-N⁵-(2-(morpholin-2-yl)ethyl)-2-oxo-1,2-dihydropyridine-3,5-dicarboxamide;
(R)-1-benzyl-N³-ethyl-N⁵-(3-(morpholin-2-yl)propyl)-2-oxo-1,2-dihydropyridine-3,5-dicarboxamide;
tert-butyl (2-((1R,5S,6s)-6-(1-((1H-indol-4-yl)methyl)-5-(methylcarbamoyl)-6-oxo-1,6-dihydropyridine-3-carboxamido)-3-azabicyclo[3.1.0]hexan-3-yl)ethyl)carbamate;
1-((1H-indol-4-yl)methyl)-N-((1R,5S,6s)-3-(2-aminoethyl)-3-azabicyclo[3.1.0]hexan-6-yl)-N³-methyl-2-oxo-1,2-dihydropyridine-3,5-dicarboxamide;
1-((1H-indol-4-yl)methyl)-N⁵-((1R,5S,6s)-3-(2-acetamidoethyl)-3-azabicyclo[3.1.0]hexan-6-yl)-N³-methyl-2-oxo-1,2-dihydropyridine-3,5-dicarboxamide;
N⁵-(3-((2r,5r)-5-amino-1,3-dioxan-2-yl)propyl)-1-benzyl-N³-methyl-2-oxo-1,2-dihydropyridine-3,5-dicarboxamide;
1-benzyl-N³-methyl-2-oxo-N⁵-(2-(piperidin-4-yloxy)ethyl)-1,2-dihydropyridine-3,5-dicarboxamide;
1-benzyl-N³-methyl-N⁵-(1-(methylsulfonyl)azetidin-3-yl)-2-oxo-1,2-dihydropyridine-3,5-dicarboxamide; and
1-benzyl-N³-methyl-N⁵-(oxetan-3-yl)-2-oxo-1,2-dihydropyridine-3,5-dicarboxamide
or a salt thereof.

In one embodiment the compound of formula (I) is
1-benzyl-N³-methyl-2-oxo-N⁵-(3-(piperidin-4-yl)propyl)-1,2-dihydropyridine-3,5-dicarboxamide;
1-benzyl-N³-methyl-N⁵-(3-(1-methylpiperidin-4-yl)propyl)-2-oxo-1,2-dihydropyridine-3,5-dicarboxamide;
1-benzyl-N⁵-(3-(1-(2-hydroxyethyl)piperidin-4-yl)propyl)-N³-methyl-2-oxo-1,2-dihydropyridine-3,5-dicarboxamide;
1-benzyl-N⁵-(3-(1-(2-fluoroethyl)piperidin-4-yl)propyl)-N³-methyl-2-oxo-1,2-dihydropyridine-3,5-dicarboxamide;
or a salt thereof.

In one embodiment the compound of formula (I) is 1-benzyl-N³-methyl-2-oxo-N⁵-(3-(piperidin-4-yl)propyl)-1,2-dihydropyridine-3,5-dicarboxamide or a salt thereof. In another embodiment the compound of formula (I) is 1-benzyl-N³-methyl-2-oxo-N⁵-(3-(piperidin-4-yl)propyl)-1,2-dihydropyridine-3,5-dicarboxamide or a pharmaceutically acceptable salt thereof. In another embodiment the compound of formula (I) is 1-benzyl-N³-methyl-2-oxo-N⁵-(3-(piperidin-4-yl)propyl)-1,2-dihydropyridine-3,5-dicarboxamide. In another embodiment the compound of formula (I) is a pharmaceutically acceptable salt of 1-benzyl-N³-methyl-2-oxo-N⁵-(3-(piperidin-4-yl)propyl)-1,2-dihydropyridine-3,5-dicarboxamide. In a further embodiment the compound of formula (I) or a salt thereof is 1-benzyl-N³-methyl-2-oxo-N⁵-(3-(piperidin-4-yl)propyl)-1,2-dihydropyridine-3,5-dicarboxamide hydrochloride.

In one embodiment the compound of formula (I) is

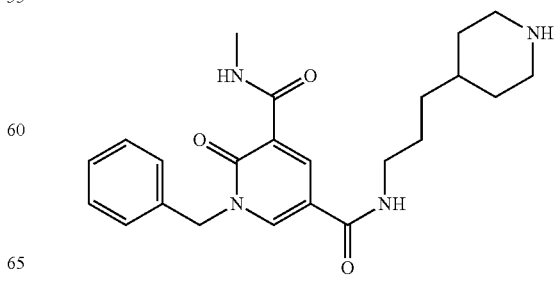

or a salt thereof. In another embodiment the compound of formula (I) is

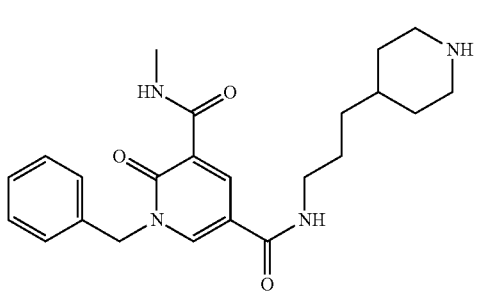 [SMILES: CNC(=O)c1cc(C(=O)NCCCC2CCNCC2)cn(Cc2ccccc2)c1=O]

or a pharmaceutically acceptable salt thereof. In another embodiment the compound of formula (I) is

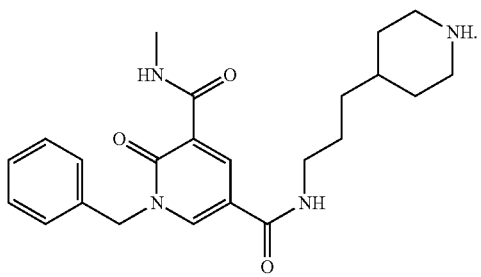 [SMILES: CNC(=O)c1cc(C(=O)NCCCC2CCNCC2)cn(Cc2ccccc2)c1=O]

In a further embodiment the compound of formula (I) is a pharmaceutically acceptable salt of

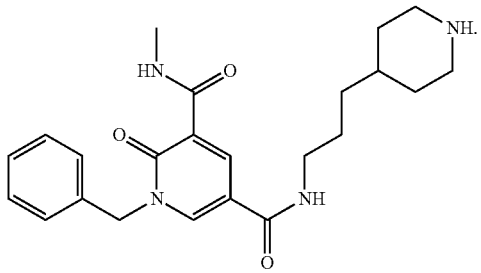 [SMILES: CNC(=O)c1cc(C(=O)NCCCC2CCNCC2)cn(Cc2ccccc2)c1=O]

In one embodiment the compound of formula (I) is 1-benzyl-$N^3$-methyl-$N^5$-(3-(1-methylpiperidin-4-yl)propyl)-2-oxo-1,2-dihydropyridine-3,5-dicarboxamide or a salt thereof. In another embodiment the compound of formula (I) is 1-benzyl-$N^3$-methyl-$N^5$-(3-(1-methylpiperidin-4-yl)propyl)-2-oxo-1,2-dihydropyridine-3,5-dicarboxamide or a pharmaceutically acceptable salt thereof. In another embodiment the compound of formula (I) is 1-benzyl-$N^3$-methyl-$N^5$-(3-(1-methylpiperidin-4-yl)propyl)-2-oxo-1,2-dihydropyridine-3,5-dicarboxamide. In a further embodiment the compound of formula (I) is a pharmaceutically acceptable salt of 1-benzyl-$N^3$-methyl-$N^5$-(3-(1-methyl piperidin-4-yl)propyl)-2-oxo-1,2-dihydropyridine-3,5-dicarboxamide.

In one embodiment the compound of formula (I) is

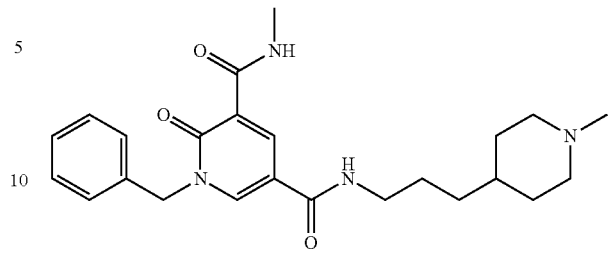

or a salt thereof. In another embodiment the compound of formula (I) is

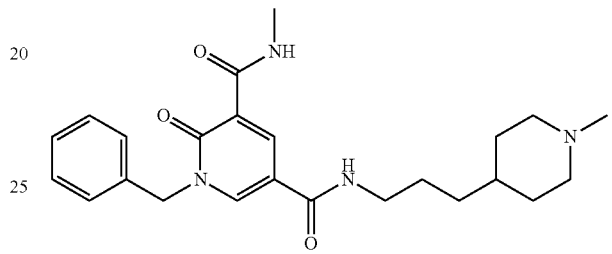

or a pharmaceutically acceptable salt thereof. In another embodiment the compound of formula (I) is

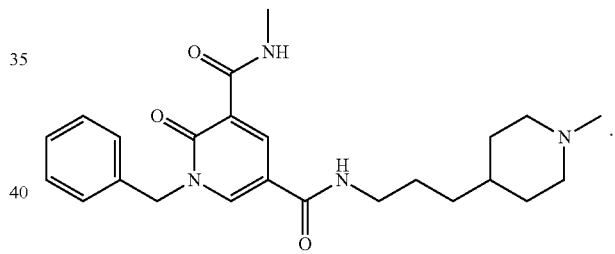

In a further embodiment the compound of formula (I) is a pharmaceutically acceptable salt of

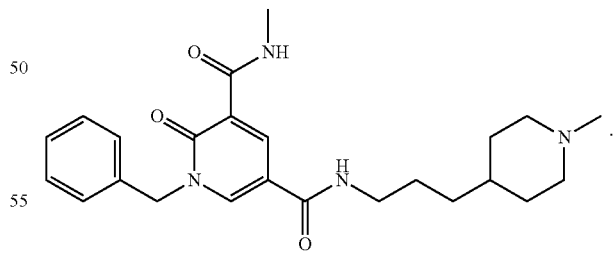

In one embodiment the compound of formula (I) is 1-benzyl-$N^5$-(3-(1-(2-hydroxyethyl)piperidin-4-yl)propyl)-$N^3$-methyl-2-oxo-1,2-dihydropyridine-3,5-dicarboxamide or a salt thereof. In another embodiment the compound of formula (I) is 1-benzyl-$N^5$-(3-(1-(2-hydroxyethyl)piperidin-4-yl)propyl)-$N^3$-methyl-2-oxo-1,2-dihydropyridine-3,5-dicarboxamide or a pharmaceutically acceptable salt thereof. In another embodiment the compound of formula (I) is 1-benzyl-$N^5$-(3-(1-(2-hydroxyethyl)piperidin-4-yl)propyl)-

$N^5$-methyl-2-oxo-1,2-dihydropyridine-3,5-dicarboxamide.

In a further embodiment the compound of formula (I) is a pharmaceutically acceptable salt of 1-benzyl-$N^5$-(3-(1-(2-hydroxyethyl)piperidin-4-yl)propyl)-$N^3$-methyl-2-oxo-1,2-dihydropyridine-3,5-dicarboxamide.

In one embodiment the compound of formula (I) is

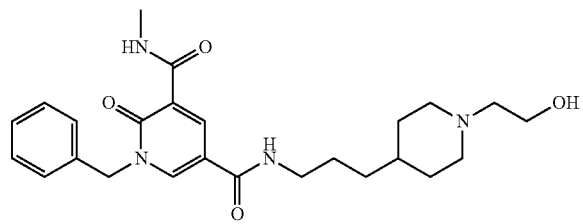 [SMILES: CNC(=O)c1cc(C(=O)NCCCC2CCN(CCO)CC2)cn(Cc2ccccc2)c1=O]

or a salt thereof. In another embodiment the compound of formula (I) is

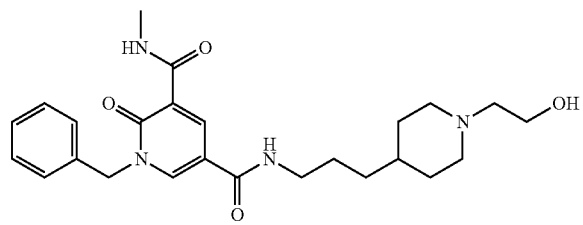 [SMILES: CNC(=O)c1cc(C(=O)NCCCC2CCN(CCO)CC2)cn(Cc2ccccc2)c1=O]

or a pharmaceutically acceptable salt thereof. In another embodiment the compound of formula (I) is

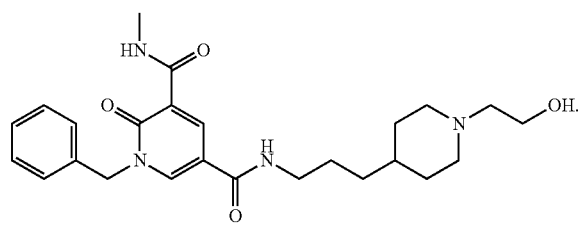 [SMILES: CNC(=O)c1cc(C(=O)NCCCC2CCN(CCO)CC2)cn(Cc2ccccc2)c1=O]

In a further embodiment the compound of formula (I) is a pharmaceutically acceptable salt of

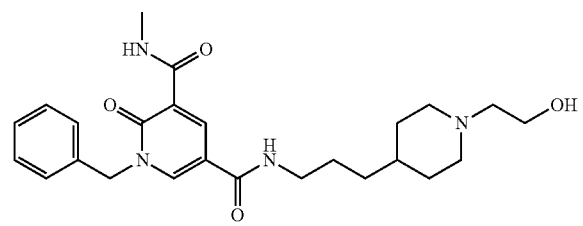 [SMILES: CNC(=O)c1cc(C(=O)NCCCC2CCN(CCO)CC2)cn(Cc2ccccc2)c1=O]

In one embodiment the compound of formula (I) is 1-benzyl-$N^5$-(3-(1-(2-fluoroethyl)piperidin-4-yl)propyl)-$N^3$-methyl-2-oxo-1,2-dihydropyridine-3,5-dicarboxamide or a salt thereof. In another embodiment the compound of formula (I) is 1-benzyl-$N^5$-(3-(1-(2-fluoroethyl)piperidin-4-yl)propyl)-$N^3$-methyl-2-oxo-1,2-dihydropyridine-3,5-dicarboxamide or a pharmaceutically acceptable salt thereof. In another embodiment the compound of formula (I) is 1-benzyl-$N^5$-(3-(1-(2-fluoroethyl)piperidin-4-yl)propyl)-$N^3$-methyl-2-oxo-1,2-dihydropyridine-3,5-dicarboxamide. In another embodiment the compound of formula (I) is a pharmaceutically acceptable salt of 1-benzyl-$N^5$-(3-(1-(2-fluoroethyl)piperidin-4-yl)propyl)-$N^3$-methyl-2-oxo-1,2-dihydropyridine-3,5-dicarboxamide. In a further embodiment the compound of formula (I) or a salt thereof is 1-benzyl-$N^5$-(3-(1-(2-fluoroethyl)piperidin-4-yl)propyl)-$N^5$-methyl-2-oxo-1,2-dihydropyridine-3,5-dicarboxamide formic acid salt.

In one embodiment the compound of formula (I) is

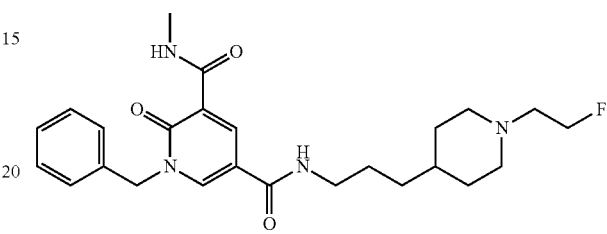

or a salt thereof. In another embodiment the compound of formula (I) is

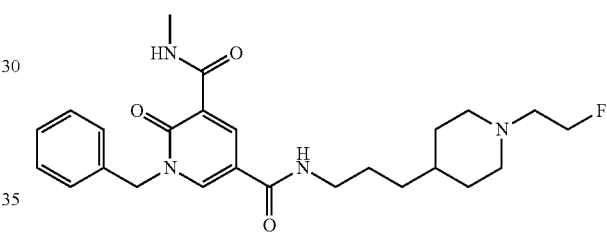

or a pharmaceutically acceptable salt thereof. In another embodiment the compound of formula (I) is

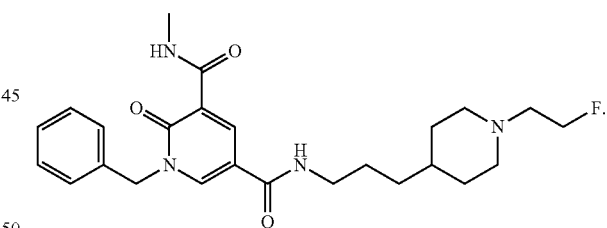

In a further embodiment the compound of formula (I) is a pharmaceutically acceptable salt of

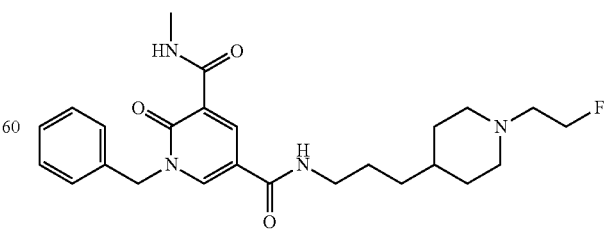

In a second aspect of the present invention, there is provided a pharmaceutical composition comprising a compound of formula (I) or a pharmaceutically acceptable salt thereof and a pharmaceutically acceptable excipient.

In a third aspect of the present invention, there is provided a compound of formula (I), or a pharmaceutically acceptable salt thereof for use in therapy, in particular in the treatment of diseases or conditions for which a bromodomain inhibitor is indicated.

In a fourth aspect of the present invention, there is provided a method of treating diseases or conditions for which a bromodomain inhibitor is indicated in a subject in need thereof which comprises administering a therapeutically effective amount of a compound of formula (I) or a pharmaceutically acceptable salt thereof.

In a fifth aspect of the present invention, there is provided the use of a compound of formula (I), or a pharmaceutically acceptable salt thereof in the manufacture of a medicament for the treatment of diseases or conditions for which a bromodomain inhibitor is indicated.

Statement of Use

The compounds of formula (I) and salts thereof are bromodomain inhibitors, and thus are believed to have potential utility in the treatment of diseases or conditions for which a bromodomain inhibitor is indicated.

Bromodomain inhibitors are believed to be useful in the treatment of a variety of diseases or conditions related to systemic or tissue inflammation, inflammatory responses to infection or hypoxia, cellular activation and proliferation, lipid metabolism, fibrosis and in the prevention and treatment of viral infections.

Bromodomain inhibitors may be useful in the treatment of a wide variety of acute or chronic autoimmune and/or inflammatory conditions such as rheumatoid arthritis, psoriatic arthritis, ankylosing spondylitis, osteoarthritis, acute gout, psoriasis, systemic lupus erythematosus, multiple sclerosis, inflammatory bowel disease (Crohn's disease and ulcerative colitis), asthma, chronic obstructive airways disease, pneumonitis, myocarditis, pericarditis, myositis, eczema, dermatitis (including atopic dermatitis), alopecia, vitiligo, bullous skin diseases, nephritis, vasculitis, hypercholesterolemia, atherosclerosis, Alzheimer's disease, Sjögren's syndrome, sialoadenitis, central retinal vein occlusion, branched retinal vein occlusion, Irvine-Gass syndrome (post cataract and post-surgical), retinitis pigmentosa, pars planitis, birdshot retinochoroidopathy, epiretinal membrane, cystic macular edema, parafoveal telengiectasis, tractional maculopathies, vitreomacular traction syndromes, retinal detachment, neuroretinitis, idiopathic macular edema, retinitis, dry eye (keratoconjunctivitis Sicca), vernal keratoconjunctivitis, atopic keratoconjunctivitis, uveitis (such as anterior uveitis, pan uveitis, posterior uveitis, uveitis-associated macular edema), scleritis, diabetic retinopathy, diabetic macula edema, age-related macular dystrophy, hepatitis, pancreatitis, primary biliary cirrhosis, sclerosing cholangitis, Addison's disease, hypophysitis, thyroiditis, Type I diabetes, Type II diabetes, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis, pyoderma gangrenosum, vasculitis with organ involvement and acute rejection of transplanted organs.

In one embodiment the acute or chronic autoimmune and/or inflammatory condition is a disorder of lipid metabolism mediated via the regulation of APO-A1 such as hypercholesterolemia, atherosclerosis or Alzheimer's disease.

In another embodiment the acute or chronic autoimmune and/or inflammatory condition is a respiratory disorder such as asthma or chronic obstructive airways disease.

In another embodiment the acute or chronic autoimmune and/or inflammatory condition is a systemic inflammatory disorder such as rheumatoid arthritis, osteoarthritis, acute gout, psoriasis, systemic lupus erythematosus, multiple sclerosis or inflammatory bowel disease (Crohn's disease or Ulcerative colitis).

In another embodiment, the acute or chronic autoimmune and/or inflammatory condition is multiple sclerosis.

In another embodiment, the acute or chronic autoimmune and/or inflammatory condition is Type I diabetes.

In another embodiment, the acute or chronic autoimmune and/or inflammatory condition is rheumatoid arthritis.

Bromodomain inhibitors may be useful in the treatment of depression.

Bromodomain inhibitors may be useful in the treatment of diseases or conditions which involve inflammatory responses to infections with bacteria, viruses, fungi, parasites or their toxins, such as sepsis, acute sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria and SIRS associated with viral infections such as influenza, herpes zoster, herpes simplex and coronavirus. In one embodiment the disease or condition which involves an inflammatory response to an infection with bacteria, a virus, fungi, a parasite or their toxins is acute sepsis.

Bromodomain inhibitors may be useful in the treatment of conditions associated with ischaemia-reperfusion injury such as myocardial infarction, cerebro-vascular ischaemia (stroke), acute coronary syndromes, renal reperfusion injury, organ transplantation, coronary artery bypass grafting, cardio-pulmonary bypass procedures, pulmonary, renal, hepatic, gastro-intestinal or peripheral limb embolism.

Bromodomain inhibitors may be useful in the treatment of cardiovascular diseases such as coronary artery diseases (for example, angina or myocardial infarction), cerebro-vascular ischaemia (stroke), hypertensive heart disease, rheumatic heart disease, cardiomyopathy, atrial fibrillation, congenital heart disease, endocarditis, aortic aneurysms or peripheral artery disease.

Bromodomain inhibitors may be useful in the treatment of fibrotic conditions such as idiopathic pulmonary fibrosis, renal fibrosis, post-operative stricture, keloid scar formation, scleroderma (including morphea) or cardiac fibrosis.

Bromodomain inhibitors may be useful in the treatment of viral infections such as herpes simplex infections and reactivations, cold sores, herpes zoster infections and reactivations, chickenpox, shingles, human papilloma virus (HPV), human immunodeficiency virus (HIV), cervical neoplasia, adenovirus infections, including acute respiratory disease, poxyirus infections such as cowpox or smallpox, or African swine fever virus. In one embodiment the viral infection is a HPV infection of skin or cervical epithelia. In another embodiment the viral infection is a latent HIV infection.

Bromodomain inhibitors may be useful in the treatment of a wide variety of bone disorders such as osteoporosis, osteopenia, osteoarthritis and ankylosing spondylitis.

Bromodomain inhibitors may be useful in the treatment of cancer, including hematological cancers (such as leukaemia, lymphoma and multiple myeloma), epithelial cancers (including lung, breast or colon carcinomas), midline carcinomas, or mesenchymal, hepatic, renal or neurological tumours.

Bromodomain inhibitors may be useful in the treatment of one or more cancers selected from brain cancer (gliomas), glioblastomas, Bannayan-Zonana syndrome, Cowden disease, Lhermitte-Duclos disease, breast cancer, inflammatory breast cancer, colorectal cancer, Wilm's tumor, Ewing's sarcoma, rhabdomyosarcoma, ependymoma, medulloblastoma, colon cancer, head and neck cancer, kidney cancer, lung cancer, liver cancer, melanoma, squamous cell carcinoma, ovarian cancer, pancreatic cancer, prostate cancer, sarcoma cancer, osteosarcoma, giant cell tumor of bone, thyroid cancer, lymphoblastic T-cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T-cell leukemia, plasmacytoma, immunoblastic large cell leukemia, mantle cell leukemia, multiple myeloma, megakaryoblastic leukemia, acute megakaryocytic leukemia, promyelocytic leukemia, mixed lineage leukaemia, erythroleukemia, malignant lymphoma, Hodgkins lymphoma, non-Hodgkins lymphoma, lymphoblastic T-cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor), NUT-midline carcinoma and testicular cancer.

In one embodiment the cancer is a leukaemia, for example a leukaemia selected from acute monocytic leukemia, acute myelogenous leukemia, chronic myelogenous leukemia, chronic lymphocytic leukemia and mixed lineage leukaemia (MLL). In another embodiment the cancer is NUT-midline carcinoma. In another embodiment the cancer is multiple myeloma. In another embodiment the cancer is a lung cancer such as small cell lung cancer (SCLC). In another embodiment the cancer is a neuroblastoma. In another embodiment the cancer is Burkitt's lymphoma. In another embodiment the cancer is cervical cancer. In another embodiment the cancer is esophageal cancer. In another embodiment the cancer is ovarian cancer. In another embodiment the cancer is breast cancer. In another embodiment the cancer is colarectal cancer.

Bromodomain inhibitors may be useful in the treatment of diseases associated with systemic inflammatory response syndrome, such as sepsis, burns, pancreatitis, major trauma, haemorrhage and ischaemia. In this embodiment the bromodomain inhibitor would be administered at the point of diagnosis to reduce the incidence of: SIRS, the onset of shock, multi-organ dysfunction syndrome, which includes the onset of acute lung injury, ARDS, acute renal, hepatic, cardiac or gastro-intestinal injury and mortality. In another embodiment the bromodomain inhibitor would be administered prior to surgical or other procedures associated with a high risk of sepsis, haemorrhage, extensive tissue damage, SIRS or MODS (multiple organ dysfunction syndrome). In a particular embodiment the disease or condition for which a bromodomain inhibitor is indicated is sepsis, sepsis syndrome, septic shock and endotoxaemia. In another embodiment, the bromodomain inhibitor is indicated for the treatment of acute or chronic pancreatitis. In another embodiment the bromodomain is indicated for the treatment of burns.

The present invention thus provides a compound of formula (I) or a pharmaceutically acceptable salt thereof for use in therapy. The compound of formula (I) or a pharmaceutically salt thereof can be used in the treatment of diseases or conditions for which a bromodomain inhibitor is indicated.

The present invention thus provides a compound of formula (I) or a pharmaceutically acceptable salt thereof for use in the treatment of a disease or condition for which a bromodomain inhibitor is indicated. In one embodiment there is provided a compound of formula (I) or a pharmaceutically acceptable salt thereof for use in the treatment of acute or chronic auto-immune and/or inflammatory conditions. In one embodiment there is provided a compound of formula (I) or a pharmaceutically acceptable salt thereof for use in the treatment of rheumatoid arthritis. In another embodiment there is provided a compound of formula (I) or a pharmaceutically acceptable salt thereof for use in the treatment of diseases or conditions which involve inflammatory responses to infections with bacteria, viruses, fungi, parasites or their toxins. In another embodiment there is provided a compound of formula (I) or a pharmaceutically acceptable salt thereof for use in the treatment of conditions associated with ischaemia-reperfusion injury. In another embodiment there is provided a compound of formula (I) or a pharmaceutically acceptable salt thereof for use in the treatment of cardiovascular diseases. In another embodiment there is provided a compound of formula (I) or a pharmaceutically acceptable salt thereof for use in the treatment of fibrotic conditions. In another embodiment there is provided a compound of formula (I) or a pharmaceutically acceptable salt thereof for use in the treatment of viral infections. In another embodiment there is provided a compound of formula (I) or a pharmaceutically acceptable salt thereof for use in the treatment of bone disorders. In another embodiment there is provided a compound of formula (I) or a pharmaceutically acceptable salt thereof for use in the treatment of cancer. In a further embodiment there is provided a compound of formula (I) or a pharmaceutically acceptable salt thereof for use in the treatment of diseases associated with systemic inflammatory response syndrome.

Also provided is the use of a compound of formula (I) or a pharmaceutically acceptable salt thereof in the manufacture of a medicament for the treatment of diseases or conditions for which a bromodomain inhibitor is indicated. In one embodiment there is provided the use of a compound of formula (I) or a pharmaceutically acceptable salt thereof in the manufacture of a medicament for the treatment of acute or chronic auto-immune and/or inflammatory conditions. In one embodiment there is provided the use of a compound of formula (I) or a pharmaceutically acceptable salt thereof in the manufacture of a medicament for the treatment of rheumatoid arthritis. In another embodiment there is provided the use of a compound of formula (I) or a pharmaceutically acceptable salt thereof in the manufacture of a medicament for the treatment of diseases or conditions which involve inflammatory responses to infections with bacteria, viruses, fungi, parasites or their toxins. In another embodiment there is provided the use of a compound of formula (I) or a pharmaceutically acceptable salt thereof in the manufacture of a medicament for the treatment of conditions associated with ischaemia-reperfusion injury. In another embodiment there is provided the use of a compound of formula (I) or a pharmaceutically acceptable salt thereof in the manufacture of a medicament for the treatment of cardiovascular diseases. In another embodiment there is provided the use of a compound of formula (I) or a pharmaceutically acceptable salt thereof in the manufacture of a medicament for the treatment of fibrotic conditions. In another embodiment there is provided the use of a compound of formula (I) or a pharmaceutically acceptable salt thereof in the manufacture of a medicament for the treatment of viral infections. In another embodiment there is provided the use of a compound of formula (I) or a pharmaceutically acceptable salt thereof in the manufacture of a medicament for the treatment of cancer. In a further embodiment there is provided the use of a compound of formula (I) or a pharmaceutically acceptable salt thereof in the manufacture of a medicament for the treatment of diseases associated with systemic inflammatory response syndrome.

Also provided is a method of treating diseases or conditions for which a bromodomain inhibitor is indicated in a subject in need thereof which comprises administering a therapeutically effective amount of compound of formula (I) or a pharmaceutically acceptable salt thereof. In one embodiment there is provided a method of treating acute or chronic auto-immune and/or inflammatory conditions in a subject in need thereof which comprises administering a therapeutically effective amount of a compound of formula (I) or a pharmaceutically acceptable salt thereof. In one embodiment there is provided a method of treating rheumatoid arthritis in a subject in need thereof which comprises administering a therapeutically effective amount of a compound of formula (I) or a pharmaceutically acceptable salt thereof. In another embodiment there is provided a method of treating diseases or conditions which involve inflammatory responses to infections with bacteria, viruses, fungi, parasites or their toxins in a subject in need thereof which comprises administering a therapeutically effective amount of a compound of formula (I) or a pharmaceutically acceptable salt thereof. In another embodiment there is provided a method of treating conditions associated with ischaemia-reperfusion injury in a subject in need thereof which comprises administering a therapeutically effective amount of a compound of formula (I) or a pharmaceutically acceptable salt thereof. In another embodiment there is provided a method of treating cardiovascular diseases in a subject in need thereof which comprises administering a therapeutically effective amount of a compound of formula (I) or a pharmaceutically acceptable salt thereof. In another embodiment there is provided a method of treating fibrotic conditions in a subject in need thereof which comprises administering a therapeutically effective amount of a compound of formula (I) or a pharmaceutically acceptable salt thereof. In another embodiment there is provided a method of treating viral infections in a subject in need thereof which comprises administering a therapeutically effective amount of a compound of formula (I) or a pharmaceutically acceptable salt thereof. In another embodiment there is provided a method of treating cancer in a subject in need thereof which comprises administering a therapeutically effective amount of a compound of formula (I) or a pharmaceutically acceptable salt thereof. In a further embodiment there is provided a method of treating diseases associated with systemic inflammatory response syndrome in a subject in need thereof which comprises administering a therapeutically effective amount of a compound of formula (I) or a pharmaceutically acceptable salt thereof.

Suitably the subject in need thereof is a mammal, particularly a human.

The invention further provides for a method for inhibiting a bromodomain which comprises contacting the bromodomain with a compound of formula (I) or a pharmaceutically acceptable salt thereof.

Pharmaceutical Compositions/Routes of Administration/Dosages

Compositions

While it is possible that for use in therapy, a compound of formula (I) as well as pharmaceutically acceptable salts thereof may be administered as the raw chemical, it is common to present the active ingredient as a pharmaceutical composition. The compounds of formula (I) and pharmaceutically acceptable salts thereof will normally, but not necessarily, be formulated into pharmaceutical compositions prior to administration to a patient. Accordingly, in another aspect there is provided a pharmaceutical composition comprising a compound of formula (I), or a pharmaceutically acceptable salt thereof, and a pharmaceutically acceptable excipient. The compounds of formula (I) and pharmaceutically acceptable salts are as described above. The excipient(s) must be acceptable in the sense of being compatible with the other ingredients of the composition and not deleterious to the recipient thereof. In accordance with another aspect of the invention there is also provided a process for the preparation of a pharmaceutical composition including admixing a compound of formula (I), or a pharmaceutically acceptable salt thereof, with a pharmaceutically acceptable excipient. The pharmaceutical composition can be used in the treatment of any of the conditions described herein.

In a further aspect the invention is directed to pharmaceutical compositions for the treatment or prophylaxis of a disease or condition for which a bromodomain inhibitor is indicated comprising a compound of formula (I) or a pharmaceutically acceptable salt thereof.

Since the compounds of formula (I) are intended for use in pharmaceutical compositions it will be readily understood that they are each preferably provided in substantially pure form, for example, at least 85% pure, especially at least 98% pure (% in a weight for weight basis).

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Pharmaceutical compositions may be adapted for administration by any appropriate route, for example by the oral (including buccal or sublingual), rectal, inhaled, intranasal, topical (including buccal, sublingual or transdermal), ocular (including topical, intraocular, subconjunctival, episcleral, sub-Tenon), vaginal or parenteral (including subcutaneous, intramuscular, intravenous or intradermal) route. Such compositions may be prepared by any method known in the art of pharmacy, for example by bringing into association the active ingredient with the carrier(s) or excipient(s).

The pharmaceutical compositions of the invention may be prepared and packaged in bulk form wherein a safe and effective amount of a compound of formula (I) or a pharmaceutically acceptable salt thereof can be extracted and then given to the patient such as with powders or syrups. Alternatively, the pharmaceutical compositions of the invention may be prepared and packaged in unit dosage form wherein each physically discrete unit contains a compound of formula (I) or a pharmaceutically acceptable salt thereof. When prepared in unit dosage form, the pharmaceutical compositions of the invention typically may contain, for example, from 0.25 mg to 1 g, or from 0.5 mg to 500 mg, or from 1 mg to 100 mg, of a compound of formula (I) or a pharmaceutically acceptable salt thereof.

The pharmaceutical compositions of the invention typically contain one compound of formula (I) or a pharmaceutically acceptable salt thereof.

The compound of formula (I) or a pharmaceutically acceptable salt thereof and the pharmaceutically acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting of the compound or compounds of formula (I) or pharmaceutically acceptable salts thereof once administered to the subject from one organ, or portion of the body, to another organ, or portion of the body. Certain pharmaceutically acceptable excipients may be chosen for their ability to enhance subjectcompliance.

Suitable pharmaceutically-acceptable excipients include the following types of excipients: diluents, fillers, binders, disintegrants, lubricants, glidants, granulating agents, coating agents, wetting agents, solvents, co-solvents, suspending agents, emulsifiers, sweetners, flavouring agents, flavour-masking agents, colouring agents, anti-caking agents, humectants, chelating agents, plasticisers, viscosity increasing agents, antioxidants, preservatives, stabilisers, surfactants, and buffering agents. The skilled artisan will appreciate that certain pharmaceutically-acceptable excipients may serve more than one function and may serve alternative functions depending on how much of the excipient is present in the formulation and what other excipients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (*Mack Publishing Company*), *The Handbook of Pharmaceutical Additives* (*Gower Publishing Limited*), and *The Handbook of Pharmaceutical Excipients* (*the American Pharmaceutical Association and the Pharmaceutical Press*).

The pharmaceutical compositions of the invention are prepared using techniques and methods known to those skilled in the art. Some of the methods commonly used in the art are described in *Remington's Pharmaceutical Sciences* (*Mack Publishing Company*).

Accordingly, in another aspect the invention is directed to process for the preparation of a pharmaceutical composition comprising a compound of formula (I) or a pharmaceutically acceptable salt thereof and one or more pharmaceutically-acceptable excipients which comprises mixing the ingredients. A pharmaceutical composition comprising a compound of formula (I) or a pharmaceutically acceptable salt thereof may be prepared by, for example, admixture at ambient temperature and atmospheric pressure.

In one embodiment the pharmaceutical composition is adapted for parenteral administration, particularly intravenous administration.

In one embodiment the pharmaceutical composition is adapted for oral administration.

In one embodiment the pharmaceutical composition is adapted for topical administration.

Pharmaceutical compositions adapted for parenteral administration include aqueous and non-aqueous sterile injection solutions (which may contain anti-oxidants, buffers, bacteriostats and solutes which render the composition isotonic with the blood of the intended recipient) and aqueous and non-aqueous sterile suspensions (which may include suspending agents and thickening agents).

The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders suitable for incorporating into tablets or capsules may be prepared by reducing the compound to a suitable fine size (e.g. by micronisation) and mixing with a similarly prepared pharmaceutical carrier such as an edible carbohydrate, for example, starch or mannitol. Flavoring, preservative, dispersing and coloring agent can also be present.

Capsules may be made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, glidants, lubricants, sweetening agents, flavours, disintegrating agents (disintegrants) and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrants include starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of formula (I) and pharmaceutically acceptable salts thereof can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Compositions for oral administration may be designed to provide a modified release profile so as to sustain or otherwise control the release of the therapeutically active agent.

Where appropriate, dosage unit compositions for oral administration can be microencapsulated. The composition may be prepared to prolong or sustain the release as for example by coating or embedding particulate material in polymers, wax or the like.

For compositions suitable and/or adapted for oral dministration, the compound of formula (I) or a pharmaceutically acceptable salt thereof, may be in a particle-size-reduced form e.g. obtained by micronisation. The preferable particle size of the size-reduced (e.g. micronised) compound or salt is defined by a $D_{50}$ value of about 0.5 to about 10 microns (for example as measured using laser diffraction).

The compounds of formula (I) and pharmaceutically acceptable salts thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Pharmaceutical compositions adapted for topical administration may be formulated as ointments, creams, suspensions, emulsions, lotions, powders, solutions, pastes, gels, foams, sprays, aerosols or oils. Such pharmaceutical compositions may include conventional additives which include, but are not limited to, preservatives, solvents to assist drug penetration, co-solvents, emollients, propellants, viscosity modifying agents (gelling agents), surfactants and carriers. In one embodiment there is provided a pharmaceutical composition adapted for topical administration which comprises between 0.01-10%, or between 0.01-1% of the compound of formula (I), or a pharmaceutically acceptable salt thereof, by weight of the composition.

For treatments of the eye or other external tissues, for example mouth and skin, the compositions are preferably applied as a topical ointment, cream, gel, spray or foam. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent. Compositions to be administered to the eye will have ophthalmically compatible pH and osmolality. One or more ophthalmically acceptable pH adjusting agents and/or buffering agents can be included in a composition of the invention, including acids such as acetic, boric, citric, lactic, phosphoric and hydrochloric acids; bases such as sodium hydroxide, sodium phosphate, sodium borate, sodium citrate, sodium acetate, and sodium lactate; and buffers such as citrate/dextrose, sodium bicarbonate and ammonium chloride. Such acids, bases, and buffers can be included in an amount required to maintain pH of the composition in an ophthalmically acceptable range. One or more ophthalmically acceptable salts can be included in the composition in an amount sufficient to bring osmolality of the composition into an ophthalmically acceptable range. Such salts include those having sodium, potassium or ammonium cations and chloride, citrate, ascorbate, borate, phosphate, bicarbonate, sulfate, thiosulfate or bisulfite anions.

The ocular delivery device may be designed for the controlled release of one or more therapeutic agents with multiple defined release rates and sustained dose kinetics and permeability. Controlled release may be obtained through the design of polymeric matrices incorporating different choices and properties of biodegradable/bioerodable polymers (e.g. poly(ethylene vinyl) acetate (EVA), superhydrolyzed PVA), hydroxyalkyl cellulose (HPC), methylcellulose (MC), hydroxypropyl methyl cellulose (HPMC), polycaprolactone, poly(glycolic) acid, poly(lactic) acid, polyanhydride, of polymer molecular weights, polymer crystallinity, copolymer ratios, processing conditions, surface finish, geometry, excipient addition and polymeric coatings that will enhance drug diffusion, erosion, dissolution and osmosis.

Pharmaceutical compositions for ocular delivery also include in situ gellable aqueous composition. Such a composition comprises a gelling agent in a concentration effective to promote gelling upon contact with the eye or with lacrimal fluid. Suitable gelling agents include but are not limited to thermosetting polymers. The term "in situ gellable" as used herein is includes not only liquids of low viscosity that form gels upon contact with the eye or with lacrimal fluid, but also includes more viscous liquids such as semi-fluid and thixotropic gels that exhibit substantially increased viscosity or gel stiffness upon administration to the eye. See, for example, Ludwig (2005) *Adv. Drug Deliv. Rev.* 3; 57:1595-639, herein incorporated by reference for purposes of its teachings of examples of polymers for use in ocular drug delivery.

Dosage forms for nasal or inhaled administration may conveniently be formulated as aerosols, solutions, suspensions, gels or dry powders.

For compositions suitable and/or adapted for inhaled administration, it is preferred that the compound of formula (I) or a pharmaceutically acceptable salt thereof, is in a particle-size-reduced form e.g. obtained by micronisation. The preferable particle size of the size-reduced (e.g. micronised) compound or salt is defined by a $D_{50}$ value of about 0.5 to about 10 microns (for example as measured using laser diffraction).

Aerosol formulations, e.g. for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g. co-solvents and/or surfactants to improve the dispersion characteristics and homogeneity of suspension formulations. Solution formulations may also require the addition of co-solvents such as ethanol.

For pharmaceutical compositions suitable and/or adapted for inhaled administration, the pharmaceutical composition may be a dry powder inhalable composition. Such a composition can comprise a powder base such as lactose, glucose, trehalose, mannitol or starch, the compound of formula (I) or a pharmaceutically acceptable salt thereof (preferably in particle-size-reduced form, e.g. in micronised form), and optionally a performance modifier such as L-leucine or another amino acid and/or metal salt of stearic acid such as magnesium or calcium stearate. Preferably, the dry powder inhalable composition comprises a dry powder blend of lactose e.g. lactose monohydrate and the compound of formula (I) or salt thereof. Such compositions can be administered to the patient using a suitable device such as the DISKUS® device, marketed by GlaxoSmithKline which is for example described in GB 2242134 A.

The compounds of formula (I) and pharmaceutically acceptable salts thereof may be formulated as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO-A-2005/044354.

A therapeutically effective amount of a compound of formula (I) or a pharmaceutically acceptable salt thereof, will depend upon a number of factors including, for example, the age and weight of the patient, the precise condition requiring treatment and its severity, the nature of the formulation, and the route of administration, and will ultimately be at the discretion of the attendant physician or veterinarian. In the pharmaceutical composition, each dosage unit for oral or parenteral administration preferably contains from 0.01 mg to 3000 mg, more preferably 0.5 mg to 1000 mg, of a compound of formula (I) or a pharmaceutically acceptable salt thereof, calculated as the free base. Each dosage unit for nasal or inhaled administration preferably contains from 0.001 mg to 50 mg, more preferably 0.01 mg to 5 mg, of a compound of the formula (I) or a pharmaceutically acceptable salt thereof, calculated as the free base.

The pharmaceutically acceptable compounds of formula (I) and pharmaceutically acceptable salts thereof, can be administered in a daily dose (for an adult patient) of, for example, an oral or parenteral dose of 0.01 mg to 3000 mg per day, 0.5 mg to 1000 mg per day or 100 mg to 2500 mg per day, or a nasal or inhaled dose of 0.001 mg to 50 mg per day or 0.01 mg to 5 mg per day, of the compound of the formula (I) or a pharmaceutically acceptable salt thereof, calculated as the free base. This amount may be given in a single dose per day or more usually in a number (such as two, three, four, five or six) of sub-doses per day such that the total daily dose is the same. An effective amount of a salt thereof, may be determined as a proportion of the effective amount of the compound of formula (I) per se.

The compounds of formula (I) and pharmaceutically acceptable salts thereof may be employed alone or in combination with other therapeutic agents. Combination therapies according to the present invention thus comprise the administration of at least one compound of formula (I) or a pharmaceutically acceptable salt thereof, and the use of at least one other therapeutically active agent. Preferably, combination therapies according to the present invention comprise the administration of at least one compound of formula (I) or a pharmaceutically acceptable salt thereof, and at least one other therapeutically active agent. The compound(s) of formula (I) and pharmaceutically acceptable salts thereof, and the other therapeutically active agent(s) may be administered together in a single pharmaceutical composition or separately and, when administered separately this may occur simultaneously or sequentially in any order. The amounts of the compound(s) of formula (I) and pharmaceutically acceptable salts thereof, and the other therapeutically active agent(s) and the relative timings of administration will be selected in order to achieve the desired combined therapeutic effect. Thus in a further aspect, there is provided a combination comprising a compound of formula (I) or a pharmaceutically acceptable salt thereof, together with one or more other therapeutically active agents.

Thus in one aspect, the compound of formula (I) or a pharmaceutically acceptable salt thereof, and pharmaceutical compositions comprising a compound of formula (I) or a pharmaceutically acceptable salt thereof, according to the invention may be used in combination with or include one or more other therapeutic agents, for example selected from antibiotics, anti-virals, glucocorticosteroids, muscarinic antagonists, beta-2 agonists and Vitamin D3 analogues. In a further embodiment a compound of formula (I) or a pharmaceutically acceptable salt thereof may be used in combination with a further therapeutic agent which is suitable for the treatment of cancer. Examples of such further therapeutic agents are desfibed in Cancer Principles and Practice of Oncology by V. T. Devita and S. Hellman (editors), 6th edition (2001), Lippincott Williams & Wilkins Publishers. A person of ordinary skill in the art would be able to discern which combinations of agents would be useful based on the particular characteristics of the drugs and the cancer involved. Further therapeutic agents to be used in combination with the compound of formula (I) or a pharmaceutically acceptable salt thereof include, but are not limited to, anti-microtubule agents (such as diterpenoids and vinca alkaloids); platinum coordination complexes; alkylating agents (such as nitrogen mustards, oxazaphosphorines, alkylsulphonates, nitrosoureas, and triazenes); antibiotic agents (such as anthracyclins, actinomycins and bleomycins); topoisomerase II inhibitors (such as epipodophyllotoxins); antimetabolites (such as purine and pyrimidine analogues and anti-folate compounds); topoisomerase I inhibitors (such as camptothecins; hormones and hormonal analogues); signal transduction pathway inhibitors (such as tyropsine receptor inhibitors); non-receptor tyrosine kinase angiogenesis inhibitors; immunotherapeutic agents; proapoptotic agents; epigenetic or transcriptional modulators (such as histone deacetylase inhibitors) and cell cycle signaling inhibitors.

It will be appreciated that when the compound of formula (I) or a pharmaceutically acceptable salt thereof, is administered in combination with other therapeutic agents normally administered by the inhaled, intravenous, oral or intranasal route, that the resultant pharmaceutical composition may be administered by the same routes. Alternatively the individual components of the composition may be administered by different routes.

One embodiment of the invention encompasses combinations comprising one or two other therapeutic agents.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention.

General Synthetic Routes

The compounds of the invention may be made by a variety of methods, including standard chemistry. Any previously defined variable will continue to have the previously defined meaning unless otherwise indicated. Illustrative general synthetic methods are set out in the following schemes, and can be readily adapted to prepare other compounds of the invention. Specific compounds of the invention are prepared in the Examples section.

Compounds of formula (I) may be prepared as described in any of the Schemes below:

Scheme 1:

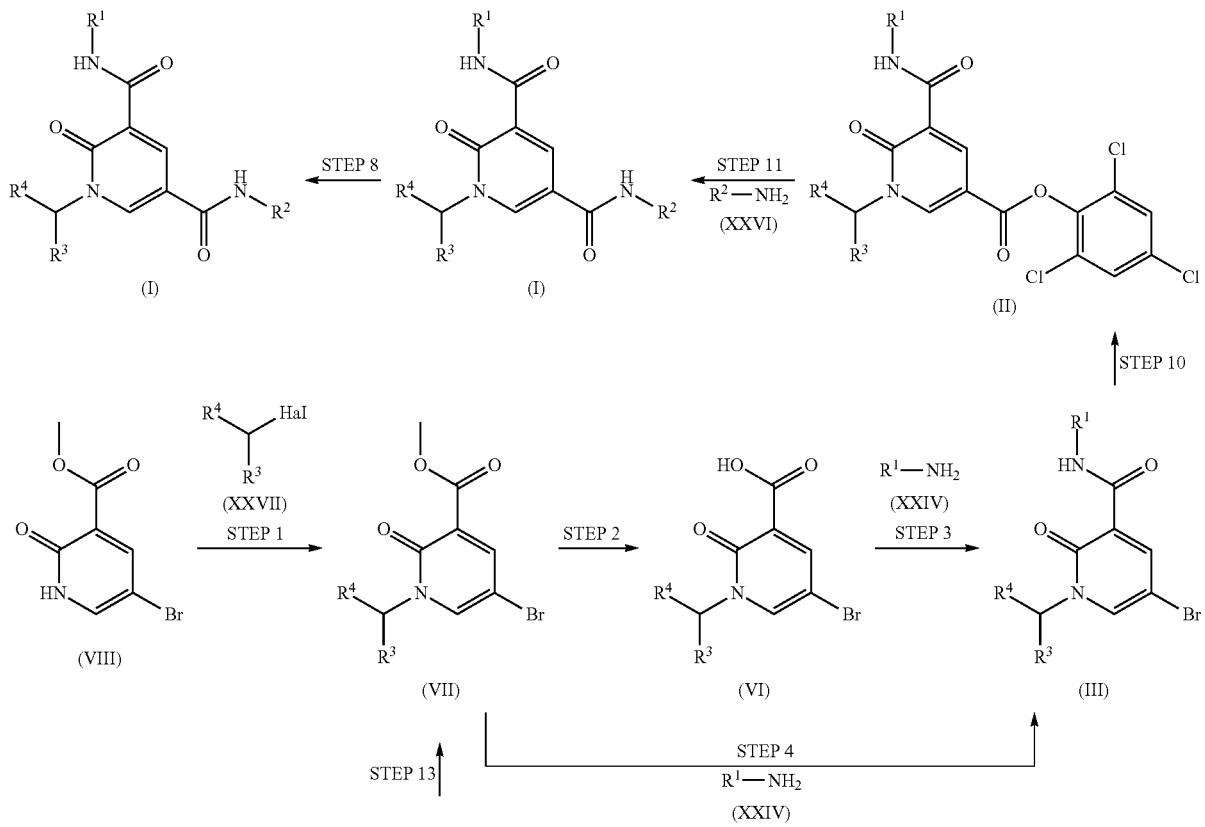

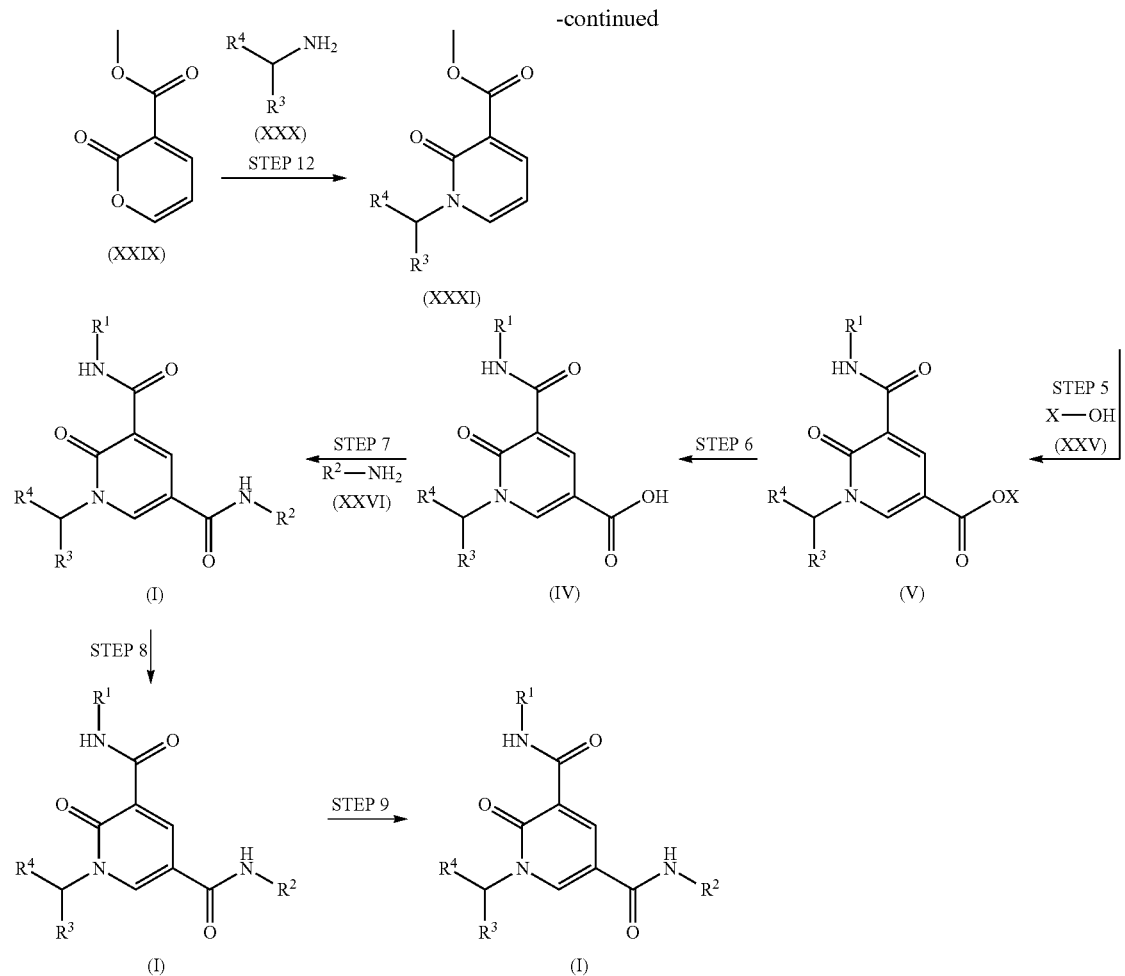

wherein $R^1$, $R^2$, $R^3$ and $R^4$ are as described above, Hal is chlorine or bromine and X is a $C_{1-6}$alkyl group.

In respect of the steps shown in Scheme 1 above the following reaction conditions may be utilised:

Step 1: is an alkylation and may be carried out using an alkyl or benzyl halide of formula $R^4CH(R^3)Hal$, such as an alkylbromide of formula $R^4CH(R^3)Br$, in the presence of an inorganic base, such as sodium hydride, in a suitable solvent, preferably an aprotic solvent, such as DMF, THF or 2-MeTHF, at a suitable temperature, such as 0° C.

Step 2: is base hydrolysis and may be carried out using any suitable inorganic base, such as LiOH, in a suitable solvent or solvent mixture, such as a mixture of methanol and THF, at a suitable temperature, such as room temperature.

Step 3: is an amide coupling reaction consisting of two steps. Step 3a, to produce the acid chloride, may be carried out using a chlorinating agent, such as oxalyl chloride, in the presence of a suitable catalyst, such as DMF, in a suitable solvent, such as DCM, at a suitable temperature, such as room temperature. Step 3b may be carried out using an amine reagent, $R^1$—$NH_2$, optionally in the presence of a tertiary amine, such as triethylamine, in a suitable solvent, such as THF, at a suitable temperature, such as 0° C.

Step 4: is an amine displacement reaction and may be carried out using an amine reagent, $R^1$—$NH_2$, in a suitable solvent or solvent mixture, such as a mixture of water and methanol, at a suitable temperature, such as 50° C.

Step 5: is a carbonylation reaction and may be carried out using an alcohol reagent, XOH (X is a $C_{1-6}$alkyl group), in the presence of a tertiary amine, such as triethylamine, in the presence of a palladium catalyst, such as palladium acetate, in the presence of a phosphine ligand, such as dppb, in the presence of carbon monoxide, in a suitable solvent, such as DMSO, at a suitable temperature, such as 100° C.

Step 6: is a hydrolysis step and may be carried out using an inorganic base, such as NaOH or LiOH, in a suitable solvent or solvent mixture, such as methanol and THF, at a suitable temperature, such as room temperature.

Step 7: is an amide coupling reaction and may be carried out using an amine reagent, $R^2$—$NH_2$, in the presence of a suitable tertiary amine, such as triethylamine or DIPEA, in the presence of a suitable amide coupling reactant, such as HATU, in a suitable solvent, such as DCM or DMF, at a suitable temperature, such as room temperature.

Step 8: is an optional deprotection step to remove a protecting group, such as BOC and may be carried out using an acid such as TFA, in the presence of a suitable solvent, such as DCM, at a suitable temperature, such as room temperature.

Step 9: is an optional salt formation and may be carried out using an acid, such as 1M hydrochloric acid in diethyl ether, in a suitable solvent, such as methanol, at a suitable temperature, such as room temperature.

Step 10: is a carbonylation reaction and may be carried out using a metal carbonyl complex, such as dicobalt octacarbonyl, in the presence of a phosphine ligand, such as Xantphos, in the presence of a suitable palladium catalyst, such as palladium (II) acetate, in the presence of a nucleophilic catalyst, such as DMAP, in the presence of a suitable solvent, such as THF, at a suitable temperature, such as 80° C.

Step 11: is a displacement reaction and may be carried out using an amine reagent, $R^2$—$NH_2$, in the presence of a nucleophilic catalyst, such as DMAP, in the presence of a tertiary amine, such as triethylamine, in the presence of a suitable solvent, such as THF, at a suitable temperature, such as 45° C.

Step 12: is a pyridone formation and may be carried out using an alkyl or benzyl amine, such as $R^4CH(R^3)NH_2$, in a suitable solvent or solvent mixture, such as DMF and THF, with the addition of a suitable amide coupling reagent, such as EDC, a suitable nucleophilic catalyst, such as DMAP, and a suitable temperature, such as room temperature.

Step 13: is a bromination reaction and may be carried out using a suitable brominating reactant, such as NBS, in a suitable solvent, such as 2-MeTHF, at a suitable temperature, such as room temperature.

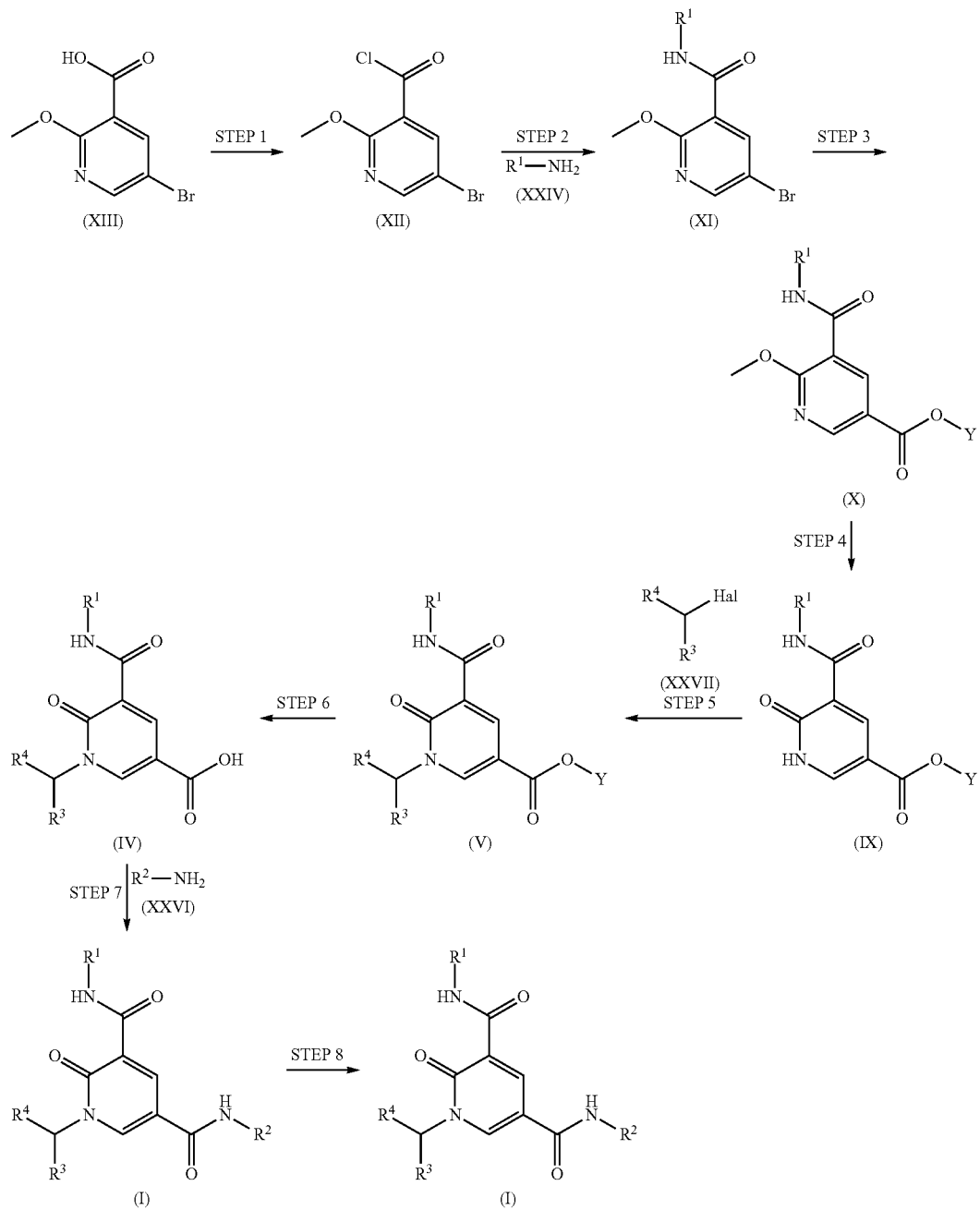

Scheme 2:

wherein $R^1$, $R^2$, $R^3$ and $R^4$ are as described above, Y is a $C_{1-6}$alkyl group and Hal is bromine or chlorine.

In respect of the steps shown in Scheme 2 above the following reaction conditions may be utilised:

Step 1: is an acid chloride formation, and may be carried out using a chlorinating agent, such as oxalyl chloride, in the presence of a suitable catalyst, such as DMF, in a suitable solvent, such as DCM, at a suitable temperature, such as room temperature.

Step 2: is an amine displacement reaction, and may be carried out using an amine reagent, $R^1$—$NH_2$, in the presence of a tertiary amine, such as triethylamine, in a suitable solvent, such as THF, at a suitable temperature, such as 0° C.

Step 3: is a carbonylation reaction and may be carried out using an alcohol reagent, YOH (Y is a $C_{1-6}$alkyl group), in the presence of a tertiary amine, such as triethylamine, in the presence of a palladium catalyst, such as palladium (II) acetate, in the presence of a phosphine ligand, such as dppb, in the presence of carbon monoxide, in a suitable solvent, such as DMSO, at a suitable temperature, such as 100° C.

Step 4: is a demethylation reaction and may be carried out using a demethylating agent, such as NaI with TMS-Cl, in a suitable solvent, such as acetonitrile, at a suitable temperature, such as room temperature.

Step 5: is an alkylation and may be carried out using an alkyl or benzyl halide such as a $R^4CH(R^3)Br$ or $R^4CH(R^3)Cl$, in the presence of an inorganic base, such as potassium carbonate, in a suitable solvent, such as DMF, at a suitable temperature, such as 90° C.

Step 6: is a hydrolysis step and may be carried out using an inorganic base, such as NaOH or LiOH, in a suitable solvent or solvent mixture, such as methanol and THF or 1,4-dioxane and water, at a suitable temperature, such as room temperature.

Step 7: is an amide coupling reaction and may be carried out using an amine reagent, $R^2$—$NH_2$, in the presence of a suitable tertiary amine, such as triethylamine or DIPEA, in the presence of an amide coupling reactant, such as HATU, in a suitable solvent, such as DCM or DMF, at a suitable temperature, such as room temperature.

Step 8: is an optional deprotection step to remove a protecting group, such as BOC and may be carried out using an acid such as TFA, in the presence of a suitable solvent, such as DCM, at a suitable temperature, such as room temperature.

Scheme 3:

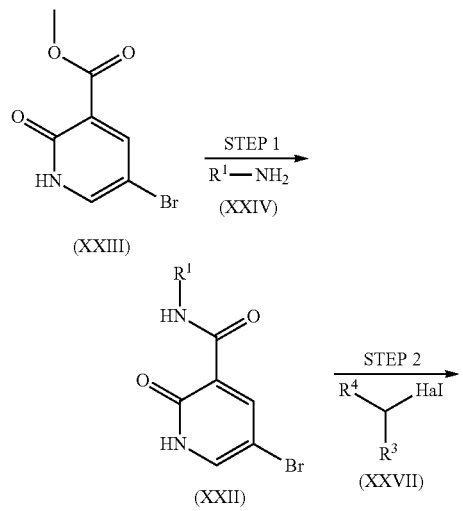

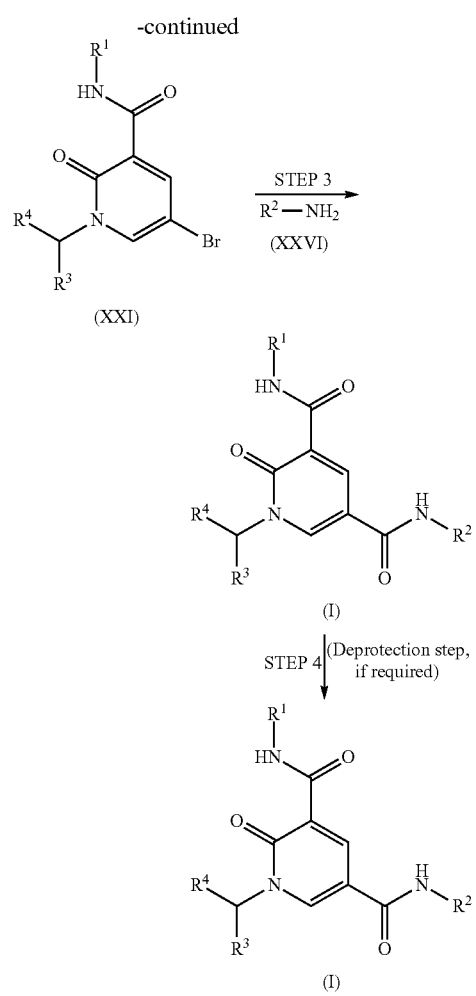

wherein $R^1$, $R^2$, $R^3$ and $R^4$ are as described above and Hal is chorine or bromine.

In respect of the steps shown in Scheme 3 above the following reaction conditions may be utilised:

Step 1: is an amine displacement reaction and may be carried out using an amine reagent, $R^1$—$NH_2$, in a suitable solvent, such as THF, at a suitable temperature, such as under reflux.

Step 2: is an alkylation and may be carried out using an alkyl or benzyl halide such as a $R^4CH(R^3)Br$ or $R^4CH(R^3)Cl$, in the presence of an inorganic base, such as potassium carbonate, in a suitable solvent, such as methanol or DMF, at a suitable temperature, such as 65° C. or 90° C.

Step 3: is an amino carbonylation reaction and may be carried out using an amine reagent such as $R^4$—$NH_2$, a metal carbonyl complex, such as dicobalt octacarbonyl, in the presence of a phosphine ligand, such as Xantphos or Catacxium A, in the presence of a suitable palladium catalyst, such as palladium (II) acetate, in the presence of a suitable nucleophilic catalyst, such as DMAP, in the presence of a suitable solvent, such as 1,4 dioxane or THF, at a suitable temperature, such as 80° C.

Step 4: is an optional deprotection step to remove a protecting group, such as BOC and may be carried out using a suitable acid, such as TFA, in the presence of a suitable solvent, such as DCM, at a suitable temperature, such as room temperature.

Compounds of Formulae (VIII), (XIII), (XXIII) and (XXIX) are commercially available from, for example, Sigma Aldrich, Fluorochem, Apollo Scientific or Combi-Blocks. Compounds of formulae (XXIV), (XXV), (XXVI), (XXVII) and (XXX) are either commercially available from the suppliers mentioned above or can by made by methods well known in the art or described herein.

Accordingly, in one embodiment there is provided a process for the preparation of a compound of formula (I) by the reaction of a compound of formula (II) with an amine of formula (XXVI)

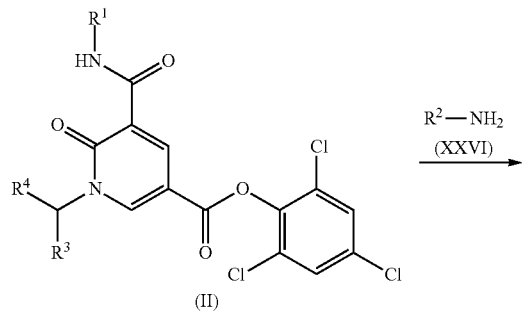

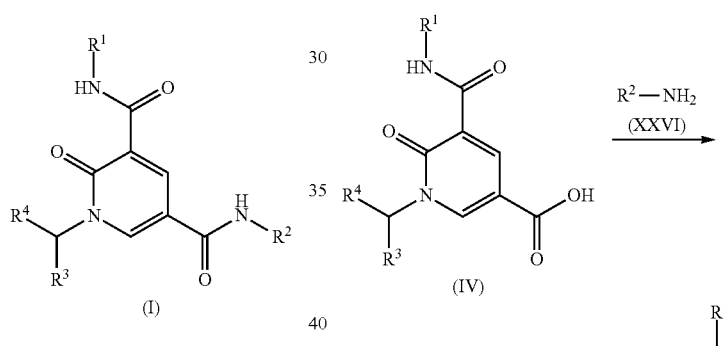

wherein $R^1$, $R^2$, $R^3$ and $R^4$ are as hereinbefore defined; in the presence of a nucleophilic catalyst, such as DMAP, in the presence of a tertiary amine, such as triethylamine, in the presence of a suitable solvent, such as THF, at a suitable temperature, such as 45° C. This step may be followed by removal of any protecting group, if required, followed by preparation of a salt, if required.

In a second embodiment there is provided a process for the preparation of a compound of formula (I) by the reaction of a compound of formula (XXI) with an amine of formula (XXVI)

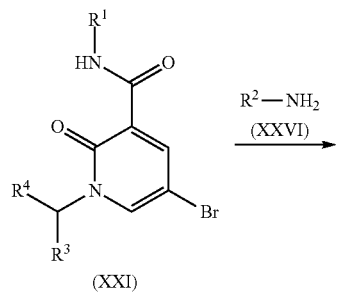

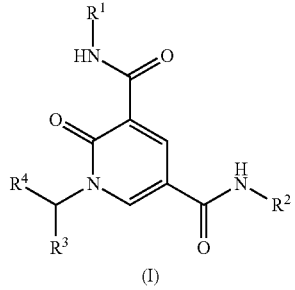

wherein $R^1$, $R^2$, $R^3$ and $R^4$ are as hereinbefore defined; in the presence of a metal carbonyl complex, such as dicobalt octacarbonyl, in the presence of a phosphine ligand, such as Xantphos or Catacxium A, in the presence of a suitable nucleophilic catalyst, such as DMAP, in the presence of a suitable solvent, such as 1,4 dioxane or THF, at a suitable temperature, such as 80° C. This step may be followed by removal of any protecting group, if required, followed by preparation of a salt, if required.

In a third embodiment there is provided a process for the preparation of a compound of formula (I) by the reaction of a compound of formula (IV) with an amine of formula (XXVI)

wherein $R^1$, $R^2$, $R^3$ and $R^4$ are as hereinbefore defined; in the presence of an amide coupling reagent, such as HATU, a tertiary amine, such as triethylamine or DIPEA, in the presence of a suitable solvent, such as DCM or DMF, at a suitable temperature, such as room temperature. This step may be followed by removal of any protecting group, if required, followed by preparation of a salt, if required.

It will be appreciated by those skilled in the art that it may be advantageous to protect one or more functional groups of the compounds described above. Examples of protecting groups and the means for their removal can be found in T. W. Greene 'Protective Groups in Organic Synthesis' (4th edition, J. Wiley and Sons, 2006), incorporated herein by reference as it relates to such procedures.

Suitable amine protecting groups include acyl (e.g. acetyl, carbamate (e.g. 2',2',2'-trichloroethoxycarbonyl, benzyloxycarbonyl or t-butoxycarbonyl) and arylalkyl (e.g. benzyl), which may be removed by acid mediated cleavage (e.g. using an acid such as hydrochloric acid in dioxane or trifluoroacetic acid in dichloromethane) or reductively (e.g. hydrogenolysis of a benzyl or benzyloxycarbonyl group or reductive removal of a 2',2',2'-trichloroethoxycarbonyl group using zinc in acetic acid) as appropriate. Other suitable amine protecting groups include trifluoroacetyl (—C(O)CF$_3$) which may be removed by base catalysed hydrolysis.

It will be appreciated that in any of the routes described above, the precise order of the synthetic steps by which the various groups and moieties are introduced into the molecule may be varied. It will be within the skill of the practitioner in the art to ensure that groups or moieties introduced at one stage of the process will not be affected by subsequent transformations and reactions, and to select the order of synthetic steps accordingly.

Certain intermediate compounds described above form a yet further aspect of the invention.

For any of the hereinbefore described reactions or processes, conventional methods of heating and cooling may be employed, for example temperature-regulated oil-baths or temperature-regulated hot-blocks, and ice/salt baths or dry ice/acetone baths respectively. Conventional methods of isolation, for example extraction from or into aqueous or non-aqueous solvents may be used. Conventional methods of drying organic solvents, solutions, or extracts, such as shaking with anhydrous magnesium sulfate, or anhydrous sodium sulfate, or passing through a hydrophobic frit, may be employed. Conventional methods of purification, for example crystallisation and chromatography, for example silica chromatography or reverse-phase chromatography, may be used as required. Crystallisation may be performed using conventional solvents such as ethyl acetate, methanol, ethanol, or butanol, or aqueous mixtures thereof. It will be appreciated that specific reaction times and temperatures may typically be determined by reaction-monitoring techniques, for example thin-layer chromatography and LC-MS.

EXAMPLES

General Methods
General Experimental Details
All temperatures referred to are in ° C.
As used herein the symbols and conventions used in these processes, schemes and examples are consistent with those used in the contemporary scientific literature, for example, the *Journal of the American Chemical Society*. Unless otherwise noted, all starting materials were obtained from commercial suppliers and used without further purification. Specifically, the following abbreviations may be used in the examples and throughout the specification:

Abbreviations

AcOH acetic acid
BBr$_3$ boron tribromide
BOC/Boc tert-butyloxycarbonyl
BuLi butyllithium
Cs$_2$CO$_3$ cesium carbonate
CHCl$_3$ chloroform
Cobalt carbonyl dicobalt octacarbonyl
CV column volume
DMSO-d$_6$ deuterated dimethylsulfoxide
DCM dichloromethane
DIAD diisopropyl azodicarboxylate
DIBAL-H diisobutylaluminium hydride
DIPEA diisopropylethylamine
DMAP 4-dimethylaminopyridine
DMF dimethylformamide
DMSO dimethylsulfoxide
DPPA diphenylphosphoryl azide
dppb 1,4-bis(diphenylphosphino)butane
EDC 1-ethyl-3-(3-dimethylaminopropyl)carbodiimide
Et$_3$N triethylamine
EtOAc ethyl acetate
h hour(s)
HATU O-(7-azabenzotriazol-1-yl)-N,N,N',N'-tetramethyluronium hexafluorophosphate
HCl hydrochloric acid
HCO$_2$H formic acid
IPA isopropyl alcohol
Isolera Biotage Flash purification system
K$_2$CO$_3$ potassium carbonate
KOH potassium hydroxide
LCMS liquid chromatography-mass spectrometry
LiOH lithium hydroxide
M molar (concentration)
MDAP mass directed autoprep
MeCN acetonitrile
MeI methyl iodide
MeOH methanol
2-MeTHF 2-methyl tetrahydrofuran
MgSO$_4$ magnesium sulphate
min minute(s)
MTBE methyl tert-butyl ether
N normal (concentration)
N$_2$ nitrogen
Na$_2$CO$_3$ sodium carbonate
NaI sodium iodide
NaH sodium hydride
NaOH sodium hydroxide
Na(OAc)$_3$BH sodium triacetoxy borohydride
Na$_2$SO$_4$ sodium sulphate
NBS N-bromosuccinimide
NEt$_3$ triethylamine
NMP N-methyl-2-pyrrolidone
NUT nuclear protein in testis
Pd/C palladium on carbon
PPh$_3$ triphenylphosphine
RBF round bottomed flask
Rt retention time
rt room temperature
sat saturated
SCX Isolute strong cation exchange sorbent SPE
SiO$_2$ silicon dioxide
SNAP Biotage (silica) flash chromatography cartridge
SP4 Biotage Flash purification system
SPE solid phase extraction
TBME tert-butyl methyl ether
Tf$_2$O trifluoromethanesulfonic anhydride
TFA trifluoroacetic acid
THF tetrahydrofuran
TMSCl/TMS-Cl trimethylsilyl chloride
TLC Thin layer chromatography
Ts tosyl
UPLC ultra performance liquid chromatograpy
XantPhos 1,1'-(9,9-dimethyl-9H-xanthene-4,5-diyl)bis[1,1-diphenylphosphine The names of the following compounds have been obtained using the compound naming programme "ACD Name Pro 6.02" or using the naming functionality of ChemDraw Ultra 12.0.

LCMS Methodology
Formic Method
LC Conditions

The UPLC analysis was conducted on an Acquity UPLC CSH C18 column (50 mm×2.1 mm, i.d. 1.7 μm packing diameter) at 40° C.

The solvents employed were:
A=0.1% v/v solution of formic acid in water
B=0.1% v/v solution of formic acid in acetonitrile
The gradient employed was:

| Time (min) | Flow rate (mL/min) | % A | % B |
|---|---|---|---|
| 0 | 1 | 97 | 3 |
| 1.5 | 1 | 5 | 95 |
| 1.9 | 1 | 5 | 95 |
| 2.0 | 1 | 97 | 3 |

The UV detection was a summed signal from wavelength of 210 nm to 350 nm.
MS Conditions
MS: Waters ZQ
Ionisation mode: Alternate-scan positive and negative electrospray
Scan range: 100 to 1000 AMU
Scan time: 0.27 sec
Inter scan delay: 0.10 sec
High pH Method
LC Conditions The UPLC analysis was conducted on an Acquity UPLC CSH C18 column (50 mm×2.1 mm, i.d. 1.7 μm packing diameter) at 40° C.

The solvents employed were:
A=10 mM ammonium hydrogen carbonate in water adjusted to pH10 with ammonia solution
B=acetonitrile
The gradient employed was:

| Time (min) | Flow rate (mL/min) | % A | % B |
|---|---|---|---|
| 0 | 1 | 97 | 3 |
| 0.05 | 1 | 97 | 3 |
| 1.5 | 1 | 5 | 95 |
| 1.9 | 1 | 5 | 95 |
| 2.0 | 1 | 97 | 3 |

The UV detection was a summed signal from wavelength of 210 nm to 350 nm.
MS Conditions
MS: Waters ZQ
Ionisation mode: Alternate-scan positive and negative electrospray
Scan range: 100 to 1000 AMU
Scan time: 0.27 sec
Inter scan delay: 0.10 sec
TFA Method
LC Conditions The UPLC analysis was conducted on an Acquity UPLC CSH C18 column (50 mm×2.1 mm, i.d. 1.7 μm packing diameter) at 40° C.

The solvents employed were:
A=0.1% v/v solution of trifluoroacetic acid in water
B=0.1% v/v solution of trifluoroacetic acid in acetonitrile The gradient employed was:

| Time (min) | Flow rate (mL/min) | % A | % B |
|---|---|---|---|
| 0 | 1 | 95 | 5 |
| 1.5 | 1 | 5 | 95 |
| 1.9 | 1 | 5 | 95 |
| 2.0 | 1 | 95 | 5 |

The UV detection was a summed signal from wavelength of 210 nm to 350 nm.
MS Conditions
MS: Waters ZQ
Ionisation mode: Alternate-scan positive and negative electrospray
Scan range: 100 to 1000 AMU
Scan time: 0.27 sec
Inter scan delay: 0.10 sec
General MDAP Purification Methods Listed below are examples of mass-directed autopreparative chromatography (MDAP) methods that have been used or may be used in compound purification.

MDAP (High pH).

The HPLC analysis was conducted on an Xselect CSH C18 column (150 mm×30 mm i.d. 5 μm packing diameter) at ambient temperature, eluting with 10 mM ammonium bicarbonate in water adjusted to pH 10 with ammonia solution (Solvent A) and acetonitrile (Solvent B) using an elution gradient of between 0 and 100% Solvent B over 15 or 25 minutes.

The UV detection was an averaged signal from wavelength of 210 nm to 350 nm. The mass spectra were recorded on a Waters ZQ Mass Spectrometer using alternate-scan positive and negative electrospray. Ionisation data was rounded to the nearest integer.

MDAP (Formic).

The HPLC analysis was conducted on an Xselect CSH C18 column (150 mm×30 mm i.d. 5 μm packing diameter) at ambient temperature, eluting with 0.1% formic acid in water (Solvent A) and 0.1% formic acid in acetonitrile (Solvent B) using an elution gradient of between 0 and 100% solvent B over 15 or 25 minutes.

The UV detection was an averaged signal from wavelength of 210 nm to 350 nm. The mass spectra were recorded on a Waters ZQ Mass Spectrometer using alternate-scan positive and negative electrospray. Ionisation data was rounded to the nearest integer.

MDAP (TFA).

The HPLC analysis was conducted on an Xselect CSH C18 column (150 mm×30 mm i.d. 5 μm packing diameter) at ambient temperature, eluting with 0.1% v/v solution of trifluoroacetic acid in water (Solvent A) and 0.1% v/v solution of trifluoroacetic acid in acetonitrile (Solvent B) using an elution gradient of between 0 and 100% solvent B over 15 or 25 minutes.

The UV detection was an averaged signal from wavelength of 210 nm to 350 nm. The mass spectra were recorded on a Waters ZQ Mass Spectrometer using alternate-scan positive and negative electrospray. Ionisation data was rounded to the nearest integer.

NMR

Spectra were run on either a 400 MHz or 600 MHz NMR machine at either 302 K or for VT spectra at 392-393 K.

Intermediate 1: 2,4,6-Trichlorophenyl Formate

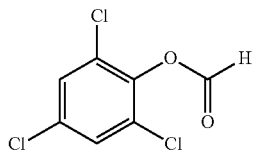 [SMILES: O=COc1c(Cl)cc(Cl)cc1Cl]

Formic acid (57.3 mL, 1519 mmol) and acetic anhydride (115 mL, 1216 mmol) were stirred and heated to 60° C. for 1.5 h then allowed to cool to ambient temperature. The resulting solution was poured into a flask containing 2,4,6-trichlorophenol (30 g, 152 mmol, commercially available from, for example, Sigma-Aldrich) and sodium acetate (12.46 g, 152 mmol). The mixture was stirred for 3.5 h, diluted with toluene (300 mL), washed with water (2×200 mL), dried with sodium sulphate, filtered and evaporated to dryness in vacuo to afford white needle-like crystals (32.45 g).

LCMS (2 min Formic): Rt=1.15 min, [M+Na]$^+$=249.8.

Intermediate 2: Methyl 1-tosyl-1H-indole-4-carboxylate

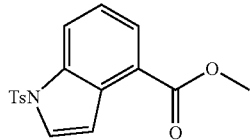 [SMILES: COC(=O)c1cccc2c1ccn2S(=O)(=O)c1ccc(C)cc1]

Methyl 1H-indole-4-carboxylate (750 mg, 4.28 mmol, commercially available from, for example, Sigma-Aldrich) was dissolved in DMF (13.591 mL) at 0° C. under nitrogen. Sodium hydride (205 mg, 5.14 mmol, 60% dispersion in mineral oil) was added in portions. The reaction was stirred at 0° C. for 10 min before warming to rt and stirring for 30 min. Tosyl-Cl (979 mg, 5.14 mmol) was added and the reaction mixture was stirred at rt for 10 min. The reaction was cooled to 0° C. and quenched by the dropwise addition of water (3.86 mL, 214 mmol), before pouring onto saturated aqueous lithium chloride (140 mL). The product was extracted with ethyl acetate (3×30 mL) and the combined organic portions were dried through a hydrophobic frit and evaporated in vacuo to yield the crude product (2056 mg). The residue was dry loaded onto a 50 g SNAP silica cartridge and purified via Biotage SP4 flash chromaotography, eluting from 0-25% ethyl acetate/cyclohexane. The relevant fractions were combined and evaporated in vacuo yield the pure product—methyl 1-tosyl-1H-indole-4-carboxylate (1039 mg, 3.15 mmol, 73.7% yield) as a white solid.

LCMS (2 min Formic): Rt=1.29 min, [MH]$^+$=330.0.

Intermediate 3: (1-Tosyl-1H-indol-4-yl)methanol

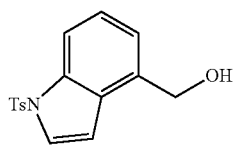

A solution of methyl 1-tosyl-1H-indole-4-carboxylate (1016 mg, 3.08 mmol) in DCM (30.361 mL) was cooled to −78° C. and DIBAL-H (1M in toluene, 13.57 mL, 13.57 mmol) was added dropwise over 1 h. The reaction mixture was stirred for a further 1.5 h, followed by a further 40 min. The reaction was quenched with methanol (0.125 mL, 3.08 mmol) when still at −78° C. and then allowed to warmed up to ambient temperature. The reaction was diluted with saturated Rochelles salt solution (60 mL) and stirred for 16 h. The layers were separated, and the aqueous phase was extracted with dichloromethane (2×50 mL). The combined organic layers were dried through a hydrophobic frit and evaporated in vacuo to yield the crude product (913 mg). The residue was loaded in dichloromethane onto a 50 g SNAP cartridge and purified via Biotage SP4, eluting from 15-75% ethyl acetate/cyclohexane. The relevant fractions were combined and evaporated in vacuo to yield the pure product—(1-tosyl-1H-indol-4-yl)methanol (901 mg, 2.84 mmol, 92% yield) as a white solid.

LCMS (2 min Formic): Rt=1.07 min, [M+Na]$^+$=324.0.

Intermediate 4: 4-(Bromomethyl)-1-tosyl-1H-indole

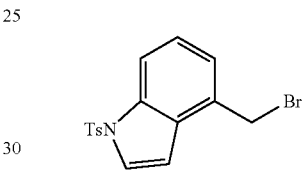

(1-Tosyl-1H-indol-4-yl)methanol (500 mg, 1.659 mmol) and HBr (3995 µL, 48% in water, 33.2 mmol) were heated at 80° C. for 4 h. The reaction mixture was poured onto water (10 mL) and the product was extracted with dichloromethane (3×20 mL). The combined organic portions were dried through a hydrophobic frit and evaporated in vacuo to yield the crude product—4-(bromomethyl)-1-tosyl-1H-indole (564 mg, 1.316 mmol, 79% yield) as a purple solid which was used without further purification.

LCMS (2 min Formic): Rt=1.35 min, [M−H]$^-$=362.0, 364.0.

Intermediate 5: 5-Bromo-N-methyl-2-oxo-1,2-dihydropyridine-3-carboxamide

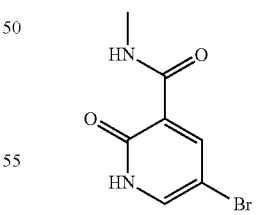

Methyl 5-bromo-2-oxo-1,2-dihydropyridine-3-carboxylate (2 g, 8.62 mmol, commercially available from, for example, CombiBlocks) and 2M methylamine in THF (13 mL, 26.0 mmol) were refluxed under N$_2$. After 4 h a white precipitate had formed. THF (15 mL) was added and the solution was refluxed for 1 h. 2M methylamine in THF (13 mL, 26.0 mmol) was added and the reaction refluxed for 2 h. Further 2M methylamine in THF (22 mL, 44.0 mmol) was added and the reaction refluxed overnight. The solution was concentrated to give a yellow solid. This was transferred to 2×20 mL microwave vials with 2M methylamine in THF (15 mL, 30.0 mmol) and THF (15 mL) and both were heated at 80° C. for 1 h. The suspension from the first microwave vial was concentrated, and triturated from diethyl ether to give 5-bromo-N-methyl-2-oxo-1,2-dihydropyridine-3-carboxamide (880 mg). The suspension from the second microwave vial was concentrated and triturated from diethyl ether to give further 5-bromo-N-methyl-2-oxo-1,2-dihydropyridine-3-carboxamide (880 mg)

LCMS (2 min Formic): Rt=0.50 min, [MH]⁺=231.0, 233.0.

Intermediate 6: 5-Bromo-2-methoxynicotinoyl chloride

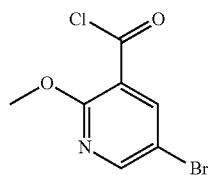

5-Bromo-2-methoxynicotinic acid (15 g, 64.6 mmol, commercially available from, for example Apollo Scientific) was suspended in DCM (100 mL) and then oxalyl chloride (16.98 mL, 194 mmol) was added, followed by DMF (5.01 mL, 64.6 mmol) and the mixture was stirred for 18 h at rt. The solvent was evaporated in vacuo and the residue was redissolved in DCM (100 mL) and evaporated to dryness to give 5-bromo-2-methoxynicotinoyl chloride (16.33 g, 65.2 mmol, 101% yield) which was used in the next step immediately.

¹H NMR (400 MHz, CDCl₃) δ ppm 8.49 (d, J=2.7 Hz, 1H) 8.44 (d, J=2.4 Hz, 1H) 4.06 (s, 3H).

Intermediate 7: 5-Bromo-2-methoxy-N-methylnicotinamide

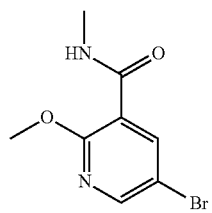

5-Bromo-2-methoxynicotinoyl chloride (16 g, 63.9 mmol) was dissolved in 2-methyltetrahydrofuran (100 mL) and Et₃N (8.90 mL, 63.9 mmol) was added, followed by methanamine (31.9 mL, 2M in THF, 63.9 mmol) and the mixture was stirred for 3 h at rt, then added to water (200 mL) and extracted with EtOAc (200 mL). The organic layer was washed with brine (200 mL), dried and evaporated in vacuo to give 5-bromo-2-methoxy-N-methylnicotinamide (14.8 g, 60.4 mmol, 95% yield) as a pale yellow solid.

LCMS (2 min High pH): Rt=0.83 min, [MH]⁺=245.1, 247.1.

Intermediate 8: Methyl 6-methoxy-5-(methylcarbamoyl)nicotinate

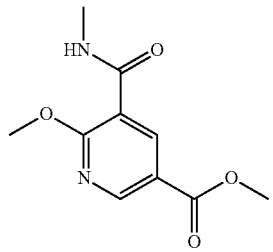

Carbon monoxide was gently bubbled through a mixture of 5-bromo-2-methoxy-N-methylnicotinamide (10.6 g, 43.3 mmol), xantphos (1.502 g, 2.60 mmol), triethylamine (12.06 mL, 87 mmol), palladium(II) acetate (0.486 g, 2.163 mmol) and methanol (17.50 mL, 433 mmol) in DMF (150 mL) until a yellow/green suspension resulted. The suspension was held under a balloon of carbon monoxide and heated to 60° C. for 5 h. LCMS showed significant SM, so the reaction was left overnight (16 h). The reaction mixture was then allowed to cool to rt. The solution was diluted with water (300 mL) and extracted with EtOAc (3×300 mL), and the combined organics back extracted with brine (3×100 mL). The combined organics were then dried (Na₂SO₄) and evaporated in vacuo to a brown solid. The residue was dissolved in DCM, loaded on to a 340 g Biotage silica SNAP column and eluted with 20→80% EtOAc/cyclohexane. The product containing fractions were evaporated in vacuo to a yellow solid—methyl 6-methoxy-5-(methylcarbamoyl) nicotinate (4 g, 17.84 mmol, 41.2% yield)

As the yield was lower than expected, the retained aqueous layer was analysed by LCMS and found to contain further product. This was therefore further extracted with DCM (3×100 mL), the combined organics were dried (Na₂SO₄) and concentrated in vacuo (for a prolonged period to remove DMF). The aqueous layer was re-analysed by LCMS and found to no longer contain product. The crude product from the organic phase, a yellow solid was taken up in DCM and added to a SNAP silica cartridge (100 g) and eluted with 20→80% EtOAc/cyclohexane. The product containing fractions were evaporated in vacuo to a yellow solid—methyl 6-methoxy-5-(methylcarbamoyl)nicotinate (1.9 g, 8.47 mmol, 19.59% yield)

LCMS (2 min Formic): Rt=0.67 min, [MH]+=225.1.

1H NMR (400 MHz, DMSO-d6) δ ppm 8.82 (d, J=2.2 Hz, 1H) 8.55 (d, J=2.4 Hz, 1H) 8.30 (br. d, J=3.9 Hz, 1H) 4.05 (s, 3H) 3.87 (s, 3H) 2.82 (d, J=4.6 Hz, 3H).

Intermediate 9: Butyl 6-methoxy-5-(methylcarbamoyl)nicotinate

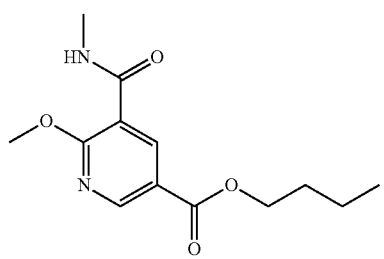 [SMILES: CCCCOC(=O)c1cnc(OC)c(C(=O)NC)c1]

(9,9-Dimethyl-9H-xanthene-4,5-diyl)bis(diphenylphosphine) (2.479 g, 4.28 mmol), triethylamine (18.58 g, 184 mmol), diacetoxypalladium (0.962 g, 4.28 mmol) and 5-bromo-2-methoxy-N-methylnicotinamide (15 g, 61.2 mmol) were combined in a 500 mL RBF, then DMF (100 mL) and 1-butanol (28.0 mL, 306 mmol) were added and the mixture was purged with carbon monoxide for 10 min, then a balloon containing around 1.5 liter of CO was added and the mixture was heated overnight at 90° C. The mixture was then cooled, diluted with water (500 mL) and extracted with EtOAc (2×500 mL). The organics were washed with water (200 mL), dried and evaporated in vacuo and the resulting black oil was purified by chromatography on a 340 g silica column eluting with 0-100% EtOAc/cyclohexane to give butyl 6-methoxy-5-(methylcarbamoyl)nicotinate (11 g, 41.3 mmol, 67.5% yield) as a pale yellow crystalline solid.

LCMS (2 min High pH): Rt=1.04 min, [MH]$^+$=267.2.

Intermediate 10: Methyl 1-benzyl-5-bromo-2-oxo-1,2-dihydropyridine-3-carboxylate

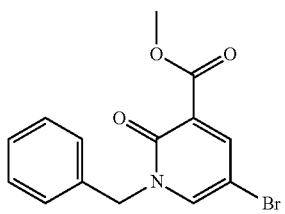 [SMILES: COC(=O)c1cc(Br)cn(Cc2ccccc2)c1=O]

Sodium hydride (5.17 g, 60% dispersion in mineral oil, 129 mmol) was added to a solution of methyl 5-bromo-2-oxo-1,2-dihydro-3-pyridinecarboxylate (25 g, 108 mmol, commercially available from, for example, Fluorochem) in DMF (200 mL) and THF (200 mL) at 0° C. and the mixture was stirred for 30 min, giving a dense suspension. Benzyl bromide (14.10 mL, 119 mmol) was added and the mixture stirred for a further 2 h, allowing to warm to rt, then the resulting clear brown solution was added to water (400 mL) and extracted with EtOAc (2×300 mL). The combined organics were washed with water (2×200 mL), dried and evaporated in vacuo to give methyl 1-benzyl-5-bromo-2-oxo-1,2-dihydropyridine-3-carboxylate (31 g, 96 mmol, 89% yield) as a beige solid. This material was carried through to the next step without purification.

LCMS (2 min High pH): Rt=0.98 min, [MH]$^+$=322.0 & 324.1.

1H NMR (400 MHz, CHCl$_3$-d) d ppm 8.16 (d, J=2.9 Hz, 1H) 7.62 (d, J=2.9 Hz, 1H) 7.30-7.43 (m, 5H) 5.15 (s, 2H) 3.92 (s, 3H).

Intermediate 11: 1-Benzyl-5-bromo-2-oxo-1,2-dihydropyridine-3-carboxylic acid

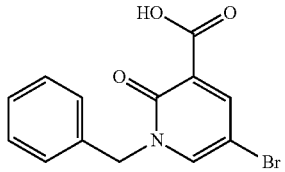 [SMILES: O=C(O)c1cc(Br)cn(Cc2ccccc2)c1=O]

Lithium hydroxide (6.91 g, 289 mmol) in water (200 mL) was added to a mixture of methyl 1-benzyl-5-bromo-2-oxo-1,2-dihydropyridine-3-carboxylate (31 g, 96 mmol), THF (200 mL) and methanol (200 mL) and the mixture was stirred at rt for 2 h, then evaporated in vacuo to about half volume, giving a dense suspension. This was diluted with water (200 mL) and acidified with acetic acid to pH 5, then extracted with EtOAc (2×300 mL). The combined organics were dried over sodium sulphate and evaporated in vacuo to give an off-white solid. The product was suspended in ether (200 mL), sonicated, diluted with cyclohexane (100 mL) and collected by filtration to give 1-benzyl-5-bromo-2-oxo-1,2-dihydropyridine-3-carboxylic acid (23 g, 74.6 mmol, 78% yield).

LCMS (2 min Formic): Rt=1.01 min, [MH]$^+$=308.0 & 310.1.

1H NMR (400 MHz, CHCl$_3$-d) d ppm 14.02 (br. s., 1H) 8.55 (d, J=2.7 Hz, 1H) 7.73 (d, J=2.7 Hz, 1H) 7.40-7.47 (m, 3H) 7.31-7.37 (m, 2H) 5.25 (s, 2H).

Intermediate 12: (R)-Methyl 2-oxo-1-(1-phenylethyl)-1,2-dihydropyridine-3-carboxylate

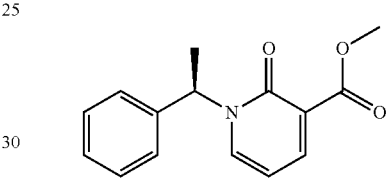

(R)-1-Phenylethanamine (8.93 mL, 70.2 mmol) was added to a stirred solution of methyl 2-oxo-2H-pyran-3-carboxylate (10.3 g, 66.8 mmol, commercially available from, for example, Sigma-Aldrich) in a mixture of dry DMF (43 mL) and dry THF (173 mL). The resulting dark red solution was stirred for 30 min, under N$_2$. EDC (16.66 g, 87 mmol) and DMAP (0.506 g, 4.14 mmol) were added and the resulting suspension stirred over the weekend. The reaction mixture was evaporated in vacuo to a brown slurry. The residue was partitioned between EtOAc and water and the aqueous layer removed. The organic layer was washed (3×2 M aq. HCl, 1× brine), dried over MgSO$_4$ and filtered through silica eluting with EtOAc. The filtrate was evaporated in vacuo to give the product as a brown oil (12.94 g).

LCMS (2 min TFA): Rt=0.84 min, [MH]$^+$=258.1.

Intermediate 13: (R)-Methyl 5-bromo-2-oxo-1-(1-phenylethyl)-1,2-dihydropyridine-3-carboxylate

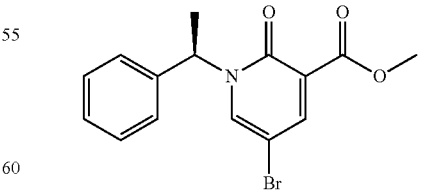

NBS (10.74 g, 60.4 mmol) was added in one portion to a dark brown solution of (R)-methyl 2-oxo-1-(1-phenylethyl)-1,2-dihydropyridine-3-carboxylate (12.94 g, 50.3 mmol). The initial suspension became a light brown solution and was stirred for 15 min whereupon it was a dark brown solution. The reaction mixture was washed [3× sat. aq. NaHCO$_3$ (40 mL), 1× aq. 10% sodium thiosulfate (20 mL), 1× brine (10 mL)], dried over MgSO$_4$ and evaporated in vacuo to a black oil. The residue was dissolved in toluene (40 mL), filtered through celite washing with toluene (80 mL) and evaporated in vacuo give the product (19.62 g) as a black oil.

LCMS (2 min TFA): Rt=1.02 min, [MH]$^+$=336.0 & 337.9.

Intermediate 14: 1-Benzyl-5-bromo-N-methyl-2-oxo-1,2-dihydropyridine-3-carboxamide

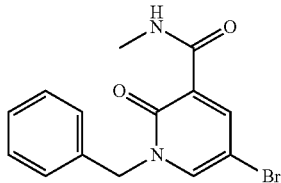 [SMILES: CNC(=O)c1cc(Br)cn(Cc2ccccc2)c1=O]

1-Benzyl-5-bromo-2-oxo-1,2-dihydropyridine-3-carboxylic acid (28 g, 91 mmol) was suspended in DCM (300 mL) and oxalyl chloride (23.86 mL, 273 mmol) and DMF (0.352 mL, 4.54 mmol) were added, then the mixture was stirred for 2 h at rt. The solvent was evaporated in vacuo to give a brown residue, which was then dissolved in THF (300 mL) and Et$_3$N (12.67 mL, 91 mmol) was added. The mixture was cooled in an ice bath, then methanamine (91 mL, 2M in THF, 182 mmol) was added dropwise over 30 min and the mixture stirred for a further 1 h at 0° C. The solvent was evaporated in vacuo and the solid residue was partitioned between water (300 mL) and DCM (300 mL), the organic layer was washed with brine, dried and evaporated in vacuo to give 1-benzyl-5-bromo-N-methyl-2-oxo-1,2-dihydropyridine-3-carboxamide (27.6 g, 86 mmol, 95% yield) as a brown solid.

LCMS (2 min Formic): Rt=0.97 min, [MH]$^+$=321.0 & 323.1.

1H NMR (400 MHz, CHCl$_3$-d) ppm 9.57 (br. s., 1H) 8.60 (d, J=2.9 Hz, 1H) 7.62 (d, J=2.9 Hz, 1H) 7.34-7.48 (m, 3H) 7.29-7.33 (m, 2H) 5.20 (s, 2H) 3.00 (d, J=4.9 Hz, 3H).

Intermediate 15: 5-Bromo-1-(2-fluorobenzyl)-N-methyl-2-oxo-1,2-dihydropyridine-3-carboxamide

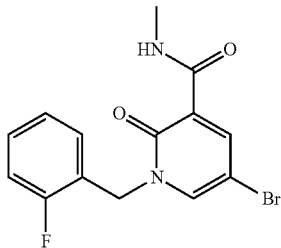 [SMILES: CNC(=O)c1cc(Br)cn(Cc2ccccc2F)c1=O]

1-(Bromomethyl)-2-fluorobenzene (0.392 mL, 3.25 mmol) was added to a suspension of 5-bromo-N-methyl-2-oxo-1,2-dihydropyridine-3-carboxamide (500 mg, 2.164 mmol) and potassium carbonate (598 mg, 4.33 mmol) in DMF (8 mL). The reaction mixture was stirred at rt under nitrogen for 2 h, partitioned between ethyl acetate and water and the organic layer washed with 2× water. The organic layer was passed through a hydrophobic frit and the solvent removed under reduced pressure. The yellow oil was dissolved in DCM and loaded onto a 50 g Biotage SNAP column which was eluted in cyclohexane:ethyl acetate (0-75%). The product-containing fractions were combined and the solvent removed under reduced pressure. The product was left to dry in vacuo overnight to give the product (536.3 mg) as a pale yellow solid.

LCMS (2 min Formic): Rt=0.98 min, [MH]$^+$=338.9 & 340.9.

Intermediate 16: (R)-5-Bromo-N-methyl-2-oxo-1-(1-phenylethyl)-1,2-dihydropyridine-3-carboxamide

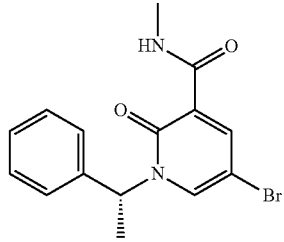 [SMILES: CNC(=O)c1cc(Br)cn([C@H](C)c2ccccc2)c1=O]

Methylamine solution (74 mL, 40% aq., 855 mmol) was added to a solution of (R)-methyl 5-bromo-2-oxo-1-(1-phenylethyl)-1,2-dihydropyridine-3-carboxylate (19.2 g, 40.0 mmol) in methanol (133 mL). The resulting solution was heated to 50° C. with a balloon fitted to the top of a condenser. The reaction mixture was stirred for 90 min. The reaction mixture was evaporated in vacuo to a black gum that was suspended in EtOAc. The suspension was filtered through silica eluting with EtOAc and the filtrate evaporated to give the product (13.1 g) as a brown gum.

LCMS (2 min TFA): Rt=1.01 min, [MH]$^+$=335.1 & 337.1.

Intermediate 17: 2,4,6-Trichlorophenyl 1-benzyl-5-(methylcarbamoyl)-6-oxo-1,6-dihydropyridine-3-carboxylate

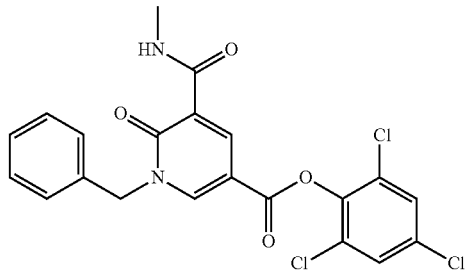 [SMILES: CNC(=O)c1cc(C(=O)Oc2c(Cl)cc(Cl)cc2Cl)cn(Cc2ccccc2)c1=O]

1-Benzyl-5-bromo-N-methyl-2-oxo-1,2-dihydropyridine-3-carboxamide (2 g, 6.23 mmol), Xantphos (0.360 g, 0.623 mmol), palladium acetate (0.070 g, 0.311 mmol) and Et$_3$N (1.302 mL, 9.34 mmol) were combined in a three necked flask equipped with a dropping funnel and a condenser with a nitrogen bubbler on the top. Toluene (30 mL) was added and the mixture was heated at 80° C. under nitrogen for 20 min, then a solution of 2,4,6-trichlorophenyl formate (2.106 g, 9.34 mmol) in toluene (20 mL) was added dropwise over 30 min and heating continued for 2 h. The reaction mixture was diluted with EtOAc (50 mL) and washed with water (50 mL) and brine (50 mL), dried and evaporated in vacuo to give an orange oil. This was dissolved in DCM (10 mL) and loaded onto a 50 g silica column, then eluted with 0-50% EtOAc/cyclohexane and the product-containing fractions evaporated in vacuo to give 2,4,6-trichlorophenyl 1-benzyl-5-(methylcarbamoyl)-6-oxo-1,6-dihydropyridine-3-carboxylate (2.52 g, 5.41 mmol, 87% yield) as a beige solid LCMS (2 min Formic): Rt=1.36 min, [MH]⁺=465, 467.

Intermediate 18: Methyl 5-(methylcarbamoyl)-6-oxo-1,6-dihydropyridine-3-carboxylate

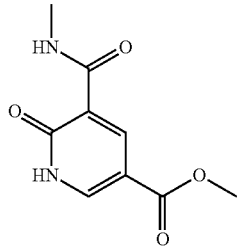

Sodium iodide (4.88 g, 32.6 mmol) was added to a solution of methyl 6-methoxy-5-(methylcarbamoyl)nicotinate (3.65 g, 16.28 mmol) in acetonitrile (100 mL) and this solution was stirred for 10 min under nitrogen. TMS-Cl (10.40 mL, 81 mmol) was added dropwise, and the reaction mixture was stirred at rt for 1 h. The reaction was quenched with water (100 mL) and the mixture was extracted five times with a mix of DCM/MeOH and the combined organic phase was dried over a hydrophobic frit and evaporated under vacuum. The crude material was dissolved in DCM and loaded onto a 100 g SNAP silica cartridge and eluted with 0-100% ethanol in EtOAc. The appropriate fractions were evaporated under vacuum, and the desired product was obtained -methyl 5-(methylcarbamoyl)-6-oxo-1,6-dihydropyridine-3-carboxylate (1.5 g, 7.14 mmol, 43.8% yield).

LCMS (2 min Formic): Rt=0.47 min, [MH]+=211.1.

1H NMR (400 MHz, DMSO-d6) δ ppm 10.25 (br. s, 1H) 9.55 (br. d, J=4.4 Hz, 1H) 8.63 (d, J=2.7 Hz, 1H) 8.32 (d, J=2.7 Hz, 1H) 3.80 (s, 3H) 2.82 (d, J=4.9 Hz, 3H).

Intermediate 19: Butyl 5-(methylcarbamoyl)-6-oxo-1,6-dihydropyridine-3-carboxylate

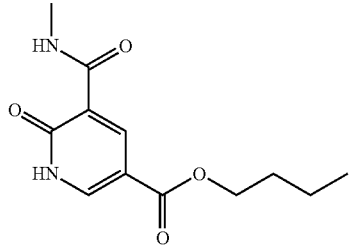 [SMILES: CCCCOC(=O)c1c[nH]c(=O)c(C(=O)NC)c1]

TMSCl (15.84 mL, 124 mmol) and sodium iodide (18.58 g, 124 mmol) were added to a solution of butyl 6-methoxy-5-(methylcarbamoyl)nicotinate (11 g, 41.3 mmol) in acetonitrile (200 mL) at rt, and the mixture was stirred for 1 h, then evaporated in vacuo and the residue partitioned between EtOAc (200 mL) and saturated sodium thiosulphate solution (200 mL). The organic layer was washed with brine, dried and evaporated in vacuo give butyl 5-(methylcarbamoyl)-6-oxo-1,6-dihydropyridine-3-carboxylate (6.5 g, 25.8 mmol, 62.4% yield) as a pale yellow solid.

LCMS (2 min High pH): Rt=0.66 min, [MH]⁺=253.2.

Intermediate 20: Ethyl 1-benzyl-5-(methylcarbamoyl)-6-oxo-1,6-dihydropyridine-3-carboxylate

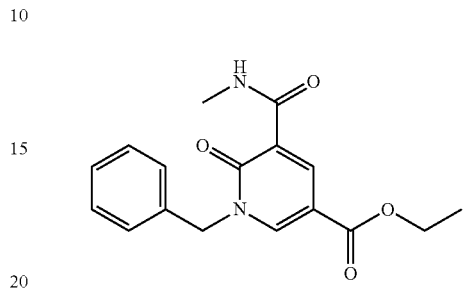

1-Benzyl-5-bromo-N-methyl-2-oxo-1,2-dihydropyridine-3-carboxamide (23 g, 71.6 mmol), DMSO (60 mL), ethanol (70 g, 1519 mmol), Et₃N (19.96 mL, 143 mmol), dppb (3.05 g, 7.16 mmol) and palladium acetate (1.608 g, 7.16 mmol) were placed in a steel Parr vessel, which was then purged with carbon monoxide by filling to 50 psi, then releasing the pressure, then refilled to 50 psi and heated overnight at 100° C. The mixture was diluted with water (200 mL) and extracted with EtOAc (2×300 mL), the organic layer washed with water (2×300 mL), then dried and evaporated in vacuo and the residue was triturated with ether (200 mL) and the solid collected by filtration to give ethyl 1-benzyl-5-(methylcarbamoyl)-6-oxo-1,6-dihydropyridine-3-carboxylate (21.2 g, 67.4 mmol, 94% yield).

LCMS (2 min Formic): Rt=0.99 min, [MH]⁺=315.2.

1H NMR (400 MHz, CHCl₃-d) ppm 9.37 (br. s., 1H) 9.03 (d, J=2.4 Hz, 1H) 8.38 (d, J=2.7 Hz, 1H) 7.34-7.42 (m, 3H) 7.28-7.34 (m, 2H) 5.25 (s, 2H) 4.35 (q, J=7.1 Hz, 2H) 2.99 (d, J=4.9 Hz, 3H) 1.37 (t, J=7.2 Hz, 3H).

Intermediate 21: Methyl 1-(3-methylbenzyl)-5-(methylcarbamoyl)-6-oxo-1,6-dihydropyridine-3-carboxylate

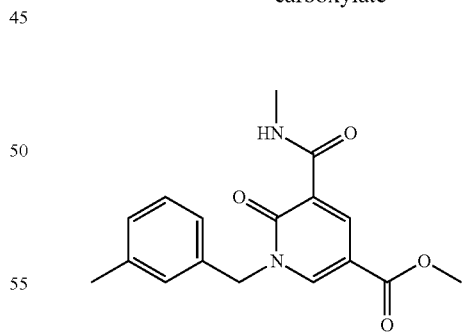

Methyl 5-(methylcarbamoyl)-6-oxo-1,6-dihydropyridine-3-carboxylate (500.2 mg, 2.380 mmol), 1-(bromomethyl)-3-methylbenzene (0.354 mL, 2.62 mmol) and potassium carbonate (140 mg, 1.013 mmol) were stirred in anhydrous DMF (10 mL) at rt under nitrogen for 4 h. The reaction mixture was concentrated in vacuo before being partitioned between water (20 mL) and ethyl acetate (20 mL). The aqueous phase was extracted with further ethyl acetate (2×20 mL) and the combined organic phases were dried by filtering through a cartridge fitted with a hydrophobic frit. The solvent was evaporated and dried in vacuo to give the desired product, as a pale yellow gum (588.2 mg). The product was used in the subsequent reaction without further purification.

LCMS (2 min Formic): Rt=1.00 min, [MH]+=315.2.

Intermediate 22: (R)-Methyl 5-(methylcarbamoyl)-6-oxo-1-(1-phenylethyl)-1,6-dihydropyridine-3-carboxylate

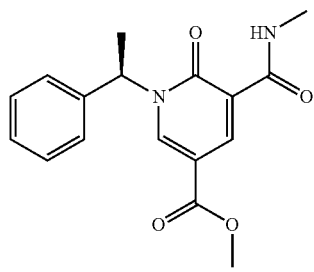 [SMILES: CNC(=O)c1cc(C(=O)OC)cn([C@H](C)c2ccccc2)c1=O]

Xantphos (1.65 g, 2.85 mmol) and palladium(II) acetate (0.877 g, 3.91 mmol) were added to a solution of (R)-5-bromo-N-methyl-2-oxo-1-(1-phenylethyl)-1,2-dihydropyridine-3-carboxamide (13.1 g, 39.1 mmol), triethylamine (16.34 mL, 117 mmol) and methanol (15.81 mL, 391 mmol) in DMF (220 mL). Carbon monoxide was sparged through the mixture until a brown suspension formed. The reaction was held under a balloon of carbon monoxide and heated to 60° C. for 4 h. The reaction mixture was cooled to rt and sparged with $N_2$ to remove any residual carbon monoxide. The reaction mixture was filtered through celite, rinsing with EtOAc and the filtrate evaporated in vacuo to a black slurry. The residue was partitioned between EtOAc (350 mL) and water (100 mL). The aqueous layer was removed, the organic layer washed (2× water [50 mL], 1× brine [50 mL]), dried over $MgSO_4$ and evaporated in vacuo to a black gum. The gum was dissolved in toluene (60 mL) and loaded on to a Biotage 340 g silica column. The column was eluted with cyclohexane:EtOAc (20→66%). The product containing fractions were evaporated to give the product (7.43 g) as a brown gum.

LCMS (2 min TFA): Rt=0.94 min, [MH]⁺=315.2.

Intermediate 23: Methyl 1-(3-methoxybenzyl)-5-(methylcarbamoyl)-6-oxo-1,6-dihydropyridine-3-carboxylate

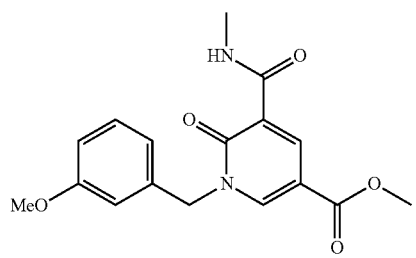 [SMILES: CNC(=O)c1cc(C(=O)OC)cn(Cc2cccc(OC)c2)c1=O]

Methyl 5-(methylcarbamoyl)-6-oxo-1,6-dihydropyridine-3-carboxylate (580 mg, 2.76 mmol), 1-(bromomethyl)-3-methoxybenzene (0.580 mL, 4.14 mmol), potassium carbonate (770 mg, 5.57 mmol) and DMF (5 mL) were stirred at 90° C. for 1 h. This was washed with a saturated aqueous LiCl solution (20 mL), partitioned between EtOAc (40 mL) and water (40 mL), the aqueous phase was extracted with EtOAc (2×40 mL), dried over a hydrophobic frit and concentrated to give a colourless oil. This was purified by chromatography on $SiO_2$ (Biotage SNAP 100 g cartridge, eluting with 0-100% EtOAc/cyclohexane). The appropriate fractions were concentrated to give methyl 1-(3-methoxybenzyl)-5-(methylcarbamoyl)-6-oxo-1,6-dihydropyridine-3-carboxylate (683 mg, 1.861 mmol, 67.4% yield) as a white solid.

LCMS (2 min Formic): Rt=0.91 min, [MH]+=331.0.

1H NMR (400 MHz, DMSO-d6) δ ppm 9.22 (br. d, J=4.6 Hz, 1H) 8.93 (d, J=2.7 Hz, 1H) 8.70 (d, J=2.7 Hz, 1H) 7.27 (t, J=7.9 Hz, 1H) 6.92 (m, J=1.7 Hz, 1H) 6.84-6.90 (m, 2H) 5.30 (s, 2H) 3.84 (s, 3H) 3.73 (s, 3H) 2.83 (s, 3H).

Intermediate 24: Butyl 1-(4-fluoro-3-methylbenzyl)-5-(methylcarbamoyl)-6-oxo-1,6-dihydropyridine-3-carboxylate

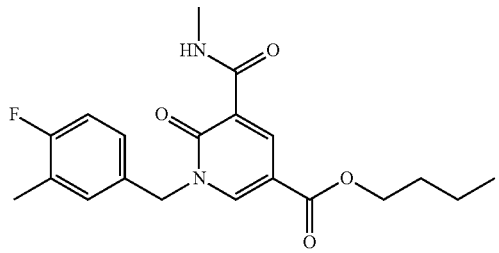 [SMILES: CCCCOC(=O)c1cc(C(=O)NC)c(=O)n(Cc2ccc(F)c(C)c2)c1]

4-(Bromomethyl)-1-fluoro-2-methylbenzene (0.805 g, 3.96 mmol) was added to a solution of butyl 5-(methylcarbamoyl)-6-oxo-1,6-dihydropyridine-3-carboxylate (1 g, 3.96 mmol) and potassium carbonate (1.096 g, 7.93 mmol) in DMF (20 mL). The reaction mixture was left to stir at rt for 2 h. The reaction mixture was concentrated under vacuum and partitioned between DCM (20 mL) and water (20 mL). The organic layer was concentrated under vacuum, loaded in DCM (3 mL) and purified by Biotage Isolera SNAP 25 g silica flash chromatography using a gradient of 0-60% cyclohexane/ethyl acetate. The appropriate fractions were combined and concentrated under vacuum to give the product (900 mg) as a white solid.

LCMS (2 min Formic): Rt=1.24 mins, [MH]⁺=375.1

Intermediate 25: Methyl 1-(4-fluorobenzyl)-5-(methylcarbamoyl)-6-oxo-1,6-dihydropyridine-3-carboxylate

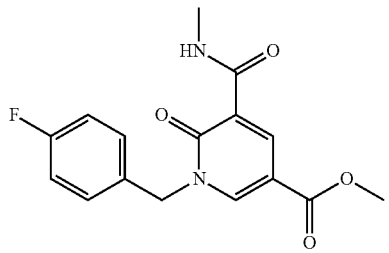 [SMILES: CNC(=O)c1cc(C(=O)OC)cn(Cc2ccc(F)cc2)c1=O]

1-(Bromomethyl)-4-fluorobenzene (0.207 mL, 1.665 mmol) was added to a solution of methyl 5-(methylcarbamoyl)-6-oxo-1,6-dihydropyridine-3-carboxylate (350 mg, 1.665 mmol) and potassium carbonate (460 mg, 3.33 mmol), in DMF (15 mL). The reaction mixture was left to stir at rt for 2 h. The reaction mixture was concentrated under vacuum and separated between DCM (20 mL) and water (20 mL). The organic solution was concentrated under vacuum, loaded in DCM (3 mL) and purified by Biotage Isolera SNAP 25 g silica flash chromatography using a gradient of 0-60% cyclohexane/ethyl acetate. The appropriate fractions were combined and concentrated under vacuum to give the product (428 mg) as a white solid.

LCMS (2 min Formic): Rt=0.92 mins, [MH]$^+$=319.0

Intermediate 26: Methyl 1-(3-hydroxybenzyl)-5-(methylcarbamoyl)-6-oxo-1,6-dihydropyridine-3-carboxylate

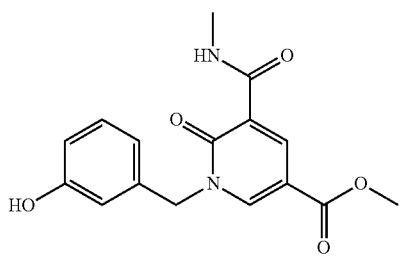 [SMILES: CNC(=O)c1cc(C(=O)OC)cn(Cc2cccc(O)c2)c1=O]

Methyl 1-(3-methoxybenzyl)-5-(methylcarbamoyl)-6-oxo-1,6-dihydropyridine-3-carboxylate (0.990 g, 3.00 mmol) in DCM (5 mL) was cooled to 0° C. under $N_2$ and $BBr_3$ (15 mL, 1 M in DCM, 15 mmol) was added dropwise and the reaction stirred for 1.5 h. The reaction was quenched with water (30 mL), extracted with DCM (2×30 mL), the aqueous layer was then extracted with EtOAc (2×30 mL). The combined organic layers were dried over a hydrophobic frit and concentrated to give 675 mg of a yellow solid. This was purified by chromatography on $SiO_2$ (Biotage SNAP 50 g cartridge, eluting with 40-100% EtOAc/cyclohexane). The appropriate fractions were concentrated to give methyl 1-(3-hydroxybenzyl)-5-(methylcarbamoyl)-6-oxo-1,6-dihydropyridine-3-carboxylate (473 mg, 1.346 mmol, 44.9% yield) as a white solid.

LCMS (2 min Formic): Rt=0.74 min, [MH]+=317.0.

1H NMR (400 MHz, DMSO-d6) δ ppm 9.46 (br. s, 1H) 9.23 (br. d, J=4.6 Hz, 1H) 8.90 (d, J=2.7 Hz, 1H) 8.70 (d, J=2.7 Hz, 1H) 7.05-7.20 (m, 1H) 6.65-6.76 (m, 3H) 5.26 (s, 2H) 3.78-3.90 (m, 3H) 2.82 (d, J=4.9 Hz, 3H).

Intermediate 27: Methyl 1-(3-(2-hydroxyethoxy)benzyl)-5-(methylcarbamoyl)-6-oxo-1,6-dihydropyridine-3-carboxylate

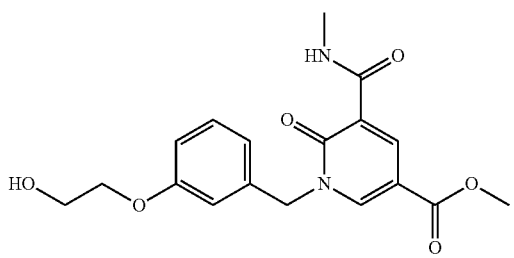 [SMILES: CNC(=O)c1cc(C(=O)OC)cn(Cc2cccc(OCCO)c2)c1=O]

Methyl 1-(3-hydroxybenzyl)-5-(methylcarbamoyl)-6-oxo-1,6-dihydropyridine-3-carboxylate (450 mg, 1.423 mmol), 1,3-dioxolan-2-one (475 mg, 5.39 mmol), potassium carbonate (600 mg, 4.34 mmol) and DMF (10 mL) were heated at 90° C. for 5 h. The solution was partitioned between EtOAc (40 mL) and a saturated aqueous LiCl solution (40 mL), the aqueous phase was extracted with EtOAc (2×40 mL), dried over a hydrophobic frit and concentrated to give 900 mg of a yellow oil. This was purified by chromatography on $SiO_2$ (Biotage SNAP 10 g cartridge, eluting with 0-100% (25% EtOH in EtOAc)/cyclohexane). The appropriate fractions were concentrated to give methyl 1-(3-(2-hydroxyethoxy)benzyl)-5-(methylcarbamoyl)-6-oxo-1,6-dihydropyridine-3-carboxylate (446 mg, 1.114 mmol, 78% yield) as a colourless oil.

LCMS (2 min Formic): Rt=0.74 min, [MH]+=361.1.

1H NMR (400 MHz, DMSO-d6) δ ppm 9.22 (br. q, J=4.9, 4.9, 4.9 Hz, 1H) 8.94 (d, J=2.7 Hz, 1H) 8.70 (d, J=2.4 Hz, 1H) 7.25 (t, J=7.8 Hz, 1H) 6.82-6.94 (m, 3H) 5.30 (s, 2H) 4.81 (t, J=5.6 Hz, 1H) 3.95 (t, J=5.0 Hz, 2H) 3.84 (s, 3H) 3.69 (q, J=5.3 Hz, 2H) 2.82 (d, J=4.6 Hz, 3H).

Intermediate 28: Butyl 1-(2-fluoro-3-methylbenzyl)-5-(methylcarbamoyl)-6-oxo-1,6-dihydropyridine-3-carboxylate

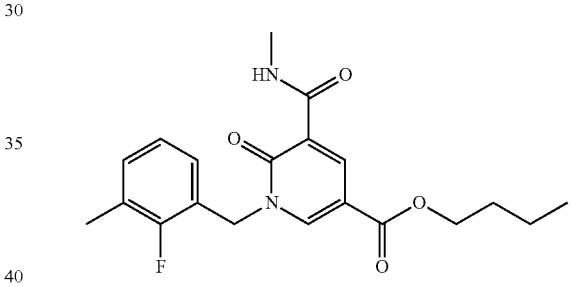

A stirred suspension of butyl 5-(methylcarbamoyl)-6-oxo-1,6-dihydropyridine-3-carboxylate (695.9 mg, 2.76 mmol) and potassium carbonate (769.4 mg, 5.57 mmol) in DMF (4 mL) at rt had a solution of 1-(bromomethyl)-2-fluoro-3-methylbenzene (607.4 mg, 2.99 mmol) in DMF (6 mL) added to it. The mixture was stirred at rt under nitrogen for 73 h before being partitioned between water (20 mL) and ethyl acetate (25 mL). The organic phase was washed with further water (20 mL) and the combined aqueous phases back-extracted with ethyl acetate (25 mL). The combined organic phases were dried by filtering through a cartridge fitted with a hydrophobic frit and the solvent was evaporated in vacuo to give a pale yellow oil which crystallised upon standing overnight to a pale yellow solid. The solid was purified by being re-dissolved in dichloromethane (ca. 5 mL) and applied to a 50 g SNAP silica cartridge which was eluted with a gradient of 20-60% ethyl acetate in cyclohexane. The required fractions were combined and evaporated in vacuo to give the desired product as a white solid (958.7 mg).

LCMS (2 min Formic): Rt=1.26 min, [MH]$^+$=375.2

Intermediate 29: Butyl 5-(methylcarbamoyl)-6-oxo-1-((1-tosyl-1H-indol-4-yl)methyl)-1,6-dihydropyridine-3-carboxylate

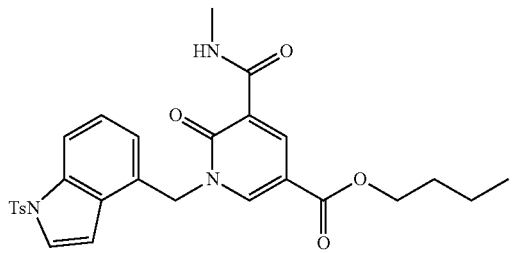 [SMILES: CCCCOC(=O)c1cc(C(=O)NC)c(=O)n(Cc2cccc3c2ccn3S(=O)(=O)c2ccc(C)cc2)c1]

To a solution of butyl 5-(methylcarbamoyl)-6-oxo-1,6-dihydropyridine-3-carboxylate (447 mg, 1.772 mmol) in DMF (11.8 mL) was added potassium carbonate (490 mg, 3.54 mmol) and 4-(bromomethyl)-1-tosyl-1H-indole (1033 mg, 2.84 mmol). The mixture was stirred at rt for 2 h. The reaction was quenched with water (1.596 mL, 89 mmol) and poured onto water (100 mL) and saturated aqueous lithium chloride (20 mL). The aqueous phase was extracted with ethyl acetate (3×30 mL) and the combined organics were washed with brine (10 mL), dried through a hydrophobic frit and evaporated in vacuo to yield the crude product (1.74 g). The residue was loaded in dichloromethane onto a 50 g SNAP silica cartridge and purified via Biotage SP4 flash chromatography, eluting from 20-100% ethyl acetate/cyclohexane. The relevant fractions were combined and evaporated in vacuo to yield the pure product—butyl 5-(methylcarbamoyl)-6-oxo-1-((1-tosyl-1H-indol-4-yl)methyl)-1,6-dihydropyridine-3-carboxylate (907 mg, 1.609 mmol, 91% yield) as a white solid.

LCMS (2 min Formic): Rt=1.34 min, [MH]$^+$=536.1.

Intermediate 30: 1-Benzyl-5-(methylcarbamoyl)-6-oxo-1,6-dihydropyridine-3-carboxylic acid

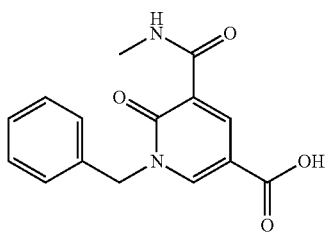 [SMILES: CNC(=O)c1cc(C(=O)O)cn(Cc2ccccc2)c1=O]

Sodium hydroxide (99 mL, 199 mmol) was added to a solution of ethyl 1-benzyl-5-(methylcarbamoyl)-6-oxo-1,6-dihydropyridine-3-carboxylate (20.8 g, 66.2 mmol) in a mixture of methanol (100 mL) and THF (100 mL) and the resulting solution was stirred for 2 h at rt, then evaporated in vacuo to approximately 100 mL volume. The mixture was diluted with water (200 mL), then filtered to remove a dark grey solid, the filtrate was washed with MTBE (200 mL), then acidified to pH 4 with 2M HCl and the resulting suspension stirred for 2 h, then filtered and the product washed with water, then dried in the vacuum oven to give 1-benzyl-5-(methylcarbamoyl)-6-oxo-1,6-dihydropyridine-3-carboxylic acid (15.2 g, 53.1 mmol, 80% yield).

LCMS (2 min High pH): Rt=0.58 min, [MH]$^+$=287.2.

1H NMR (400 MHz, DMSO-d6) δ ppm 13.19 (br. s., 1H) 9.14-9.34 (m, 1H) 8.88 (d, J=2.7 Hz, 1H) 8.70 (d, J=2.7 Hz, 1H) 7.25-7.42 (m, 5H) 5.33 (s, 2H) 2.82 (d, J=4.6 Hz, 3H).

Intermediate 31: 1-(3-Methylbenzyl)-5-(methylcarbamoyl)-6-oxo-1,6-dihydropyridine-3-carboxylic acid

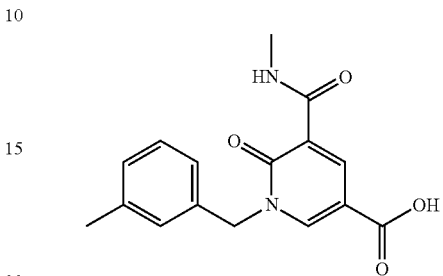

A mixture of methyl 1-(3-methylbenzyl)-5-(methylcarbamoyl)-6-oxo-1,6-dihydropyridine-3-carboxylate (583.9 mg, 1.858 mmol) and lithium hydroxide (92.4 mg, 3.86 mmol) in THF (10 mL) and water (5.00 mL) was stirred at rt under nitrogen for 16.75 h. The mixture was then acidified to pH 0 with a 2M solution of hydrochloric acid (2 mL). Water (30 mL) was added and the resulting precipitate extracted with ethyl acetate (20 mL). The layers were separated and the aqueous layer further extracted with ethyl acetate (2×20 mL). The organic layers were combined and filtered through a cartridge containing a hydrophobic frit before being concentrated in vacuo. The residue was applied to a 25 g SNAP silica cartridge as a suspension in ethyl acetate. The precipitate remaining on the top of the cartridge was removed and retained as a portion of the desired product. The cartridge was eluted with a gradient of 0-7.5% ethanol (with 0.3% acetic acid) in ethyl acetate. The required fractions were combined with the previously obtained solid, evaporated and dried in vacuo to give the desired product as a white solid (355.4 mg).

LCMS (2 min Formic): Rt=0.88 min, [MH]$^+$=301.2.

Intermediate 32: (R)-5-(Methylcarbamoyl)-6-oxo-1-(1-phenylethyl)-1,6-dihydropyridine-3-carboxylic acid

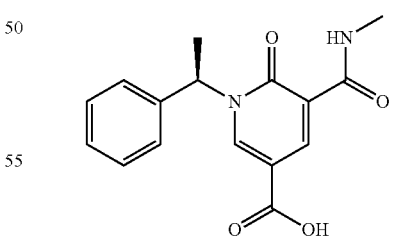

Sodium hydroxide (1.891 g, 47.3 mmol) was added to a solution of (R)-methyl 5-(methylcarbamoyl)-6-oxo-1-(1-phenylethyl)-1,6-dihydropyridine-3-carboxylate (7.43 g, 23.64 mmol) in methanol (70 mL). Water was added to the stirred suspension and the resulting solution stirred overnight. The reaction mixture was evaporated in vacuo to a pale brown solid and acidified with 2M aq. HCl (100 mL). Acetone (10 mL) was added and the suspension stirred for 15 min and filtered. The filtercake was washed [water: acetone (1:1, 20 mL), acetone (20 mL)] and dried in vacuo to give the product (6.40 g) as a beige solid.

LCMS (2 min TFA): Rt=0.82 min, [MH]$^+$=301.0.

Intermediate 33: 1-(3-Methoxybenzyl)-5-(methylcarbamoyl)-6-oxo-1,6-dihydropyridine-3-carboxylic acid

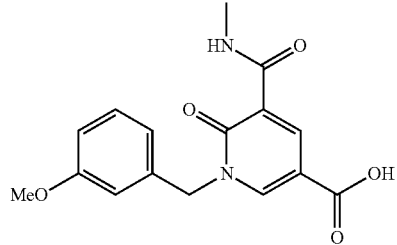 [SMILES: CNC(=O)c1cc(C(=O)O)cn(Cc2cccc(OC)c2)c1=O]

Methyl 1-(3-methoxybenzyl)-5-(methylcarbamoyl)-6-oxo-1,6-dihydropyridine-3-carboxylate (670 mg, 2.028 mmol), lithium hydroxide (146 mg, 6.08 mmol), 1,4-dioxane (3 mL) and water (3 mL) were stirred at rt for 30 min. Acetic acid (1 mL, 17.47 mmol) was added and the solution was partitioned between EtOAc (20 mL) and water (20 mL), the aqueous phase was extracted with EtOAc (2×20 mL), dried over a hydrophobic frit and concentrated to give 1-(3-methoxybenzyl)-5-(methylcarbamoyl)-6-oxo-1,6-dihydropyridine-3-carboxylic acid (641 mg, 1.824 mmol, 90% yield) as a white solid.

LCMS (2 min Formic): Rt=0.81 min, [MH]+=317.0.

1H NMR (400 MHz, DMSO-d6) δ ppm 13.09 (br. s, 1H) 9.26 (br. q, J=4.4, 4.4, 4.4 Hz, 1H) 8.84 (d, J=2.7 Hz, 1H) 8.70 (d, J=2.4 Hz, 1H) 7.27 (t, J=7.9 Hz, 1H) 6.91-6.94 (m, 1H) 6.84-6.90 (m, 2H) 5.29 (s, 2H) 3.73 (s, 3H) 2.82 (d, J=4.9 Hz, 3H).

Intermediate 34: 1-(4-Fluoro-3-methylbenzyl)-5-(methylcarbamoyl)-6-oxo-1,6-dihydropyridine-3-carboxylic acid

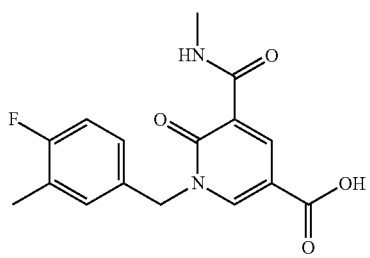 [SMILES: CNC(=O)c1cc(C(=O)O)cn(Cc2ccc(F)c(C)c2)c1=O]

Butyl 1-(4-fluoro-3-methylbenzyl)-5-(methylcarbamoyl)-6-oxo-1,6-dihydropyridine-3-carboxylate (900 mg, 2.404 mmol) was taken up in THF (10 mL) and water (10 mL). Lithium hydroxide (115 mg, 4.81 mmol) was added to the solution and the reaction stirred overnight at rt. 2M aq. HCl (3.61 mL, 7.21 mmol) was added and the resulting solid was washed with water to give the product (1 g) as a white solid.

LCMS (2 min Formic): Rt=0.91 mins, [MH]$^+$=319.0

Intermediate 35: 1-(4-Fluorobenzyl)-5-(methylcarbamoyl)-6-oxo-1,6-dihydropyridine-3-carboxylic acid

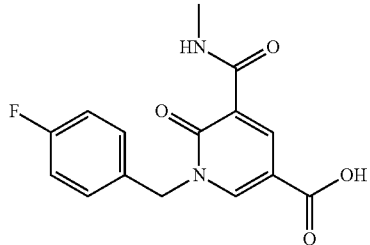 [SMILES: CNC(=O)c1cc(C(=O)O)cn(Cc2ccc(F)cc2)c1=O]

Methyl 1-(4-fluorobenzyl)-5-(methylcarbamoyl)-6-oxo-1,6-dihydropyridine-3-carboxylate (330 mg, 1.037 mmol) was taken up in THF (4 mL) and water (4.00 mL). Lithium hydroxide (49.7 mg, 2.074 mmol) was added to the solution and the reaction stirred overnight at rt. 2M aq. HCl (1.555 mL, 3.11 mmol) was added and the reaction mixture partitioned between water (10 mL) and 10% MeOH/DCM (10 mL). The aqueous layer was washed further with 10% MeOH/DCM (2×10 mL). The organic layers were combined, passed through a hydrophobic frit and concentrated under vacuum to give the product (123.5 mg) as a white solid.

LCMS (2 min Formic): Rt=0.82 mins, [MH]$^+$=305.0

Intermediate 36: 1-(3-(2-Hydroxyethoxy)benzyl)-5-(methylcarbamoyl)-6-oxo-1,6-dihydropyridine-3-carboxylic acid

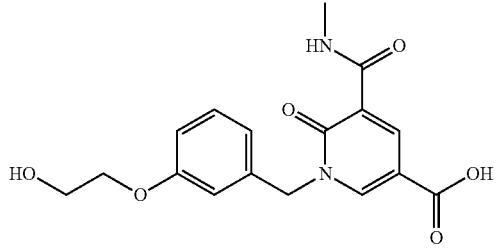 [SMILES: CNC(=O)c1cc(C(=O)O)cn(Cc2cccc(OCCO)c2)c1=O]

Methyl 1-(3-(2-hydroxyethoxy)benzyl)-5-(methylcarbamoyl)-6-oxo-1,6-dihydropyridine-3-carboxylate (440 mg, 1.221 mmol), lithium hydroxide (86 mg, 3.59 mmol), 1,4-dioxane (3 mL) and water (3 mL) were stirred at rt for 1 h. Acetic acid (1 mL, 17.47 mmol) was added and the solution was partitioned between EtOAc (20 mL) and water (20 mL), the aqueous phase was extracted with EtOAc (2×20 mL), dried over a hydrophobic frit and concentrated to give 1-(3-(2-hydroxyethoxy)benzyl)-5-(methylcarbamoyl)-6-oxo-1,6-dihydropyridine-3-carboxylic acid (343 mg, 0.891 mmol, 73.0% yield) as a white solid.

LCMS (2 min Formic): Rt=0.66 min, [MH]+=347.0.

1H NMR (400 MHz, DMSO-d6) δ ppm 9.27 (br. q, J=4.2, 4.2, 4.2 Hz, 1H) 8.85 (d, J=2.4 Hz, 1H) 8.71 (d, J=2.4 Hz, 1H) 7.27 (t, J=7.8 Hz, 1H) 6.80-6.99 (m, 3H) 5.30 (s, 2H) 4.82 (t, J=5.5 Hz, 1H) 3.96 (app. t, J=5.0 Hz, 2H) 3.70 (ABq, J=5.1 Hz, 2H) 2.83 (d, J=4.9 Hz, 3H).

Intermediate 37: 1-(2-Fluoro-3-methylbenzyl)-5-(methylcarbamoyl)-6-oxo-1,6-dihydropyridine-3-carboxylic acid

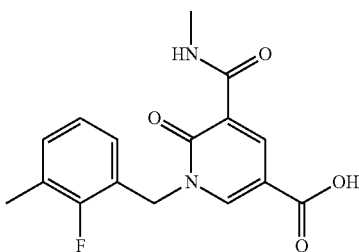 [SMILES: CNC(=O)c1cc(C(=O)O)cn(Cc2cccc(C)c2F)c1=O]

To a stirred solution of butyl 1-(2-fluoro-3-methylbenzyl)-5-(methylcarbamoyl)-6-oxo-1,6-dihydropyridine-3-carboxylate (953.7 mg, 2.55 mmol) in acetonitrile (10 mL) and THF (10 mL) under nitrogen was added lithium hydroxide (1.0 M aqueous solution) (5.1 mL, 5.10 mmol) and the mixture was stirred at rt for 2.5 h. The volatiles were evaporated from the mixture in vacuo and the residue dried in vacuo before being partitioned between 2 M aqueous hydrochloric acid (20 mL) and ethyl acetate (150 mL) [solid was poorly soluble in both phases]. The aqueous phase was extracted with further ethyl acetate (75 mL) and the combined organic phases washed with water (20 mL) and saturated brine solution (30 mL). The organic phase was dried by filtering through a cartridge fitted with a hydrophobic frit and the solvent evaporated in vacuo. The solid residue was triturated twice with methanol (10 mL+5 mL) and the solid dried in vacuo to give the desired product as a white solid (621.7 mg).

LCMS (2 min Formic): Rt=0.90 min, [MH]$^+$=319.1.

Intermediate 38: 1-((1H-Indol-4-yl)methyl)-5-(methylcarbamoyl)-6-oxo-1,6-dihydropyridine-3-carboxylic acid

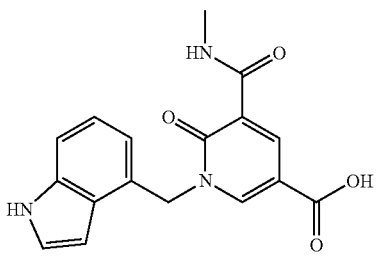 [SMILES: CNC(=O)c1cc(C(=O)O)cn(Cc2cccc3[nH]ccc23)c1=O]

To a solution of butyl 5-(methylcarbamoyl)-6-oxo-1-((1-tosyl-1H-indol-4-yl)methyl)-1,6-dihydropyridine-3-carboxylate (821 mg, 1.533 mmol) in methanol (1.703 mL) and THF (3.406 mL) stirred under nitrogen at rt was added solid cesium carbonate (3995 mg, 12.26 mmol) in one charge. The reaction mixture was stirred at 70° C. for 3 h. The reaction mixture was concentrated in vacuo, before diluting with 1,4-dioxane (1.703 mL) and water (1.703 mL). The mixture was stirred at 70° C. for 4.5 h. The reaction mixture was poured onto saturated sodium bicarbonate (30 mL) and extracted with ethyl acetate (3×10 mL). The aqueous phase was acidified with 2M HCl and extracted with ethyl acetate (8×30 mL). Following extraction a solid precipitate remained in the organic phase which was filtered off to give some desired crude product (251 mg). The filtrate from workup was dried through a hydrophobic frit and evaporated in vacuo to yield a brown solid. The solid was triturated with ether (30 mL) and filtered to give further product (539 mg). This residue was suspended in water (20 mL) and brought to pH 4 with 2M HCl. The suspension was filtered, washed with water (2×5 mL) and diethyl ether (2×10 mL). The collected solid (213 mg) was suspended in dichloromethane (10 mL) and combined with the previous batch of crude product. The combined suspension was sonicated and blown down under a stream of nitrogen and dried in vacuo to give the final product 1-((1H-indol-4-yl)methyl)-5-(methylcarbamoyl)-6-oxo-1,6-dihydropyridine-3-carboxylic acid (432 mg, 1.222 mmol, 80% yield).

LCMS (2 min Formic): Rt=0.77 min, [MH]$^+$=326.2.

Intermediate 39: tert-Butyl 4-(2-(1-benzyl-5-(methylcarbamoyl)-6-oxo-1,6-dihydropyridine-3-carboxamido)ethyl)piperidine-1-carboxylate

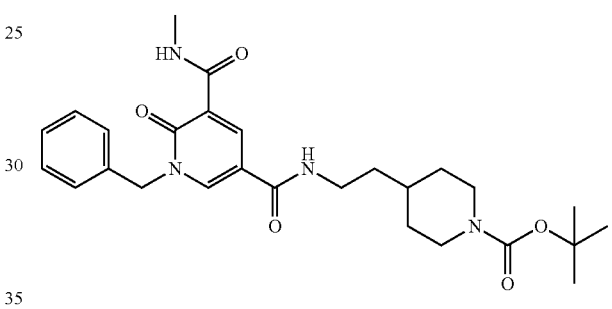

2,4,6-Trichlorophenyl 1-benzyl-5-(methylcarbamoyl)-6-oxo-1,6-dihydropyridine-3-carboxylate (81 mg, 0.174 mmol), tert-butyl 4-(2-aminoethyl)piperidine-1-carboxylate (0.078 mL, 0.348 mmol), N,N-dimethylpyridin-4-amine (5 mg, 0.041 mmol), triethylamine (0.073 mL, 0.522 mmol) and THF (1 mL) were stirred at 45° C. for 1 h. The solution was concentrated to give 233 mg of a colourless oil which was purified by chromatography on SiO$_2$ (Biotage SNAP 25 g cartridge, eluting with 0-100% ethyl acetate/cyclohexane). The appropriate fractions were concentrated to give tert-butyl 4-(2-(1-benzyl-5-(methylcarbamoyl)-6-oxo-1,6-dihydropyridine-3-carboxamido)ethyl)piperidine-1-carboxylate (80 mg, 0.129 mmol, 74.1% yield) as an off white solid.

LCMS (2 min Formic): Rt=1.14 min, [MH]$^+$=497.

Intermediate 40: tert-Butyl 4-(3-(1-benzyl-5-(methylcarbamoyl)-6-oxo-1,6-dihydropyridine-3-carboxamido)propyl)piperazine-1-carboxylate

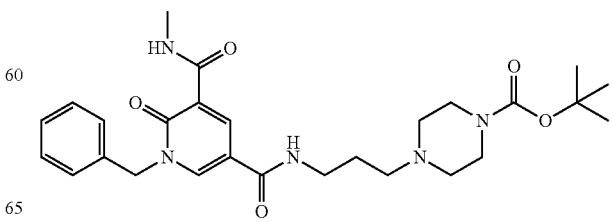

1-Benzyl-5-(methylcarbamoyl)-6-oxo-1,6-dihydropyridine-3-carboxylic acid (205 mg, 0.716 mmol), HATU (412 mg, 1.084 mmol), DIPEA (0.38 mL, 2.176 mmol), tert-butyl 4-(3-aminopropyl)piperazine-1-carboxylate (344 mg, 1.414 mmol) and DMF (4 mL) were stirred at rt under $N_2$ for 1 h. The solution was concentrated to give 1.18 g of a red oil which was purified by chromatography on $SiO_2$ (Biotage SNAP 25 g cartridge, eluting with 0-50% (20% (2M ammonia in MeOH) in DCM)/DCM). The appropriate fractions were concentrated to give tert-butyl 4-(3-(1-benzyl-5-(methylcarbamoyl)-6-oxo-1,6-dihydropyridine-3-carboxamido)propyl)piperazine-1-carboxylate (497 mg) as a pink solid.

LCMS (2 min Formic): Rt=0.66 min, $[MH]^+$=512.

Intermediate 41: tert-Butyl 4-(3-(1-(2-fluorobenzyl)-5-(methylcarbamoyl)-6-oxo-1,6-dihydropyridine-3-carboxamido)propyl)piperidine-1-carboxylate

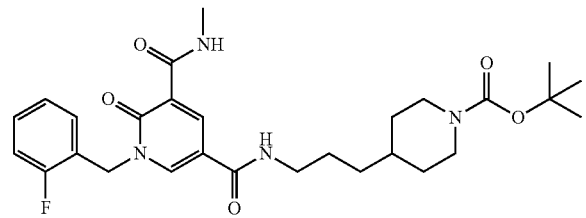 [SMILES: CNC(=O)c1cc(C(=O)NCCCC2CCN(C(=O)OC(C)(C)C)CC2)cn(Cc2ccccc2F)c1=O]

5-Bromo-1-(2-fluorobenzyl)-N-methyl-2-oxo-1,2-dihydropyridine-3-carboxamide (100 mg, 0.295 mmol), cobalt carbonyl (25.2 mg, 0.074 mmol), DMAP (72.0 mg, 0.590 mmol), palladium (II) acetate (3.31 mg, 0.015 mmol), tert-butyl 4-(3-aminopropyl)piperidine-1-carboxylate (71.5 mg, 0.295 mmol) and xantphos (8.53 mg, 0.015 mmol) were added to a microwave vial. The vial was sealed and THF (2.5 mL) added and the reaction heated in a Biotage Initiator microwave at 80° C. for 30 min. The reaction mixture was heated for a further 30 min in a Biotage Initiator microwave at 80° C. The resulting mixture was diluted with water (20 mL) and extracted with ethyl acetate (20 mL). The organic layer was dried, concentrated under vacuum and purified by Biotage Isolera SNAP 10 g silica flash chromatography using a gradient of 0-60% cyclohexane/ethyl acetate. The product containing fractions were combined and concentrated under vacuum to give the product (30 mg) as a white solid.

LCMS (2 min Formic): Rt=1.19 min, $[MH]^+$=529.2.

Intermediate 42: tert-Butyl 4-(3-(1-(4-fluoro-3-methylbenzyl)-5-(methylcarbamoyl)-6-oxo-1,6-dihydropyridine-3-carboxamido)propyl)piperidine-1-carboxylate

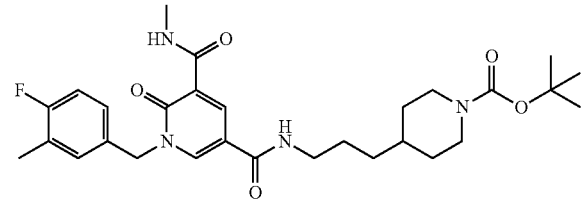 [SMILES: CNC(=O)c1cc(C(=O)NCCCC2CCN(C(=O)OC(C)(C)C)CC2)cn(Cc2ccc(F)c(C)c2)c1=O]

1-(4-Fluoro-3-methylbenzyl)-5-(methylcarbamoyl)-6-oxo-1,6-dihydropyridine-3-carboxylic acid (100 mg, 0.314 mmol) was added to a solution of HATU (119 mg, 0.314 mmol) and DIPEA (0.055 mL, 0.314 mmol) in DMF (3 mL). The reaction mixture was left to stir at rt for 5 min. tert-Butyl 4-(3-aminopropyl)piperidine-1-carboxylate (76 mg, 0.314 mmol) was added to the reaction mixture, which was then left to stir at rt overnight. The reaction mixture was concentrated under vacuum and partitioned between DCM (20 mL) and water (20 mL). The organic layer was concentrated under vacuum, loaded in DCM (3 mL) and purified by Biotage Isolera SNAP 10 g silica flash chromatography using a gradient of 0-100% cyclohexane/ethyl acetate. The appropriate fractions were combined and concentrated under vacuum to give the product (172 mg) as a yellow solid.

LCMS (2 min Formic): Rt=1.25 min, $[MH]^+$=543.3.

Intermediate 43: tert-Butyl 4-(3-(1-(4-fluorobenzyl)-5-(methylcarbamoyl)-6-oxo-1,6-dihydropyridine-3-carboxamido)propyl)piperidine-1-carboxylate

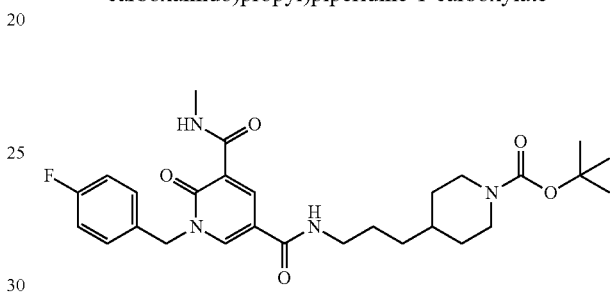

1-(4-Fluorobenzyl)-5-(methylcarbamoyl)-6-oxo-1,6-dihydropyridine-3-carboxylic acid (100 mg, 0.329 mmol) was added to a solution of HATU (125 mg, 0.329 mmol) and DIPEA (0.057 mL, 0.329 mmol) in DMF (3 mL). The reaction mixture was left to stir at rt for 5 min. tert-Butyl 4-(3-aminopropyl)piperidine-1-carboxylate (80 mg, 0.329 mmol) was added to the reaction mixture which was then left to stir at rt overnight. The reaction mixture was concentrated under vacuum and partitioned between DCM (20 mL) and water (20 mL). The organic layer was concentrated under vacuum, loaded in DCM (3 mL) and purified by Biotage Isolera SNAP 10 g silica flash chromatography using a gradient of 0-100% cyclohexane/ethyl acetate. The appropriate fractions were combined and concentrated under vacuum to give the product (195 mg, 0.369 mmol, quant yield) as a yellow solid.

LCMS (2 min Formic): Rt=1.19 min, $[MH]^+$=529.2.

Intermediate 44: tert-Butyl 4-(3-(1-benzyl-5-(methylcarbamoyl)-6-oxo-1,6-dihydropyridine-3-carboxamido)propyl)piperidine-1-carboxylate

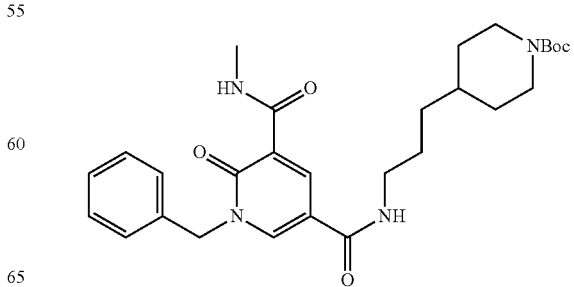

1-Benzyl-5-(methylcarbamoyl)-6-oxo-1,6-dihydropyridine-3-carboxylic acid (2.2 g, 7.68 mmol) was suspended in DCM (50 mL), then Et₃N (1.285 mL, 9.22 mmol) and HATU (3.51 g, 9.22 mmol) were added, and the mixture was stirred for 10 min before the addition of tert-butyl 4-(3-aminopropyl)piperidine-1-carboxylate (1.862 g, 7.68 mmol, commercially available from, for example, Milestone PharmTech). The resulting solution was stirred for 2 h at rt, then washed with water (50 mL), 0.5 M NaOH (50 mL) and 0.5 M HCl (50 mL). The solvent was dried and evaporated in vacuo and the residue triturated with ether (20 mL), filtered and the solid dried in vacuo to give tert-butyl 4-(3-(1-benzyl-5-(methylcarbamoyl)-6-oxo-1,6-dihydropyridine-3-carboxamido)propyl)piperidine-1-carboxylate (3.43 g, 6.72 mmol, 87% yield)

LCMS (2 min formic): Rt=1.20 min, [MH]+=511.

1H NMR (400 MHz, DMSO-d6) δ ppm 9.37 (br. q, J=4.4, 4.4, 4.4 Hz, 1H) 8.82 (d, J=2.9 Hz, 1H) 8.72 (d, J=2.7 Hz, 1H) 8.55 (br. t, J=5.4, 5.4 Hz, 1H) 7.27-7.39 (m, 5H) 5.30 (s, 2H) 3.91 (br. d, J=12.5 Hz, 2H) 3.21 (br. q, J=6.8, 6.8, 6.8 Hz, 2H) 3.08 (br. q, J=6.8, 6.8, 6.8 Hz, 2H) 2.83 (d, J=4.9 Hz, 3H) 1.62 (br. d, J=12.5 Hz, 2H) 1.52 (br. dt, J=15.0, 7.4, 7.4 Hz, 2H) 1.33-1.45 (m, 10H) 1.19-1.27 (m, 2H) 0.94 (br. qd, J=12.2, 12.2, 12.2, 4.2 Hz, 2H).

Intermediate 45: tert-butyl 4-(2-cyanoethyl)-4-hydroxypiperidine-1-carboxylate

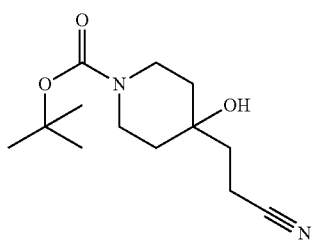 [SMILES: CC(C)(C)OC(=O)N1CCC(O)(CCC#N)CC1]

To a solution of MeCN (0.551 mL, 10.55 mmol) in tetrahydrofuran (8 mL) stirred under N₂ at −78° C. was added BuLi (1.6M in Hexanes) (6.59 mL, 10.55 mmol) dropwise over 5 mins (forming a light orange precipitate). After the reaction mixture was stirred for 30 mins at ~78° C. solution of tert-butyl 1-oxa-6-azaspiro[2.5]octane-6-carboxylate (Commercially available from e.g. Manchester Organics, 1500 mg, 7.03 mmol) in THF (5 mL) was added dropwise over 5 mins. Reaction mixture was stirred at −78° C. for 1 hr then left to warm to r.t. (Reaction mixture turned dark red solution and then dark red suspension). Reaction mixture left over w/e which went to a brown solid. This was re-dissolved in ethyl acetate and quenched with a saturated solution of ammonium chloride and extracted with ethyl acetate. Combined organic layers were dried (Na₂SO₄) and concentrated under reduced pressure to give ~2.19 g of crude brown oil. This crude product was purified by silica gel column chromatography, eluting with 5-70% ethyl acetate/cyclohexane over 1320 mL to give the title compound (1.65 g, 5.51 mmol, 78% yield) as a yellow oil.

¹H NMR (400 MHz, METHANOL-d₄) δ 3.79 (d, J=13.20 Hz, 2H), 3.11-3.25 (m, 2H), 2.48-2.59 (m, 2H), 1.77-1.88 (m, 2H), 1.48-1.62 (m, 4H), 1.47 (s, 9H)

Intermediate 46: tert-butyl 4-(3-aminopropyl)-4-hydroxypiperidine-1-carboxylate

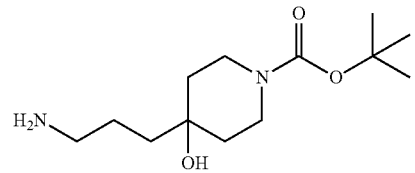 [SMILES: CC(C)(C)OC(=O)N1CCC(O)(CCCN)CC1]

Tert-butyl 4-(2-cyanoethyl)-4-hydroxypiperidine-1-carboxylate (200 mg, 0.786 mmol) was dissolved in tetrahydrofuran (3 mL) and cooled in an ice-bath under N₂. Borane tetrahydrofuran complex (1M solution in THF) (1.573 mL, 1.573 mmol) was added and reaction mixture heated at reflux for 1.5 hrs and then cooled to r.t. A further portion of borane tetrahydrofuran complex (1M solution in THF) (1.573 mL, 0.786 mmol) was added and reaction mixture heated at reflux. After a further 2 hrs, reaction mixture was cooled to r.t. and quenched with a mixture of ammonium chloride and sat. NaHCO₃ solution. Reaction mixture was extracted with ethyl acetate and combined organic layers were dried (Na₂SO₄) and concentrated under reduced pressure to give 173 mg of white oily solid. This crude product was loaded onto a 5 g SCX cartridge (pre-conditioned with MeOH) and washed with MeOH (40 mL) followed by 2M NH₃ in MeOH (40 mL). Ammonia fractions were combined and concentrated under reduced pressure to give the title compound (108 mg) as a pale yellow oil.

LCMS (2 min Formic): Rt=0.44 min, [MH]⁺=259

Intermediate 47: tert-butyl 4-(3-(1-benzyl-5-(methylcarbamoyl)-6-oxo-1,6-dihydropyridine-3-carboxamido)propyl)-4-hydroxypiperidine-1-carboxylate

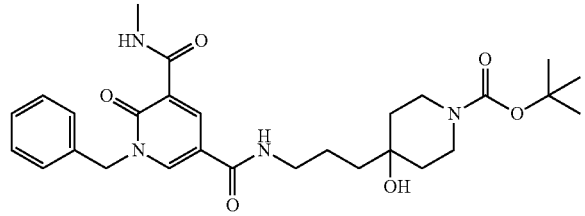 [SMILES: CNC(=O)c1cc(C(=O)NCCCC2(O)CCN(C(=O)OC(C)(C)C)CC2)cn(Cc2ccccc2)c1=O]

To a solution of 1-benzyl-5-(methylcarbamoyl)-6-oxo-1,6-dihydropyridine-3-carboxylic acid (50 mg, 0.175 mmol) in N,N-Dimethylformamide (2 mL) was added HATU (100 mg, 0.262 mmol) followed by tert-butyl 4-(3-aminopropyl)-4-hydroxypiperidine-1-carboxylate (54 mg, 0.209 mmol) and DIPEA (0.122 mL, 0.699 mmol). The resulting reaction mixture was stirred at r.t. under N₂ (formed yellow solution). Crude reaction mixture was combined with partitioned between ethyl acetate and a sat. solution of LiCl. The organic layer was separated and aqueous layer further extracted with ethyl acetate. Combined organic layers were dried (Na₂SO₄) and conc. to give ~258 mg crude orange residue. This was purified by chromatography, eluting with 10-65% of (25% Ethanol in ethyl acetate)/ethyl acetate to give the title compound (159 mg, 0.272 mmol) as a colourless oil. Product was used in subsequent reactions without further purification.

LCMS (2 min Formic): Rt=1.00 min, [MH]⁺=527

Intermediate 48: tert-butyl 4-(3-(1-benzyl-5-(methylcarbamoyl)-6-oxo-1,6-dihydropyridine-3-carboxamido)propyl)-4-fluoropiperidine-1-carboxylate

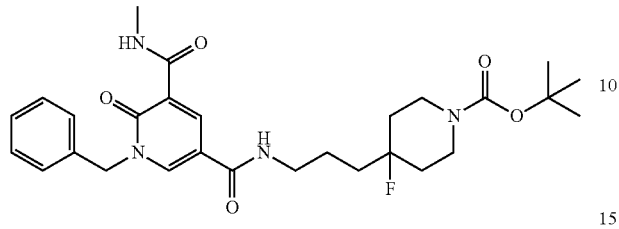

To a solution of tert-butyl 4-(3-(1-benzyl-5-(methylcarbamoyl)-6-oxo-1,6-dihydropyridine-3-carboxamido)propyl)-4-hydroxypiperidine-1-carboxylate (79 mg, 0.150 mmol) in dry dichloromethane (4 mL) cooled to −78° C. was added was added DAST (0.040 mL, 0.300 mmol). The reaction mixture was allowed to warm slowly to r.t. Reaction temp was 0° C. after 2 hours at which point reaction was left to stir at r.t. for a further 1.5 h. Reaction mixture was quenched by addition of saturated NaHCO$_3$ solution and organic layer was separated, dried (Na$_2$SO$_4$) and concentrated to give 76 mg of crude white solid. The crude product was purified by HPLC, eluting with 0.1% TFA acid in water/0.1% TFA acid in acetonitrile solvent system. Product was re-dissolved in MeOH (3 mL), concentrated and dried to give the title compound (76 mg, 0.072 mmol, 47.9% yield) as a white solid LCMS (2 min Formic): Rt=1.15 min, [MH]$^+$=529

Intermediate 49: Tert-butyl 2-(3-(1-benzyl-5-(methylcarbamoyl)-6-oxo-1,6-dihydropyridine-3-carboxamido)propyl)morpholine-4-carboxylate

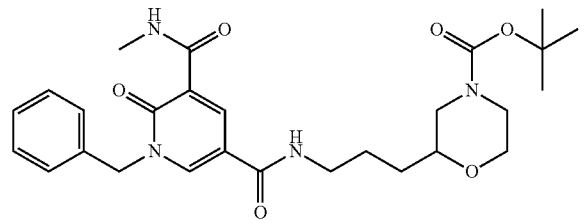 [SMILES: CNC(=O)c1cc(C(=O)NCCCC2CN(C(=O)OC(C)(C)C)CCO2)cn(Cc2ccccc2)c1=O]

2,4,6-Trichlorophenyl 1-benzyl-5-(methylcarbamoyl)-6-oxo-1,6-dihydropyridine-3-carboxylate (25.7 mg, 0.055 mmol), tert-butyl 2-(3-aminopropyl)morpholine-4-carboxylate (18 mg, 0.037 mmol), DMAP (0.450 mg, 3.68 μmol), triethylamine (10.3 μL, 0.074 mmol) and tetrahydrofuran (2 mL) were stirred at 45° C. under N$_2$ for 2 h. The reaction was concentrated and purified by silica gel column chromatography, eluting with 0-50% 25% ethanol in ethyl acetate/cyclohexane. The desired fractions were concentrated to give tert-butyl 2-(3-(1-benzyl-5-(methylcarbamoyl)-6-oxo-1,6-dihydropyridine-3-carboxamido)propyl)morpholine-4-carboxylate (8 mg, 0.012 mmol, 33.9% yield) as a colourless oil.

LCMS (2 min Formic): Rt=1.07 min, [MH]+=513.5

Intermediate 50: tert-butyl 2-(2-(1-benzyl-5-(methylcarbamoyl)-6-oxo-1,6-dihydropyridine-3-carboxamido)ethyl)morpholine-4-carboxylate

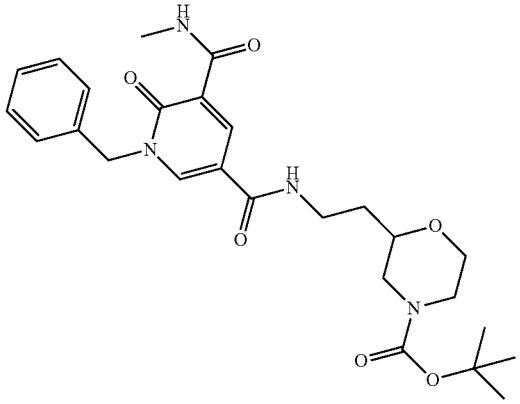 [SMILES: CNC(=O)c1cc(C(=O)NCCC2CN(C(=O)OC(C)(C)C)CCO2)cn(Cc2ccccc2)c1=O]

To 1-benzyl-5-(methylcarbamoyl)-6-oxo-1,6-dihydropyridine-3-carboxylic acid (56 mg, 0.196 mmol) and HATU (90.4 mg, 0.238 mmol) was added a solution of (±)-tert-butyl 2-(2-aminoethyl)morpholine-4-carboxylate (50 mg, 0.217 mmol; for a preparation see WO03097618) in DMF (1.5 mL). DIPEA (0.068 mL, 0.391 mmol) was added and the reaction mixture was stirred at room temperature for 1.25 hr. The mixture was concentrated under a stream of nitrogen before being made up to 3 mL with DMSO and directly purified by MDAP (high pH). The required fraction was concentrated under a stream of nitrogen before being dissolved in a 1:1 mixture of dichloromethane/methanol (6 mL), concentrated under a stream of nitrogen and dried in vacuo to give the desired product as a white solid (75 mg, 0.150 mmol, 77% yield).

LCMS (2 min Formic): Rt=1.04 min, [MH]$^+$=499

Intermediate 51: tert-butyl 3-(2-(1-benzyl-5-(methylcarbamoyl)-6-oxo-1,6-dihydropyridine-3-carboxamido)ethoxy)pyrrolidine-1-carboxylate

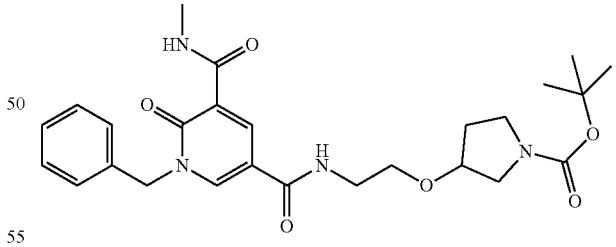

To a solution of 1-benzyl-5-(methylcarbamoyl)-6-oxo-1,6-dihydropyridine-3-carboxylic acid (92.5 mg, 0.323 mmol), HATU (161 mg, 0.423 mmol) and crude tert-butyl 3-(2-aminoethoxy)pyrrolidine-1-carboxylate (74 mg, 0.321 mmol) in N,N-Dimethylformamide (2 mL) was added N,N-diisopropylethylamine (0.112 mL, 0.643 mmol) and the reaction mixture was stirred at room temperature for 7 hr before being concentrated under a stream of nitrogen. The residue was made up to 6 mL with dimethylsulphoxide and directly purified by MDAP (high pH). The required fractions were combined, concentrated under a stream of nitrogen and dried in vacuo to tert-butyl 3-(2-(1-benzyl-5-(methylcarbamoyl)-6-oxo-1,6-dihydropyridine-3-carboxamido)ethoxy)pyrrolidine-1-carboxylate (79.3 mg, 0.159 mmol, 49.5% yield) as a cream coloured solid. LCMS (2 min Formic): Rt=1.04 min, [MH]⁺=499.4.

Intermediate 52: tert-butyl 3-(2-aminoethoxy)pyrrolidine-1-carboxylate

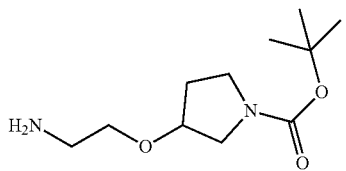 [SMILES: CC(C)(C)OC(=O)N1CCC(OCCN)C1]

A solution of tert-butyl 3-(2-((benzyloxy)imino)ethoxy)pyrrolidine-1-carboxylate (140.9 mg, 0.421 mmol) was dissolved in ethanol (2 mL) and hydrogenated at 50° C. and 40 atmospheres of pressure, using an H-cube apparatus and a Raney-Nickel catalyst cartridge. The resulting solution was concentrated under a stream of nitrogen to give a crude brown oil which was re-dissolved in ethanol (2 mL) and hydrogenated twice at 75° C. and 80 atmospheres of pressure, using an H-cube apparatus and a Raney-Nickel catalyst cartridge and the resulting solution concentrated under a stream of nitrogen to give an orange oil. This was dissolved in methanol and loaded onto a 2 g SCX cartridge which was eluted with methanol (3×5 mL) followed with a 2M solution of ammonia in methanol (4×5 mL). Ammonia fractions were concentrated under a stream of nitrogen and dried in vacuo to give tert-butyl 3-(2-aminoethoxy)pyrrolidine-1-carboxylate (74.1 mg, 0.322 mmol, 76% yield) as an amber oil which was used without further purification.

$^1$H NMR (400 MHz, CDCl$_3$) δ ppm 4.04 (m, J=3.4 Hz, 1H) 3.33-3.60 (m, 6H) 2.86 (t, J=5.1 Hz, 1H) 2.80 (t, J=5.4 Hz, 1H) 1.96 (d, J=13.7 Hz, 2H) 1.49-1.56 (m, 2H) 1.47 (s, 9H)

Intermediate 53: (E)-tert-butyl 3-(2-((benzyloxy)imino)ethoxy)pyrrolidine-1-carboxylate

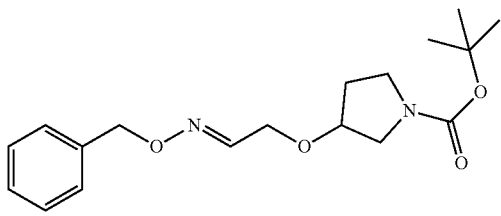 [SMILES: CC(C)(C)OC(=O)N1CCC(OC/C=N/OCc2ccccc2)C1]

To a suspension of sodium periodate (552.7 mg, 2.58 mmol) in water (0.25 mL) was added a suspension of osmium tetroxide (2.3 mg, 9.05 μmol) in water (0.75 mL). a solution of tert-butyl 3-(allyloxy)pyrrolidine-1-carboxylate (146.9 mg, 0.646 mmol) in diethyl ether (1.0 mL) was added and the reaction mixture stirred at room temperature for 6.5 hrs. Methanol (2.0 mL) was added and the reaction mixture filtered through a celite cartridge, and washed through with methanol (3×3 mL). The combined fractions were concentrated in vacuo before being dissolved in Ethanol (3.0 mL). Pyridine (1.5 mL, 18.55 mmol) and O-benzylhydroxylamine hydrochloride (237.1 mg, 1.485 mmol) were added and the reaction mixture stirred at room temperature for 18 hrs. The reaction mixture was concentrated in vacuo before being partitioned between water (25 mL) and dichloromethane (25 mL). The phases were separated and the aqueous phase further extracted with dichloromethane (2×25 mL). The organic phases were combined and filtered through a cartridge containing a hyrdophobic frit before being concentrated in vacuo to give a brown oil. This was dissolved in dichloromethane (4 mL) and loaded onto a 25 g SNAP silica cartridge which was eluted with a gradient of 0-100% ethyl acetate in cyclohexane. The required fractions were combined and concentrated in vacuo before being dissolved in a 1:1 mixture of dichloromethane/methanol (6 mL), concentrated under a stream of nitrogen and dried in vacuo to give tert-butyl 3-(2-((benzyloxy)imino)ethoxy)pyrrolidine-1-carboxylate (177.1 mg, 0.530 mmol, 82% yield) as an orange oil.

LCMS (2 min High pH): Rt=1.28 min, 1.30 min, [MH]⁺=335.3.

Intermediate 54: tert-butyl 3-(allyloxy)pyrrolidine-1-carboxylate

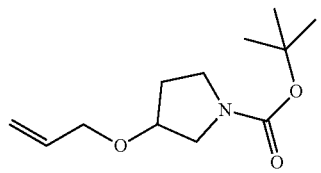 [SMILES: C=CCOC1CCN(C(=O)OC(C)(C)C)C1]

To a solution of tert-butyl 3-hydroxypyrrolidine-1-carboxylate (284 mg, 1.517 mmol, commercially available from, for example, Sigma Aldrich) in N,N-Dimethylformamide (3 mL) was added 3-bromoprop-1-ene (0.130 mL, 1.502 mmol). The solution was stirred at room temperature under nitrogen for 10 mins before sodium hydride (as a 60% wt dispersion in mineral oils) (92.5 mg, 2.313 mmol) was added in small portions and the reaction mixture stirred at room temperature for 21 hr. A 1:1 mixture of saturated ammonium chloride solution and water (10 mL) was added and the reaction mixture extracted with diethyl ether (10 mL). The layers were separated and the aqueous layer extracted with further diethyl ether (2×10 mL). The combined organic phases were washed with a 1:1 mixture of saturated ammonium chloride solution and water (2×10 mL) before being filtered through a cartridge containing a hydrophobic frit and concentrated in vacuo before being dissolved in dichloromethane (5 mL) and concentrated under a stream of nitrogen to give a colourless oil, approximately 335 mg. This was dissolved in dichloromethane (1.5 mL) and loaded onto a 25 g SNAP silica cartridge which was eluted with a 0-50% gradient of ethyl acetate in cyclohexane. The required fractions were combined, concentrated in vacuo before being dissolved in a 1:1 mixture of dichloromethane/methanol (6 mL), concentrated under a stream of nitrogen and dried in vacuo to give tert-butyl 3-(allyloxy)pyrrolidine-1-carboxylate (152.7 mg, 0.672 mmol, 44.3% yield) as a colourless oil. LCMS (2 min High pH): Rt=1.08 min, [MH]⁺=228.3

Intermediate 55: tert-butyl 3-(2-(1-benzyl-5-(methylcarbamoyl)-6-oxo-1,6-dihydropyridine-3-carboxamido)ethoxy)piperidine-1-carboxylate

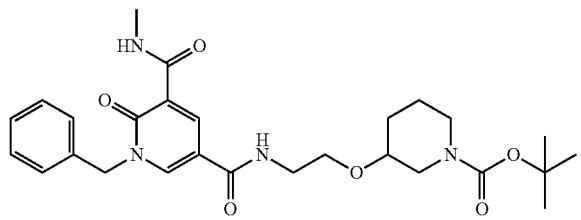 [SMILES: CNC(=O)c1cc(C(=O)NCCOC2CCCN(C(=O)OC(C)(C)C)C2)cn(Cc2ccccc2)c1=O]

To a solution of 1-benzyl-5-(methylcarbamoyl)-6-oxo-1,6-dihydropyridine-3-carboxylic acid (44.5 mg, 0.155 mmol), HATU (77.2 mg, 0.203 mmol) and crude tert-butyl 3-(2-aminoethoxy)piperidine-1-carboxylate (37.5 mg, 0.153 mmol) in N,N-Dimethylformamide (1.5 mL) was added N,N-diisopropylethylamine (0.054 mL, 0.307 mmol) and the reaction mixture was stirred at room temperature for 7 hr before being concentrated under a stream of nitrogen. The residue was made up to 3 mL with dimethylsulphoxide and directly purified by mass MDAP (high pH). The required fractions were individually concentrated under a stream of nitrogen before being dissolved in a 1:1 mixture of dichloromethane/methanol (2×4 mL), individually concentrated under a stream of nitrogen and dried in vacuo to give tert-butyl 3-(2-(1-benzyl-5-(methylcarbamoyl)-6-oxo-1,6-dihydropyridine-3-carboxamido)ethoxy)piperidine-1-carboxylate (33.5 mg, 0.065 mmol, 42.6% yield) as a cream coloured solid. LCMS (2 min Formic): Rt=1.10 min, [MH]$^+$=513.4.

Intermediate 56: tert-butyl 3-(2-aminoethoxy)piperidine-1-carboxylate

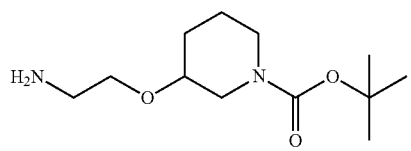 [SMILES: CC(C)(C)OC(=O)N1CCCC(OCCN)C1]

A solution of tert-butyl 3-(2-((benzyloxy)imino)ethoxy)piperidine-1-carboxylate (95 mg, 0.273 mmol) was dissolved in ethanol (2 mL) and hydrogenated at 75° C. and 80 atmospheres of pressure, using an H-cube apparatus and a Raney-nickel catalyst cartridge. The resulting solution was concentrated under a stream of nitrogen to give a yellow oil which was re-dissolved in ethanol (2 mL) and rehydrogenated at 75° C. and 80 atmospheres of pressure, using an H-cube apparatus and a Raney-nickel catalyst cartridge. The resulting solution was concentrated under a stream of nitrogen to give a yellow oil which was dissolved in methanol and loaded onto a 2 g SCX cartridge and eluted with methanol (3×5 mL). The cartridge was then eluted with a 2M solution of ammonia in methanol (4×5 mL). The ammonia fractions were concentrated under a stream of nitrogen and dried in vacuo to give tert-butyl 3-(2-aminoethoxy)piperidine-1-carboxylate (37.8 mg, 0.155 mmol, 56.7% yield) as an amber oil.

$^1$H NMR (400 MHz, CDCl$_3$) δ ppm 3.83 (m, J=10.5 Hz, 1H) 3.43-3.69 (m, 3H) 3.24-3.37 (m, 1H) 2.92-3.15 (m, 2H) 2.74-2.89 (m, 2H) 1.85-2.02 (m, 1H) 1.75 (dtd, J=12.8, 6.4, 6.4, 3.3 Hz, 1H) 1.49-1.61 (m, 3H) 1.46 (s, 9H) 1.37-1.44 (m, 1H)

Intermediate 57: (E)-tert-butyl 3-(2-((benzyloxy)imino)ethoxy)piperidine-1-carboxylate

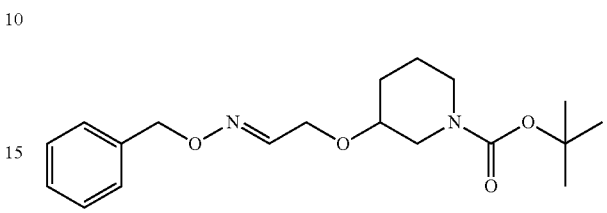

To a suspension of sodium periodate (351.2 mg, 1.642 mmol) in water (0.25 mL) was added a suspension of osmium tetroxide (2.3 mg, 9.05 µmol) in water (0.75 mL). A solution of tert-butyl 3-(allyloxy)piperidine-1-carboxylate (98.2 mg, 0.407 mmol) in diethyl ether (1.000 mL) was added and the reaction mixture stirred at room temperature for 6.5 hrs. Methanol (2.000 mL) was added and the reaction mixture filtered through a celite cartridge, and washed through with methanol (3×3 mL). The combined fractions were concentrated in vacuo before being dissolved in Ethanol (3.000 mL). pyridine (1 mL, 12.36 mmol) and O-benzylhydroxylamine, Hydrochloride (151.5 mg, 0.949 mmol) were added and the reaction mixture stirred at room temperature for 18 hrs. The reaction mixture was concentrated in vacuo before being partitioned between water (25 mL) and dichloromethane (25 mL). The phases were separated and the aqueous phase further extracted with dichloromethane (2×25 mL). The organic phases were combined and filtered through a cartridge containing a hydrophobic frit before being concentrated in vacuo to give a dark orange oil, approximately 225 mg. This was dissolved in dichloromethane (4 mL) and loaded onto a 25 g SNAP silica cartridge which was eluted with a gradient of 0-100% ethyl acetate in cyclohexane. The required fractions were combined and concentrated in vacuo before being dissolved in a 1:1 mixture of dichloromethane/methanol (6 mL), concentrated under a stream of nitrogen and dried in vacuo to give tert-butyl 3-(2-((benzyloxy)imino)ethoxy)piperidine-1-carboxylate (108 mg, 0.310 mmol, 76% yield) as an orange oil. LCMS (2 min High pH): Rt=1.36 min, 1.37 min, [MH]$^+$=349.3

Intermediate 58: tert-butyl 3-(allyloxy)piperidine-1-carboxylate

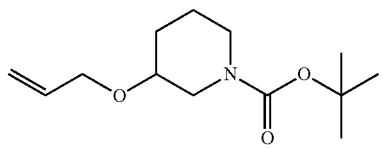 [SMILES: C=CCOC1CCCN(C(=O)OC(C)(C)C)C1]

To a solution of tert-butyl 3-hydroxypiperidine-1-carboxylate (304 mg, 1.510 mmol, commercially available from, for example, Apollo Scientific) in N,N-Dimethylformamide (3 mL) was added 3-bromoprop-1-ene (0.130 ml, 1.502 mmol). The solution was stirred at room temperature under Nitrogen for 10 mins before sodium hydride (as a 60% wt dispersion in mineral oils) (90.2 mg, 2.255 mmol) was added in small portions and the reaction mixture stirred at room temperature for 21.5 hr. A 1:1 mixture of saturated ammonium chloride solution and water (10 mL) was added and the reaction mixture extracted with diethyl ether (10 mL). The layers were separated and the aqueous layer extracted with further diethyl ether (2×10 mL). The combined organic phases were washed with a 1:1 mixture of saturated ammonium chloride solution and water (2×10 mL), filtered through a cartridge containing a hydrophobic frit and concentrated in vacuo before being dissolved in dichloromethane (5 mL) and concentrated under a stream of nitrogen to give a colourless oil, approximately 350 mg. This was dissolved in dichloromethane (1.5 mL) and loaded onto a 25 g SNAP silica cartridge which was eluted with a 0-50% gradient of ethyl acetate in cyclohexane. The required fractions were combined and concentrated in vacuo before being dissolved in a 1:1 mixture of dichloromethane/methanol (6 mL), concentrated under a stream of nitrogen and dried in vacuo give tert-butyl 3-(allyloxy)piperidine-1-carboxylate (105 mg, 0.435 mmol, 28.8% yield) as a colourless oil. LCMS (2 min High pH): Rt=1.18 min, [MH]⁺=242.2

Intermediate 59: tert-butyl 4-(3-(1-benzyl-5-(ethylcarbamoyl)-6-oxo-1,6-dihydropyridine-3-carboxamido)propyl)piperidine-1-carboxylate

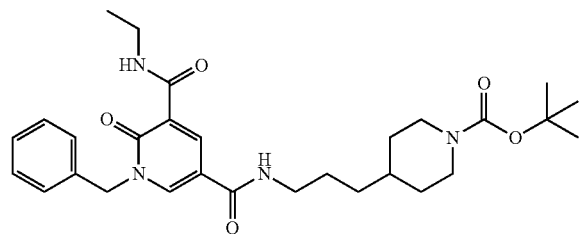 [SMILES: CCNC(=O)c1cc(C(=O)NCCCC2CCN(C(=O)OC(C)(C)C)CC2)cn(Cc2ccccc2)c1=O]

To a solution of 1-benzyl-5-(ethylcarbamoyl)-6-oxo-1,6-dihydropyridine-3-carboxylic acid (200 mg, 0.666 mmol) in N,N-Dimethylformamide (10 mL) and cooled to 0° C., was added DIPEA (0.233 mL, 1.332 mmol), HATU (380 mg, 0.999 mmol) followed by tert-butyl 4-(3-aminopropyl)piperidine-1-carboxylate (0.161 mL, 0.666 mmol, commercially available from, for example, Fluorochem) was added slowly at 0° C. The reaction mixture was stirred for 3 hr at RT. Water was added and extracted with ethyl acetate (2×75 mL). The organic layer was separated, dried over Na2SO4, filtered and concentrated to get crude product. This was purified by column chromatography silica gel 100-200 column and was eluted with 18% EtOAc in n-hexane and collected pure fractions were concentrated under reduced pressure to get tert-butyl 4-(3-(1-benzyl-5-(ethylcarbamoyl)-6-oxo-1,6-dihydropyridine-3-carboxamido)propyl)piperidine-1-carboxylate (180 mg, 0.341 mmol, 51.2% yield). as a off-white solid.

LCMS (10 min RND-FA-10-MIN=REV): Rt=5.67 min, [MH]⁺=525.1.

LCMS Conditions: RND-FA-10-MIN:
Column: Acquity BEH C18 (100 mm×2.1 mm, 1.7 μm)
Mobile Phase: A: 0.05% formic acid in ACN; B: 0.05% formic acid in water
Time (min)/% B: 0/97, 0.4/97, 7.5/2, 9.5/2, 9.6/97, 10/97
Column Temp: 35° C., Flow Rate: 0.45 mL/min Intermediate 60: 1-benzyl-5-(ethylcarbamoyl)-6-oxo-1,6-dihydropyridine-3-carboxylic acid

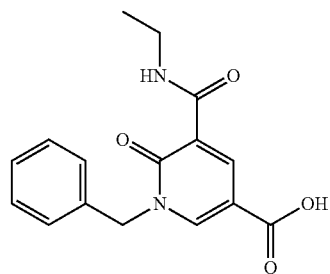 [SMILES: CCNC(=O)c1cc(C(=O)O)cn(Cc2ccccc2)c1=O]

Butyl 1-benzyl-5-(ethylcarbamoyl)-6-oxo-1,6-dihydropyridine-3-carboxylate (2.4600 g, 6.90 mmol) was taken up in Tetrahydrofuran (12 mL) and Water (12.00 mL). lithium hydroxide (0.165 g, 6.90 mmol) was added and the reaction stirred for 3 h at RT. A further portion of lithium hydroxide (0.083 g, 3.45 mmol) was added and the reaction mixture was stirred overnight. 2M HCl (aq) (5.18 mL, 10.35 mmol) was added and the reaction mixture was stirred at r.t during 10 mins then the reaction mixture mixture was extracted with EtOAc 3 times and the combined organic phases were dried over magnesium sulfate then solvent was removed in vacuo to give the title compound (2.0773 g, 6.57 mmol, 95% yield).

LCMS (2 min Formic): Rt=0.89 min, [MH]⁺=301.1.

Intermediate 61: butyl 1-benzyl-5-(ethylcarbamoyl)-6-oxo-1,6-dihydropyridine-3-carboxylate

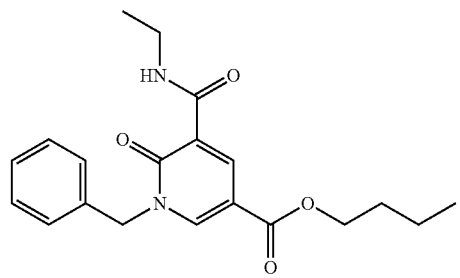 [SMILES: CCCCOC(=O)c1cc(C(=O)NCC)c(=O)n(Cc2ccccc2)c1]

To a solution of butyl 5-(ethylcarbamoyl)-6-oxo-1,6-dihydropyridine-3-carboxylate (1.998 g, 7.50 mmol) in N,N-Dimethylformamide (25 mL), was added (bromomethyl)benzene (0.97 mL, 8.16 mmol)) and K₂CO₃ (2.093 g, 15.14 mmol) at 0° C. The reaction mixture was stirred at RT for 2 hours. Water was added and extracted with ethyl acetate (2×30 mL). The organic phase was washed with a saturated solution of LiCl then dried over magnesium sulfate and concentrated under vacuum to get crude product. This was then purified by silica gel column chromatography' eluting with ethyl acetate/cyclohexane 0-40%. The combined desired fractions were concentrated in vacuo to give the title compound (2.4600 g, 6.56 mmol, 87% yield) as a pale yellow solid.

LCMS (2 min Formic): Rt=1.24 min, [MH]⁺=357.3.

Intermediate 62: butyl 5-(ethylcarbamoyl)-6-oxo-1,6-dihydropyridine-3-carboxylate

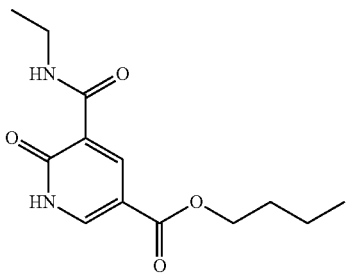 [SMILES: CCCCOC(=O)c1c[nH]c(=O)c(C(=O)NCC)c1]

To a solution of butyl 5-(ethylcarbamoyl)-6-methoxynicotinate (5.55 g, 18.57 mmol) in acetonitrile (100 mL) and cooled to 0° C., was added sodium iodide (8.35 g, 55.7 mmol) followed by TMSCl (7.12 mL, 55.7 mmol) slowly was added. The reaction mixture was stirred at RT for 1 hr. After the reaction was quenched with saturated sodium thiosulphate and water was added, extracted with ethyl acetate (2×20 ml). The organic phase was washed with saturated brine, dried over Na2SO4 and concentrated under vacuum to get crude product, which was washed with n-pentane (2×25 ml) to get pure compound butyl 5-(ethylcarbamoyl)-6-oxo-1,6-dihydropyridine-3-carboxylate (5.15 g, 18.63 mmol, 100% yield) as an off-white solid.

LCMS (4.5 min RND-FA-4.5-MIN): Rt=1.82 min, $[MH]^+=267.2$.

LCMS Conditions: RND-FA-4.5-MIN

Column: Acquity BEH C18 (50 mm×2.1 mm, 1.7 μm)

Mobile Phase: A: 0.05% formic acid in water; B: 0.05% formic acid in ACN

Time (min)/% B: 0/3, 0.4/3, 3.2/98, 3.8/98, 4.2/3, 4.5/3

Column Temp: 35° C., Flow Rate: 0.6 mL/min

Intermediate 63: Butyl 5-(ethylcarbamoyl)-6-methoxynicotinate

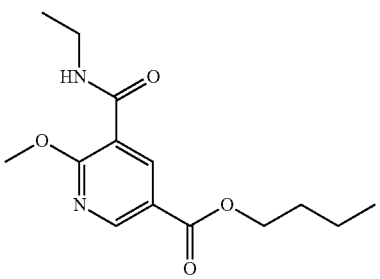 [SMILES: CCCCOC(=O)c1cnc(OC)c(C(=O)NCC)c1]

To a solution of 5-bromo-N-ethyl-2-methoxynicotinamide (11 g, 41.0 mmol) in DMF (100 mL) was added triethylamine (17.16 mL, 123 mmol), 1-butanol (11.98 mL, 205 mmol) and xantphos (1.662 g, 2.87 mmol) in a steel bomb. The reaction mixture was degassed for 10 min with argon. Then palladium(II) acetate (0.921 g, 4.10 mmol) was added and the reaction stirred under a carbon monoxide atmosphere at rt. Then the steel bomb was closed and the reaction was stirred under a carbon monoxide atmosphere (100 psi) at 110° C. for 18 h. After cooling, the reaction mixture was filtered through a Celite pad and washed with ethyl acetate. The filtrate was partitioned between ethyl acetate & cold water. The organic phase was washed with saturated brine, dried over Na2SO4 and concentrated under vacuum to afford the crude product. The crude product was purified by column chromatography on a silica gel 100-200 column which was eluted with 25% EtOAc/n-hexane. The collected pure fractions were concentrated under reduced pressure to give the desired product—butyl 5-(ethylcarbamoyl)-6-methoxynicotinate (4.4 g, 12.57 mmol, 30.6% yield).

LCMS (10 min RND-ABC-10-MIN-V): Rt=4.70 min, $[MH]^+=281.1$.

LCMS Conditions: RND-ABC-10-MIN-V

Column: Xbridge C18 (50 mm×4.6 mm, 2.5 μm),

Mobile Phase: A: 5 mM ammonium bicarbonate in water (pH 10); B: ACN

Time (min)/% ACN: 0/5, 0.5/5, 1/15, 6/98, 9/98, 9.5/5, 10/5

Column temp: 35° C., Flow Rate: 1.3 mL

Intermediate 64: 5-Bromo-N-ethyl-2-methoxynicotinamide

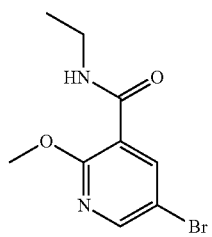

To a solution of 5-bromo-2-methoxynicotinic acid (15 g, 64.6 mmol, commercially available from, for example, Combiblocks) in DCM (100 mL) cooled to 0° C., was added oxalyl dichloride (16.98 mL, 194.0 mmol) followed by the slow addition of DMF (5.01 mL, 64.6 mmol) at 0° C. The reaction mixture was then stirred for 18 h at rt. A small aliquot of the reaction mixture was taken and quenched with MeOH, the TLC shows the complete conversion of SM. The reaction mixture was then concentrated and re-dissolved in DCM (150 mL) and treated with ethanamine hydrochloride (7.91 g, 97 mmol). The reaction mixture was stirred for 3 h at rt. After the reaction, water was added and the organics extracted with ethyl acetate (2×300 mL). The organic layer was separated, dried over Na2SO4, filtered and concentrated to obtain the crude product. The crude product was purified by column chromatography on a silica gel 100-200 column and was eluted with 16% EtOAc/n-hexane. The collected pure fractions were concentrated under reduced pressure to afford the desired product 5-bromo-N-ethyl-2-methoxynicotinamide (11 g, 41.0 mmol, 64% yield) as an off-white solid.

LCMS (10 min RND-FA-10-MIN): Rt=4.22 min, $[MH]^+=261$.

LCMS Conditions: RND-FA-10-MIN:

Column: Acquity BEH C18 (100 mm×2.1 mm, 1.7 μm)

Mobile Phase: A: 0.05% formic acid in ACN; B: 0.05% formic acid in water

Time (min)/% B: 0/97, 0.4/97, 7.5/2, 9.5/2, 9.6/97, 10/97

Column Temp: 35° C., Flow Rate: 0.45 mL/min

Intermediate 65: (S)-tert-butyl 3-(3-(1-benzyl-5-(ethylcarbamoyl)-6-oxo-1,6-dihydropyridine-3-carboxamido)propyl)-3-fluoropiperidine-1-carboxylate

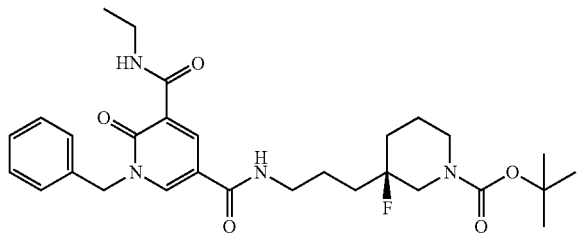 [SMILES: CCNC(=O)c1cc(C(=O)NCCC[C@]2(F)CCCN(C(=O)OC(C)(C)C)C2)cn(Cc2ccccc2)c1=O]

To a solution of 1-benzyl-5-(ethylcarbamoyl)-6-oxo-1,6-dihydropyridine-3-carboxylic acid (47.9 mg, 0.160 mmol) in N,N-Dimethylformamide (0.8 mL) was added HATU (91 mg, 0.239 mmol) followed by (5)-tert-butyl 3-(3-aminopropyl)-3-fluoropiperidine-1-carboxylate (41.5 mg, 0.160 mmol) and N-ethyl-N-isopropylpropan-2-amine (0.10 ml, 0.573 mmol). The resulting reaction mixture was stirred at r.t. during 3 hours. Reaction mixture was purified directly by MDAP (high pH). Fractions containing desired product were concentrated in vacuo to give (5)-tert-butyl 3-(3-(1-benzyl-5-(ethylcarbamoyl)-6-oxo-1,6-dihydropyridine-3-carboxamido)propyl)-3-fluoropiperidine-1-carboxylate (105 mg, 0.155 mmol, 97% yield) as a colorless oil.

LCMS (2 min Formic): Rt=1.21 min, [MH]$^+$=543.3.

Intermediate 66: (S)-tert-butyl 3-(3-aminopropyl)-3-fluoropiperidine-1-carboxylate

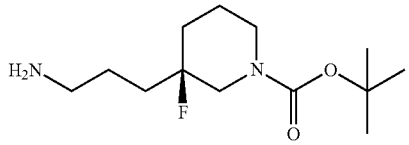 [SMILES: CC(C)(C)OC(=O)N1CCC[C@@](F)(CCCN)C1]

(R)-tert-butyl 3-(3-azidopropyl)-3-fluoropiperidine-1-carboxylate (5.0 g, 17.46 mmol) was dissolved in THF (50 mL) and PPh$_3$ (5.50 g, 20.95 mmol) was added, then the mixture was stirred at rt over the weekend. Water (50 mL) was added and the mixture stirred vigorously for 2 h, then diluted with EtOAc (100 mL) and brine (50 mL) and the organic layer separated, dried and evaporated in vacuo to give a pale yellow oil. The crude product was dissolved in DCM (20 mL) and loaded onto a 100 g silica column, then eluted with 0-20% 2M methanoic ammonia/DCM and the product-containing fractions (visualised by ninhydrin) were evaporated in vacuo to give (S)-tert-butyl 3-(3-aminopropyl)-3-fluoropiperidine-1-carboxylate (4.0 g, 15.36 mmol, 88% yield) as a colourless oil.

$^1$H NMR (400 MHz, CDCl$_3$) δ ppm 3.72-4.02 (m, 2H) 2.89-3.12 (m, 2H) 2.72 (t, J=6.6 Hz, 2H) 1.86-1.98 (m, 1H) 1.72-1.85 (m, 1H) 1.48-1.70 (m, 6H) 1.46 (s, 9H)

Intermediate 67: (R)-tert-butyl 3-(3-azidopropyl)-3-fluoropiperidine-1-carboxylate

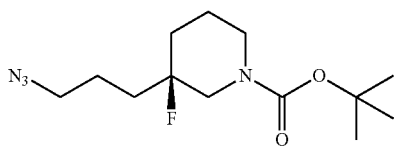 [SMILES: CC(C)(C)OC(=O)N1CCC[C@@](F)(CCCN=[N+]=[N-])C1]

Sodium azide (2.68 g, 41.2 mmol) was added to a solution of (R)-tert-butyl 3-fluoro-3-(3-((methylsulfonyl)oxy)propyl)piperidine-1-carboxylate (7 g, 20.62 mmol) in DMF (50 mL) and the mixture was heated at 70° C. for 2 h, then diluted with water (200 mL) and extracted with EtOAc (2×100 mL). The combined organics were washed with water (2×100 mL), dried and evaporated in vacuo give the crude product as a colourless oil. The crude product was dissolved in DCM (10 mL) and loaded onto a 100 g silica column, then eluted with 0-50% EtOAc/cyclohexane and the product-containing fractions (visualised by ninhydrin) were evaporated in vacuo to give (R)-tert-butyl 3-(3-azidopropyl)-3-fluoropiperidine-1-carboxylate (5.2 g, 18.16 mmol, 88% yield) as a colourless oil which was carried though to the next step without further purification.

$^1$H NMR (400 MHz, CDCl$_3$) δ ppm 3.69-3.99 (m, 2H) 3.33 (t, J=6.5 Hz, 2H) 2.96-3.17 (m, 2H) 1.86-1.98 (m, 1H) 1.58-1.83 (m, 6H) 1.49-1.58 (m, 1H) 1.47 (s, 9H)

Intermediate 68: (R)-tert-butyl 3-fluoro-3-(3-((methylsulfonyl)oxy)propyl)piperidine-1-carboxylate

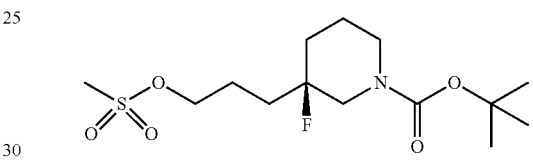

(R)-tert-butyl 3-fluoro-3-(3-hydroxypropyl)piperidine-1-carboxylate (6 g, 22.96 mmol) was dissolved in DCM (100 mL), Et$_3$N (4.80 mL, 34.4 mmol) was added and the mixture was cooled in an ice bath, then Ms-Cl (2.326 mL, 29.8 mmol) was added dropwise (exotherm!) and the mixture was stirred for 2 h, allowing it to warm to rt. The solution was washed with water (100 mL) and brine (100 mL). The organic layer was dried and evaporated in vacuo to give (R)-tert-butyl 3-fluoro-3-(3-((methylsulfonyl)oxy)propyl)piperidine-1-carboxylate (7.2 g, 21.21 mmol, 92% yield) as a colourless oil which was used in the next step.

$^1$H NMR (400 MHz, CDCl$_3$) δ ppm 4.20-4.32 (m, 2H) 3.70-3.96 (m, 2H) 3.68 (s, 1H) 3.04-3.15 (m, 1H) 3.00-3.03 (m, 3H) 1.88-1.99 (m, 3H) 1.49-1.83 (m, 5H) 1.43-1.48 (m, 9H)

Intermediate 69: (R)-tert-butyl 3-fluoro-3-(3-hydroxypropyl)piperidine-1-carboxylate

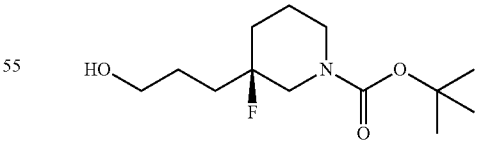

LiBH$_4$ (2.046 g, 94 mmol) was added to a solution of (R)-tert-butyl 3-(3-ethoxy-3-oxopropyl)-3-fluoropiperidine-1-carboxylate (9.5 g, 31.3 mmol) in THF (100 mL) and the mixture was stirred at rt under N$_2$ for 48 h, then cooled in an ice bath and quenched by very cautious, initially dropwise addition of ammonium chloride solution (100 mL) (strong effervescence on addition!), then the mixture was stirred for 20 min, diluted with EtOAc (100 mL) and the combined organics separated, dried over Na$_2$SO$_4$ and evaporated in vacuo to give a pale yellow oil. The crude material was dissolved in DCM and loaded onto a 100 g silica column, then eluted with 0-100% EtOAc/cyclohexane and the product-containing fractions were evaporated in vacuo to give (R)-tert-butyl 3-fluoro-3-(3-hydroxypropyl)piperidine-1-carboxylate (6.0 g, 22.96 mmol, 73.3% yield) which was carried though to the next step immediately.

$^1$H NMR (400 MHz, CDCl$_3$) δ ppm 3.61-3.93 (m, 4H) 2.94-3.14 (m, 2H) 1.87-1.99 (m, 1H) 1.48-1.86 (m, 7H) 1.45 (s, 9H)

Intermediate 70: (R)-tert-butyl 3-(3-ethoxy-3-oxopropyl)-3-fluoropiperidine-1-carboxylate

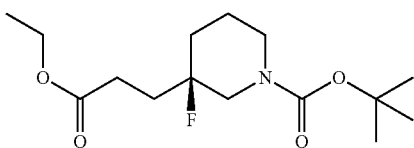 [SMILES: CCOC(=O)CC[C@]1(F)CCCN(C(=O)OC(C)(C)C)C1]

(R,E)-tert-butyl 3-(3-ethoxy-3-oxoprop-1-en-1-yl)-3-fluoropiperidine-1-carboxylate (10 g, 33.2 mmol) was dissolved in EtOH (100 mL) and added to 5% Pd—C (2 g, 18.79 mmol) under N$_2$, then the mixture was hydrogenated at atmospheric pressure for 6 h, giving the expected uptake of hydrogen. The mixture was filtered though Celite® under N$_2$ and the filtrate evaporated in vacuo to give (R)-tert-butyl 3-(3-ethoxy-3-oxopropyl)-3-fluoropiperidine-1-carboxylate (9.5 g, 31.3 mmol, 94% yield) as a pale yellow oil.

$^1$H NMR (400 MHz, CDCl$_3$) δ ppm 4.05-4.22 (m, 2H) 3.66-4.01 (m, 2H) 2.88-3.23 (m, 2H) 2.47 (t, J=8.1 Hz, 2H) 1.84-2.12 (m, 3H) 1.71-1.84 (m, 1H) 1.47-1.71 (m, 2H) 1.45 (s, 9H) 1.21-1.32 (m, 3H)

Intermediate 71: (R,E)-tert-butyl 3-(3-ethoxy-3-oxoprop-1-en-1-yl)-3-fluoropiperidine-1-carboxylate

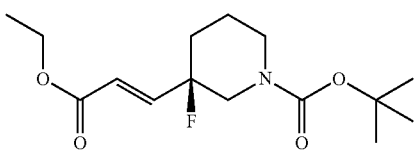 [SMILES: CCOC(=O)/C=C/[C@]1(F)CCCN(C(=O)OC(C)(C)C)C1]

(S)-tert-butyl 3-fluoro-3-(hydroxymethyl)piperidine-1-carboxylate (10 g, 42.9 mmol, preparation described in the literature: Org. Process Res. Dev. 2015, 19, 7, 865-871)) was dissolved in DCM (60 mL) and Dess-Martin periodinane (23.64 g, 55.7 mmol) was added and the mixture was stirred at rt for 18 h, then washed with water and the organic layer dried over Na$_2$SO$_4$ and decanted into a clean, dry flask. Ethyl 2-(triphenylphosphoranylidene)acetate (19.41 g, 55.7 mmol) was added and the mixture was stirred overnight, then washed with water and the organic layer dried and evaporated in vacuo. The residue was purifed on a 50 g silica column eluting with 0-50% EtOAc/cyclohexane and the product-containing fractions were evaporated in vacuo to give (R,E)-tert-butyl 3-(3-ethoxy-3-oxoprop-1-en-1-yl)-3-fluoropiperidine-1-carboxylate (10.5 g, 34.8 mmol, 81% yield) as a colourless oil.

$^1$H NMR (400 MHz, CDCl$_3$) δ ppm 6.89 (dd, J=19.6, 15.7 Hz, 1H) 6.15 (d, J=15.7 Hz, 1H) 4.13-4.28 (m, 2H) 3.80-4.10 (m, 2H) 2.86-3.25 (m, 2H) 1.52-2.04 (m, 4H) 1.46 (s, 9H) 1.30 (t, J=7.1 Hz, 3H)

Intermediate 72: (R)-tert-butyl 2-(2-(1-benzyl-5-(ethylcarbamoyl)-6-oxo-1,6-dihydropyridine-3-carboxamido)ethyl)morpholine-4-carboxylate

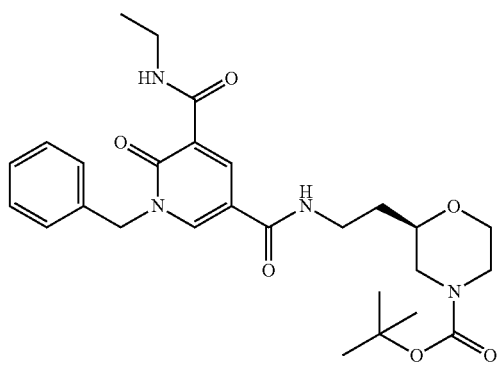 [SMILES: CCNC(=O)c1cc(C(=O)NCC[C@@H]2CN(C(=O)OC(C)(C)C)CCO2)cn(Cc2ccccc2)c1=O]

To a solution of 1-benzyl-5-(ethylcarbamoyl)-6-oxo-1,6-dihydropyridine-3-carboxylic acid (75 mg, 0.250 mmol) in N,N-Dimethylformamide (0.8 mL) was added HATU (142 mg, 0.375 mmol) followed by (R)-tert-butyl 2-(2-aminoethyl)morpholine-4-carboxylate (86 mg, 0.375 mmol) and N-ethyl-N-isopropylpropan-2-amine (0.10 ml, 0.573 mmol). The resulting reaction mixture was stirred at r.t. during 3 hours. Reaction mixture was purified directly by MDAP (high pH). Fractions containing desired product were concentrated in vacuo to give (R)-tert-butyl 2-(2-(1-benzyl-5-(ethylcarbamoyl)-6-oxo-1,6-dihydropyridine-3-carboxamido)ethyl)morpholine-4-carboxylate (125 mg, 0.232 mmol, 93% yield) as a colorless oil.

LCMS (2 min Formic): Rt=1.12 min, [MH]$^+$=513.2.

Intermediate 73: (R)-tert-Butyl 2-(2-aminoethyl)morpholine-4-carboxylate

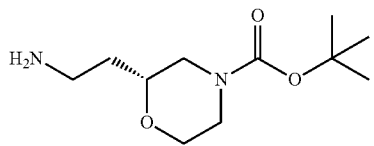 [SMILES: CC(C)(C)OC(=O)N1CCO[C@H](CCN)C1]

(R)-tert-Butyl 2-(cyanomethyl)morpholine-4-carboxylate (2.39 g, 10.56 mmol) was taken up in THF (20 mL) and stirred at rt, BH$_3$.THF (1M in THF, 15.84 mL, 15.84 mmol) was added over 10 min and the reaction stirred at rt for 2 h. The reaction was quenched by the careful addition of MeOH until all effervesence had stopped. The reaction was concentrated and diluted with MeOH and treated with 1M NaOH (50 mL) and stirred at rt for 2 h, a precipitate resulted. The reaction was concentrated to remove the MeOH and was diluted with water and extracted with EtOAc. The combined organics were washed with water, dried using a hydrophobic frit and concentrated to give the crude product as a colourless oil. This was further purified using SP4 flash chromatography, using a SNAP 50 g Si column and eluting with 0-8% 2M NH₃ in MeOH:DCM to give (R)-tert-butyl 2-(2-aminoethyl)morpholine-4-carboxylate (965 mg, 4.19 mmol, 39.7% yield) as a colourless oil.

¹H NMR (400 MHz, DMSO-d₆) δ ppm: 3.56-3.90 (m, 3H) 3.23-3.46 (m, 2H) 2.01-3.11 (obs m, 6H) 1.28-1.62 (m, 11H).

Intermediate 74: (S)-tert-Butyl 2-(cyanomethyl)morpholine-4-carboxylate

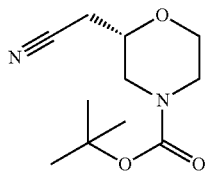

(R)-tert-Butyl 2-(((methylsulfonyl)oxy)methyl)morpholine-4-carboxylate (4 g, 13.54 mmol, commercially available from, for example, Matrix Scientific), KCN (0.926 g, 14.22 mmol) and KI (3.37 g, 20.31 mmol) were stirred at 80° C. in DMSO (30 mL) for 4 h and then at 100° C. for 3 h. The reaction was diluted with water and was extracted with EtOAc, the organic layer was washed with water and brine, dried using a hydrophobic frit and concentrated to a yellow oil. This oil was purified using a 50 g silica column, eluting with 0-50% EtOAc:Cyclohexane. The appropriate fractions were collected and concentrated in vacuo to give (S)-tert-butyl 2-(cyanomethyl)morpholine-4-carboxylate (2.693 g, 11.90 mmol, 88% yield) as a white solid.

¹H NMR (400 MHz, DMSO-d₆) δ ppm 3.78-3.92 (m, 2H) 3.70 (br. d, J=13.4 Hz, 1H) 3.53-3.63 (m, 1H) 3.45 (td, J=11.6, 2.9 Hz, 1H) 2.80-2.92 (m, 2H) 2.73 (dd, J=17.1, 7.1 Hz, 1H) 2.59-2.68 (m, 1H) 1.41 (s, 9H)

Intermediate 75: (R)-tert-butyl 2-(3-(1-benzyl-5-(ethylcarbamoyl)-6-oxo-1,6-dihydropyridine-3-carboxamido)propyl)morpholine-4-carboxylate

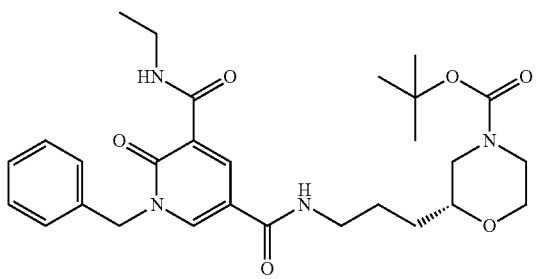 [SMILES: CCNC(=O)c1cc(C(=O)NCCC[C@@H]2CN(C(=O)OC(C)(C)C)CCO2)cn(Cc2ccccc2)c1=O]

To a solution of 1-benzyl-5-(ethylcarbamoyl)-6-oxo-1,6-dihydropyridine-3-carboxylic acid (65 mg, 0.216 mmol) in N,N-Dimethylformamide (0.8 mL) was added HATU (123 mg, 0.325 mmol) followed by (R)-tert-butyl 2-(3-aminopropyl)morpholine-4-carboxylate (79 mg, 0.325 mmol) and N-ethyl-N-isopropylpropan-2-amine (0.10 mL, 0.573 mmol). The resulting reaction mixture was stirred at r.t. during 1 hour. Reaction mixture was purified directly by MDAP (high pH). Fractions containing desired product were concentrated in vacuo to give (R)-tert-butyl 2-(3-(1-benzyl-5-(ethylcarbamoyl)-6-oxo-1,6-dihydropyridine-3-carboxamido)propyl)morpholine-4-carboxylate (100 mg, 0.169 mmol, 78% yield) as a colorless oil.

LCMS (2 min Formic): Rt=1.15 min, [MH]⁺=527.2.

Intermediate 76: (R)-tert-butyl 2-(3-aminopropyl)morpholine-4-carboxylate

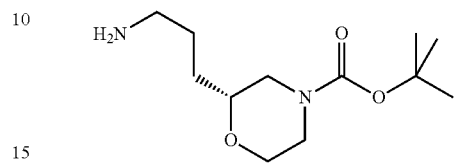

(R)-tert-butyl 2-(3-azidopropyl)morpholine-4-carboxylate (0.96 g, 3.55 mmol) was dissolved in EtOH (30 mL) and was hydrogenated in an H-Cube on full mode at 1 mL/min flow rate over a Pd/C cat cart. The eluant was evaporated in vacuo to give (R)-tert-butyl 2-(3-aminopropyl)morpholine-4-carboxylate (0.81 g, 3.32 mmol, 93% yield).

¹H NMR (400 MHz, CDCl₃-d) 6 ppm 3.70-4.00 (m, 3H) 3.41-3.56 (m, 1H) 3.23-3.40 (m, 2H) 2.79-3.12 (m, 2H) 2.47-2.69 (m, 1H) 1.80-1.98 (m, 1H) 1.25-1.72 (m, 12H)

Intermediate 77: (R)-tertbutyl 2-(3-azidopropyl)morpholine-4-carboxylate

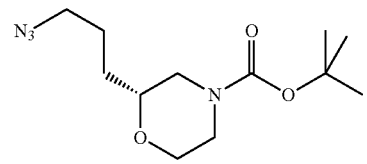 [SMILES: CC(C)(C)OC(=O)N1CCO[C@H](CCCN=[N+]=[N-])C1]

(R)-tert-Butyl 2-(3-((methylsulfonyl)oxy)propyl)morpholine-4-carboxylate (1.2 g, 3.71 mmol) was dissolved in DMF (5 mL) and sodium azide (0.724 g, 11.13 mmol) was added, then the mixture was heated at 80° C. for 2 h. The mixture was diluted with water (20 mL) and extracted with EtOAc (20 mL). The organic layer was washed with water (2×10 mL), dried and evaporated in vacuo to give (R)-tert-butyl 2-(3-azidopropyl)morpholine-4-carboxylate (0.96 g, 3.55 mmol, 96% yield) as a colourless gum.

¹H NMR (400 MHz, CDCl₃) δ ppm 4.12 (q, J=7.3 Hz, 1H) 3.74-3.97 (m, 3H) 3.49 (td, J=11.7, 2.8 Hz, 1H) 3.20-3.41 (m, 2H) 2.89-2.95 (m, 1H) 2.59 (br. s., 1H) 1.60-1.85 (m, 2H) 1.49-1.56 (m, 2H) 1.47 (s, 9H)

Intermediate 78: (R)-tert-butyl 2-(3-(methylsulfonyl)oxy)propyl)morpholine-4-carboxylate

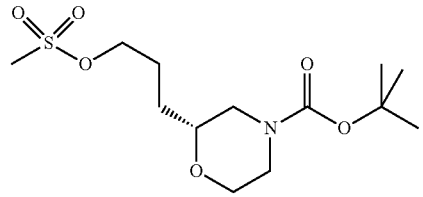 [SMILES: CC(C)(C)OC(=O)N1CCO[C@H](CCCOS(C)(=O)=O)C1]

(R)-tert-butyl 2-(3-hydroxypropyl)morpholine-4-carboxylate (1.34 g, 5.46 mmol) was dissolved in DCM (10 mL) and Et₃N (1.142 mL, 8.19 mmol) and Ms-Cl (0.553 mL, 7.10 mmol) were added. The solution was stirred for 2 h, then washed with water and the organic layer dried and evaporated in vacuo to give a pale yellow oil. This was purified by chromatography on a 50 g silica column, eluting with 0-100% EtOAc/cyclohexane and the product-containing fractions were evaporated in vacuo to give (R)-tert-butyl 2-(3-((methylsulfonyl)oxy)propyl)morpholine-4-carboxylate (1.22 g, 3.77 mmol, 69.1% yield).

¹H NMR (400 MHz, CDCl₃) δ ppm 4.21-4.35 (m, 2H) 3.76-3.95 (m, 3H) 3.45-3.55 (m, 1H) 3.32-3.41 (m, 1H) 3.02 (s, 3H) 2.84-2.97 (m, 1H) 2.55-2.66 (m, 1H) 1.91-2.02 (m, 1H) 1.78-1.90 (m, 1H) 1.52-1.65 (m, 2H) 1.48 (s, 9H)

Intermediate 79: (R)-tertbutyl 2-(3-hydroxypropyl)morpholine-4-carboxylate

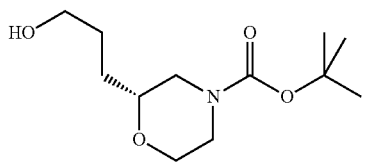 [SMILES: CC(C)(C)OC(=O)N1CCO[C@H](CCCO)C1]

LiBH₄ (0.121 g, 5.57 mmol) was added to a solution of (S)-tert-butyl 2-(3-ethoxy-3-oxopropyl)morpholine-4-carboxylate (0.40 g, 1.392 mmol) in THF (10 mL) at 0° C., then the mixture was stirred overnight, allowing it to warm to rt. The reaction mixture was quenched by very cautious addition of ammonium chloride solution (20 mL) and extracted with EtOAc (2×20 mL). The combined organics were dried and evaporated in vacuo to give (S)-tert-butyl 2-(3-hydroxypropyl)morpholine-4-carboxylate (0.30 g, 1.223 mmol, 88% yield).

¹H NMR (400 MHz, CDCl₃) δ ppm 5.32 (s, 1H) 3.88 (br. s., 3H) 3.75-3.80 (m, 1H) 3.67 (br. d, J=2.2 Hz, 1H) 3.53 (td, J=11.0, 3.0 Hz, 1H) 3.34-3.43 (m, 1H) 2.88-2.99 (m, 1H) 2.57-2.68 (m, 1H) 1.71 (q, J=6.6 Hz, 2H) 1.53-1.62 (m, 2H) 1.48 (s, 9H)

Intermediate 80: (R)-tertbutyl 2-(3-ethoxy-3-oxopropyl)morpholine-4-carboxylate

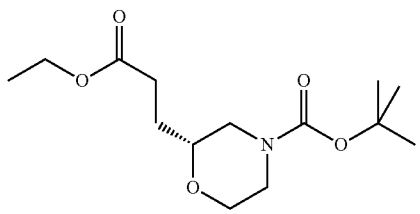 [SMILES: CCOC(=O)CC[C@@H]1CN(C(=O)OC(C)(C)C)CCO1]

(R,E)-tert-butyl 2-(3-ethoxy-3-oxoprop-1-en-1-yl)morpholine-4-carboxylate (1.8 g, 6.31 mmol) was dissolved in EtOH (60 mL) and hydrogenated in an H-Cube on full mode at 1 mL/min flow rate over a Pd/C cat cart. The eluant was evaporated in vacuo to give (R)-tert-butyl 2-(3-ethoxy-3-oxopropyl)morpholine-4-carboxylate (1.7 g, 5.92 mmol, 94% yield) as a colourless gum.

¹H NMR (400 MHz, CDCl₃) δ ppm 4.14 (q, J=7.1 Hz, 2H) 3.73-3.95 (m, 3H) 3.43-3.53 (m, 1H) 3.26-3.40 (m, 1H) 2.86-2.97 (m, 1H) 2.56-2.65 (m, 1H) 2.44 (spt, J=7.5 Hz, 2H) 1.72-1.82 (m, 2H) 1.44-1.48 (m, 9H) 1.26 (t, J=7.1 Hz, 3H)

Intermediate 81: (R,E)-tert-butyl 2-(3-ethoxy-3-oxoprop-1-en-1-yl)morpholine-4-carboxylate

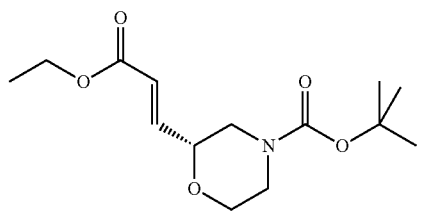 [SMILES: CCOC(=O)/C=C/[C@@H]1CN(C(=O)OC(C)(C)C)CCO1]

(S)-tert-Butyl 2-(hydroxymethyl)morpholine-4-carboxylate (5 g, 23.01 mmol, commercially available from, for example, AOK Chem) was dissolved in DCM (10 mL) and Dess-Martin periodinane (11.71 g, 27.6 mmol) was added, then the solution was stirred at rt for 2 h. The mixture was washed with NaHCO₃ solution (20 mL) and the organic layer dried and evaporated to give a colourless solid. NMR shows the presence of the desired aldehyde. The crude intermediate was dissolved in toluene (20 mL) and ethyl 2-(triphenylphosphoranylidene)acetate (10.42 g, 29.9 mmol) was added, then the mixture was heated at 90° C. overnight. The resulting suspension was filtered and the filtrate washed with water, then the organic layer was dried and evaporated in vacuo. The residue was purified by chromatography on a 25 g silica column eluting with 0-50% EtOAc/cyclohexane and the product-containing fractions were evaporated in vacuo to give (R,E)-tert-butyl 2-(3-ethoxy-3-oxoprop-1-en-1-yl)morpholine-4-carboxylate (1.9 g, 6.66 mmol, 28.9% yield) as a colourless gum.

¹H NMR (400 MHz, CDCl₃) δ ppm 6.84 (dd, 7-15.9, 4.2 Hz, 1H) 6.02-6.24 (m, 1H) 4.15-4.34 (m, 2H) 4.02-4.12 (m, 1H) 3.80-3.99 (m, 2H) 3.49-3.67 (m, 1H) 2.98 (t, 7-10.6 Hz, 1H) 2.70 (br. s., 1H) 1.49 (s, 9H) 1.26-1.36 (m, 4H)

Intermediate 82: 1-Benzyl-N⁵-(4,4-diethoxybutyl)-N³-methyl-2-oxo-1,2-dihydropyridine-3,5-dicarboxamide

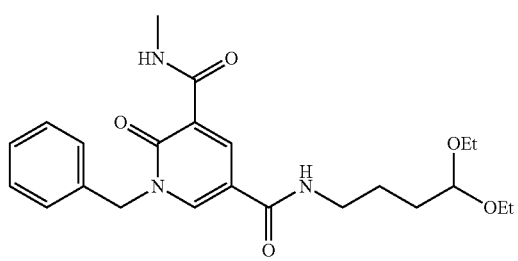 [SMILES: CCOC(CCCNC(=O)c1cc(C(=O)NC)c(=O)n(Cc2ccccc2)c1)OCC]

To a solution of 1-benzyl-5-(methylcarbamoyl)-6-oxo-1,6-dihydropyridine-3-carboxylic acid (350 mg, 1.22 mmol) and HATU (511 mg, 1.35 mmol) in DMF (7 mL) was added DIPEA (0.427 mL, 2.45 mmol) followed by 4,4-diethoxybutan-1-amine (0.232 mL, 1.35 mmol). The resulting solution was stirred at rt for 30 min, after which sat. aqueous LiCl solution (20 mL), sat. aqueous Na₂CO₃ solution (1 mL) and ethyl acetate (20 mL) were added and the layers separated. The aqueous layer was extracted with further ethyl acetate (2×20 mL). The organic layers were combined, back extracted with water (2×10 mL) and filtered through a cartridge fitted with a hydrophobic frit. The filtrate was evaporated in vacuo to give an orange crystalline solid. This was redissolved in DCM and directly applied to the top of a 25 g SNAP silica cartridge and purified by SP4 flash column chromatography. The column was eluted with a gradient of 40-80% ethyl acetate in cyclohexane. The appropriate fractions were collected and concentrated in vacuo afford the product as a cream solid—1-benzyl-N⁵-(4,4-diethoxybutyl)-N³-methyl-2-oxo-1,2-dihydropyridine-3,5-dicarboxamide (448 mg, 1.04 mmol, 85% yield)

LCMS (2 min high pH): Rt=0.99 min, [M−H]⁻=428.4.

Intermediate 83: (1R,5S,6r)-3-Oxabicyclo[3.1.0]hexane-6-carboxylic acid

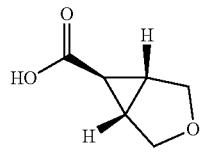

LiOH (751 mg, 31.4 mmol) was added to a solution of (1R,5S,6r)-ethyl 3-oxabicyclo[3.1.0]hexane-6-carboxylate (1000 mg, 6.27 mmol, commercially available from, for example, Pharmablock) in water (10 mL), THF (10 mL) and MeOH (10 mL) at rt. The resulting suspension was stirred for 3 h. For work-up, the mixture was evaporated, the remaining crude solid was dissolved in a minimum amount of water, and quenched with HCl (5 mL, 25% m/m), and extracted 4 times with MeOH/DCM solvent, the combined organic phases were dried over a hydrophobic frit, evaporated in vacuo, to yield the desired compound (1R,5S,6r)-3-oxabicyclo[3.1.0]hexane-6-carboxylic acid (750 mg, 5.85 mmol, 93% yield)

¹H NMR (400 MHz, DMSO-d₆) δ ppm 12.13 (s, 1H) 3.80 (d, J=8.6 Hz, 2H) 3.62 (d, J=8.6 Hz, 2H) 2.00-2.15 (m, 2H) 1.32 (t, J=3.1 Hz, 1H)

Intermediate 84: Benzyl (1R,5S,6r)-3-oxabicyclo[3.1.0]hexan-6-ylcarbamate

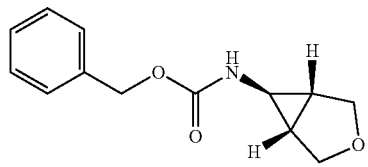 [SMILES: O=C(N[C@H]1[C@@H]2COC[C@@H]21)OCc1ccccc1]

(1R,5S,6r)-3-Oxabicyclo[3.1.0]hexane-6-carboxylic acid (340 mg, 2.65 mmol) was dissolved in toluene (12 mL), then Et₃N (1.110 mL, 7.96 mmol), diphenyl phosphorazidate (0.686 mL, 3.18 mmol) and benzyl alcohol (0.552 mL, 5.31 mmol) were added and the mixture was heated at reflux for 2 h. The solution was diluted with EtOAc (10 mL) and washed with water (10 mL) and NaHCO₃ solution (10 mL), the organic layer was dried and evaporated and the residue purified by chromatography on a 25 g silica column eluting with 0-50% EtOAc/cyclohexane and the product-containing fractions were evaporated in vacuo to give benzyl (1R,5S,6r)-3-oxabicyclo[3.1.0]hexan-6-ylcarbamate (460 mg, 1.972 mmol, 74.3% yield) as a white solid.

LCMS (2 min Formic): Rt=0.83 min, [MH]⁺=234.3.

¹H NMR (400 MHz, CDCl₃) δ ppm 7.29-7.41 (m, 5H) 5.11 (br. s., 2H) 4.86 (br. s., 1H) 3.98 (d, J=8.3 Hz, 2H) 3.72 (d, J=8.6 Hz, 2H) 2.45-2.52 (m, 1H) 1.80 (br. s, 2H)

Intermediate 85: (1R,5S,6r)-3-Oxabicyclo[3.1.0]hexan-6-amine, hydrochloride

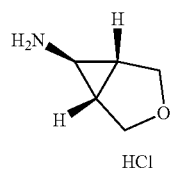

Benzyl (1R,5S,6r)-3-oxabicyclo[3.1.0]hexan-6-ylcarbamate (460 mg, 1.972 mmol) was dissolved in EtOH (20 mL) and the reaction was hydrogenated using an H-cube (settings: rt, 1 bar, 1 mL/min flow rate) and 10% Pd/C CatCart 30 as the catalyst. The reaction was cycled though the H-Cube for 1.5 h before acidifying the mixture with HCl (7M aqueous, 1.332 mL, 9.86 mmol) and evaporating in vacuo to yield an oily solid. The solid was dried in vacuo over 2 days to yield the desired product (1R,5S,6r)-3-oxabicyclo[3.1.0]hexan-6-amine, hydrochloride (262 mg, 1.836 mmol, 93% yield) as an off-white solid.

¹H NMR (400 MHz, DMSO-d₆) δ ppm 8.48 (br. s., 3H) 3.80 (d, J=8.8 Hz, 2H) 3.59 (d, J=8.6 Hz, 2H) 2.24 (t, J=2.3 Hz, 1H) 2.07 (t, J=2.6 Hz, 2H).

Intermediate 86: 1-Benzyl-N⁵-(3-((2r,5r)-5-(1,3-dioxoisoindolin-2-yl)-1,3-dioxan-2-yl)propyl)-N³-methyl-2-oxo-1,2-dihydropyridine-3,5-dicarboxamide

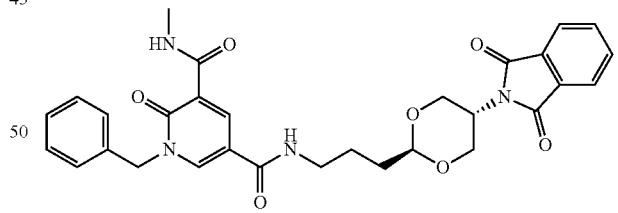

To a solution of 1-benzyl-N⁵-(4,4-diethoxybutyl)-N³-methyl-2-oxo-1,2-dihydropyridine-3,5-dicarboxamide (200 mg, 0.47 mmol) in toluene (4 mL) was added 2-(1,3-dihydroxypropan-2-yl)isoindoline-1,3-dione (103 mg, 0.466 mmol, the preparation of which is described in patent: WO 2015011252) and p-toluenesulfonic acid monohydrate (17.7 mg, 0.09 mmol). The resulting suspension was stirred at 90° C. under nitrogen for 2 h, after which the reaction mixture was allowed to cool to rt and partitioned between ethyl acetate (30 mL), and sat. aq. sodium bicarbonate solution (30 mL) and the layers separated. The aqueous phase was extracted with further ethyl acetate (2×30 mL) and the organic phases were combined, dried (Na₂SO₄) and filtered through a hydrophobic frit. The filtrate was evaporated under a stream of nitrogen to give a yellow crystalline solid. This was redissolved in DMSO (3 mL) and purified by MDAP (3×1 mL injections, high pH). The required fractions were combined and evaporated in vacuo to give the desired product—1-benzyl-$N^5$-(3-((2r,5r)-5-(1,3-dioxoisoindolin-2-yl)-1,3-dioxan-2-yl)propyl)-$N^3$-methyl-2-oxo-1,2-dihydropyridine-3,5-dicarboxamide (117 mg, 0.21 mmol, 45% yield).

LCMS (2 min high pH): Rt=1.04 min, [MH]$^+$=559.3.

EXAMPLES

Example 1: 1-Benzyl-N3-methyl-2-oxo-N5-(2-(tetrahydro-2H-pyran-4-yl)ethyl)-1,2-dihydropyridine-3, 5-dicarboxamide

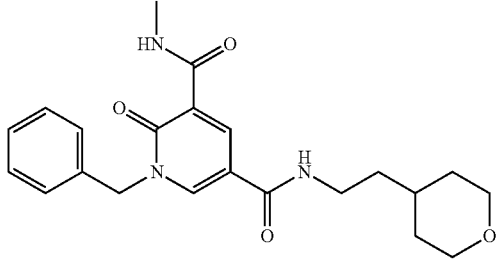

2,4,6-Trichlorophenyl 1-benzyl-5-(methylcarbamoyl)-6-oxo-1,6-dihydropyridine-3-carboxylate (61 mg, 0.131 mmol), 2-(tetrahydro-2H-pyran-4-yl)ethanamine (33.8 mg, 0.262 mmol), N,N-dimethylpyridin-4-amine (4 mg, 0.033 mmol), triethylamine (0.05 mL, 0.359 mmol) and THF (1 mL) were stirred at 45° C. for 4 h. A white precipitate formed which was filtered to give 31 mg of a white solid. This was purified by chromatography on SiO$_2$ (Biotage SNAP 10 g cartridge, eluting with 0-100% ethyl acetate/(25% ethanol in ethyl acetate)). The appropriate fractions were collected and concentrated to give 1-benzyl-N3-methyl-2-oxo-N5-(2-(tetrahydro-2H-pyran-4-yl)ethyl)-1,2-dihydropyridine-3,5-dicarboxamide (9 mg, 0.020 mmol, 15.56% yield) as a white solid LCMS (2 min Formic): Rt=0.89 min, [MH]$^+$=398.

Example 2: 1-Benzyl-$N^3$-methyl-2-oxo-$N^5$-(2-(piperidin-4-yl)ethyl)-1,2-dihydropyridine-3,5-dicarboxamide

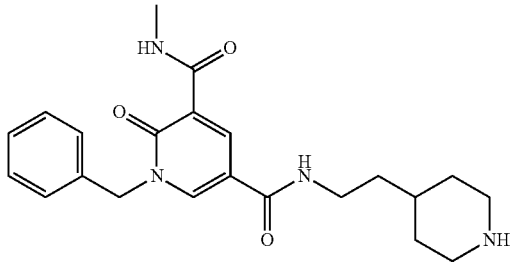 [SMILES: CNC(=O)c1cc(C(=O)NCCC2CCNCC2)cn(Cc2ccccc2)c1=O]

tert-Butyl 4-(2-(1-benzyl-5-(methylcarbamoyl)-6-oxo-1,6-dihydropyridine-3-carboxamido)ethyl)piperidine-1-carboxylate (76 mg, 0.153 mmol) was dissolved in DCM (5 mL). TFA (1 mL, 12.98 mmol) was added and the reaction stirred under N$_2$ at rt for 3 h. The reaction mixture was concentrated and loaded onto a 2 g SCX cartridge (preconditioned with MeOH) and eluted with MeOH (40 mL) followed by 2M NH$_3$ in MeOH (40 mL). The ammonia fractions containing product were combined and concentrated to give 1-benzyl-N3-methyl-2-oxo-N5-(2-(piperidin-4-yl)ethyl)-1,2-dihydropyridine-3,5-dicarboxamide (52 mg, 0.118 mmol, 77% yield) as a white solid.

LCMS (2 min Formic): Rt=0.56 min, [MH]$^+$=397.

Example 3: 1-Benzyl-$N^3$-methyl-$N^5$-(2-(1-methylpiperidin-4-yl)ethyl)-2-oxo-1,2-dihydropyridine-3,5-dicarboxamide

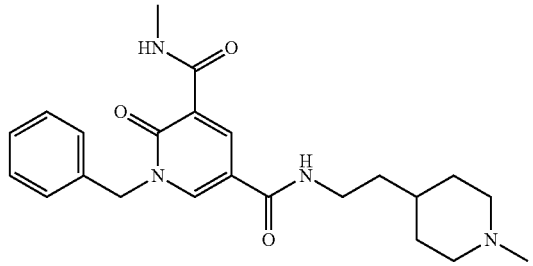 [SMILES: CNC(=O)c1cc(C(=O)NCCC2CCN(C)CC2)cn(Cc2ccccc2)c1=O]

1-Benzyl-N3-methyl-2-oxo-N5-(2-(piperidin-4-yl)ethyl)-1,2-dihydropyridine-3,5-dicarboxamide (50 mg, 0.126 mmol), formic acid (0.01 mL, 0.261 mmol), 37% formaldehyde in water (0.05 mL, 0.672 mmol) and methanol (2 mL) were refluxed for 2 h under N$_2$. Further formic acid (0.013 mL, 0.348 mmol), 37% formaldehyde in water (0.05 mL, 0.672 mmol) and methanol (2 mL) were added and the reaction was stirred overnight. The solution was concentrated to give 58 mg of a colourless oil. Sodium bicarbonate solution (30 mL) was added and the reaction mixture extracted with DCM (3×40 mL), dried over a hydrophobic frit and concentrated to give 73 mg of an off white solid. This was purified by chromatography on SiO$_2$ (Biotage SNAP 50 g cartridge), eluting the column with 0-100% ethyl acetate/cyclohexane, followed by 0-100% ethyl acetate/(25% EtOH in ethyl acetate). The column was then flushed with 20% (2M NH$_3$ in MeOH) in DCM. The appropriate fractions were concentrated to give 1-benzyl-N3-methyl-N5-(2-(1-methylpiperidin-4-yl)ethyl)-2-oxo-1,2-dihydropyridine-3,5-dicarboxamide (39 mg, 0.086 mmol, 67.8% yield) as a colourless oil.

LCMS (2 min Formic): Rt=0.56 min, [MH]$^+$=411.

Example 4: tert-Butyl 3-(1-benzyl-5-(methylcarbamoyl)-6-oxo-1,6-dihydropyridine-3-carboxamido) azetidine-1-carboxylate

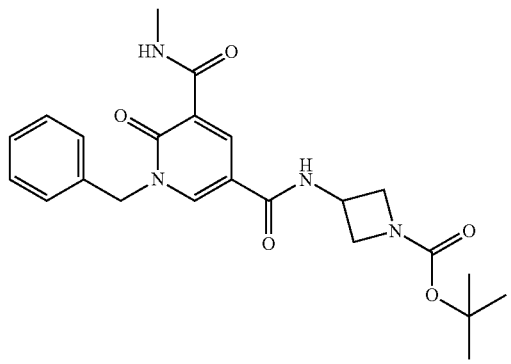 [SMILES: CNC(=O)c1cc(C(=O)NC2CN(C(=O)OC(C)(C)C)C2)cn(Cc2ccccc2)c1=O]

2,4,6-Trichlorophenyl 1-benzyl-5-(methylcarbamoyl)-6-oxo-1,6-dihydropyridine-3-carboxylate (196 mg, 0.421 mmol), tert-butyl 3-aminoazetidine-1-carboxylate hydrochloride (180 mg, 0.863 mmol, commercially available from, for example, Acesys Pharmatech), N,N-dimethylpyridin-4-amine (10 mg, 0.082 mmol) and triethylamine (0.24 mL, 1.722 mmol) were stirred in THF (4 mL) at 45° C. for 5 h. The white precipitate formed was filtered under suction to give a white solid. The filtrate and solid were combined and concentrated to give 500 mg of an off white solid. This was purified by chromatography on SiO$_2$ (Biotage SNAP 25 g cartridge, eluting with 0-100% ethyl acetate/cyclohexane). The desired fractions were concentrated to give tert-butyl 3-(1-benzyl-5-(methylcarbamoyl)-6-oxo-1,6-dihydropyridine-3-carboxamido)azetidine-1-carboxylate (155 mg, 0.317 mmol, 75% yield) as a colourless oil.

LCMS (2 min Formic): Rt=1.04 min, [MH]$^+$=441.

Example 5: tert-Butyl 4-(3-(1-benzyl-5-(methylcarbamoyl)-6-oxo-1,6-dihydropyridine-3-carboxamido) propylpiperidine-1-carboxylate

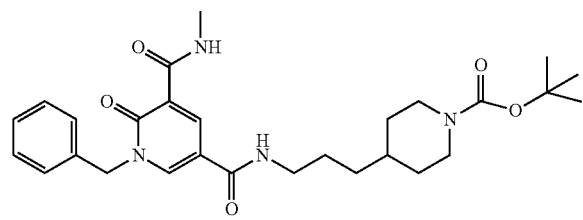 [SMILES: CNC(=O)c1cc(C(=O)NCCCC2CCN(C(=O)OC(C)(C)C)CC2)cn(Cc2ccccc2)c1=O]

1-Benzyl-5-(methylcarbamoyl)-6-oxo-1,6-dihydropyridine-3-carboxylic acid (250 mg, 0.873 mmol) was taken up in DMF (4 mL) and HATU (365 mg, 0.961 mmol) followed by DIPEA (0.302 mL, 1.747 mmol) were added. The reaction mixture was allowed to stir for 5 min, then tert-butyl 4-(3-aminopropyl)piperidine-1-carboxylate (233 mg, 0.961 mmol, commercially available from, for example, Milestone PharmTech) was added and the reaction allowed to stir for 1 h. The solution was concentrated under vacuum and redissolved in ethyl acetate (15 mL) and washed with citric acid (1 M, 3×10 mL), saturated NaHCO$_3$ (3×10 mL), water (10 mL) and brine (10 mL). The solution was dried and concentrated under vacuum to give the desired product (456 mg, 0.893 mmol, quant. yield).

LCMS (2 min Formic): Rt=1.18 min, [MH]$^+$=511.

Example 6a: 1-Benzyl-N$^3$-methyl-2-oxo-N$^5$-(3-(piperidin-4-yl)propyl)-1,2-dihydropyridine-3,5-dicarboxamide

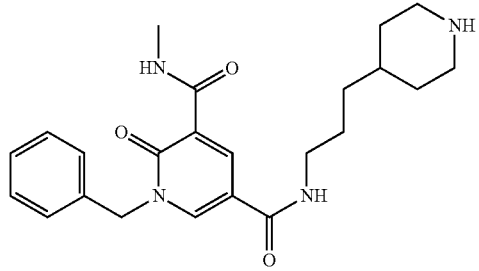 [SMILES: CNC(=O)c1cc(C(=O)NCCCC2CCNCC2)cn(Cc2ccccc2)c1=O]

tert-Butyl 4-(3-(1-benzyl-5-(methylcarbamoyl)-6-oxo-1,6-dihydropyridine-3-carboxamido)propyl)piperidine-1-carboxylate (3.43 g, 6.72 mmol) was dissolved in DCM (10 mL) and TFA (5 mL) and the mixture was stirred for 2 h, then evaporated in vacuo. The residue was dissolved in methanol (30 mL) and loaded onto a 20 g SCX2 cartridge and this was washed with methanol (50 mL), then the product eluted with 2M methanolic ammonia (100 mL) and the eluent evaporated in vacuo to give 1-benzyl-N3-methyl-2-oxo-N5-(3-(piperidin-4-yl)propyl)-1,2-dihydropyridine-3,5-dicarboxamide (2.7 g, 6.58 mmol, 98% yield) as a pale yellow solid.

LCMS (2 min formic): Rt=0.56 min, [MH]+=411.

1H NMR (400 MHz, DMSO-d6) δ ppm 9.37 (br. q, J=4.6, 4.6, 4.6 Hz, 1H) 8.82 (d, J=2.7 Hz, 1H) 8.73 (d, J=2.7 Hz, 1H) 8.55 (br. t, J=5.5, 5.5 Hz, 1H) 7.27-7.40 (m, 5H) 5.30 (s, 2H) 3.18-3.25 (m, 2H) 2.93 (br. d, J=12.0 Hz, 2H) 2.83 (d, J=4.9 Hz, 3H) 2.41-2.50 (m, 2H) 1.59 (br. d, J=11.0 Hz, 2H) 1.51 (br. dt, J=14.9, 7.6, 7.6 Hz, 2H) 1.25-1.40 (m, 1H) 1.16-1.24 (m, 2H) 1.00 (br. qd, J=12.1, 12.1, 12.1, 3.9 Hz, 2H)

Example 6b: 1-Benzyl-N$^3$-methyl-2-oxo-N$^5$-(3-(piperidin-4-yl)propyl)-1,2-dihydropyridine-3,5-dicarboxamide hydrochloride

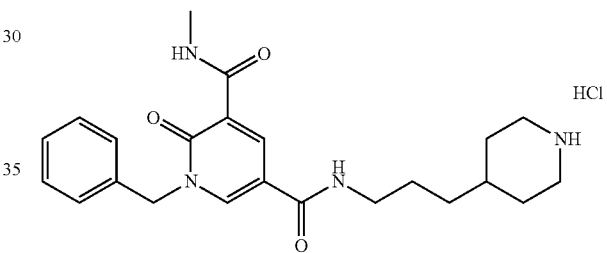

1 M HCl in ether (134 μL, 0.134 mmol) was added to a solution of 1-benzyl-N3-methyl-2-oxo-N5-(3-(piperidin-4-yl)propyl)-1,2-dihydropyridine-3,5-dicarboxamide (50 mg, 0.122 mmol) in methanol (1 mL) and the reaction left for 10 min. The solvent was removed in a blow down unit to give the product (35 mg) as a yellow solid.

LCMS (2 min Formic): Rt=0.56 min, [MH]$^+$=411.2.

Example 7: 1-Benzyl-N$^3$-methyl-N$^5$-(3-(1-methylpiperidin-4-yl)propyl)-2-oxo-1,2-dihydropyridine-3,5-dicarboxamide

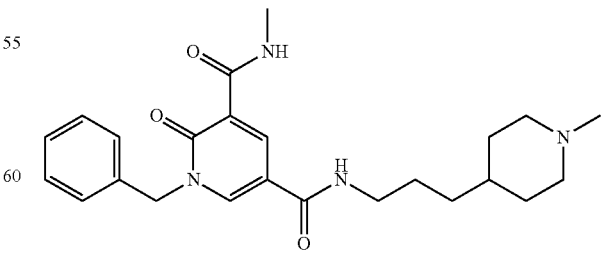

1-Benzyl-N3-methyl-2-oxo-N5-(3-(piperidin-4-yl)propyl)-1,2-dihydropyridine-3,5-dicarboxamide (230 mg, 0.560 mmol) was dissolved in a solution of methanol (4 mL). Formic acid (0.043 mL, 1.121 mmol) and formaldehyde (0.077 mL, 35% in water, 0.979 mmol) were added to the solution which was stirred at 45° C. for two days. The reaction temperature was raised to 65° C. and formaldehyde (0.077 mL, 35% in water, 0.979 mmol) and formic acid (0.043 mL, 1.121 mmol) were added. The mixture was stirred for 24 h. The mixture was concentrated under vacuum, partitioned between DCM (30 mL) and sodium bicarbonate (30 mL). The aqueous layer was extracted with DCM (2×20 mL) and the organic layers combined and concentrated under vacuum. The solid was loaded in DCM and purified by MDAP (High pH). The product containing fractions were combined and concentrated under vacuum to give the product (92 mg) as a white solid.

LCMS (2 min Formic): Rt=0.56 min, [MH]$^+$=425.2.

1H NMR (400 MHz, DMSO-d6) δ ppm 9.37 (br. q, J=4.6, 4.6, 4.6, 4.6 Hz, 1H) 8.82 (d, J=2.7 Hz, 1H) 8.72 (d, J=2.7 Hz, 1H) 8.54 (t, J=5.5 Hz, 1H) 7.27-7.40 (m, 5H) 5.30 (s, 2H) 3.16-3.24 (m, 2H) 2.83 (d, J=4.6 Hz, 3H) 2.71 (br. d, J=11.7 Hz, 2H) 2.11 (s, 3H) 1.74-1.83 (m, 2H) 1.59 (br. d, J=11.7 Hz, 2H) 1.51 (br. quin, J=7.3, 7.3, 7.3, 7.3 Hz, 2H) 1.03-1.26 (m, 5H).

Example 8: $N^5$-(3-(1-Acetylpiperidin-4-yl)propyl)-1-benzyl-$N^3$-methyl-2-oxo-1,2-dihydropyridine-3,5-dicarboxamide

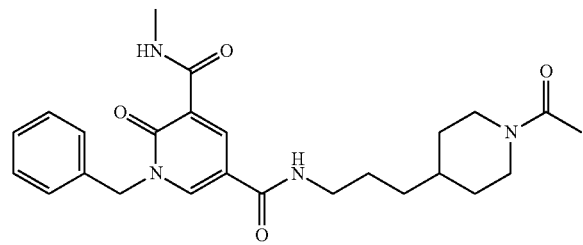 [SMILES: CNC(=O)c1cc(C(=O)NCCCC2CCN(C(C)=O)CC2)cn(Cc2ccccc2)c1=O]

1-Benzyl-N3-methyl-2-oxo-N5-(3-(piperidin-4-yl)propyl)-1,2-dihydropyridine-3,5-dicarboxamide (135 mg, 0.329 mmol) was dissolved in DCM (6.5 mL) and triethylamine (0.07 mL, 0.502 mmol) was added. The solution was cooled to 0° C. and acetic anhydride (0.031 mL, 0.329 mmol) was added. The reaction mixture was stirred at 0° C. for 1 h. The solution was concentrated to give 226 mg of a white solid which was purified by chromatography on SiO$_2$ (Biotage SNAP 25 g cartridge, eluting with 0-100% (25% EtOH in EtOAc)/EtOAc). The appropriate fractions were concentrated to give N5-(3-(1-acetylpiperidin-4-yl)propyl)-1-benzyl-N3-methyl-2-oxo-1,2-dihydropyridine-3,5-dicarboxamide (160 mg, 0.318 mmol, 97% yield) as a white solid.

LCMS (2 min Formic): Rt=0.86 min, [MH]+=453.

Example 9: 1-Benzyl-$N^3$-methyl-2-oxo-$N^5$-(2-(tetrahydrofuran-3-yl)ethyl)-1,2-dihydropyridine-3,5-dicarboxamide

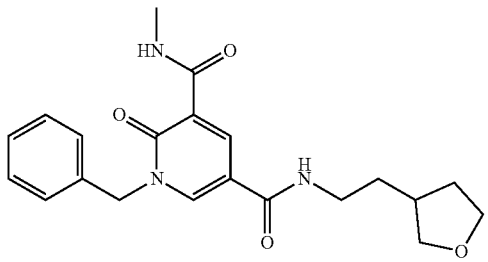 [SMILES: CNC(=O)c1cc(C(=O)NCCC2CCOC2)cn(Cc2ccccc2)c1=O]

1-Benzyl-5-(methylcarbamoyl)-6-oxo-1,6-dihydropyridine-3-carboxylic acid (50 mg, 0.175 mmol) was taken up in DMF (2 mL) and HATU (73.0 mg, 0.192 mmol) was added followed by DIPEA (0.061 mL, 0.349 mmol). The reaction mixture was allowed to stir for 5 min, then 2-(tetrahydrofuran-3-yl)ethanamine (20.12 mg, 0.175 mmol, commercially available from, for example, Fluorochem) was added and the reaction allowed to stir for 1 h. The reaction mixture was concentrated under vacuum and purified by MDAP (High pH). The appropriate fractions were combined and concentrated under vacuum to give the desired product (54 mg, 0.141 mmol, 81% yield).

LCMS (2 min Formic): Rt=0.83 min, [MH]$^+$=384.2.

Example 10: 1-Benzyl-$N^3$-methyl-2-oxo-$N^5$-(3-(1-(2,2,2-trifluoroethyl)piperidin-4-yl)propyl-1,2-dihydropyridine-3,5-dicarboxamide

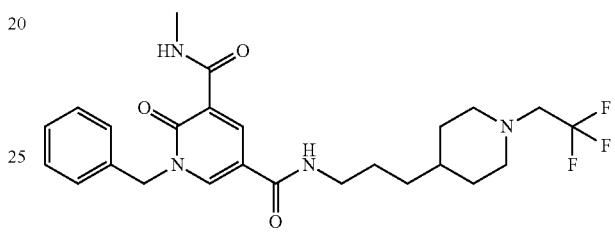

To a solution of 1-benzyl-N3-methyl-2-oxo-N5-(3-(piperidin-4-yl)propyl)-1,2-dihydropyridine-3,5-dicarboxamide (40 mg, 0.097 mmol), cesium carbonate (63.5 mg, 0.195 mmol) in DMF (0.8 mL), cooled to 0° C., was added 2,2,2-trifluoroethyl trifluoromethanesulfonate (0.015 mL, 0.107 mmol). The reaction was stirred overnight while warming to rt. The reaction mixture was concentrated under vacuum and purified by MDAP (High pH). The product containing fractions were combined and concentrated under vacuum to give the product (15 mg) as a white solid.

LCMS (2 min Formic): Rt=0.75 min, [MH]$^+$=493.2.

Example 11: 1-Benzyl-$N^5$-(3-(1-ethylpiperidin-4-yl)propyl)-$N^3$-methyl-2-oxo-1,2-dihydropyridine-3,5-dicarboxamide

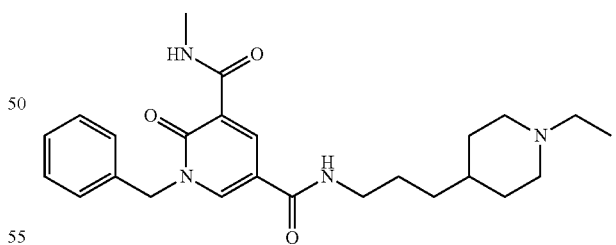

A solution of 1-benzyl-$N^3$-methyl-2-oxo-$N^5$-(3-(piperidin-4-yl)propyl)-1,2-dihydropyridine-3,5-dicarboxamide (50 mg, 0.122 mmol), acetaldehyde (0.034 mL, 0.609 mmol), methanol (1 mL) and acetic acid (0.100 mL) was left to stir at rt for 1 h. 2-Picoline borane complex (14.33 mg, 0.134 mmol) was added and the reaction stirred for 2 h at rt. The reaction mixture was concentrated under vacuum and purified by MDAP (High pH). The product containing fractions were combined and concentrated under vacuum to give the product (25 mg) as a white solid.

LCMS (2 min Formic): Rt=0.58 min, [MH]$^+$=439.3.

Example 12: 1-Benzyl-$N^3$-methyl-2-oxo-$N^5$-(3-(piperazin-1-yl)propyl)-1,2-dihydropyridine-3,5-dicarboxamide, hydrochloride

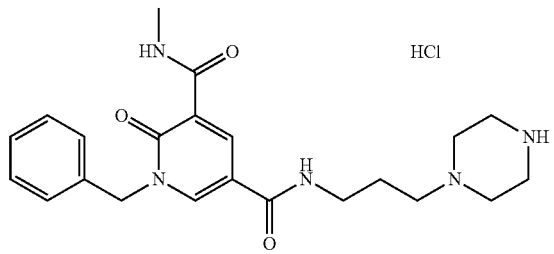 [SMILES: CNC(=O)c1cc(C(=O)NCCCN2CCNCC2)cn(Cc2ccccc2)c1=O ; Cl]

tert-Butyl 4-(3-(1-benzyl-5-(methylcarbamoyl)-6-oxo-1,6-dihydropyridine-3-carboxamido)propyl)piperazine-1-carboxylate (495 mg, 0.968 mmol) and TFA (1 mL, 12.98 mmol) were stirred at rt in DCM (4 mL) for 1 h. The reaction mixture was concentrated and loaded onto a 2 g SCX cartridge (pre-conditioned with MeOH) and eluted with MeOH (40 mL) followed by 2M $NH_3$ in MeOH (40 mL). The ammonia fractions containing product were combined and concentrated to give 1-benzyl-N3-methyl-2-oxo-N5-(3-(piperazin-1-yl)propyl)-1,2-dihydropyridine-3,5-dicarboxamide (304 mg) as an orange solid. This was dissolved in MeOH (1 mL) and HCl (0.12 mL, 0.120 mmol, 1 M in diethyl ether) was added and blown down to give 1-benzyl-N3-methyl-2-oxo-N5-(3-(piperazin-1-yl)propyl)-1,2-dihydropyridine-3,5-dicarboxamide, hydrochloride (55 mg, 0.104 mmol, 10.79% yield) as a pink solid.

LCMS (2 min Formic): Rt=0.42 min, $[MH]^+$=412.

Example 13: 1-Benzyl-$N^5$-(2-(1,1-dioxidotetrahydro-2H-thiopyran-4-yl)ethyl)-$N^3$-methyl-2-oxo-1,2-dihydropyridine-3,5-dicarboxamide

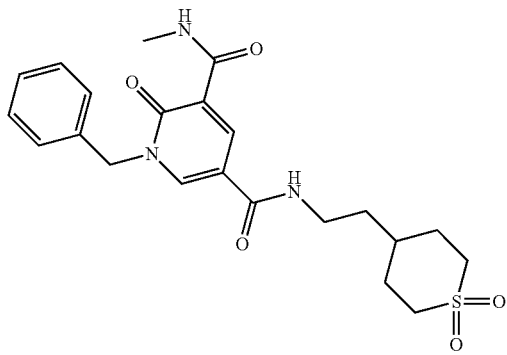 [SMILES: CNC(=O)c1cc(C(=O)NCCC2CCS(=O)(=O)CC2)cn(Cc2ccccc2)c1=O]

To a solution of 1-benzyl-5-(methylcarbamoyl)-6-oxo-1,6-dihydropyridine-3-carboxylic acid (51.9 mg, 0.181 mmol), 4-(2-aminoethyl)tetrahydro-2H-thiopyran 1,1-dioxide hydrochloride (78.8 mg, 0.369 mmol, commercially available from, for example, Alfa Aesar) and 2-(3H-[1,2,3]triazolo[4,5-b]pyridin-3-yl)-1,1,3,3-tetramethylisouronium hexafluorophosphate(V) (HATU) (84 mg, 0.221 mmol) in DMF (1 mL) was added DIPEA (0.127 mL, 0.725 mmol). The mixture was stirred at rt for 1.5 h before being concentrated under a stream of nitrogen. The solution was made up to 2 mL with DMSO and directly purified by MDAP (formic). The required fractions were individually evaporated under a stream of nitrogen before being dissolved in a 1:1 mixture of dichloromethane/methanol (2×4 mL), combined, concentrated under a stream of nitrogen and dried in vacuo to give the desired product as a white solid—1-benzyl-N5-(2-(1,1-dioxidotetrahydro-2H-thiopyran-4-yl)ethyl)-N3-methyl-2-oxo-1,2-dihydropyridine-3,5-dicarboxamide (73.4 mg, 0.165 mmol, 91% yield).

LCMS (2 min Formic) Rt=0.81 min, $[MH]^+$=446.3.

Example 14: 1-(2-Fluorobenzyl)-$N^3$-methyl-2-oxo-$N^5$-(3-(piperidin-4-yl)propyl)-1,2-dihydropyridine-3,5-dicarboxamide

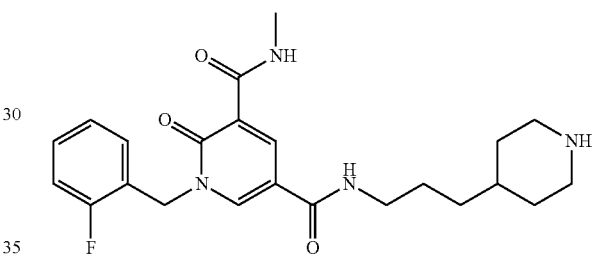

tert-Butyl 4-(3-(1-(2-fluorobenzyl)-5-(methylcarbamoyl)-6-oxo-1,6-dihydropyridine-3-carboxamido)propyl)piperidine-1-carboxylate (28 mg, 0.053 mmol) was dissolved in a solution of 2M HCl in IPA (0.8 mL 1.600 mmol). The reaction mixture was stirred at rt for 1 h. The reaction mixture was concentrated under vacuum and purified by MDAP (High pH). The appropriate fractions were combined and concentrated under vacuum to give the product (8 mg) as a colourless residue.

LCMS (2 min Formic): Rt=0.57 min, $[MH]^+$=429.2.

Examples 15-16: Amide Array of 1-(3-methylbenzyl)-5-(methylcarbamoyl)-6-oxo-1,6-dihydropyridine-3-carboxylic acid Monomers

| Ex No. | Reagent Name | Structure | MW | Reagent Mass (g) | Reagent Volume (mL) | mmol |
|---|---|---|---|---|---|---|
| 15 | tert-butyl 4-(3-aminopropyl)piperidine-1-carboxylate | 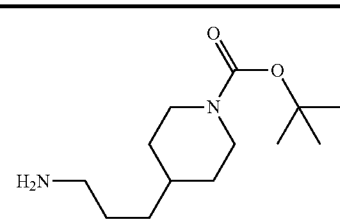 | 242.36 | 0.0291 | — | 0.120 |

-continued

| Ex No. | Reagent Name | Structure | MW | Reagent Mass (g) | Reagent Volume (mL) | mmol |
|---|---|---|---|---|---|---|
| 16 | tert-butyl 4-(2-aminoethyl)piperidine-1-carboxylate | 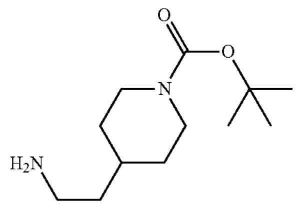 [SMILES: CC(C)(C)OC(=O)N1CCC(CCN)CC1] | 228.33 | 0.0274 | — | 0.120 |

To a stock solution of 1-(3-methylbenzyl)-5-(methylcarbamoyl)-6-oxo-1,6-dihydropyridine-3-carboxylic acid (300 mg, 1.0 mmol) and HATU (380 mg, 1.0 mmol) dissolved in DMF (5 mL) was added DIPEA (520 μL, 3.0 mmol). The mixture was shaken and sonicated to aid dispersion. An aliquot (0.5 mL) of this mixture was added to the appropriate amine (0.12 mmol) in a vial which was subsequently sealed. Each vial was shaken before being allowed to stand at rt for 18 h. (NOTE: to the reaction containing monomer amine used to prepare example 15 was added further HATU (0.038 g, 0.100 mmol) and DIPEA (0.052 mL, 0.300 mmol) before this mixture was left to stand at rt for 1 h. The samples were injected as is and purified by MDAP (High pH). The solvent was dried under a stream of nitrogen in the plate blowdown apparatus. The products derived from the amine monomers used to prepare example 15 and 16 were dissolved in DCM (0.5 mL). TFA (0.5 mL) was added and the vials were capped and sonicated to aid dispersement. Each mixture was left to stand at rt for 2 h. The solvent was then concentrated to dryness and the residues were redissolved in MeOH (0.5 mL) and applied to the top of a SCX-2 SPE cartridge (100 mg, preconditioned with MeOH (1 mL)). Each cartridge was eluted with further MeOH (1 mL) followed by 2M NH$_3$/MeOH (1 mL). The solvent was removed to dryness to give the required products as shown in the table below.

EXAMPLES

| Ex No. | Name | Structure | Mass (mg) | Yield (%) | [MH]$^+$ | Rt (min)* |
|---|---|---|---|---|---|---|
| 15 | N$^3$-Methyl-1-(3-methylbenzyl)-2-oxo-N$^5$-(3-(piperidin-4-yl)propyl)-1,2-dihydropyridine-3,5-dicarboxamide | 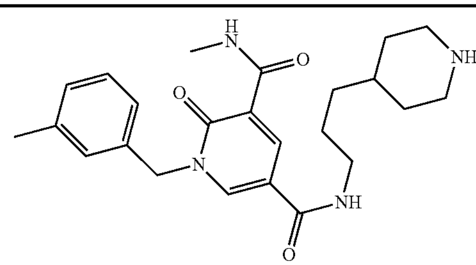 | 6.5 | 11.5 | 425 | 0.59 |
| 16 | N$^3$-Methyl-1-(3-methylbenzyl)-2-oxo-N$^5$-(2-(piperidin-4-yl)ethyl)-1,2-dihydropyridine-3,5-dicarboxamide | 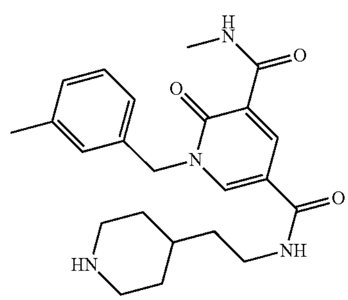 [SMILES: CNC(=O)c1cc(C(=O)NCCC2CCNCC2)cn(Cc2cccc(C)c2)c1=O] | 11.9 | 22 | 411 | 0.57 |

*All LCMS were conducted using 2 min Formic.

Examples 17-18: Amide Array of (R)-5-(methylcarbamoyl)-6-oxo-1-(1-phenylethyl)-1,6-dihydropyridine-3-carboxylic acid To a stock solution of (R)-5-(methylcarbamoyl)-6-oxo-1-(1-phenylethyl)-1,6-dihydropyridine-3-carboxylic acid (30 mg, 0.1 mmol) and HATU (380 mg) in DMF (5 mL) was added DIPEA (520 μL). The mixture was shaken and sonicated to aid dispersion. The mixture was aliquoted (0.5 mL) to a set of preweighed amines (0.100 mmol) in micronic vials. These were capped and shaken and left to stand at rt for 18 h. The samples were purified by MDAP (High pH). The solvent was dried under a stream of nitrogen to give the required products. Examples 17 and 18 were dissolved in DCM (0.5 mL) and treated with TFA (0.5 mL) and the solutions left to stand in capped vials at rt for 2 h. The reaction mixtures were evaporated and the residues dissolved in MeOH (0.5 mL). The solutions were applied to MeOH-preconditioned 100 mg SCX-2 cartridges which were then washed with MeOH (1 mL) followed by 2M ammonia in MeOH solution (1 mL). The basic washes were evaporated to dryness to give final deprotected compounds as the free base.

mL) to a set of preweighed amines (as shown in table below). These were capped and shaken and left to stand at rt for 18 h. The samples were purified by MDAP (High pH). The solvent was dried under a stream of nitrogen to give the required products. Examples 19 and 20 were dissolved in

| Ex No. | Reagent Name | Structure | MW | Reagent Mass (g) | Reagent Volume (mL) | mmol |
|---|---|---|---|---|---|---|
| 17 | tert-butyl 4-(3-aminopropyl)piperidine-1-carboxylate | 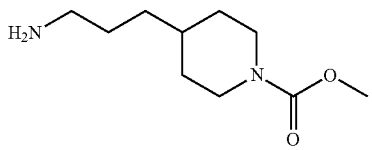 | 242.36 | 0.024 | | 0.100 |
| 18 | tert-butyl 4-(2-aminoethyl)piperidine-1-carboxylate | 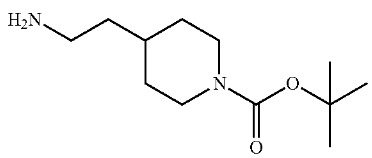 [SMILES: CC(C)(C)OC(=O)N1CCC(CCN)CC1] | 228.33 | 0.023 | | 0.100 |

| Ex no. | Name | Structure | Mass (mg) | Yield (%) | [MH]+ | Rt (min) |
|---|---|---|---|---|---|---|
| 17 | (R)-$N^3$-Methyl-2-oxo-1-(1-phenylethyl)-$N^5$-(3-(piperidin-4-yl)propyl)-1,2-dihydropyridine-3,5-dicarboxamide | 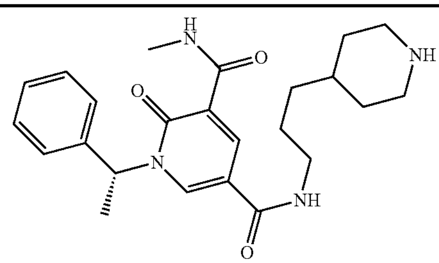 | 3.3 | 7.0 | 425.0 | 0.57 |
| 18 | (R)-$N^3$-Methyl-2-oxo-1-(1-phenylethyl)-$N^5$-(2-(piperidin-4-yl)ethyl)-1,2-dihydropyridine-3,5-dicarboxamide | 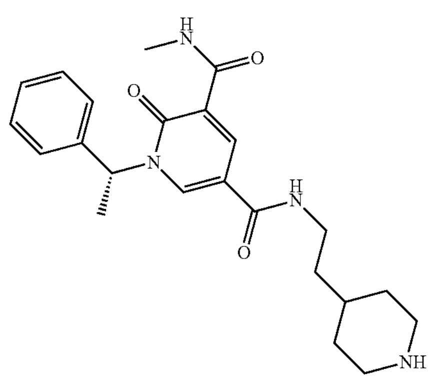 [SMILES: CNC(=O)c1cc(C(=O)NCCC2CCNCC2)cn([C@H](C)c2ccccc2)c1=O] | 5.3 | 11.6 | 411.0 | 0.56 |

All LCMS were conducted using 2 min Formic method.

Examples 19-20: Amide Array of 1-(3-methoxybenzyl)-5-(methylcarbamoyl)-6-oxo-1,6-dihydropyridine-3-carboxylic acid To a stock solution of 1-(3-methoxybenzyl)-5-(methylcarbamoyl)-6-oxo-1,6-dihydropyridine-3-carboxylic acid (316 mg, 1 mmol) and HATU (380 mg) in DMF (5 mL) was added DIPEA (520 μL). The mixture was shaken and sonicated to aid dispersion. The mixture was aliquoted (0.55 mL) to a set of preweighed amines (as shown in table below). These were capped and shaken and left to stand at rt for 18 h. The samples were purified by MDAP (High pH). The solvent was dried under a stream of nitrogen to give the required products. Examples 19 and 20 were dissolved in DCM (0.5 mL) and treated with TFA (0.5 mL) and the solutions left to stand in capped vials at rt for 2 h. The reaction mixtures were evaporated and the residues dissolved in MeOH (0.5 mL). The solutions were applied to MeOH-preconditioned 100 mg SCX-2 cartridges which were then washed with MeOH (1 mL) followed by 2M ammonia in MeOH solution (1 mL). The basic washes were evaporated to dryness to give final deprotected compounds as the free base (as shown in the table below).

Monomers

| Ex No. | Reagent Name | Structure | MW | Reagent Mass (g) | Reagent Volume (mL) | mmol |
|---|---|---|---|---|---|---|
| 19 | tert-butyl 4-(3-aminopropyl)piperidine-1-carboxylate | 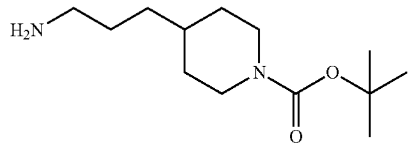 [SMILES: CC(C)(C)OC(=O)N1CCC(CCCN)CC1] | 242.36 | 0.029 | — | 0.120 |
| 20 | tert-butyl 4-(2-aminoethyl)piperidine-1-carboxylate | 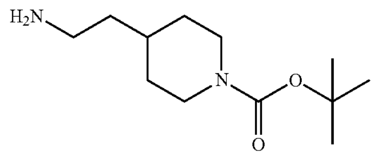 [SMILES: CC(C)(C)OC(=O)N1CCC(CCN)CC1] | 228.33 | 0.027 | — | 0.120 |

EXAMPLES

| Ex no. | Name | Structure | Mass (mg) | Yield (%) | [MH]+ | Rt (min) |
|---|---|---|---|---|---|---|
| 19 | 1-(3-Methoxybenzyl)-N³-methyl-2-oxo-N⁵-(3-(piperidin-4-yl)propyl)-1,2-dihydropyridine-3,5-dicarboxamide | 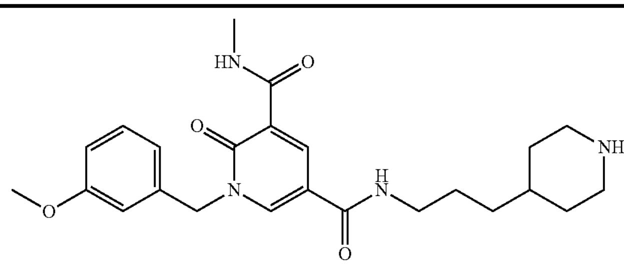 | 9.5 | 19.4 | 441 | 0.57 |
| 20 | 1-(3-Methoxybenzyl)-N³-methyl-2-oxo-N⁵-(2-(piperidin-4-yl)ethyl)-1,2-dihydropyridine-3,5-dicarboxamide | 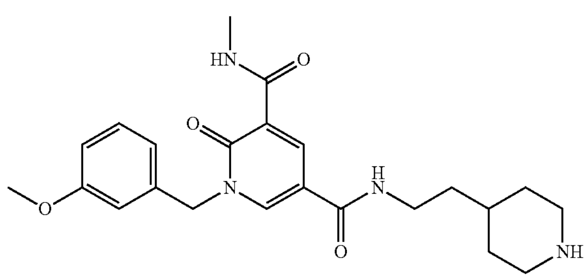 [SMILES: CNC(=O)c1cc(C(=O)NCCC2CCNCC2)cn(Cc2cccc(OC)c2)c1=O] | 6.9 | 14.6 | 427 | 0.55 |

All LCMS were conducted using 2 min Formic method.

Example 21: 1-(4-Fluoro-3-methylbenzyl)-$N^3$-methyl-2-oxo-$N^5$-(3-(piperidin-4-yl)propyl)-1,2-dihydropyridine-3,5-dicarboxamide

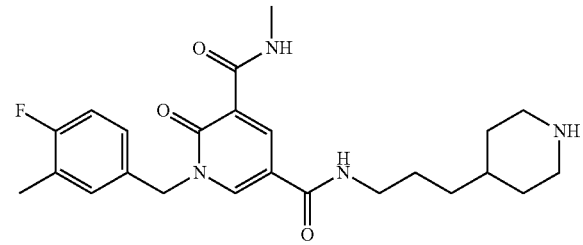 [SMILES: CNC(=O)c1cc(C(=O)NCCCC2CCNCC2)cn(Cc2ccc(F)c(C)c2)c1=O]

tert-Butyl 4-(3-(1-(2-fluorobenzyl)-5-(methylcarbamoyl)-6-oxo-1,6-dihydropyridine-3-carboxamido)propyl)piperidine-1-carboxylate (28 mg, 0.053 mmol) was dissolved in a solution of 2M HCl in IPA (0.8 mL, 1.600 mmol). The reaction mixture was stirred at rt for 1 h. The reaction mixture was concentrated under vacuum and purified by MDAP (High pH). The appropriate fractions were combined and concentrated under vacuum to give the product (60 mg) as a colourless residue.

LCMS (2 min Formic): Rt=0.64 min, [MH]⁺=443.2.

Example 22: 1-(4-Fluorobenzyl)-N³-methyl-2-oxo-N-(3-(piperidin-4-1)propyl)-1,2-dihydropyridine-3,5-dicarboxamide

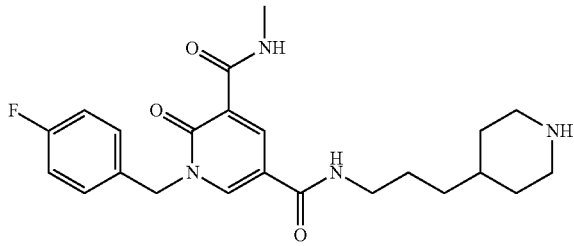 [SMILES: CNC(=O)c1cc(C(=O)NCCCC2CCNCC2)cn(Cc2ccc(F)cc2)c1=O]

tert-Butyl 4-(3-(1-(2-fluorobenzyl)-5-(methylcarbamoyl)-6-oxo-1,6-dihydropyridine-3-carboxamido)propyl)piperidine-1-carboxylate (28 mg, 0.053 mmol) was dissolved in a solution of 2M HCl in IPA (0.8 mL, 1.600 mmol). The reaction mixture was stirred at rt for 1 h. The reaction mixture was concentrated under vacuum and purified by MDAP (High pH). The appropriate fractions were combined and concentrated under vacuum to give the product (87 mg, 0.428 mmol, 54.8% yield) as a colourless residue.

LCMS (2 min Formic): Rt=0.58 min, [MH]⁺=429.2.

Examples 23-24: Amide Array of 1-(3-(2-hydroxyethoxy)benzyl)-5-(methylcarbamoyl)-6-oxo-1,6-dihydropyridine-3-carboxylic acid To a stock solution of 1-(3-(2-hydroxyethoxy)benzyl)-5-(methylcarbamoyl)-6-oxo-1,6-dihydropyridine-3-carboxylic acid (337 mg, 0.97 mmol) and HATU (374 mg) in DMF (5.5 mL) was added DIPEA (550 µL). The solution was shaken and sonicated to aid dispersion and aliquoted (0.55 mL) to a set of preweighed amines (as shown in table below). The samples were injected as is and purified by MDAP (High pH). The solvent was dried under a stream of nitrogen to give the required products. Examples 23 and 24 were dissolved in DCM (0.5 mL) and treated with TFA (0.5 mL) and the solutions left to stand in capped vials at rt for 2 h. The reaction mixtures were evaporated and examples 23 and 24 were dissolved in MeOH (0.5 mL). The solutions were applied to MeOH-preconditioned 100 mg SCX-2 cartridges which were then washed with MeOH (1 mL) followed by 2M ammonia in MeOH solution (1 mL). The basic washes were evaporated to dryness to give final deprotected compounds as the free base (as shown in table below). Examples 24 was re-purified by MDAP (High pH). The solvent was dried under a stream of nitrogen to give the required product.

Monomers

| Ex No. | Reagent Name | Structure | MW | Reagent Mass (g) | Reagent Volume (mL) | mmol |
|---|---|---|---|---|---|---|
| 23 | tert-butyl 4-(3-aminopropyl)piperidine-1-carboxylate | 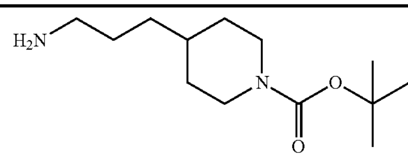 | 242.36 | 0.028 | — | 0.114 |
| 24 | tert-butyl 4-(2-aminoethyl)piperidine-1-carboxylate | 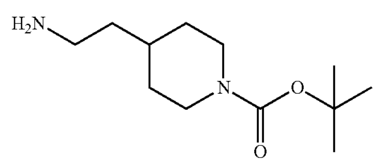 | 228.33 | 0.026 | — | 0.114 |

EXAMPLES

| Ex no. | Name | Structure | Mass (mg) | Yield (%) | [MH]⁺ | Rt (min) |
|---|---|---|---|---|---|---|
| 23 | 1-(3-(2-Hydroxyethoxy)benzyl)-N³-methyl-2-oxo-N⁵-(3-(piperidin-4-yl)propyl)-1,2-dihydropyridine-3,5-dicarboxamide | 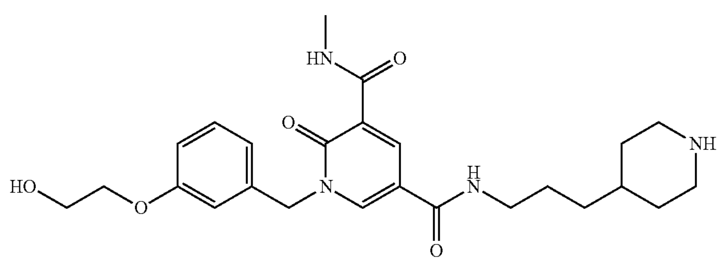 [SMILES: CNC(=O)c1cc(C(=O)NCCCC2CCNCC2)cn(Cc2cccc(OCCO)c2)c1=O] | 3.6 | 7.7 | 471 | 0.49 |

| Ex no. | Name | Structure | Mass (mg) | Yield (%) | [MH]+ | Rt (min) |
|---|---|---|---|---|---|---|
| 24 | 1-(3-(2-Hydroxyethoxy)benzyl)-N³-methyl-2-oxo-N⁵-(2-(piperidin-4-yl)ethyl)-1,2-dihydropyridine-3,5-dicarboxamide | 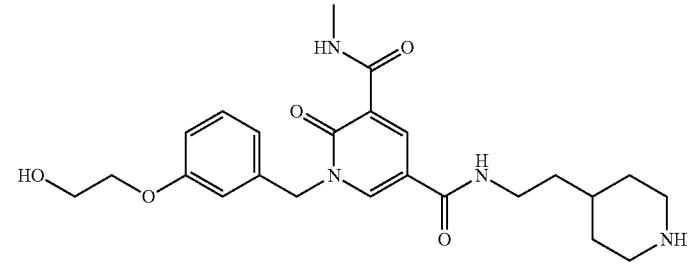 [SMILES: CNC(=O)c1cc(C(=O)NCCC2CCNCC2)cn(Cc2cccc(OCCO)c2)c1=O] | 6.2 | 13.7 | 457 | 0.47 |

All LCMS were conducted using 2 min Formic method.

Example 25: 1-Benzyl-N⁵-(3-(1-(2-hydroxyethyl)piperidin-4-yl)propyl-N³-methyl-2-oxo-1,2-dihydropyridine-3,5-dicarboxamide

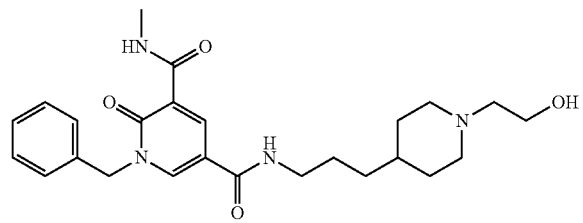 [SMILES: CNC(=O)c1cc(C(=O)NCCCC2CCN(CCO)CC2)cn(Cc2ccccc2)c1=O]

1-Benzyl-N3-methyl-2-oxo-N5-(3-(piperidin-4-yl)propyl)-1,2-dihydropyridine-3,5-dicarboxamide (99 mg, 0.241 mmol), 1,3-dioxolan-2-one (120 mg, 1.363 mmol), potassium carbonate (136 mg, 0.984 mmol) and DMF (2 mL) were heated at 90° C. under $N_2$ overnight. The solution was partitioned between EtOAc (10 mL) and water (10 mL). The aqueous phase was extracted with EtOAc (2×10 mL) and the combined organic layers were dried over a hydrobobic frit and concentrated to give 143 mg of a yellow solid. This was purified by chromatography on $SiO_2$ (Biotage SNAP 25 g cartridge, eluting with 0-100% (25% EtOH in EtOAc)/cyclohexane followed by 20% of (2M $NH_3$ in MeOH)/DCM. The appropriate fractions were concentrated to give 1-benzyl-N⁵-(3-(1-(2-hydroxyethyl)piperidin-4-yl)propyl)-N³-methyl-2-oxo-1,2-dihydropyridine-3,5-dicarboxamide (19 mg, 0.038 mmol, 15.60% yield) as a colourless oil.

LCMS (2 min Formic): Rt=0.56 min, [MH]+=455.

1H NMR (400 MHz, MeOH-d4) δ ppm 8.84 (d, J=2.7 Hz, 1H) 8.55 (d, J=2.7 Hz, 1H) 7.28-7.40 (m, 5H) 5.32 (s, 2H) 3.71 (t, J=6.1 Hz, 2H) 3.31-3.36 (obs., 2H) 3.06 (br. d, J=11.7 Hz, 2 H) 2.95 (s, 3H) 2.63 (t, J=5.9 Hz, 2H) 2.22 (br. t, J=11.2, 11.2 Hz, 2H) 1.76 (br. d, J=12.2 Hz, 2H) 1.62 (br. dt, J=14.7, 7.4, 7.4 Hz, 2H) 1.23-1.42 (m, 5H).

Examples 26-27: Amide Array of 1-(2-fluoro-3-methylbenzyl)-5-(methylcarbamoyl)-6-oxo-1,6-dihydropyridine-3-carboxylic acid Monomers

| Ex No. | Reagent Name | Structure | MW | Reagent Mass (g) | Reagent Volume (mL) | mmol |
|---|---|---|---|---|---|---|
| 26 | tert-butyl 4-(3-aminopropyl)piperidine-1-carboxylate | 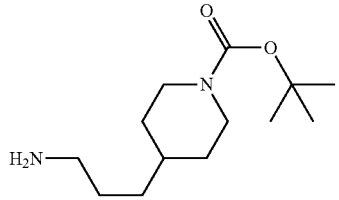 [SMILES: CC(C)(C)OC(=O)N1CCC(CCCN)CC1] | 242.36 | 0.0291 | — | 0.120 |
| 27 | tert-butyl 4-(2-aminoethyl)piperidine-1-carboxylate | 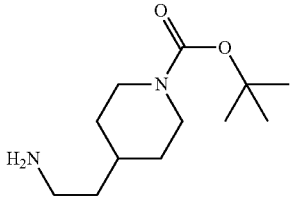 [SMILES: CC(C)(C)OC(=O)N1CCC(CCN)CC1] | 228.33 | 0.0274 | — | 0.120 |

To a stock solution of 1-(2-fluoro-3-methylbenzyl)-5-(methylcarbamoyl)-6-oxo-1,6-dihydropyridine-3-carboxylic acid (350 mg, 1.1 mmol) dissolved in DMF (5.5 mL) was added HATU (502 mg, 2.13 mmol) and DIPEA (570 μL, 3.3 mmol). The mixture was sonicated to aid dispersion and further DMF (5.5 mL) was added. An aliquot (1.0 mL) of this mixture was added to the appropriate amine (0.12 mmol) in DMF (0.3 mL) in a vial, which was subsequently sealed, sonicated and left to stand at rt for 3 h. The samples were reduced to 1 mL, then injected as is and purified by MDAP (High pH). The solvent was removed using a plate dryer to give the required products.

DCM (0.5 mL) and TFA (0.5 mL) were added to the products derived from the amine monomers used to prepare examples 26 and 27 and the vials were capped and left to stand at rt for 2 h. The solvents were removed using a plate dryer. The residues were redissolved in MeOH (0.5 mL) and applied to a SCX-2 SPE cartridge (1 g, preconditioned with MeOH (1 mL)). Each cartridge was eluted with further MeOH (1 mL) followed by 2 M $NH_3$/MeOH (1 mL). The solvent was evaporated from each sample under a stream of nitrogen. The residues were each dissolved in DCM (1 mL) and applied to an aminopropyl cartridge (100 mg), (preconditioned with $CHCl_3$), and were eluted with further $CHCl_3$ (1 mL). The products derived from the amine monomers used to prepare examples 26 and 27 were further purified by being dissolved in DMSO (1 mL) and purified by MDAP (High pH). The solvent was removed using a plate dryer to give the required products as shown in the table below.

1-Benzyl-N3-methyl-2-oxo-N5-(3-(piperidin-4-yl)propyl)-1,2-dihydropyridine-3,5-dicarboxamide (125 mg, 0.304 mmol) and cesium carbonate (202 mg, 0.620 mmol) were dissolved in DMF (3 mL) at 0° C. and 2-bromo-1,1-difluoroethane (53 mg, 0.366 mmol) was added. The reaction mixture was stirred at 0° C. for 1 h and then allowed to warm to rt and stirred for a further 1 h. A further portion of 2-bromo-1,1-difluoroethane (88 mg, 0.609 mmol) was added and the reaction was heated at 90° C. for 2 h. The solution was partitioned between EtOAc (10 mL) and water (10 mL). The aqueous phase was extracted with EtOAc (2×10 mL) and combined organic layers were dried over a hydrophobic frit and concentrated to give 160 mg of an orange solid. This was purified by chromatography on $SiO_2$ (Biotage SNAP 25 g cartridge, eluting with 0-100% (25% EtOH in EtOAc)/cyclohexane). The appropriate fractions were concentrated to give 111 mg of a pale brown solid. This was further purified by MDAP (Formic). The appropriate fractions were concentrated to give 1-benzyl-$N^5$-(3-(1-(2,2-difluoroethyl)piperidin-4-yl)propyl)-$N^3$-methyl-2-oxo-1,2-dihydropyridine-3,5-dicarboxamide (47 mg, 0.089 mmol, 29.3% yield) as a white solid.

LCMS (2 min Formic): Rt=0.59 min, [MH]+=475.

EXAMPLES

| Ex No. | Name | Structure | Mass (mg) | Yield (%) | [MH]+ | Rt (min)* |
|---|---|---|---|---|---|---|
| 26 | 1-(2-Fluoro-3-methylbenzyl)-$N^3$-methyl-2-oxo-$N^5$-(3-(piperidin-4-yl)propyl)-1,2-dihydropyridine-3,5-dicarboxamide | 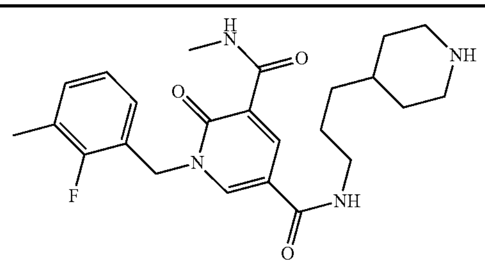 | 3.5 | 5.9 | 443 | 0.62 |
| 27 | 1-(2-Fluoro-3-methylbenzyl)-$N^3$-methyl-2-oxo-$N^5$-(2-(piperidin-4-yl)ethyl)-1,2-dihydropyridine-3,5-dicarboxamide | 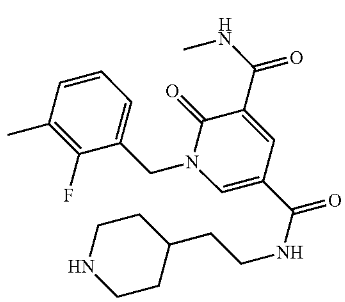 [SMILES: CNC(=O)c1cc(C(=O)NCCC2CCNCC2)cn(Cc2cccc(C)c2F)c1=O] | 3.1 | 5.4 | 429 | 0.59 |

All LCMS were conducted using 2 min Formic method.

Example 28: 1-Benzyl-$N^5$-(3-(1-(2,2-difluoroethyl)piperidin-4-yl)propyl-$N^3$-methyl-2-oxo-1,2-dihydropyridine-3,5-dicarboxamide

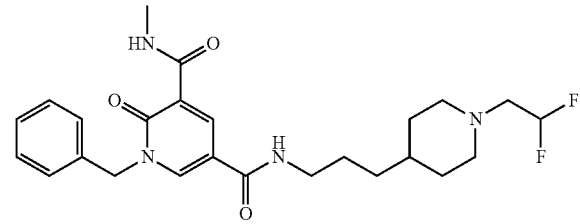 [SMILES: CNC(=O)c1cc(C(=O)NCCCC2CCN(CC(F)F)CC2)cn(Cc2ccccc2)c1=O]

Example 29: 1-Benzyl-$N^5$-(3-(1-(2-fluoroethyl)piperidin-4-yl)propyl)-$N^3$-methyl-2-oxo-1,2-dihydropyridine-3,5-dicarboxamide. formic acid salt

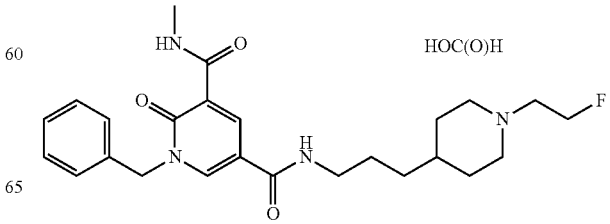

1-Benzyl-N3-methyl-2-oxo-N5-(3-(piperidin-4-yl)propyl)-1,2-dihydropyridine-3,5-dicarboxamide (100 mg, 0.244 mmol) and cesium carbonate (155 mg, 0.476 mmol) were dissolved in DMF (2 mL) at 90° C. and 1-bromo-2-fluoroethane (41 mg, 0.323 mmol) was added. The reaction mixture was stirred at 90° C. for 1 h. The resulting suspension was concentrated to give 300 mg of an orange solid. This was partitioned between EtOAc (20 mL) and water (20 mL). The aqueous phase was extracted with EtOAc (2×10 mL) and the combined organic layers were dried over a hydrophobic frit and concentrated to give 120 mg of a cream solid. This was purified by MDAP (Formic). The appropriate fractions were concentrated to give 1-benzyl-N5-(3-(1-(2-fluoroethyl)piperidin-4-yl)propyl)-N3-methyl-2-oxo-1,2-dihydropyridine-3,5-dicarboxamide (30 mg, 0.056 mmol, 22.93% yield) as a colourless oil.

LCMS (2 min Formic): Rt=0.58 min, [MH]+=457.

1H NMR (400 MHz, MeOH-d4) δ ppm 9.78 (br. d, J=4.4 Hz, 1H) 8.83 (d, J=2.7 Hz, 1H) 8.56 (d, J=2.9 Hz, 1H) 8.38 (s, 1H) 7.27-7.40 (m, 5H) 5.32 (s, 2H) 4.72-4.89 (obs, 2H) 3.52 (br. d, J=12.2 Hz, 2H) 3.33-3.46 (m, 4H) 2.88-3.01 (m, 5H) 1.97 (br. d, J=13.9 Hz, 2H) 1.55-1.70 (m, 3H) 1.32-1.53 (m, 4H).

Examples 30: Amide Array of 1-((1H-Indol-4-yl)methyl)-5-(methylcarbamoyl)-6-oxo-1,6-dihydropyridine-3-carboxylic acid Monomers

| Ex No. | Reagent Name | Structure | MW | Reagent Mass (g) | Reagent Volume (mL) | mmol |
|---|---|---|---|---|---|---|
| 30 | tert-Butyl 4-(3-aminopropyl)piperidine-1-carboxylate | 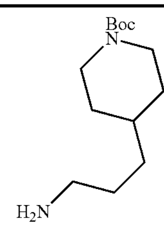 | 242.36 | 0.029 | — | 0.120 |

A stock solution of 1-((1H-indol-4-yl)methyl)-5-(methylcarbamoyl)-6-oxo-1,6-dihydropyridine-3-carboxylic acid (358 mg) was prepared in DMF (7.7 mL), along with HATU (502 mg), and DIPEA (0.57 mL), and was then capped and sonicated, before being aliquoted (0.7 mL) into a vial containing the listed amine monomer (0.12 mmol). This was sealed and sonicated, then allowed to stand at rt for 18 h. The sample was then directly injected and purified by MDAP (High pH). The solvent was removed using a plate dryer to give the required Boc-protected intermediate. This was dissolved in DCM (0.5 mL), and HCl in dioxane (4M, 0.5 mL) was added to the sample. This was sealed and sonicated before leaving to stand for 2 h. The solvent was removed using a blow down unit. The sample was found to be impure by LCMS. The sample was dissolved in DMSO (1 mL) and purified by MDAP (Formic). The solvent was removed using a plate dryer to give the required example 30 as indicated in the example table.

EXAMPLES

| Ex No. | Name | Structure | Mass (mg) | Yield (5) | [MH]+ | Rt (min)* |
|---|---|---|---|---|---|---|
| 30 | 1-((1H-Indol-4-yl)methyl)-N3-methyl-2-oxo-N5-(3-(piperidin-4-yl)propyl)-1,2-dihydropyridine-3,5-dicarboxamide | 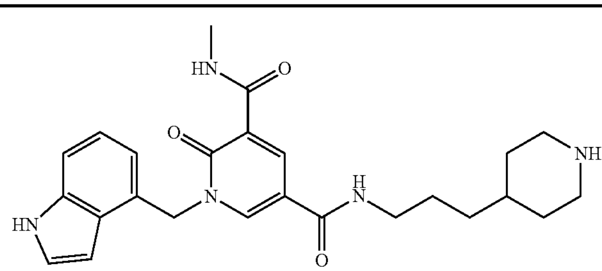 | 5.7 | 11 | 450 | 0.55 |

*All LCMS were conducted using 2 min Formic.

Examples 31-61

Examples 31-61 were prepared in an analogous manner to the previous examples

| Ex No. | Name | Structure | [MH]+ | Rt (min)* |
|---|---|---|---|---|
| 31 | 1-Benzyl-N³-methyl-2-oxo-N⁵-(2-(tetrahydro-2H-pyran-3-yl)ethyl)-1,2-dihydropyridine-3,5-dicarboxamide | 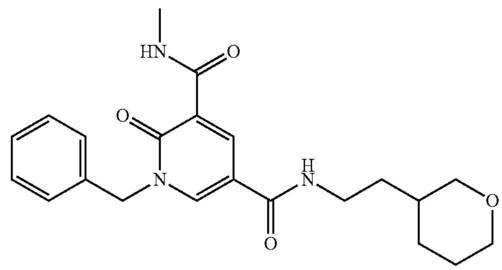 [SMILES: CNC(=O)c1cc(C(=O)NCCC2CCCOC2)cn(Cc2ccccc2)c1=O] | 398.1 (formic) | 0.91 |
| 32 | tert-Butyl 4-(2-(1-benzyl-5-(methylcarbamoyl)-6-oxo-1,6-dihydropyridine-3-carboxamido)ethyl)piperidine-1-carboxylate | 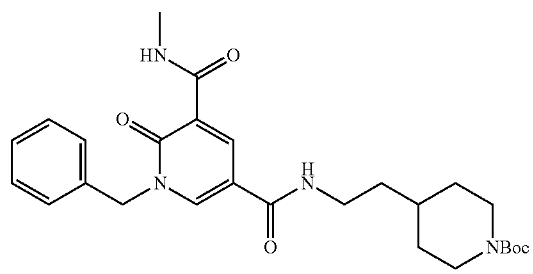 [SMILES: CNC(=O)c1cc(C(=O)NCCC2CCN(C(=O)OC(C)(C)C)CC2)cn(Cc2ccccc2)c1=O] | 497.3 (formic) | 1.14 |
| 33 | N⁵-(Azetidin-3-1)-1-benzyl-N³-methyl-2-oxo-1,2-dihydropyridine-3,5-dicarboxamide | 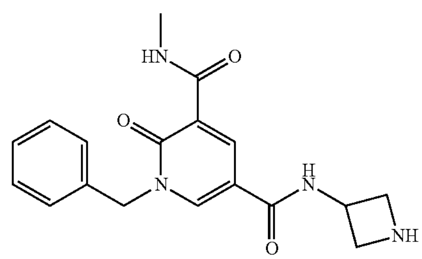 [SMILES: CNC(=O)c1cc(C(=O)NC2CNC2)cn(Cc2ccccc2)c1=O] | 341.0 (formic) | 0.53 |
| 34 | 1-Benzyl-N³-methyl-N⁵-(1-methylazetidin-3-yl)-2-oxo-1,2-dihdyropyridine-3,5-dicarboxamide | 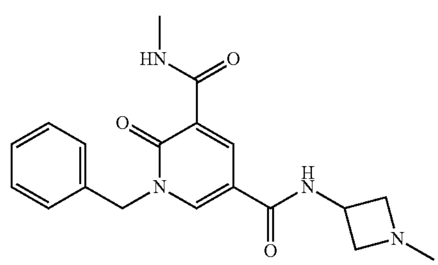 [SMILES: CNC(=O)c1cc(C(=O)NC2CN(C)C2)cn(Cc2ccccc2)c1=O] | 355.0 (formic) | 0.51 |
| 35 | 1-Benzyl-N⁵-(2-oxabicyclo[4.2.0]octan-7-yl)-N³-methyl-2-oxo-1,2-dihydropyridine-3,5-dicarboxamide | 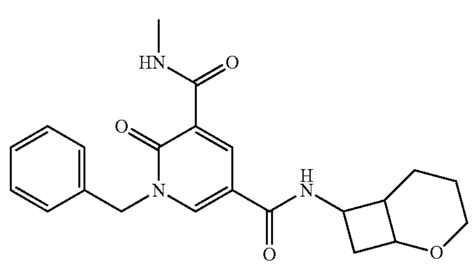 [SMILES: CNC(=O)c1cc(C(=O)NC2CC3OCCCC23)cn(Cc2ccccc2)c1=O] | 396.1 (formic) | 0.87 |

-continued

| Ex No. | Name | Structure | [MH]+ | Rt (min)* |
|---|---|---|---|---|
| 36 | 1-Benzyl-$N^3$-methyl-$N^5$-(2-(1-methylpyrrolidin-3-yl)ethyl)-2-oxo-1,2-dihydropyridine-3,5-dicarboxamide | 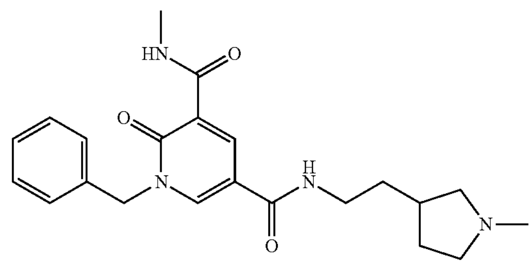 [SMILES: CNC(=O)c1cc(C(=O)NCCC2CCN(C)C2)cn(Cc2ccccc2)c1=O] | 397.3 (formic) | 0.53 |
| 37 | 1-Benzyl-$N^3$-methyl-$N^5$-(3-morpholinopropyl)-2-oxo-1,2-dihydropyridine-3,5-dicarboxamide | 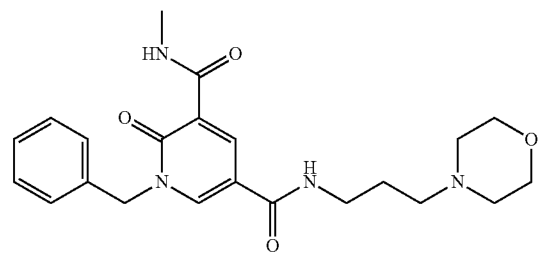 [SMILES: CNC(=O)c1cc(C(=O)NCCCN2CCOCC2)cn(Cc2ccccc2)c1=O] | 413.2 (formic) | 0.52 |
| 38 | tert-Butyl 3-(2-(1-benzyl-5-(methylcarbamoyl)-6-oxo-1,6-dihydropyridine-3-carboxamido)ethyl)piperidine-1-carbxylate | 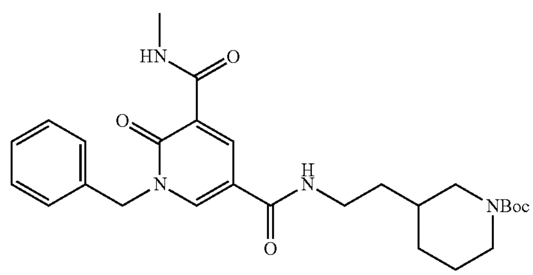 [SMILES: CNC(=O)c1cc(C(=O)NCCC2CCCN(C(=O)OC(C)(C)C)C2)cn(Cc2ccccc2)c1=O] | 397.2 (formic) | 1.18 |
| 39 | 1-Benzyl-$N^3$-methyl-2-oxo-$N^5$-(2-(piperidin-3-yl)ethyl)-1,2-dihydropyridine-3,5-dicarboxamide, hydrochloride | 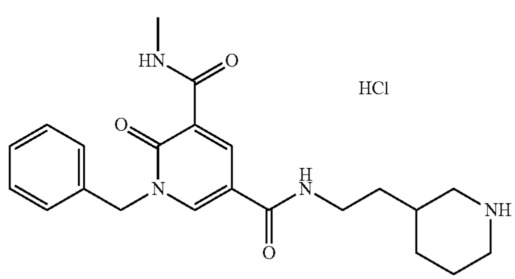 [SMILES: CNC(=O)c1cc(C(=O)NCCC2CCCNC2)cn(Cc2ccccc2)c1=O ; Cl] | 397.2 (formic) | 0.54 |
| 40 | 1-Benzyl-$N^3$-methyl-2-oxo-$N^5$-(2-(piperidin-2-yl)ethyl)-1,2-dihydropyridine-3,5-dicarboxamide hydrochloride | 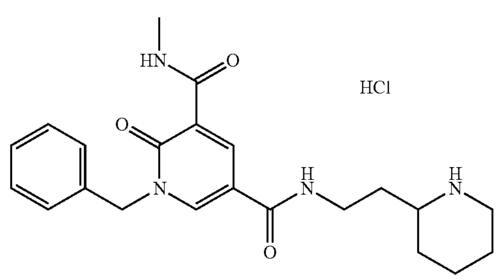 [SMILES: CNC(=O)c1cc(C(=O)NCCC2CCCCN2)cn(Cc2ccccc2)c1=O ; Cl] | 397.2 (formic) | 0.56 |

| Ex No. | Name | Structure | [MH]⁺ | Rt (min)* |
|---|---|---|---|---|
| 41 | 1-Benzyl-$N^3$-methyl-2-oxo-$N^5$-(tetrahydro-2H-pyran-4-yl)-1,2-dihydropyridine-3,5-dicarboxamide | 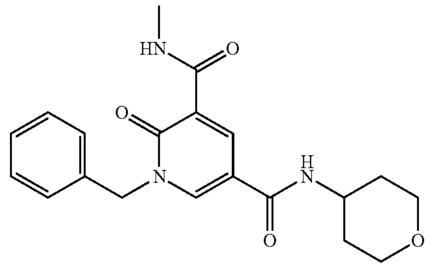 [SMILES: CNC(=O)c1cc(C(=O)NC2CCOCC2)cn(Cc2ccccc2)c1=O] | 370.3 (formic) | 0.81 |
| 42 | 1-Benzyl-$N^5$-(1,1-dioxidotetrahydro-2H-thiopyran-3-yl)-$N^3$-methyl-2-oxo-1,2-dihdyropyridine-3,5-dicarboxamide | 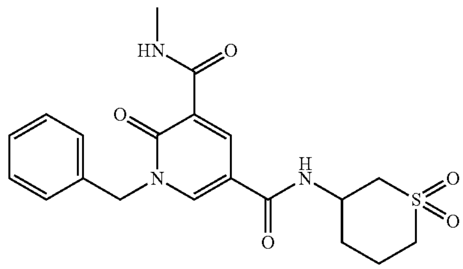 [SMILES: CNC(=O)c1cc(C(=O)NC2CCCS(=O)(=O)C2)cn(Cc2ccccc2)c1=O] | 418.3 (formic) | 0.79 |
| 43 | 1-Benzyl-$N^5$-(1,1-dioxidotetrahydrothiophen-3-yl)-$N^3$-methyl-2-oxo-1,2-dihydroypridine-3,5-dicarboxamide | 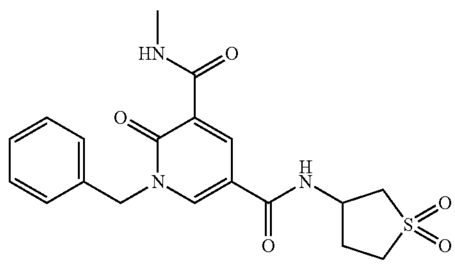 [SMILES: CNC(=O)c1cc(C(=O)NC2CCS(=O)(=O)C2)cn(Cc2ccccc2)c1=O] | 404.2 (formic) | 0.78 |
| 44 | 1-Benzyl-$N^5$-(1,1-dioxidotetrahydro-2H-thiopyran-4-yl)-$N^3$-methyl-2-oxo-1,2-dihydropyridine-3,5-dicarboxamide | 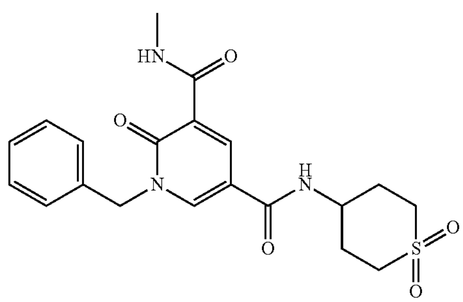 [SMILES: CNC(=O)c1cc(C(=O)NC2CCS(=O)(=O)CC2)cn(Cc2ccccc2)c1=O] | 418.3 (formic) | 0.77 |
| 45 | 1-Benzyl-$N^3$-methyl-2-oxo-$N^5$-(3-(piperidin-1-yl)propyl)-1,2-dihydropyridine-3,5-dicarboxamide hydrochloride | 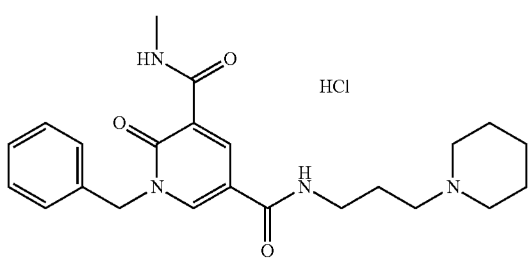 [SMILES: CNC(=O)c1cc(C(=O)NCCCN2CCCCC2)cn(Cc2ccccc2)c1=O ; Cl] | 411.3 (formic) | 0.56 |

-continued

| Ex No. | Name | Structure | [MH]+ | Rt (min)* |
|---|---|---|---|---|
| 46 | (R)-1-Benzyl-$N^3$-methyl-2-oxo-$N^5$-((tetrahydro-2H-pyran-3-yl)methyl)-1,2-dihydropyridine-3,5-dicarboxamide | 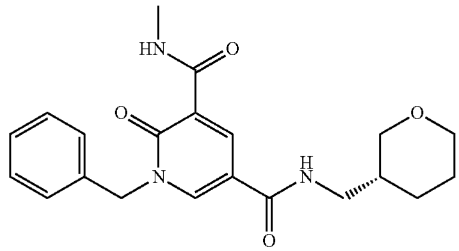 [SMILES: CNC(=O)c1cc(C(=O)NC[C@H]2CCCOC2)cn(Cc2ccccc2)c1=O] | 384.2 (formic) | 0.85 |
| 47 | (S)-1-Benzyl-$N^3$-methyl-2-oxo-$N^5$-((tetrahydro-2H-pyran-3-yl)methyl)-1,2-dihydropyridine-3,5-dicarboxamide | 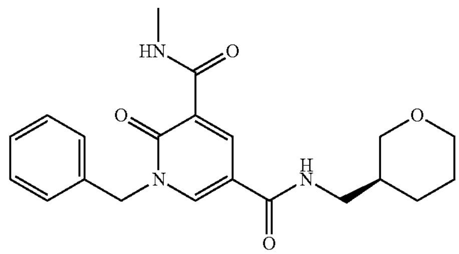 [SMILES: CNC(=O)c1cc(C(=O)NC[C@@H]2CCCOC2)cn(Cc2ccccc2)c1=O] | 384.2 (formic) | 0.85 |
| 48 | 1-Benzyl-$N^5$-((1,1-dioxidotetrahydrothiophen-3-yl)methyl)-$N^3$-methyl-2-oxo-1,2-dihydropyridine-3,5-dicarboxamide | 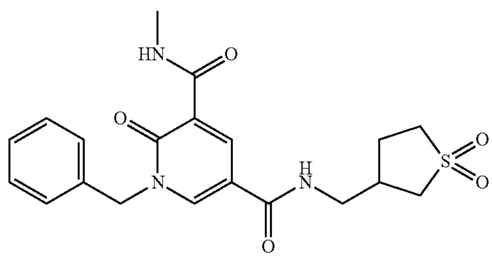 [SMILES: CNC(=O)c1cc(C(=O)NCC2CCS(=O)(=O)C2)cn(Cc2ccccc2)c1=O] | 418.3 (formic) | 0.77 |
| 49 | 1-Benzyl-$N^3$-methyl-2-oxo-$N^5$-((tetrahydro-2H-pyran-4-yl)methyl)-1,2-dihydroopyridine-3,5-dicarboxamide | 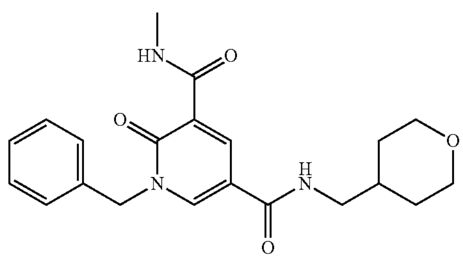 [SMILES: CNC(=O)c1cc(C(=O)NCC2CCOCC2)cn(Cc2ccccc2)c1=O] | 384.3 (High pH) | 0.85 |
| 50 | 1-Benzyl-$N^3$-methyl-2-oxo-$N^5$-(tetrahydro-2H-pyran-3-yl)-1,2-dihdyropyridine-3,5-dicarboxamide | 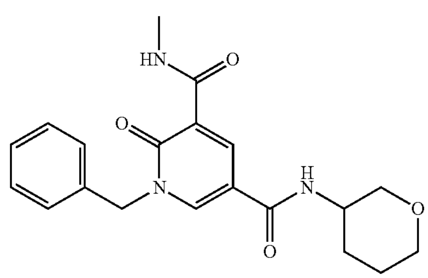 [SMILES: CNC(=O)c1cc(C(=O)NC2CCCOC2)cn(Cc2ccccc2)c1=O] | 370.2 (formic) | 0.84 |
| 51 | 1-Benzyl-$N^3$-methyl-$N^5$-(3-(4-methylpiperazin-1-yl)propyl)-2-oxo-1,2-dihydropyridine-3,5-dicarboxamide | 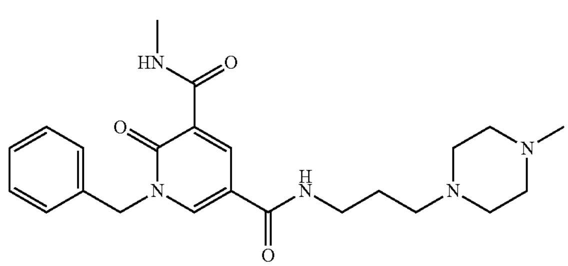 [SMILES: CNC(=O)c1cc(C(=O)NCCCN2CCN(C)CC2)cn(Cc2ccccc2)c1=O] | 426.3 (formic) | 0.44 |

| Ex No. | Name | Structure | [MH]+ | Rt (min)* |
|---|---|---|---|---|
| 52 | 1-Benzyl-N⁵-(3-(1,1-dioxidothiomorpholino)propyl)-N³-methyl-2-oxo-1,2-dihydropyridine-3,5-dicarboxamide | 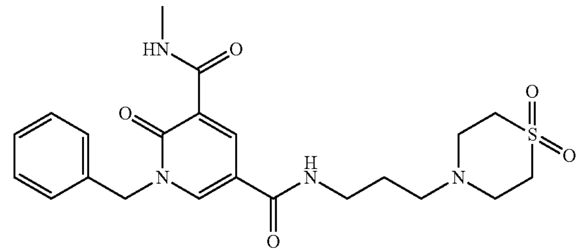 [SMILES: CNC(=O)c1cc(C(=O)NCCCN2CCS(=O)(=O)CC2)cn(Cc2ccccc2)c1=O] | 461.2 (formic) | 0.59 |
| 53 | 1-Benzyl-N⁵-((1,1-dioxidotetrahydro-2H-thiopyran-4-yl)methyl)-N³-methyl-2-oxo-1,2-dihydropyridine-3,5-dicarboxamide | 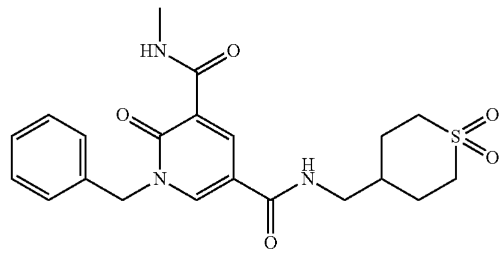 [SMILES: CNC(=O)c1cc(C(=O)NCC2CCS(=O)(=O)CC2)cn(Cc2ccccc2)c1=O] | 432.3 (formic) | 0.78 |
| 54 | N³-Methyl-1-(3-methylbenzyl)-2-oxo-N⁵-(3-(piperidin-4-yl)propyl)-1,2-dihydropyridine-3,5-dicarboxamide hydrochloride | 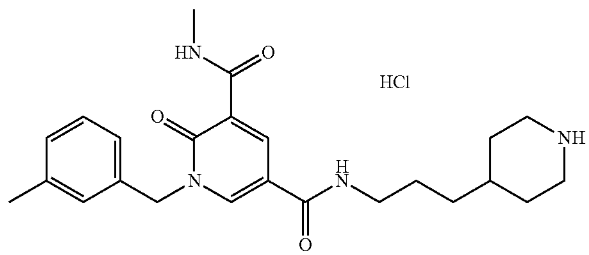 [SMILES: CNC(=O)c1cc(C(=O)NCCCC2CCNCC2)cn(Cc2cccc(C)c2)c1=O ; Cl] | 425.4 (formic) | 0.61 |
| 55 | (R)-N³-Methyl-2-oxo-1-(1-phenylethyl)-N⁵-(3-(piperidin-4-yl)propyl)-1,2-dihydropyridine-3,5-dicarboxamide hydrochloride | 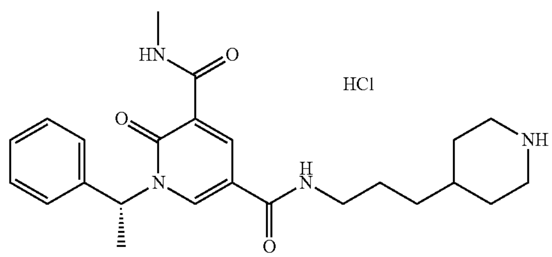 [SMILES: CNC(=O)c1cc(C(=O)NCCCC2CCNCC2)cn([C@H](C)c2ccccc2)c1=O ; Cl] | 425.4 (formic) | 0.60 |
| 56 | 1-((1H-Indol-4-yl)methyl)-N³-methyl-2-oxo-N5-(2-(piperidin-4-yl)ethyl)-1,2-dihydropyridine-3,5-dicarboxamide | 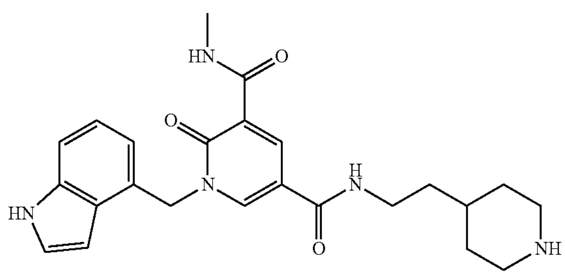 [SMILES: CNC(=O)c1cc(C(=O)NCCC2CCNCC2)cn(Cc2cccc3[nH]ccc23)c1=O] | 435.9 (formic) | 0.53 |
| 57 | 1-Benzyl-N⁵-(3-(4-hydroxypiperidin-4-yl)propyl)-N³-methyl-2-oxo-1,2-dihydropyridine-3,5-dicarboxamide | 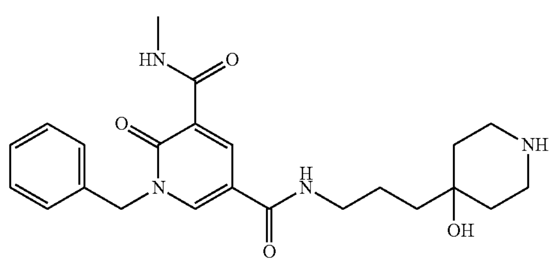 [SMILES: CNC(=O)c1cc(C(=O)NCCCC2(O)CCNCC2)cn(Cc2ccccc2)c1=O] | 427.3 (formic) | 0.56 |

| Ex No. | Name | Structure | [MH]+ | Rt (min)* |
|---|---|---|---|---|
| 58 | 1-(3-Fluorobenzyl)-N³-methyl-2-oxo-N⁵-(3-(piperidin-4-yl)propyl)-1,2-dihydropyridine-3,5-dicarboxamide | 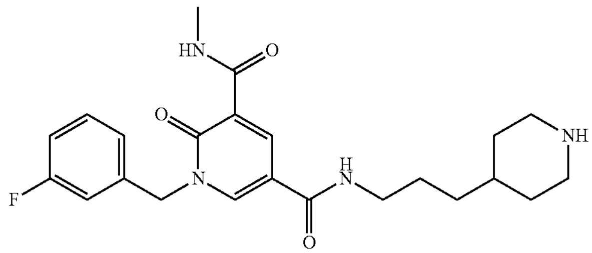 [SMILES: CNC(=O)c1cc(C(=O)NCCCC2CCNCC2)cn(Cc2cccc(F)c2)c1=O] | 429.2 (formic) | 0.58 |
| 59 | tert-Butyl 3-(3-(1-benzyl-5-(methylcarbamoyl)-6-oxo-1,6-dihydropyridine-3-carboxamido)propyl)piperidine-1-carboxylate | 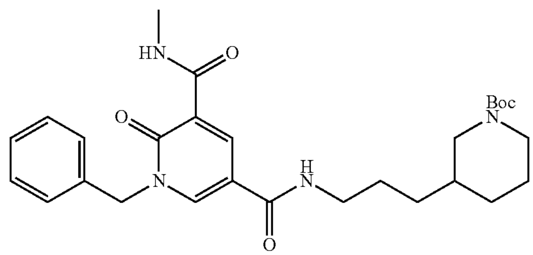 [SMILES: CNC(=O)c1cc(C(=O)NCCCC2CCCN(C(=O)OC(C)(C)C)C2)cn(Cc2ccccc2)c1=O] | 511.2 (formic) | 1.20 |
| 60 | 1-Benzyl-N³-methyl-2-oxo-N⁵-(3-(piperidin-3-yl)propyl)-1,2-dihdyropyridine-3,5-dicarboxamide hydrochloride | 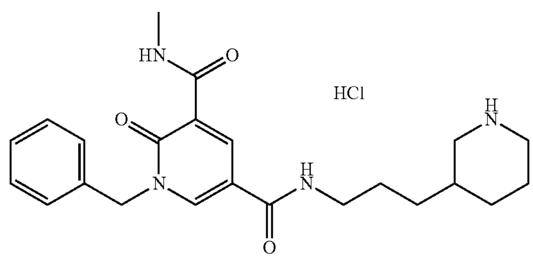 [SMILES: CNC(=O)c1cc(C(=O)NCCCC2CCCNC2)cn(Cc2ccccc2)c1=O ; Cl] | 411.2 (formic) | 0.57 |
| 61 | 1-Benzyl-N⁵-(3-(4-fluoropiperidin-4-yl)propyl)-N³-methyl-2-oxo-1,2-dihydropyridine-3,5-dicarboxamide hydrochloride | 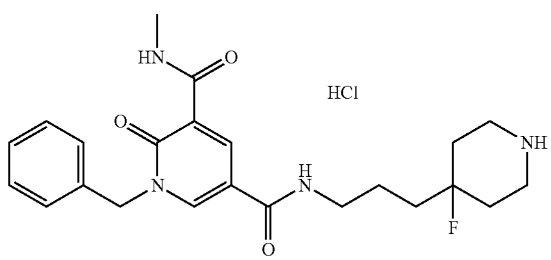 [SMILES: CNC(=O)c1cc(C(=O)NCCCC2(F)CCNCC2)cn(Cc2ccccc2)c1=O ; Cl] | 429.2 (formic) | 0.56 |

Example 62: 1-((1H-Indol-4-yl)methyl)-N³-methyl-2-oxo-N⁵-(3-(piperidin-4-yl)propyl)-1,2-dihydropyridine-3,5-dicarboxamide hydrochloride

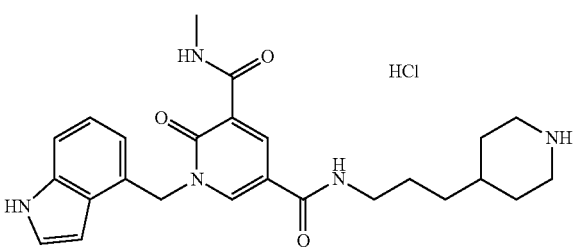 [SMILES: CNC(=O)c1cc(C(=O)NCCCC2CCNCC2)cn(Cc2cccc3[nH]ccc23)c1=O ; Cl]

tert-Butyl 4-(3-(1-((1H-indol-4-yl)methyl)-5-(methylcarbamoyl)-6-oxo-1,6-dihydropyridine-3-carboxamido)propyl)piperidine-1-carboxylate (283 mg, 0.52 mmol) was taken up in DCM (5 mL) and TFA (1 mL, 12.98 mmol) was added. The reaction was stirred at rt for 2 h. The solvent was removed in vacuo and the residue applied to a 2 g SCX cartridge in the minimum of MeOH. The cartridge was eluted with MeOH then 2N NH₃ in MeOH (20 mL each) and the ammonia fraction concentrated in vacuo to give a yellow oil. This was purified by MDAP (high pH). The appropriate fractions were concentrated in vacuo to give 1-((1H-indol-4-yl)methyl)-N³-methyl-2-oxo-N-(3-(piperidin-4-yl)propyl)-1,2-dihydropyridine-3,5-dicarboxamide (110 mg, 0.23 mmol, 45% yield) as a yellow oil. 85 mg of this was taken up in the minimum of DCM and 2N HCl in Et₂O (104 μL, 1.1 eq.) was added. The solvent was removed under a stream of nitrogen to give 1-((1H-indol-4-yl)methyl)-N³-methyl-2-oxo-N⁵-(3-(piperidin-4-yl)propyl)-1,2-dihydropyridine-3,5-dicarboxamide, hydrochloride (77 mg, 0.15 mmol, 29% yield) as a cream solid.

LCMS (2 min High pH): Rt=0.77 min, [MH]+=450.4.

Example 63: 1-benzyl-$N^5$-(3-(4-fluoropiperidin-4-yl)propyl)-$N^3$-methyl-2-oxo-1,2-dihydropyridine-3,5-dicarboxamide

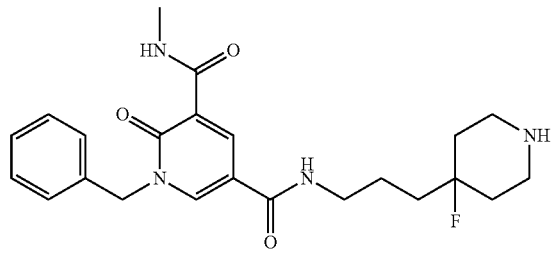

To a solution of tert-butyl 4-(3-(1-benzyl-5-(methylcarbamoyl)-6-oxo-1,6-dihydropyridine-3-carboxamido)propyl)-4-fluoropiperidine-1-carboxylate (76 mg, 0.144 mmol) in dichloromethane (2 mL) was added TFA (0.5 mL, 6.49 mmol) and the reaction mixture stirred under $N_2$ at r.t. for 16 h. Reaction mixture was concentrated to give 59 mg of crude pale pink oil. This was loaded onto a 1 g SCX cartridge (pre-conditioned with MeOH) and eluted with MeOH (40 mL) followed by 2M $NH_3$ in MeOH (40 mL). Ammonia fractions were combined and concentrated to give the title compound (20 mg, 0.042 mmol, 29.2% yield) as an off-white solid LCMS (2 min Formic): Rt=0.56 min, $[MH]^+$=429

Example 64: 1-benzyl-$N^3$-methyl-$N^5$-(2-(4-methylmorpholin-2-yl)ethyl)-2-oxo-1,2-dihydropyridine-3,5-dicarboxamide

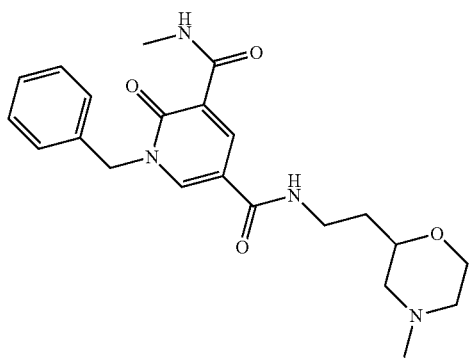 [SMILES: CNC(=O)c1cc(C(=O)NCCC2CN(C)CCO2)cn(Cc2ccccc2)c1=O]

To a suspension of 1-benzyl-5-(methylcarbamoyl)-6-oxo-1,6-dihydropyridine-3-carboxylic acid (59.6 mg, 0.208 mmol), HATU (98.7 mg, 0.260 mmol) and (+)-2-(4-methylmorpholin-2-yl)ethanamine, dihydrochloride (52.2 mg, 0.240 mmol; free base commercially available from Aurora Building blocks) in N,N-dimethylformamide (2 mL) was added DIPEA (0.145 mL, 0.833 mmol). The reaction mixture was stirred at room temperature for 1.25 hr before being concentrated under a stream of nitrogen and made up to 6 mL with DMSO and directly purified by MDAP (high pH). The required fractions were individually concentrated under a stream of nitrogen before being dissolved in a 1:1 mixture of dichloromethane/methanol (2×6 mL), combined, concentrated under a stream of nitrogen and dried in vacuo give the desired product as a white solid (88 mg, 0.213 mmol, 102% yield). LCMS (2 min Formic): Rt=0.52 min, $[MH]^+$=413

Example 65: $N^5$-(2-(4-acetylmorpholin-2-yl)ethyl)-1-benzyl-$N^3$-methyl-2-oxo-1,2-dihydropyridine-3,5-dicarboxamide

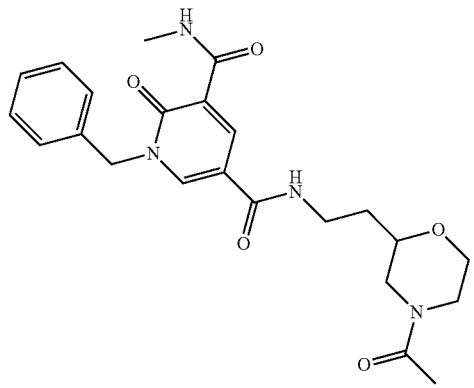 [SMILES: CNC(=O)c1cc(C(=O)NCCC2CN(C(C)=O)CCO2)cn(Cc2ccccc2)c1=O]

To 1-benzyl-5-(methylcarbamoyl)-6-oxo-1,6-dihydropyridine-3-carboxylic acid (73.7 mg, 0.257 mmol) and HATU (117 mg, 0.309 mmol) was added a solution of (+)-1-(2-(2-aminoethyl)morpholino)ethanone (54 mg, 0.314 mmol; commercially available from Aurora Building blocks) in DMF (2 mL). DIPEA (0.090 mL, 0.515 mmol) was added and the reaction mixture was stirred at room temperature for 17 hr. The reaction mixture was concentrated under a stream of nitrogen before being made up to 3 mL with dimethylsulphoxide and directly purified by MDAP (high pH). The required fraction was concentrated under a stream of nitrogen before being dissolved in a 1:1 mixture of dichloromethane/methanol, concentrated under a stream of nitrogen and dried in vacuo to give the desired product as a pale yellow solid (42.5 mg, 0.096 mmol, 37.5% yield).

LCMS (2 min Formic): Rt=0.76 min, $[MH]^+$=441

Example 66: 1-benzyl-$N^3$-methyl-$N^5$-(2-(morpholin-2-yl)ethyl)-2-oxo-1,2-dihydropyridine-3,5-dicarboxamide hydrochloride

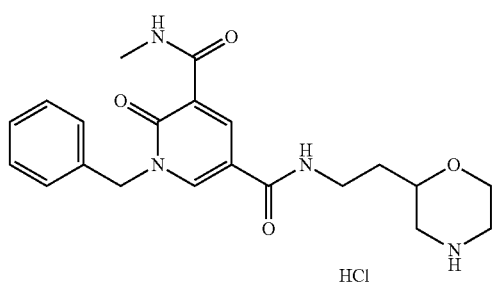 [SMILES: CNC(=O)c1cc(C(=O)NCCC2CNCCO2)cn(Cc2ccccc2)c1=O ; Cl]

To a solution of (±)-tert-butyl 2-(2-(1-benzyl-5-(methylcarbamoyl)-6-oxo-1,6-dihydropyridine-3-carboxamido)ethyl)morpholine-4-carboxylate (71.6 mg, 0.144 mmol) in 1,4-dioxane (1 mL) was added hydrogen chloride (4M solution in 1,4-dioxane) (1.5 mL, 6.00 mmol) and the reaction mixture stirred at room temperature for 1.25 hr. The mixture was concentrated under a stream of nitrogen and dried in vacuo to give the desired product as a yellow solid, (65.2 mg, 0.150 mmol, 104% yield). LCMS (2 min Formic): Rt=0.51 min, [MH]+=399

Example 67: 1-benzyl-N3-methyl-2-oxo-N5-(2-(pyrrolidin-3-yloxy)ethyl)-1,2-dihydropyridine-3,5-dicarboxamide, hydrochloride

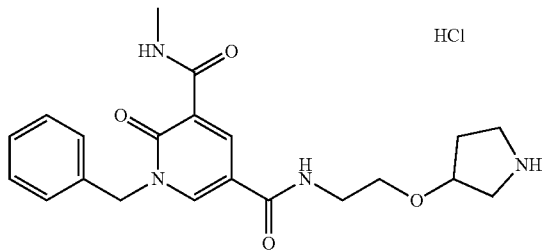 [SMILES: CNC(=O)c1cc(C(=O)NCCOC2CCNC2)cn(Cc2ccccc2)c1=O ; Cl]

To a solution of (±)-tert-butyl 3-(2-(1-benzyl-5-(methylcarbamoyl)-6-oxo-1,6-dihydropyridine-3-carboxamido)ethoxy)pyrrolidine-1-carboxylate (79.3 mg, 0.159 mmol) in 1,4-dioxane (1.5 mL) was added hydrogen chloride (4M solution in 1,4-dioxane) (1.5 mL, 6.00 mmol) and the reaction mixture stirred at room temperature for 1.5 hr. The reaction mixture was concentrated under a stream of nitrogen and dried in vacuo to give (+)-1-benzyl-$N^3$-methyl-2-oxo-$N^5$-(2-(pyrrolidin-3-yloxy)ethyl)-1,2-dihydropyridine-3,5-dicarboxamide, hydrochloride (60.7 mg, 0.140 mmol, 88% yield) as a yellow solid. LCMS (2 min Formic): Rt=0.51 min, [MH]+=399.4

Example 68: 1-benzyl-$N^3$-methyl-2-oxo-$N^5$-(2-(piperidin-3-yloxy)ethyl)-1,2-dihydropyridine-3,5-dicarboxamide

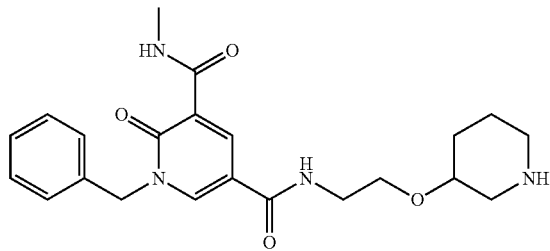 [SMILES: CNC(=O)c1cc(C(=O)NCCOC2CCCNC2)cn(Cc2ccccc2)c1=O]

To a suspension of (±)-tert-butyl 3-(2-(1-benzyl-5-(methylcarbamoyl)-6-oxo-1,6-dihydropyridine-3-carboxamido)ethoxy)piperidine-1-carboxylate (32.2 mg, 0.063 mmol) in 1,4-dioxane (0.5 mL) was added hydrogen chloride (4M solution in 1,4-dioxane) (0.75 mL, 3.00 mmol) and the reaction mixture stirred at room temperature for 1.5 hr. The reaction mixture was concentrated under a stream of nitrogen before being made up to 1 mL with methanol and directly purified by MDAP (formic). The required fraction was concentrated under a stream of nitrogen before being dissolved in a 1:1 mixture of dichloromethane/methanol (6 mL), concentrated under a stream of nitrogen and dried in vacuo. The residue was dissolved in methanol and loaded onto an SCX cartridge which was eluted with methanol (3×3 mL). These washings were discarded. The cartridge was then eluted with ammonia in methanol solution (2M) (4×3 mL). These washings were combined, concentrated under a stream of nitrogen and dried in vacuo give 1-benzyl-$N^3$-methyl-2-oxo-$N^5$-(2-(piperidin-3-yloxy)ethyl)-1,2-dihydropyridine-3,5-dicarboxamide (11.6 mg, 0.028 mmol, 44.8% yield) as a white solid. LCMS (2 min Formic): Rt=0.52 min, [MH]+=413.4.

Example 69: 1-Benzyl-$N^5$-((1R,5S,6r)-3-oxabicyclo[3.1.0]hexan-6-yl)-$N^3$-methyl-2-oxo-1,2-dihydropyridine-3,5-dicarboxamide

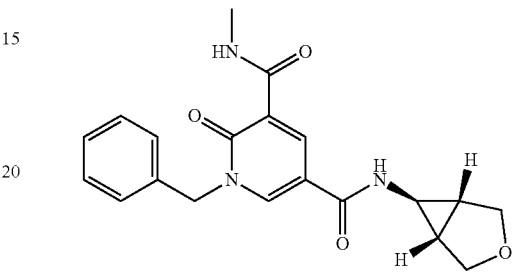

DIPEA (0.099 mL, 0.566 mmol), HATU (86 mg, 0.226 mmol) and (1R,5S,6r)-3-oxabicyclo[3.1.0]hexan-6-amine (22.44 mg, 0.226 mmol) were successively added to a solution of 1-benzyl-5-(methylcarbamoyl)-6-oxo-1,6-dihydropyridine-3-carboxylic acid (54 mg, 0.189 mmol) in DMF (1 mL). After 10 min stirring. The reaction mixture was directly purified by MDAP (formic), and the appropriate fraction were collected and evaporated in vacuo, to afford the desired compound (9 mg, 0.024 mmol, 12.99% yield). LCMS (2 min Formic): Rt=0.79 min, [MH]+=368.3

Example 70: 1-Benzyl-$N^3$-methyl-$N^5$-(3-(1-methylpiperidin-3-yl)propyl)-2-oxo-1,2-dihydropyridine-3,5-dicarboxamide

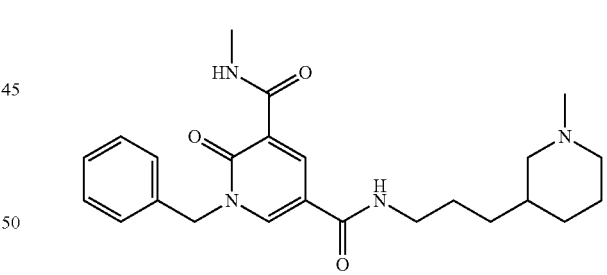

A solution of 1-benzyl-$N^3$-methyl-2-oxo-$N^5$-(3-(piperidin-3-yl)propyl)-1,2-dihydropyridine-3,5-dicarboxamide (42 mg, 0.102 mmol) in dry methanol (2 mL) was treated with paraformaldehyde (7 mg, 0.233 mmol) and formic acid (8.33 µL, 0.217 mmol). The reaction mixture was stirred at r.t. for 10 mins and then sodium cyanoborohydride (14 mg, 0.223 mmol) was added. Reaction mixture was then stirred at r.t. under $N_2$ o/n. Further portions of paraformaldehyde (7 mg, 0.233 mmol) and formic acid (8.33 µL, 0.217 mmol) were added followed after 30 mins by addition of sodium triacetoxyborohydride (44 mg, 0.208 mmol). Reaction mixture left sitting for a further 9 days at r.t. Reaction mixture was concentrated and partitioned between sat. $NaHCO_3$ solution (10 mL) and DCM. Organic layer was separated and aqueous layer further extracted with DCM (2×10 mL). Combined organic layers were dried (Na$_2$SO$_4$) and conc. to give 38 mg of crude residue. This was purified by silica gel chromatography, eluting with 0-10% of 2M Ammonia in MeOH in DCM/DCM over 120 mL) to give the title compound (23 mg, 0.049 mmol, 47.7% yield) as a white solid.

LCMS (2 min Formic): Rt=0.57 min, [MH]+=425.3

Example 71: 1-Benzyl-N$^3$-methyl-N$^5$-(3-(1-methyl-piperidin-3-yl)propyl)-2-oxo-1,2-dihydropyridine-3,5-dicarboxamide

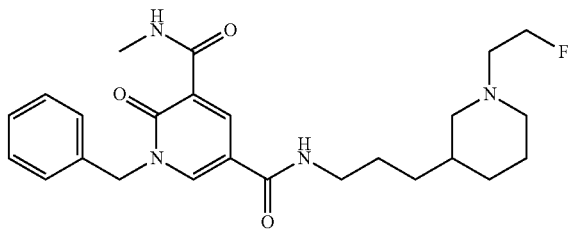 [SMILES: CNC(=O)c1cc(C(=O)NCCCC2CCCN(CCF)C2)cn(Cc2ccccc2)c1=O]

1-Benzyl-N$^3$-methyl-2-oxo-N$^5$-(3-(piperidin-3-yl)propyl)-1,2-dihydropyridine-3,5-dicarboxamide (46 mg, 0.112 mmol) and cesium carbonate (73.0 mg, 0.224 mmol) were dissolved in N,N-dimethylformamide (2 mL) at 90° C. and 1-bromo-2-fluoroethane (20 mg, 0.158 mmol) was added. The resulting mixture was stirred at this temperature for 2.5 h then the suspension was concentrated and partitioned between EtOAc (20 mL) and water (20 mL), the aqueous phase was extracted with EtOAc (2×10 mL), dried over a hydrobobic frit and concentrated to give ~75 mg of a crude solid. This was purified by silica gel chromatography, eluting with 0-100% of 25% ethanol in ethyl acetate/ethyl acetate over 120 mL) to give 1-benzyl-N$^5$-(3-(1-(2-fluoroethyl)piperidin-3-yl)propyl)-N$^3$-methyl-2-oxo-1,2-dihydropyridine-3,5-dicarboxamide (28 mg, 0.055 mmol, 49.3% yield) as a white solid.

LCMS (2 min Formic): Rt=0.58 min, [MH]+=457.5

Example 72: N5-((1R,5S,6r)-3-Oxabicyclo[3.1.0]hexan-6-yl)-1-(3-methoxybenzyl)-N$^3$-methyl-2-oxo-1,2-dihydropyridine-3,5-dicarboxamide

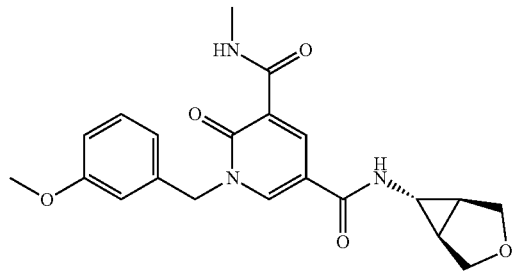 [SMILES: CNC(=O)c1cc(C(=O)N[C@H]2[C@@H]3COC[C@@H]32)cn(Cc2cccc(OC)c2)c1=O]

To a solution of 1-(3-methoxybenzyl)-5-(methylcarbamoyl)-6-oxo-1,6-dihydropyridine-3-carboxylic acid (80 mg, 0.253 mmol) in N,N-dimethylformamide (2 mL) was added HATU (144 mg, 0.379 mmol) followed by (1R,5S,6r)-3-oxabicyclo[3.1.0]hexan-6-amine hydrochloride (64 mg, 0.472 mmol) and DIPEA (0.221 mL, 1.265 mmol). The resulting reaction mixture was stirred at r.t. under N$_2$ for 4 h (formed yellow solution). Then the reaction mixture partitioned between ethyl acetate and water. Organic layer was separated and aqueous layer was extracted with more ethyl acetate. Combined organic layer were dried (Na2SO4) and conc. to give ~180 mg of crude residue. This was purified by chromatography on SiO$_2$ (Biotage SNAP 10 g cartridge, eluting with 0-100% ethyl acetate/cyclohexane over 120 mL followed by 10% EtOH in ethylacetate over 120 mL) to give the title compound (96 mg, 0.217 mmol, 86% yield) as a colourless oil.

LCMS (2 min Formic): Rt=0.80 min, [MH]+=398.4

Example 73: 1-Benzyl-N$^3$-methyl-N$^5$-(3-(morpholin-2-yl)propyl-2-oxo-1,2-dihydropyridine-3,5-dicarboxamide

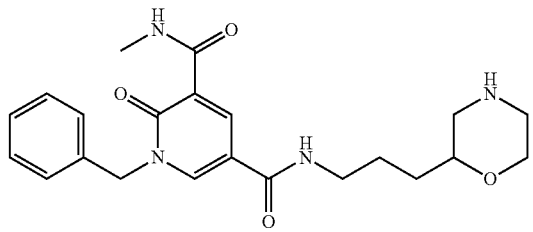 [SMILES: CNC(=O)c1cc(C(=O)NCCCC2CNCCO2)cn(Cc2ccccc2)c1=O]

tert-Butyl 2-(3-(1-benzyl-5-(methylcarbamoyl)-6-oxo-1,6-dihydropyridine-3-carboxamido)propyl)morpholine-4-carboxylate (11 mg, 0.017 mmol) and TFA (0.1 mL, 1.298 mmol) were stirred at r.t. in dichloromethane (0.4 mL) for 30 min. the reaction mixture was then concentrated and loaded onto a 500 mg SCX cartridge (pre-conditioned with MeOH) and eluted with MeOH (4 CV's) followed by 2M NH$_3$ in MeOH (4 CV's). Ammonia fractions containing product were combined and concentrated to give 15 mg of a colourless oil. This oil was purified by MDAP (High pH). The appropriate fractions were concentrated to give 1-benzyl-N3-methyl-N5-(3-(morpholin-2-yl)propyl)-2-oxo-1,2-dihydropyridine-3,5-dicarboxamide (2 mg, 4.36 µmol, 25.4% yield) as a white solid. LCMS (2 min Formic): Rt=0.54 min, [MH]+=413.5

Example 74: 1-((1H-indol-4-yl)methyl-N$^5$-(3-(1-acetylpiperidin-4-yl)propyl-N$^3$-methyl-2-oxo-1,2-dihydropyridine-3,5-dicarboxamide

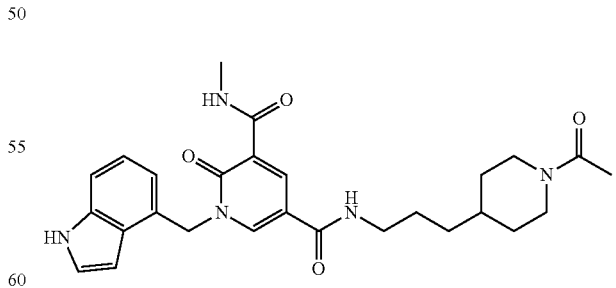

1-((1H-indol-4-yl)methyl)-N$^3$-methyl-2-oxo-N$^5$-(3-(piperidin-4-yl)propyl)-1,2-dihydropyridine-3,5-dicarboxamide (25 mg, 0.056 mmol) was taken up in dichloromethane (2 mL). Et$_3$N (0.016 mL, 0.111 mmol) then AcCl (4.35 µL, 0.061 mmol) were added and the reaction stirred at room temperature for 2 hrs. The reaction was diluted with DCM (10 mL) and washed with sat. NaHCO₃ (15 mL) then eluted through a hydrophobic frit and concentrated in vacuo to give a clear oil. The crude product was applied to a 10 g SNAP cartridge in the minimum of DCM and eluted with 1% 2M NH₃ in methanol in DCM for 2CV then 1-10% 2M NH₃ in methanol in DCM over 10CV then held at 10% for 5CV. The appropriate fractions were concentrated in vacuo to give the title compound (21.5 mg, 0.042 mmol, 74.7% yield) as a cream solid.

LCMS (2 min High pH): Rt=0.86 min, [MH]⁺=492.4.

Example 75: (1R,5S,6s)-Tert-butyl 6-(1-benzyl-5-(methylcarbamoyl)-6-oxo-1,6-dihydropyridine-3-carboxamido)-3-azabicyclo[3.1.0]hexane-3-carboxylate

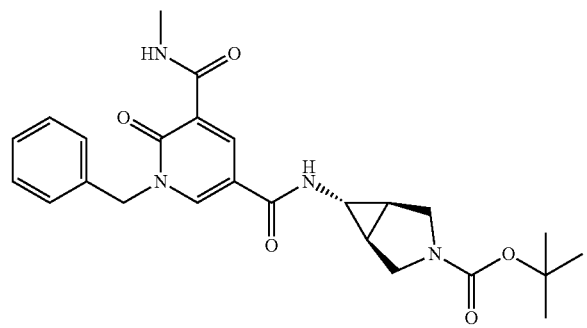 [SMILES: CNC(=O)c1cc(C(=O)N[C@H]2[C@@H]3CN(C(=O)OC(C)(C)C)C[C@@H]32)cn(Cc2ccccc2)c1=O]

To a solution of 2,4,6-trichlorophenyl 1-benzyl-5-(methylcarbamoyl)-6-oxo-1,6-dihydropyridine-3-carboxylate (450 mg, 0.966 mmol) in tetrahydrofuran (5 mL) was added (1R,5S,6s)-tert-butyl 6-amino-3-azabicyclo[3.1.0]hexane-3-carboxylate (230 mg, 1.160 mmol) followed by Et₃N (0.269 mL, 1.933 mmol) and DMAP (11.80 mg, 0.097 mmol). The resulting reaction mixture was stirred at 45° C. under N₂. Reaction mixture partitioned between ethyl acetate and water. Organic layer was separated and aqueous layer was extracted with more ethyl acetate. Combined organic layer were dried (Na₂SO₄) and conc. to give ~714 mg of crude cream foam. This was purified by silica gel chromatography, eluting with 0-100% ethyl acetate/cyclohexane over 330 mL to give the title compound (402 mg, 0.776 mmol, 80% yield) as a white solid LCMS (2 min Formic): Rt=1.03 min, [MH]+=467.5

Example 76: 1-Benzyl-N⁵-((1R,5S,6s)-3-azabicyclo[3.1.0]hexan-6-yl)-N³-methyl-2-oxo-1,2-dihydropyridine-3,5-dicarboxamide

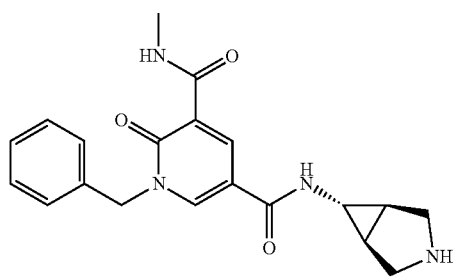 [SMILES: CNC(=O)c1cc(C(=O)N[C@H]2[C@@H]3CNC[C@@H]32)cn(Cc2ccccc2)c1=O]

To a solution of (1R,5S,6s)-tert-butyl 6-(1-benzyl-5-(methylcarbamoyl)-6-oxo-1,6-dihydropyridine-3-carboxamido)-3-azabicyclo[3.1.0]hexane-3-carboxylate (381 mg, 0.817 mmol) in DCM (5 mL) was added TFA (1 mL, 12.98 mmol) and reaction mixture was stirred at under N₂ at r.t. for 1 h then the reaction mixture was concentrated and loaded onto a 5 g SCX cartridge (pre-conditioned with MeOH) and eluted with MeOH (30 mL) followed by 2M NH₃ in MeOH (30 mL). Ammonia fractions containing product were combined and concentrated under reduced pressure to give the title compound (294 mg, 0.722 mmol, 88% yield) as a pale yellow solid.

LCMS (2 min Formic): Rt=0.51 min, [MH]+=367.5

Example 77: 1-Benzyl-N³-methyl-N⁵-(3-(morpholin-2-yl)propyl)-2-oxo-1,2-dihydropyridine-3,5-dicarboxamide (Single Enantiomer of Unknown Configuration)

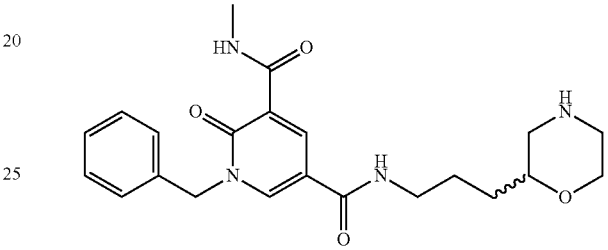

(+/−)-1-Benzyl-N³-methyl-N⁵-(3-(morpholin-2-yl)propyl)-2-oxo-1,2-dihydropyridine-3,5-dicarboxamide (23 mg) was submitted for chiral separation. The racemate (23 mg) was dissolved in EtOH (1.5 mL). Injection: 1.5 mL of the solution was injected onto the column (80% EtOH (+0.2% isopropylamine)/heptane (+0.2% isopropylamine), flow rate=30 mL/min, detection wavelength=215 nm, 4. Ref 550, 100, Column 30 mm×25 cm Chiralpak IA (5 μm), Lot No. IA11157-01). Total number of injections=1. Fractions from 13.5-16.5 min were bulked and labelled peak 1. Fractions from 20-28 min were bulked and labelled peak 2. The bulked fractions were concentrated in vacuo and then transferred to weighed flasks. Final compounds were recovered from DCM and heptane in order to obtain a solid.

The fractions corresponding to peak 1 were collected to afford the title compound (8 mg) as an off white solid.

LCMS (2 min Formic): Rt=0.55 min, [MH]⁺=413.3.

The fractions corresponding to the opposite enantiomer were collected but found to be of insufficient purity for screening.

Example 78: 1-benzyl-N³-ethyl-2-oxo-N⁵-(3-(piperidin-4-yl)propyl)-1,2-dihydropyridine-3,5-dicarboxamide

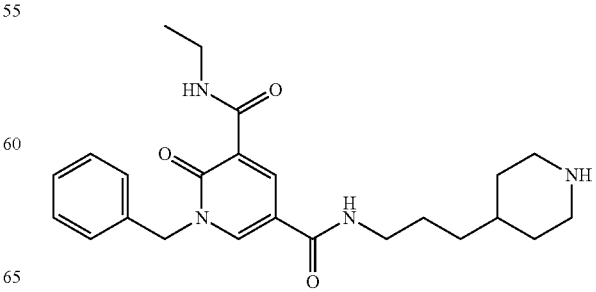

tert-Butyl 4-(3-(1-benzyl-5-(ethylcarbamoyl)-6-oxo-1,6-dihydropyridine-3-carboxamido)propyl)piperidine-1-carboxylate (160 mg, 0.303 mmol) was taken into round neck RB and HCl (18.44 µL, 0.607 mmol) was added at RT. The reaction mixture was stirred at RT for 2 hr. Solvent was evaporated in vacuum under reduced pressure to get crude product, which was washed with n-pentane (2×10 mL) to give 1-benzyl-$N^3$-ethyl-2-oxo-$N^5$-(3-(piperidin-4-yl)propyl)-1,2-dihydropyridine-3,5-dicarboxamide hydrochloride (110 mg, 0.238 mmol, 78% yield). This was then dissolved in methanol and adsorbed on SCX cartridge. Then eluted with water (5 mL), MeOH/NH4OH (19:1) 20 mL in four fractions. The appropriate fractions were concentrated. The residue obtained was then dissolved in ACN/Water (1:1 1 mL) and lyopholized to get 1-benzyl-$N^3$-ethyl-2-oxo-$N^5$-(3-(piperidin-4-yl)propyl)-1,2-dihydropyridine-3,5-dicarboxamide (68 mg, 0.160 mmol, 67.3% yield) as an off-white solid.

LCMS (4.5 min RND-FA-4.5-MIN): Rt=1.60 min, [MH]$^+$=425.4.

LCMS Conditions: RND-FA-4.5-MIN
Column: Acquity BEH C18 (50 mm×2.1 mm, 1.7 µm)
Mobile Phase: A: 0.05% formic acid in water; B: 0.05% formic acid in ACN
Time (min)/% B: 0/3, 0.4/3, 3.2/98, 3.8/98, 4.2/3, 4.5/3
Column Temp: 35° C., Flow Rate: 0.6 mL/min Example 79: (1R,5S,6s)-tert-Butyl 6-(1-((1H-indol-4-yl)methyl)-5-(methylcarbamoyl)-6-oxo-1,6-dihydropyridine-3-carboxamido)-3-azabicyclo[3.1.0]hexane-3-carboxylate

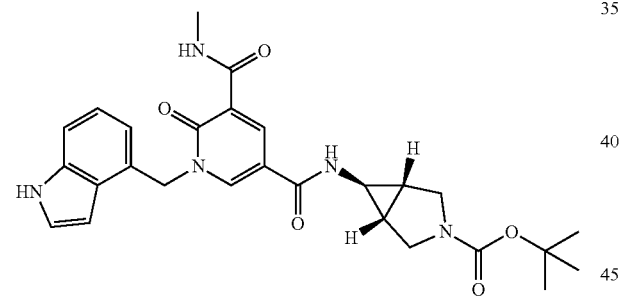

1-((1H-Indol-4-yl)methyl)-5-(methylcarbamoyl)-6-oxo-1,6-dihydropyridine-3-carboxylic acid (200 mg, 0.62 mmol) was taken up in DMF (2 mL). DIPEA (0.322 mL, 1.84 mmol) then HATU (351 mg, 0.92 mmol) were added and the reaction stirred at rt for 5 min. (1R,5S,6s)-tert-butyl 6-amino-3-azabicyclo[3.1.0]hexane-3-carboxylate (146 mg, 0.74 mmol, commercially available from, for example, Fluorochem) was added and the reaction stirred at rt overnight. The reaction was concentrated in vacuo and the residue partitioned between EtOAc and sat. aq. NaHCO$_3$ solution (20 mL each). The organic layer was washed with brine (20 mL) and eluted through a hydrophobic frit then concentrated in vacuo to yield an orange oil. The crude product was applied to a 25 g SNAP cartridge in the minimum of DCM and purified by flash chromatography, eluting with 5-50% (3:1 EtOAc:EtOH) in cyclohexane. The appropriate fractions were concentrated in vacuo to give (1R,5S,6s)-tert-butyl 6-(1-((1H-indol-4-yl)methyl)-5-(methylcarbamoyl)-6-oxo-1,6-dihydropyridine-3-carboxamido)-3-azabicyclo[3.1.0]hexane-3-carboxylate (324 mg, 0.61 mmol, 99% yield) as a cream solid. LCMS (2 min High pH): Rt=1.01 min, [MH]$^+$=506.4.

Example 80: 1-((1H-Indol-4-yl)methyl)-$N^5$-((1R,5S,6s)-3-azabicyclo[3.1.0]hexan-6-yl-$N^3$-methyl-2-oxo-1,2-dihydropyridine-3,5-dicarboxamide

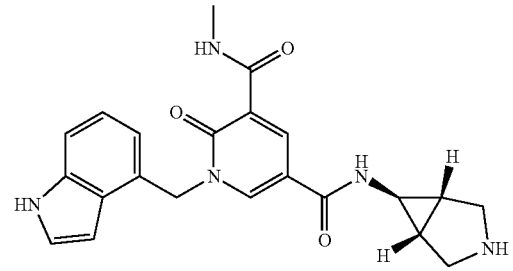 [SMILES: CNC(=O)c1cc(C(=O)N[C@H]2[C@@H]3CNC[C@@H]32)cn(Cc2cccc3[nH]ccc23)c1=O]

(1R,5S,6s)-tert-Butyl 6-(1-((1H-indol-4-yl)methyl)-5-(methylcarbamoyl)-6-oxo-1,6-dihydropyridine-3-carboxamido)-3-azabicyclo[3.1.0]hexane-3-carboxylate (324 mg, 0.64 mmol) was taken up in DCM (4.5 mL) and TFA (0.5 mL, 6.49 mmol) was added. The reaction was stirred at rt and monitored by LCMS. After 2 h, the solvent was removed in vacuo and the residue applied to a 5 g SCX cartridge in the minimum of MeOH. The cartridge was eluted with MeOH then 2N NH$_3$ in MeOH (30 mL each). The ammonia fractions was concentrated in vacuo to give 1-((1H-indol-4-yl)methyl)-N5-((1R,5S,6s)-3-azabicyclo[3.1.0]hexan-6-yl)-$N^3$-methyl-2-oxo-1,2-dihydropyridine-3,5-dicarboxamide (211 mg, 0.49 mmol, 77% yield) as a purple oil which solidified to a light purple solid.

LCMS (2 min High pH): Rt=0.72 min, [MH]$^+$=406.4.

Example 81: 1-((1H-Indol-4-yl)methyl)-$N^5$-((1R,5S,6s)-3-acetyl-3-azabicyclo[3.1.0]hexan-6-yl)-$N^3$-methyl-2-oxo-1,2-dihydropyridine-3,5-dicarboxamide

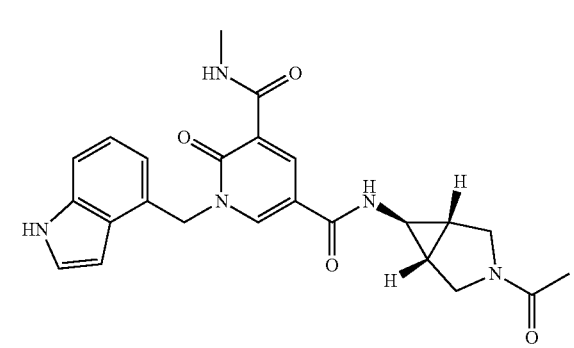 [SMILES: CNC(=O)c1cc(C(=O)N[C@H]2[C@@H]3CN(C(C)=O)C[C@@H]32)cn(Cc2cccc3[nH]ccc23)c1=O]

1-((1H-Indol-4-yl)methyl)-$N^5$-((1R,5S,6s)-3-azabicyclo[3.1.0]hexan-6-yl)-$N^3$-methyl-2-oxo-1,2-dihydropyridine-3,5-dicarboxamide (50 mg, 0.123 mmol) was suspended in DCM. Et$_3$N (34 µL, 0.25 mmol) then acetyl chloride (9.7 µL, 0.14 mmol) was added and the reaction became a clear orange oil. The reaction was stirred for 1 h and then diluted with DCM (10 mL) and washed with sat. aq. NaHCO$_3$ solution (10 mL), then eluted through a hydrophobic frit and concentrated in vacuo to give an orange solid. The crude product was purified by MDAP (high pH). The appropriate fractions were concentrated in vacuo to give 1-((1H-indol-4-yl)methyl)-N⁵-((1R,5S,6s)-3-acetyl-3-azabicyclo[3.1.0]hexan-6-yl)-N³-methyl-2-oxo-1,2-dihydropyridine-3,5-dicarboxamide (24.4 mg, 0.05 mmol, 42% yield) as a cream solid.

LCMS (2 min High pH): Rt=0.76 min, [MH]⁺=448.4.

Example 82: (R)-1-benzyl-N³-ethyl-N⁵-(3-(3-fluoropiperidin-3-yl)propyl-2-oxo-1,2-dihydropyridine-3,5-dicarboxamide

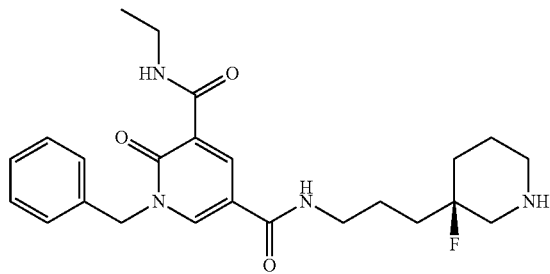 [SMILES: CCNC(=O)c1cc(C(=O)NCCC[C@]2(F)CCCNC2)cn(Cc2ccccc2)c1=O]

To a solution of (S)-tert-butyl 3-(3-(1-benzyl-5-(ethylcarbamoyl)-6-oxo-1,6-dihydropyridine-3-carboxamido)propyl)-3-fluoropiperidine-1-carboxylate (105 mg, 0.193 mmol) in dichloromethane (DCM) (1 mL) was added 2,2,2-trifluoroacetic acid (0.2 ml, 2.60 mmol) and reaction mixture was stirred during 3 hours. The reaction mixture was concentrated under vacuum. Purification by SCX 2 g (eluent 2M NH3 in MeOH). The desired fractions were combined and concentrated in vacuo to give (R)-1-benzyl-N³-ethyl-N⁵-(3-(3-fluoropiperidin-3-yl)propyl)-2-oxo-1,2-dihydropyridine-3,5-dicarboxamide (84 mg, 0.171 mmol, 88% yield).

LCMS (2 min Formic): Rt=0.62 min, [MH]⁺=443.2

Example 83: (R)-1-benzyl-N³-ethyl-N⁵-(2-(morpholin-2-yl)ethyl)-2-oxo-1,2-dihydropyridine-3,5-dicarboxamide

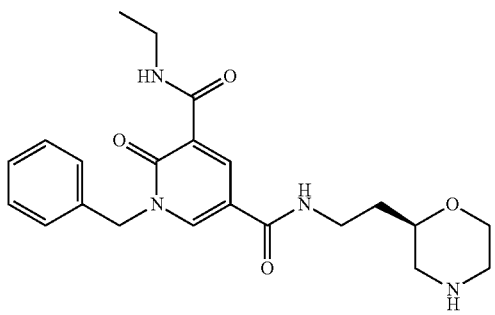 [SMILES: CCNC(=O)c1cc(C(=O)NCC[C@@H]2CNCCO2)cn(Cc2ccccc2)c1=O]

To a solution of (R)-tert-butyl 2-(2-(1-benzyl-5-(ethylcarbamoyl)-6-oxo-1,6-dihydropyridine-3-carboxamido)ethyl)morpholine-4-carboxylate (125 mg, 0.244 mmol) in dichloromethane (1 mL) was added 2,2,2-trifluoroacetic acid (0.2 mL, 2.60 mmol) and reaction mixture was stirred during 3 hours. The reaction mixture was concentrated under vacuum. Purification by SCX 2 g (eluent 2M NH₃ in MeOH). The desired fractions were combined and concentrated in vacuo to give (R)-1-benzyl-N³-ethyl-N⁵-(2-(morpholin-2-yl)ethyl)-2-oxo-1,2-dihydropyridine-3,5-dicarboxamide (80 mg, 0.175 mmol, 71.6% yield). LCMS (2 min Formic): Rt=0.59 min, [MH]⁺=413.2

Example 84: (R)-1-benzyl-N³-ethyl-N⁵-(3-(morpholin-2-yl)propyl)-2-oxo-1,2-dihydropyridine-3,5-dicarboxamide

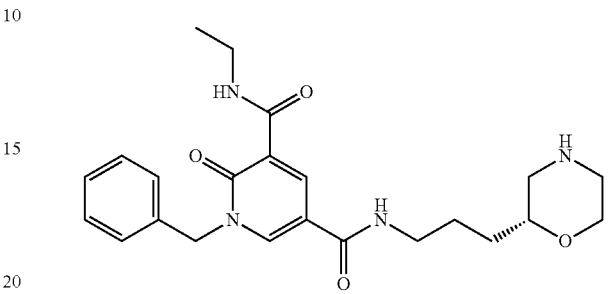

To a solution of (R)-tert-butyl 2-(3-(1-benzyl-5-(ethylcarbamoyl)-6-oxo-1,6-dihydropyridine-3-carboxamido)propyl)morpholine-4-carboxylate (100 mg, 0.190 mmol) in dichloromethane (1 mL) was added 2,2,2-trifluoroacetic acid (0.15 mL, 1.947 mmol) and reaction mixture was stirred during 2 hours. The reaction mixture was concentrated under vacuum. Purification by SCX 2 g (eluent 2M NH3 in MeOH). The desired fractions were combined and concentrated in vacuo to give the title compound (77.5 mg, 0.164 mmol, 86% yield).

LCMS (2 min Formic): Rt=0.62 min, [MH]⁺=427.3

Example 85: tert-Butyl (2-((1R,5S,6s)-6-(1-((1H-indol-4-yl)methyl)-5-(methylcarbamoyl)-6-oxo-1,6-dihydropyridine-3-carboxamido)-3-azabicyclo[3.1.0]hexan-3-yl)ethyl)carbamate

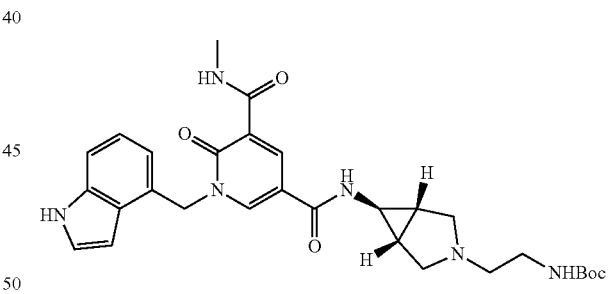

1-((1H-Indol-4-yl)methyl)-N⁵-((1R,5S,6s)-3-azabicyclo[3.1.0]hexan-6-yl)-N³-methyl-2-oxo-1,2-dihydropyridine-3,5-dicarboxamide (50 mg, 0.123 mmol) and tert-butyl (2-oxoethyl)carbamate (29.4 mg, 0.19 mmol, commercially available from, for example, Sigma-Aldrich) were combined in DCM (2 mL) and stirred at rt for 30 min. Sodium triacetoxyborohydride (39.2 mg, 0.19 mmol) was added and stirring at rt continued overnight. The reaction was quenched with sat. aq. NaHCO₃ solution (5 mL) and then stirred for 20 min. The mixture was extracted with DCM (10 mL×2) and the combined organics eluted through a hydrophobic frit then concentrated in vacuo to a clear oil. The crude product was applied to a 10 g SNAP cartridge in the minimum of DCM and eluted with 5-50% (3:1 EtOAc:EtOH) in cyclohexane. The appropriate fractions were concentrated in vacuo give tert-butyl (2-((1R,5S,6s)-6-(1-((1H-indol-4-yl)

methyl)-5-(methylcarbamoyl)-6-oxo-1,6-dihydropyridine-3-carboxamido)-3-azabicyclo[3.1.0]hexan-3-yl)ethyl)carbamate (10 mg, 0.02 mmol, 14% yield) as a cream solid. Some mixed fractions were observed and these were recolumned by dry loading onto silica and using the same column conditions as above, but again no separation was seen, so the crude product was purified by MDAP (high pH). The appropriate fraction was concentrated in vacuo to give further tert-butyl (2-((1R,5S,6s)-6-(1-((1H-indol-4-yl)methyl)-5-(methylcarbamoyl)-6-oxo-1,6-dihydropyridine-3-carboxamido)-3-azabicyclo[3.1.0]hexan-3-yl)ethyl)carbamate (4.1 mg, 7.10 μmol, 5.76% yield) as a cream solid. LCMS (2 min High pH): Rt=1.00 min, [MH]$^+$=549.2.

Example 86: 1-((1H-Indol-4-yl)methyl)-N$^5$-((1R,5S,6s)-3-(2-aminoethyl)-3-azabicyclo[3.1.0]hexan-6-yl)-N$^3$-methyl-2-oxo-1,2-dihydropyridine-3,5-dicarboxamide

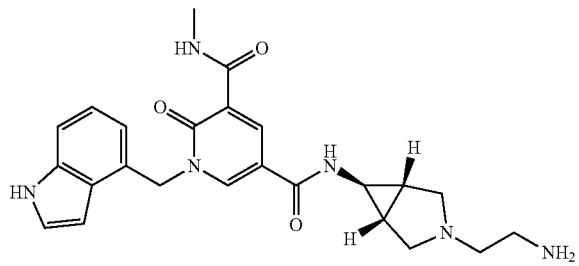 [SMILES: CNC(=O)c1cc(C(=O)N[C@H]2[C@@H]3CN(CCN)C[C@@H]32)cn(Cc2cccc3[nH]ccc23)c1=O]

tert-Butyl (2-((1R,5S,6s)-6-(1-((1H-indol-4-yl)methyl)-5-(methylcarbamoyl)-6-oxo-1,6-dihydropyridine-3-carboxamido)-3-azabicyclo[3.1.0]hexan-3-yl)ethyl)carbamate (83 mg, 0.151 mmol) was taken up in DCM (5 mL) and TFA (0.5 mL, 6.49 mmol) was added. The reaction was stirred at rt for 2.5 h and then concentrated in vacuo. The crude product was purified by MDAP (high pH). The appropriate fractions were concentrated in vacuo to give 1-((1H-indol-4-yl)methyl)-N$^5$-((1R,5S,6s)-3-(2-aminoethyl)-3-azabicyclo[3.1.0]hexan-6-yl)-N$^3$-methyl-2-oxo-1,2-dihydropyridine-3,5-dicarboxamide (19.7 mg, 0.04 mmol, 28% yield) as a cream solid.
LCMS (2 min High pH): Rt=0.79 min, [MH]$^+$=449.4.

Example 87: 1-((1H-Indol-4-yl)methyl)-N$^5$-((1R,5S,6s)-3-(2-acetamidoethyl)-3-azabicyclo[3.1.0]hexan-6-yl)-N$^3$-methyl-2-oxo-1,2-dihydrouridine-3,5-dicarboxamide

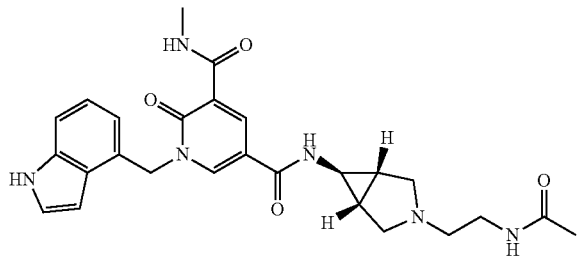 [SMILES: CNC(=O)c1cc(C(=O)N[C@H]2[C@@H]3CN(CCNC(C)=O)C[C@@H]32)cn(Cc2cccc3[nH]ccc23)c1=O]

1-((1H-Indol-4-yl)methyl)-N$^5$-((1R,5S,6s)-3-(2-aminoethyl)-3-azabicyclo[3.1.0]hexan-6-yl)-N$^3$-methyl-2-oxo-1,2-dihydropyridine-3,5-dicarboxamide (12 mg, 0.03 mmol) was suspended in DCM (2 mL). Et$_3$N (7.5 μL, 0.05 mmol) then AcCl (2.3 μL, 0.03 mmol) was added and the reaction stirred at rt for 4 h. The reaction was concentrated and purified by MDAP (high pH). The appropriate fractions were concentrated in vacuo to give 1-((1H-indol-4-yl)methyl)-N$^5$-((1R,5S,6s)-3-(2-acetamidoethyl)-3-azabicyclo[3.1.0]hexan-6-yl)-N$^3$-methyl-2-oxo-1,2-dihydropyridine-3,5-dicarboxamide (7.8 mg, 0.02 mmol, 57% yield) as a cream solid.

LCMS (2 min high pH): Rt=0.76 min, [MH]$^+$=491.4.

Example 88: N$^5$-(3-((2r,5r)-5-Amino-1,3-dioxan-2-yl)propyl)-1-benzyl-N$^3$-methyl-2-oxo-1,2-dihydropyridine-3,5-dicarboxamide

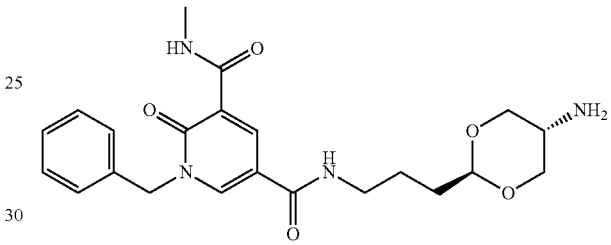

To a suspension of 1-benzyl-N$^5$-(3-((2r,5r)-5-(1,3-dioxoisoindolin-2-yl)-1,3-dioxan-2-yl)propyl)-N$^{3}$-methyl-2-oxo-1,2-dihydropyridine-3,5-dicarboxamide (117 mg, 0.21 mmol) in ethanol (1 mL) was added hydrazine hydrate (0.030 mL, 0.628 mmol). The resulting suspension was stirred at rt for 2 h. Further ethanol (3 mL) was added to aid stirring and further hydrazine hydrate (0.030 mL, 0.628 mmol) was added. The reaction was stirred for a further ~2 h and then overnight. The reaction was then heated at 40° C. for ~7.5 h in total. The reaction mixture was allowed to cool, after which it was filtered and the solid washed with ethanol (3×5 mL). The filtrate was evaporated in vacuo to give a white solid. This was redissolved in DMSO (1.8 mL) and directly purified by MDAP (2×1 mL injections, formic). The required fractions were passed through a 20 g NH$_2$ SPE cartridge and eluted with MeOH. The filtrate was evaporated in vacuo to give a poorly soluble white solid which was taken up in 10% MeOH/DCM (10 mL) and partitioned with water (20 mL). The layers were separated and the aqueous layer extracted with further 10% MeOH/DCM (2×10 mL). The combined organics were dried (Na$_2$SO$_4$) and concentrated in vacuo to afford the desired product as a white solid—N$^5$-(3-((2r,5r)-5-amino-1,3-dioxan-2-yl)propyl)-1-benzyl-N$^3$-methyl-2-oxo-1,2-dihydropyridine-3,5-dicarboxamide (40 mg, 0.09 mmol, 45% yield)

LCMS (2 min formic): Rt=0.54 min, [MH]$^+$=429.4.

| Ex No. | Name | Structure | Mass (mg) | Yield (%) | [MH]+ | Rt (min)* |
|---|---|---|---|---|---|---|
| 89 | 1-benzyl-N³-methyl-2-oxo-N⁵-(2-(piperidin-4-yloxy)ethyl)-1,2-dihydropyridine-3,5-dicarboxamide hydrochloride | 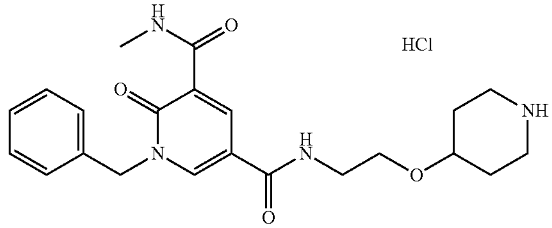 [SMILES: CNC(=O)c1cc(C(=O)NCCOC2CCNCC2)cn(Cc2ccccc2)c1=O ; Cl] | 2.2 | 100 | 413 | 0.52 |
| 90 | 1-benzyl-N³-methyl-N⁵-(1-(methylsulfonyl)azetidin-3-yl)-2-oxo-1,2-dihydropyridine-3,5-dicarboxamide | 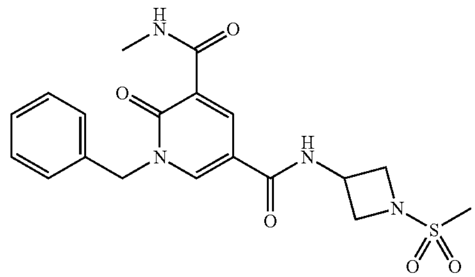 [SMILES: CNC(=O)c1cc(C(=O)NC2CN(S(C)(=O)=O)C2)cn(Cc2ccccc2)c1=O] | 53.8 | 89 | 342 | 0.75 |
| 91 | 1-benzyl-N³-methyl-N⁵-(oxetan-3-yl)-2-oxo-1,2-dihydropyridine-3,5-dicarboxamide | 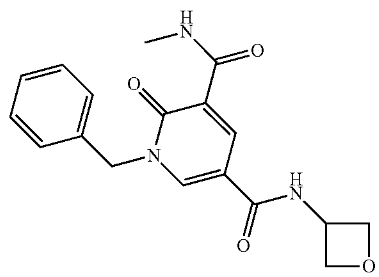 [SMILES: CNC(=O)c1cc(C(=O)NC2COC2)cn(Cc2ccccc2)c1=O] | 68.0 | 92 | 419 | 0.80 |

Biological Data

The compounds of formula (I) may be tested in one or more of the following assays:

Time Resolved Fluorescence Resonance Energy Transfer (TR-FRET) Assay

Bromodomain binding was assessed utilising a time resolved fluorescent resonance energy transfer (TR-FRET) competition assay. To enable this approach a known, high affinity, pan-BET interacting small molecule was labelled with Alexa Fluor® 647, which is a far-red-fluorescent dye (Reference Compound X). Reference Compound X acts as a reporter of bromodomain binding and is the acceptor fluorophore component of the TR-FRET pair. Europium chelate, conjugated to an anti-6*His antibody, was utilised as the donor fluorophore in the TR-FRET pair. The anti-6*His antibody binds selectively to a six Histidine purification epitope added to the amino-terminus of each of the BET tandem bromodomain protein constructs used in this study. A TR-FRET signal is generated when the donor and acceptor fluorophores are in close proximity, between 20-80 A, which is enabled in this assay by binding of Reference Compound X to the bromodomain protein.

Reference Compound X: 4-((Z)-3-(6-((5-(2-((4S)-6-(4-chlorophenyl)-8-methoxy-1-methyl-4H-benzo[f][1,2,4]tri-azolo[4,3-a][1,4]diazepin-4-yl)acetamido)pentyl)amino)-6-oxohexyl)-2-((2E,4E)-5-(3,3-dimethyl-5-sulfo-1-(4-sulfobutyl)-3H-indol-1-ium-2-yl)penta-2,4-dien-1-ylidene)-3-methyl-5-sulfoindolin-1-yl)butane-1-sulphonate)

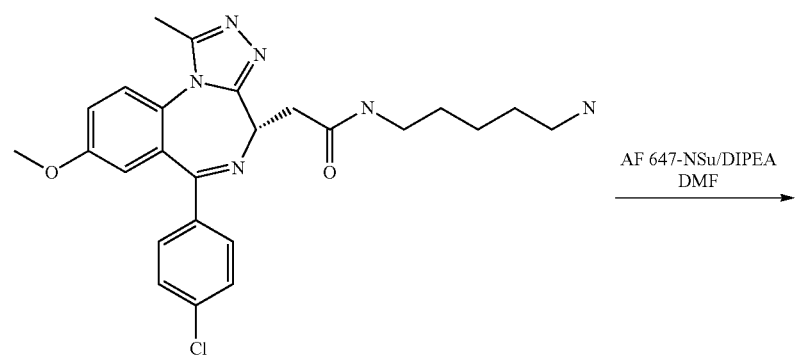

AF 647-NSu/DIPEA
DMF

-continued

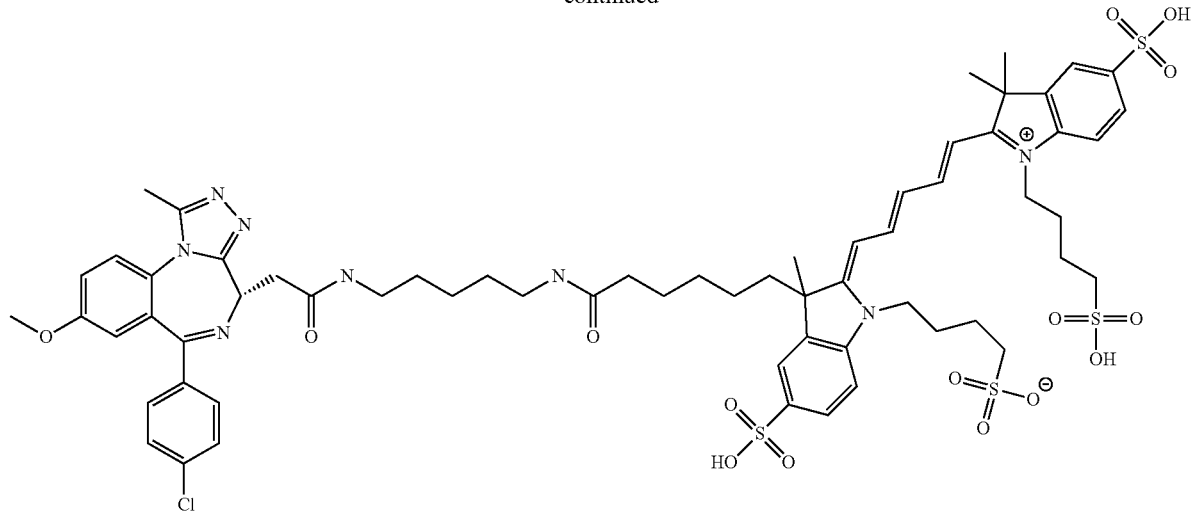

To a solution of N-(5-aminopentyl)-2-((4S)-6-(4-chlorophenyl)-8-methoxy-1-methyl-4H-benzo[f][1,2,4]triazolo[4,3-a][1,4]diazepin-4-yl)acetamide (for a preparation see Reference Compound J, WO2011/054848A1, 1.7 mg, 3.53 μmol) in DMF (40 μl) was added a solution of AlexaFluor647-ONSu (2.16 mg, 1.966 μmol) also in DMF (100 μl). The mixture was basified with DIPEA (1 μl, 5.73 μmol) and agitated overnight on a vortex mixer.

The reaction mixture was evaporated to dryness. The solid was dissolved in acetonitrile/water/acetic acid (5/4/1, <1 ml) filtered and was applied to a Phenomenex Jupiter C18 preparative column and eluted with the following gradient (A=0.1% trifluoroacetic acid in water, B=0.1% TFA/90% acetonitrile/10% water): Flow rate=10 ml/min., AU=20/10 (214 nm):

5-35%, t=0 min: B=5%; t=10 min: B=5%; t=100 min: B=35%; t=115 min: B=100% (Sep. grad: 0.33%/min)

The major component was eluted over the range 26-28% B but appeared to be composed of two peaks. The middle fraction (F1.26) which should contain "both" components was analysed by analytical HPLC (Spherisorb ODS2, 1 to 35% over 60 min): single component eluting at 28% B.

Fractions F1.25/26&27 were combined and evaporated to dryness. Transferred with DMF, evaporated to dryness, triturated with dry ether and the blue solid dried overnight at <0.2 mbar: 1.54 mg.

Analytical HPLC (Sphersisorb ODS2, 1 to 35% B over 60 min): MSM10520-1: $[M+H]^+$ (obs): 661.8/—corresponding with M-29. This equates to $[(M+2H)/2]^+$ for a calculated mass of 1320.984 which is M-29. This is a standard occurrence with the Alexa Fluor 647 dye and represents a theoretical loss of two methylene groups under the conditions of the mass spectrometer.

Assay Principle:

In order to generate a TR-FRET signal, donor fluorophore is excited by a laser at λ337 nm, which subsequently leads to emission at λ618 nm. If the acceptor fluorophore is in close proximity then energy transfer can occur, which leads to emission of Alexa Fluor® 647 at λ665 nm. In the presence of competitor compound, Reference Compound X can be displaced from binding to the bromodomain. If displacement occurs, the acceptor fluorophore is no longer in proximity to the donor fluorophore, which prevents fluorescent energy transfer and, subsequently, a loss of Alexa Fluor® 647 emission at λ665 nm.

The competition of the compounds of formula (I) with Reference Compound X for binding to the BET family (BRD2, BRD3, BRD4 and BRDT) was assessed using protein truncates spanning both bromodomain 1 (BD1) and bromodomain 2 (BD2). In order to monitor differential binding to either BD1 or BD2, single residue mutations of key tyrosines to alanine were made in the acetyl lysine binding pockets. To validate this approach, a double residue mutant tandem domain protein was produced for each of the BET family members. Utilising a Fluorescence Polarisation approach, binding affinities for each of the single and double mutants for Reference Compound X were determined. The affinities of the double mutant tandem proteins for Reference Compound X were greatly greatly reduced in comparison to the non mutated, wild type tandem BET proteins (>1000 fold reduction in Kd). The affinities of the single mutated bromdomain tandem proteins for Reference Compound X were equi-potent with the corresponding non-mutated BET protein. These data demonstrated that single mutations of Tyrosine to Alanine reduce the Kd of the interaction between the mutated bromodomain and Reference Compound X by >1000 fold. In the TR-FRET competition assay, Reference Compound X is used at a concentration that is equivalent to the Kd for the non-mutated bromodomain, which ensures that no binding at the mutated bromodomain is detected.

Protein Production:

Recombinant Human Bromodomains [(BRD2 (1-473) (Y113A) and (Y386A), BRD3 (1-435) (Y73A) and (Y348A) BRD4 (1-477) (Y97A) and (Y390A) and BRDT (1-397) (Y66A) and (Y309A)] were expressed in E. coli cells (in pET15b vector for BRD2/3/4 and in pET28a vector for BRDT) with a 6-His tag at the N-terminal. The His-tagged Bromodomain pellet was resuspended in 50 mM HEPES (pH7.5), 300 mM NaCl, 10 mM imidazole & 1 μl/ml protease inhibitor cocktail and extracted from the E. coli cells using sonication and purified using a nickel sepharose high performance column, the proteins were washed and then eluted with a linear gradient of 0-500 mM imidazole with buffer 50 mM HEPES (pH7.5), 150 mM NaCl, 500 mM imidazole, over 20 column volumes. Final purification was completed by Superdex 200 prep grade size exclusion column. Purified protein was stored at −80° C. in 20 mM HEPES pH 7.5 and 100 mM NaCl. Protein identity was confirmed by peptide mass fingerprinting and predicted molecular weight confirmed by mass spectrometry.

Protocol for Bromodomain BRD2, 3, 4 and T, BD1+BD2 Mutant TR-FRET Competition Assays:

All assay components were dissolved in an assay buffer composing of 50 mM HEPES pH7.4, 50 mM NaCl, 5% Glycerol, 1 mM DTT and 1 mM CHAPS. Reference Compound X was diluted, in assay buffer containing 20 nM single mutant, tandem bromodomain protein, to a concentration equivalent to 2*Kd for this bromodomain. The solution containing bromodomain and Reference Compound X was added to dose response dilutions of test compound or DMSO vehicle (a maximum of 0.5% DMSO is used in this assay) in Greiner 384 well black low volume microtitre plates and subsequently incubated for 30 minutes at room temperature. An equal volume of 3 nM of anti-6*His Europium chelate was added to all wells, followed by a further 30 minute incubation at room temperature. TR-FRET was detected using a Perkin Elmer Multimode plate reader, by exciting the donor fluorophore at λ337 nm and subsequently, after a delay of 50 μsecs, measuring emission of the donor and acceptor fluorophores at λ615 nm and λ665 nm, respectively. In order to control these assays, 16 replicates each of uninhibited (DMSO vehicle) and inhibited ($10*IC_{50}$ concentrations of Example 11 of WO 2011/054846A1) TR-FRET assays were included on every microtitre plate.

cA four parameter curve fit of the following form was then applied:

$$y=a+((b-a)/(1+(10\hat{\,}x/10\hat{\,}c)\hat{\,}d)$$

Where '$a$' is the minimum, '$b$' is the Hill slope, '$c$' is the $pIC_{50}$ and 'd is the maximum.

All compounds (Examples 1-61) were each tested in the BRD4 BD1 and the BRD4 BD2 TR-FRET assays described above.

All compounds were found to have a $pIC_{50} \geq 4.5$ in at least one assay.

Examples 34, 35, 38, 39, 42, 48 and 53 were found to have a $pIC_{50} \geq 4.0$ and <6.0 in the BRD4 BD2 assay.

Examples 1, 4, 5, 8, 9, 13, 20, 27, 31, 32, 33, 36, 37, 40, 41, 43-47, 49-52, 59, 64-68, 78, 83 and 89-91 were found to have a $pIC_{50} \geq 6.0$ and <7.0 in the BRD4 BD2 assay.

Examples 2, 3, 6a, 6b, 7, 10, 11, 12, 14-19, 21-26, 28-30, 54-58, 60-63, 69-77, 79-82 and 84-88 were found to have a $pIC_{50} \geq 7.0$ in the BRD4 BD2 assay.

Specific data for a selection of Examples is shown in the table below:

| Ex. No. | BRD4 BD2 $IC_{50}$ (average value) | N (total number of values recorded) |
| --- | --- | --- |
| 6a | 7.5 | 8 |
| 7 | 7.5 | 6 |
| 23 | 7.3 | 2 |
| 25 | 7.4 | 6 |
| 29 | 7.6 | 3 |
| 30 | 8 | 3 |
| 56 | 7.8 | 3 |
| 88 | 7.3 | 2 |

Those of skill in the art will recognise that in vitro binding assays and cell-based assays for functional activity are subject to experimental variability. Accordingly, it is to be understood that the $pIC_{50}$ values given above are exemplary only.

Calculation of selectivity for BRD4 BD2 over BRD4 BD1
Selectivity for BRD4 BD2 over BRD4 BD1 was calculated as follows:

Selectivity=$BRD4BD2pIC_{50}-BRD4BD1pIC_{50}$ $pIC_{50}$ values are expressed as $log_{10}$ units.

With the exception of Examples 33, 34, 38 and 39 all tested compounds were found to have selectivity for BRD4 BD2 over BRD4 BD1 of ≥1 log unit in at least one of the TR-FRET assays described above, hence are at least 10 fold selective for BRD4 BD2 over BRD4 BD1.

Examples 1-30 and 54-88 were found to have selectivity for BRD4 BD2 over BRD4 BD1 of ≥2 log unit in at least one of the TR-FRET assays described above, hence are at least 100 fold selective for BRD4 BD2 over BRD4 BD1.

The invention claimed is:

1. A compound of formula (I)

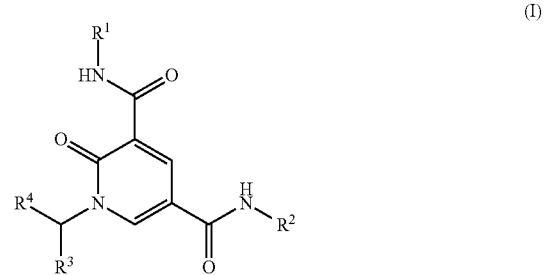

or a pharmaceutically acceptable salt thereof:
wherein
$R^1$ is $C_{1-3}$ alkyl or cyclopropyl;
$R^2$ is —$(CH_2)_n$—$C_{4-10}$heterocyclyl or —$(CH_2)_p$O—$C_{4-10}$heterocyclyl,
wherein each $C_{4-10}$heterocyclyl is optionally substituted by one or two substituents independently selected from halo, $C_{1-4}$alkyl, $C_{3-4}$cycloalkyl, —$CH_2CF_3$, —$CH_2CHF_2$, —$CH_2CH_2F$, —$OR^5$, —$OCH_2CH_2OR^5$, —$CH_2OR^5$, —$CH_2CH_2OR^5$, —$NR^6R^7$, —$CH_2NR^6R^7$, —$CH_2CH_2NR^6R^7$, —$NHCH_2CH_2OR^5$, —$NHCO_2C(CH_3)_3$, oxo, —$CO_2H$, —$SO_2C_{1-3}$ alkyl, —$CO_2C(CH_3)_3$, and —$C(O)R^5$;
$R^3$ is phenyl, $C_{5-6}$heteroaryl, $C_{9-11}$heteroaryl, or —$(CH_2)_m$-phenyl;
wherein said phenyl is optionally substituted by one, two, or three $R^8$ groups which may be the same or different; said $C_{5-6}$ heteroaryl is optionally substituted by $C_{1-3}$ alkyl, $C_{1-3}$alkoxy, or halo; or said $C_{9-11}$heteroaryl is optionally substituted by one, two, or three groups independently selected from —$C_{1-3}$ alkylR$^9$, —$OCH_3$, —$OC_{2-3}$ alkylR$^9$, halo, oxo, and cyano;
$R^4$ is —H, $C_{1-4}$ alkyl, cyclopropyl, —$CH_2OR^{10}$, or —$CH_2CH_2OR^{10}$;
$R^5$ is —H or $C_{1-3}$ alkyl;
$R^6$ and $R^7$ are each independently selected from —H, $C_{1-3}$alkyl, $COC_{1-3}$alkyl, and $CO_2C_{1-4}$ alkyl; or $R^6$ and $R^7$ taken together with the nitrogen to which they are attached form a $C_{4-7}$ heterocyclyl optionally containing a further heteroatom selected from nitrogen, oxygen, and sulphur and optionally substituted by one or two substituents independently selected from $C_{1-3}$alkyl, —OH, and fluoro;
$R^8$ is —$NR^{11}R^{12}$, halo, —CN, —$CH_2CN$, —$CO_2R^{10}$, —$C(O)C_{1-3}$ alkyl, —OH, —$OCHF_2$, —$OCF_3$, —O—$C_{2-6}$ alkylR$^9$, —$OCH_3$, —$CH_2CH_2NR^{11}R^{12}$, —$C_{1-6}$alkylR$^9$, —$OC_6$heterocyclyl, —OCH₂C₆heterocyclyl, —CH₂C₆heterocyclyl, —CH₂CH₂C₆heterocyclyl, —CO₂CH₃, —NHC(O)R¹⁰, —SO₂R¹⁰, or —SOR¹⁰;

R⁹ is —H, —OR¹⁰, or —NR¹¹R¹²;

R¹⁰ is —H or C₁₋₃alkyl;

R¹¹ and R¹² are each independently selected from —H and C₁₋₃alkyl; or R¹¹ and R¹² taken together with the nitrogen to which they are attached form a C₄₋₇heterocyclyl optionally containing a further heteroatom selected from nitrogen, oxygen, and sulphur and optionally substituted by one or two substituents independently selected from C₁₋₃alkyl, —OH, and fluoro;

n is an integer selected from 0, 1, 2, 3, and 4;

m is an integer selected from 1 and 2; and p is an integer selected from 2 and 3.

2. The compound or pharmaceutically acceptable salt thereof according to claim 1, wherein R¹ is methyl.

3. The compound or pharmaceutically acceptable salt thereof according to claim 1, wherein R² is —(CH₂)ₙ—C₄₋₁₀ heterocyclyl, wherein C₄₋₁₀ heterocyclyl is selected from tetrahydro-2H-pyranyl, piperidinyl, azetidinyl, tetrahydrofuranyl, pyrrolidinyl, piperazinyl, morpholinyl, tetrahydro-2H-thiopyranyl, tetrahydrothiophenyl, thiomorpholinyl, and 2-oxabicyclo[4.2.0]octanyl;

wherein tetrahydro-2H-pyranyl, piperidinyl, azetidinyl, tetrahydrofuranyl, pyrrolidinyl, piperazinyl, morpholinyl, tetrahydro-2H-thiopyranyl, tetrahydrothiophenyl, thiomorpholinyl, or 2-oxabicyclo[4.2.0]octanyl is optionally substituted by one or two substituents independently selected from halo, C₁₋₄ alkyl, phenyl, —CH₂CF₃, —CH₂CHF₂, —CH₂CH₂F, —OR⁵, —OCH₂CH₂OR⁵, —CH₂CH₂OR⁵, —NR⁶R⁷, —NHCH₂CH₂OR⁵, —NHCO₂C(CH₃)₃, oxo, —CO₂H, —CO₂C(CH₃)₃, and —C(O)R⁵.

4. The compound or pharmaceutically acceptable salt thereof according to claim 3, wherein R² is —(CH₂)ₙ—C₄₋₁₀ heterocyclyl, wherein C₄₋₁₀ heterocyclyl is piperidinyl or morpholinyl, wherein piperidinyl or morpholinyl is optionally substituted by one or two substituents independently selected from halo, C₁₋₄ alkyl, —CH₂CF₃, —CH₂CHF₂, —CH₂CH₂F, —OR⁵, —OCH₂CH₂OR⁵, —CH₂CH₂OR⁵, —NR⁶R⁷, —NHCH₂CH₂OR⁵, —NHCO₂C(CH₃)₃, oxo, —CO₂H, —CO₂C(CH₃)₃, and —C(O)R⁵.

5. The compound or pharmaceutically acceptable salt thereof according to claim 4, wherein piperidinyl or morpholinyl is optionally substituted by one or two substituents independently selected from fluoro, methyl, —CH₂CF₃, —CH₂CHF₂, —CH₂CH₂F, —OH, —CH₂CH₂OH, —CO₂C(CH₃)₃ —C(O)CH₃, and —C(O)CH₃.

6. The compound or pharmaceutically acceptable salt thereof according to claim 3, wherein the C₄₋₁₀ heterocyclyl is selected from:

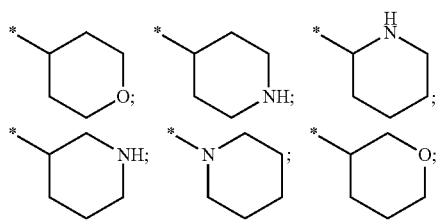

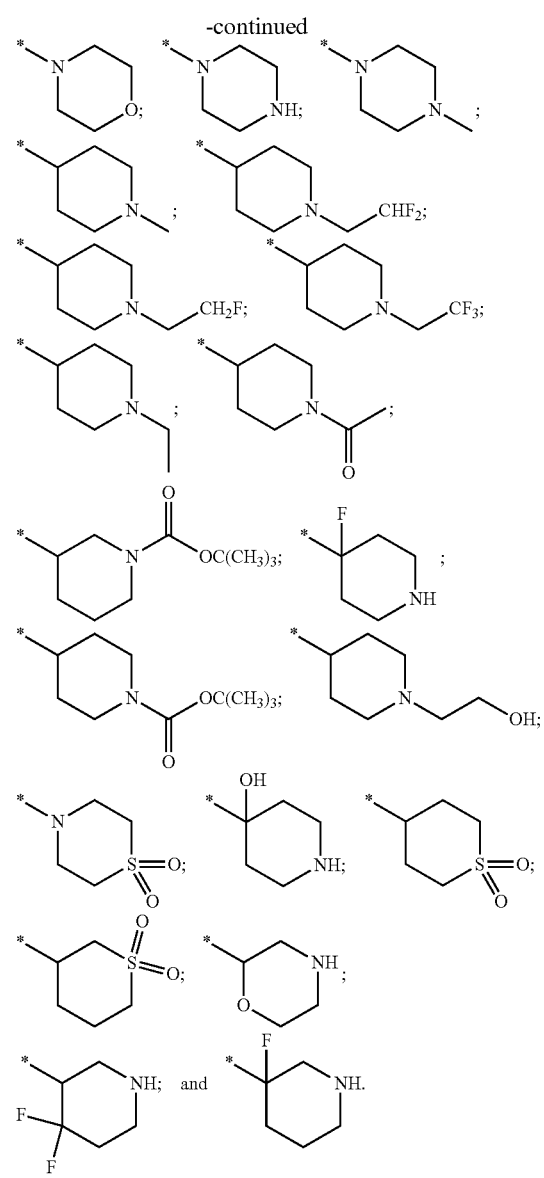

7. The compound or pharmaceutically acceptable salt thereof according to claim 1, wherein n is 3.

8. The compound or pharmaceutically acceptable salt thereof according to claim 1, wherein R³ is phenyl optionally substituted by one or two R⁸ groups independently selected from halo, O—C₁₋₆ alkylR⁹, and —C₁₋₆ alkylR⁹.

9. The compound or pharmaceutically acceptable salt thereof according to claim 8, wherein R³ is phenyl optionally substituted by one or two R⁸ groups independently selected from fluoro, —OCH₃, —OCH₂CH₂OH, and methyl.

10. The compound or pharmaceutically acceptable salt thereof according to claim 1, wherein R³ is unsubstituted indolyl.

11. The compound or pharmaceutically acceptable salt thereof according to claim 1, wherein R⁴ is —H or methyl.

12. The compound or pharmaceutically acceptable salt thereof according to claim 1, wherein p is 2.

13. The compound or pharmaceutically acceptable salt thereof according to claim 1, wherein R⁵ and R¹⁰ are each independently selected from —H and methyl.

14. The compound according to claim 1 which is:
1-benzyl-N3-methyl-2-oxo-N5-(2-(tetrahydro-2H-pyran-4-yl)ethyl)-1,2-dihydropyridine-3,5-dicarboxamide;
1-benzyl-N3-methyl-2-oxo-N5-(2-(piperidin-4-yl)ethyl)-1,2-dihydropyridine-3,5-dicarboxamide;
1-benzyl-N3-methyl-N5-(2-(1-methylpiperidin-4-yl)ethyl)-2-oxo-1,2-dihydropyridine-3,5-dicarboxamide;
tert-butyl 3-(1-benzyl-5-(methylcarbamoyl)-6-oxo-1,6-dihydropyridine-3-carboxamido)azetidine-1-carboxylate;
tert-butyl 4-(3-(1-benzyl-5-(methylcarbamoyl)-6-oxo-1,6-dihydropyridine-3-carboxamido)propyl)piperidine-1-carboxylate;
1-benzyl-N3-methyl-2-oxo-N5-(3-(piperidin-4-yl)propyl)-1,2-dihydropyridine-3,5-dicarboxamide;
1-benzyl-N3-methyl-N5-(3-(1-methylpiperidin-4-yl)propyl)-2-oxo-1,2-dihydropyridine-3,5-dicarboxamide;
N5-(3-(1-acetylpiperidin-4-yl)propyl)-1-benzyl-N3-methyl-2-oxo-1,2-dihydropyridine-3,5-dicarboxamide;
1-benzyl-N3-methyl-2-oxo-N5-(2-(tetrahydrofuran-3-yl)ethyl)-1,2-dihydropyridine-3,5-dicarboxamide;
1-benzyl-N3-methyl-2-oxo-N5-(3-(1-(2,2,2-trifluoroethyl)piperidin-4-yl)propyl)-1,2-dihydropyridine-3,5-dicarboxamide;
1-benzyl-N5-(3-(1-ethylpiperidin-4-yl)propyl)-N3-methyl-2-oxo-1,2-dihydropyridine-3,5-dicarboxamide;
1-benzyl-N3-methyl-2-oxo-N5-(3-(piperazin-1-yl)propyl)-1,2-dihydropyridine-3,5-dicarboxamide;
1-benzyl-N5-(2-(1,1-dioxidotetrahydro-2H-thiopyran-4-yl)ethyl)-N3-methyl-2-oxo-1,2-dihydropyridine-3,5-dicarboxamide;
1-(2-fluorobenzyl)-N3-methyl-2-oxo-N5-(3-(piperidin-4-yl)propyl)-1,2-dihydropyridine-3,5-dicarboxamide;
N3-methyl-1-(3-methylbenzyl)-2-oxo-N5-(3-(piperidin-4-yl)propyl)-1,2-dihydropyridine-3,5-dicarboxamide;
N3-methyl-1-(3-methylbenzyl)-2-oxo-N5-(2-(piperidin-4-yl)ethyl)-1,2-dihydropyridine-3,5-dicarboxamide;
(R)—N3-methyl-2-oxo-1-(1-phenylethyl)-N5-(3-(piperidin-4-yl)propyl)-1,2-dihydropyridine-3,5-dicarboxamide;
(R)—N3-methyl-2-oxo-1-(1-phenylethyl)-N5-(2-(piperidin-4-yl)ethyl)-1,2-dihydropyridine-3,5-dicarboxamide;
1-(3-methoxybenzyl)-N3-methyl-2-oxo-N5-(3-(piperidin-4-yl)propyl)-1,2-dihydropyridine-3,5-dicarboxamide;
1-(3-methoxybenzyl)-N3-methyl-2-oxo-N5-(2-(piperidin-4-yl)ethyl)-1,2-dihydropyridine-3,5-dicarboxamide;
1-(4-fluoro-3-methylbenzyl)-N3-methyl-2-oxo-N5-(3-(piperidin-4-yl)propyl)-1,2-dihydropyridine-3,5-dicarboxamide;
1-(4-fluorobenzyl)-N3-methyl-2-oxo-N5-(3-(piperidin-4-yl)propyl)-1,2-dihydropyridine-3,5-dicarboxamide;
1-(3-(2-hydroxyethoxy)benzyl)-N3-methyl-2-oxo-N5-(3-(piperidin-4-yl)propyl)-1,2-dihydropyridine-3,5-dicarboxamide;
1-(3-(2-hydroxyethoxy)benzyl)-N3-methyl-2-oxo-N5-(2-(piperidin-4-yl)ethyl)-1,2-dihydropyridine-3,5-dicarboxamide;
1-benzyl-N5-(3-(1-(2-hydroxyethyl)piperidin-4-yl)propyl)-N3-methyl-2-oxo-1,2-dihydropyridine-3,5-dicarboxamide;
1-(2-fluoro-3-methylbenzyl)-N3-methyl-2-oxo-N5-(3-(piperidin-4-yl)propyl)-1,2-dihydropyridine-3,5-dicarboxamide;
1-(2-fluoro-3-methylbenzyl)-N3-methyl-2-oxo-N5-(2-(piperidin-4-yl)ethyl)-1,2-dihydropyridine-3,5-dicarboxamide;
1-benzyl-N5-(3-(1-(2,2-difluoroethyl)piperidin-4-yl)propyl)-N3-methyl-2-oxo-1,2-dihydropyridine-3,5-dicarboxamide;
1-benzyl-N5-(3-(1-(2-fluoroethyl)piperidin-4-yl)propyl)-N3-methyl-2-oxo-1,2-dihydropyridine-3,5-dicarboxamide;
1-((1H-indol-4-yl)methyl)-N3-methyl-2-oxo-N5-(3-(piperidin-4-yl)propyl)-1,2-dihydropyridine-3,5-dicarboxamide;
1-benzyl-N3-methyl-2-oxo-N5-(2-(tetrahydro-2H-pyran-3-yl)ethyl)-1,2-dihydropyridine-3,5-dicarboxamide;
tert-butyl 4-(2-(1-benzyl-5-(methylcarbamoyl)-6-oxo-1,6-dihydropyridine-3-carboxamido)ethyl)piperidine-1-carboxylate;
N5-(azetidin-3-yl)-1-benzyl-N3-methyl-2-oxo-1,2-dihydropyridine-3,5-dicarboxamide;
1-benzyl-N3-methyl-N5-(1-methylazetidin-3-yl)-2-oxo-1,2-dihydropyridine-3,5-dicarboxamide;
1-benzyl-N5-(2-oxabicyclo[4.2.0]octan-7-yl)-N3-methyl-2-oxo-1,2-dihydropyridine-3,5-dicarboxamide;
1-benzyl-N3-methyl-N5-(2-(1-methylpyrrolidin-3-yl)ethyl)-2-oxo-1,2-dihydropyridine-3,5-dicarboxamide;
1-benzyl-N3-methyl-N5-(3-morpholinopropyl)-2-oxo-1,2-dihydropyridine-3,5-dicarboxamide;
tert-butyl 3-(2-(1-benzyl-5-(methylcarbamoyl)-6-oxo-1,6-dihydropyridine-3-carboxamido)ethyl)piperidine-1-carboxylate;
1-benzyl-N3-methyl-2-oxo-N5-(2-(piperidin-3-yl)ethyl)-1,2-dihydropyridine-3,5-dicarboxamide;
1-benzyl-N3-methyl-2-oxo-N5-(2-(piperidin-2-yl)ethyl)-1,2-dihydropyridine-3,5-dicarboxamide;
1-benzyl-N3-methyl-2-oxo-N5-(tetrahydro-2H-pyran-4-yl)-1,2-dihydropyridine-3,5-dicarboxamide;
1-benzyl-N5-(1,1-dioxidotetrahydro-2H-thiopyran-3-yl)-N3-methyl-2-oxo-1,2-dihydropyridine-3,5-dicarboxamide;
1-benzyl-N5-(1,1-dioxidotetrahydrothiophen-3-yl)-N3-methyl-2-oxo-1,2-dihydropyridine-3,5-dicarboxamide;
1-benzyl-N5-(1,1-dioxidotetrahydro-2H-thiopyran-4-yl)-N3-methyl-2-oxo-1,2-dihydropyridine-3,5-dicarboxamide;
1-benzyl-N3-methyl-2-oxo-N5-(3-(piperidin-1-yl)propyl)-1,2-dihydropyridine-3,5-dicarboxamide;
(R)-1-benzyl-N3-methyl-2-oxo-N5-((tetrahydro-2H-pyran-3-yl)methyl)-1,2-dihydropyridine-3,5-dicarboxamide;
(S)-1-benzyl-N3-methyl-2-oxo-N5-((tetrahydro-2H-pyran-3-yl)methyl)-1,2-dihydropyridine-3,5-dicarboxamide;
1-benzyl-N5-((1,1-dioxidotetrahydrothiophen-3-yl)methyl)-N3-methyl-2-oxo-1,2-dihydropyridine-3,5-dicarboxamide;
1-benzyl-N3-methyl-2-oxo-N5-((tetrahydro-2H-pyran-4-yl)methyl)-1,2-dihydropyridine-3,5-dicarboxamide;
1-benzyl-N3-methyl-2-oxo-N5-(tetrahydro-2H-pyran-3-yl)-1,2-dihydropyridine-3,5-dicarboxamide;
1-benzyl-N3-methyl-N5-(3-(4-methylpiperazin-1-yl)propyl)-2-oxo-1,2-dihydropyridine-3,5-dicarboxamide;
1-benzyl-N5-(3-(1,1-dioxidothiomorpholino)propyl)-N3-methyl-2-oxo-1,2-dihydropyridine-3,5-dicarboxamide;
1-benzyl-N5-((1,1-dioxidotetrahydro-2H-thiopyran-4-yl)methyl)-N3-methyl-2-oxo-1,2-dihydropyridine-3,5-dicarboxamide;

N3-methyl-1-(3-methylbenzyl)-2-oxo-N5-(3-(piperidin-4-yl)propyl)-1,2-dihydropyridine-3,5-dicarboxamide;

(R)—N3-methyl-2-oxo-1-(1-phenylethyl)-N5-(3-(piperidin-4-yl)propyl)-1,2-dihydropyridine-3,5-dicarboxamide;

1-((1H-indol-4-yl)methyl)-N3-methyl-2-oxo-N5-(2-(piperidin-4-yl)ethyl)-1,2-dihydropyridine-3,5-dicarboxamide;

1-benzyl-N5-(3-(4-hydroxypiperidin-4-yl)propyl)-N3-methyl-2-oxo-1,2-dihydropyridine-3,5-dicarboxamide;

1-(3-fluorobenzyl)-N3-methyl-2-oxo-N5-(3-(piperidin-4-yl)propyl)-1,2-dihydropyridine-3,5-dicarboxamide;

tert-butyl 3-(3-(1-benzyl-5-(methylcarbamoyl)-6-oxo-1,6-dihydropyridine-3-carboxamido)propyl)piperidine-1-carboxylate;

1-benzyl-N3-methyl-2-oxo-N5-(3-(piperidin-3-yl)propyl)-1,2-dihydropyridine-3,5-dicarboxamide;

1-benzyl-N5-(3-(4-fluoropiperidin-4-yl)propyl)-N3-methyl-2-oxo-1,2-dihydropyridine-3,5-dicarboxamide;

1-((1H-indol-4-yl)methyl)-N3-methyl-2-oxo-N5-(3-(piperidin-4-yl)propyl)-1,2-dihydropyridine-3,5-dicarboxamide;

1-benzyl-N5-(3-(4-fluoropiperidin-4-yl)propyl)-N3-methyl-2-oxo-1,2-dihydropyridine-3,5-dicarboxamide;

1-benzyl-N3-methyl-N5-(2-(4-methylmorpholin-2-yl)ethyl)-2-oxo-1,2-dihydropyridine-3,5-dicarboxamide;

N5-(2-(4-acetylmorpholin-2-yl)ethyl)-1-benzyl-N3-methyl-2-oxo-1,2-dihydropyridine-3,5-dicarboxamide;

1-benzyl-N3-methyl-N5-(2-(morpholin-2-yl)ethyl)-2-oxo-1,2-dihydropyridine-3,5-dicarboxamide;

1-benzyl-N3-methyl-2-oxo-N5-(2-(pyrrolidin-3-yloxy)ethyl)-1,2-dihydropyridine-3,5-dicarboxamide;

1-benzyl-N3-methyl-2-oxo-N5-(2-(piperidin-3-yloxy)ethyl)-1,2-dihydropyridine-3,5-dicarboxamide;

1-benzyl-N5-((1R,5S,6r)-3-oxabicyclo[3.1.0]hexan-6-yl)-N3-methyl-2-oxo-1,2-dihydropyridine-3,5-dicarboxamide;

1-benzyl-N3-methyl-N5-(3-(1-methylpiperidin-3-yl)propyl)-2-oxo-1,2-dihydropyridine-3,5-dicarboxamide;

1-benzyl-N3-methyl-N5-(3-(1-methylpiperidin-3-yl)propyl)-2-oxo-1,2-dihydropyridine-3,5-dicarboxamide;

N5-((1R,5S,6r)-3-oxabicyclo[3.1.0]hexan-6-yl)-1-(3-methoxybenzyl)-N3-methyl-2-oxo-1,2-dihydropyridine-3,5-dicarboxamide;

1-benzyl-N3-methyl-N5-(3-(morpholin-2-yl)propyl)-2-oxo-1,2-dihydropyridine-3,5-dicarboxamide;

1-((1H-indol-4-yl)methyl)-N5-(3-(1-acetylpiperidin-4-yl)propyl)-N3-methyl-2-oxo-1,2-dihydropyridine-3,5-dicarboxamide;

(1R,5S,6s)-tert-butyl 6-(1-benzyl-5-(methylcarbamoyl)-6-oxo-1,6-dihydropyridine-3-carboxamido)-3-azabicyclo[3.1.0]hexane-3-carboxylate;

1-benzyl-N5-((1R,5S,6s)-3-azabicyclo[3.1.0]hexan-6-yl)-N3-methyl-2-oxo-1,2-dihydropyridine-3,5-dicarboxamide;

1-benzyl-N3-methyl-N5-(3-(morpholin-2-yl)propyl)-2-oxo-1,2-dihydropyridine-3,5-dicarboxamide;

1-benzyl-N3-ethyl-2-oxo-N5-(3-(piperidin-4-yl)propyl)-1,2-dihydropyridine-3,5-dicarboxamide;

(1R,5S,6s)-tert-butyl 6-(1-((1H-indol-4-yl)methyl)-5-(methylcarbamoyl)-6-oxo-1,6-dihydropyridine-3-carboxamido)-3-azabicyclo[3.1.0]hexane-3-carboxylate;

1-((1H-indol-4-yl)methyl)-N5-((1R,5S,6s)-3-azabicyclo[3.1.0]hexan-6-yl)-N3-methyl-2-oxo-1,2-dihydropyridine-3,5-dicarboxamide;

1-((1H-indol-4-yl)methyl)-N5-((1R,5S,6s)-3-acetyl-3-azabicyclo[3.1.0]hexan-6-yl)-N3-methyl-2-oxo-1,2-dihydropyridine-3,5-dicarboxamide;

(R)-1-benzyl-N3-ethyl-N5-(3-(3-fluoropiperidin-3-yl)propyl)-2-oxo-1,2-dihydropyridine-3,5-dicarboxamide;

(R)-1-benzyl-N3-ethyl-N5-(2-(morpholin-2-yl)ethyl)-2-oxo-1,2-dihydropyridine-3,5-dicarboxamide;

(R)-1-benzyl-N3-ethyl-N5-(3-(morpholin-2-yl)propyl)-2-oxo-1,2-dihydropyridine-3,5-dicarboxamide;

tert-butyl (2-((1R,5S,6s)-6-(1-((1H-indol-4-yl)methyl)-5-(methylcarbamoyl)-6-oxo-1,6-dihydropyridine-3-carboxamido)-3-azabicyclo[3.1.0]hexan-3-yl)ethyl)carbamate;

1-((1H-indol-4-yl)methyl)-N5-((1R,5S,6s)-3-(2-aminoethyl)-3-azabicyclo[3.1.0]hexan-6-yl)-N3-methyl-2-oxo-1,2-dihydropyridine-3,5-dicarboxamide;

1-((1H-indol-4-yl)methyl)-N5-((1R,5S,6s)-3-(2-acetamidoethyl)-3-azabicyclo[3.1.0]hexan-6-yl)-N3-methyl-2-oxo-1,2-dihydropyridine-3,5-dicarboxamide;

N5-(3-((2r,5r)-5-amino-1,3-dioxan-2-yl)propyl)-1-benzyl-N3-methyl-2-oxo-1,2-dihydropyridine-3,5-dicarboxamide;

1-benzyl-N3-methyl-2-oxo-N5-(2-(piperidin-4-yloxy)ethyl)-1,2-dihydropyridine-3,5-dicarboxamide;

1-benzyl-N3-methyl-N5-(1-(methylsulfonyl)azetidin-3-yl)-2-oxo-1,2-dihydropyridine-3,5-dicarboxamide; and 1-benzyl-N3-methyl-N5-(oxetan-3-yl)-2-oxo-1,2-dihydropyridine-3,5-dicarboxamide;

or a pharmaceutically acceptable salt thereof.

15. A pharmaceutical composition comprising the compound or pharmaceutically acceptable salt thereof according to claim 1 and a pharmaceutically acceptable excipient.

16. A combination comprising the compound or pharmaceutically acceptable salt thereof as defined in claim 1 together with one or more other therapeutically active agents.

17. A method of treating a bromodomain-mediated disease or condition in a human in need thereof comprising administering a therapeutically effective amount of the compound, or a pharmaceutically acceptable salt thereof, according to claim 1.

18. The method according to claim 17, wherein the bromodomain-mediated disease or condition is an acute or chronic autoimmune or inflammatory condition.

19. The method according to claim 18, wherein the acute or chronic autoimmune or inflammatory condition is rheumatoid arthritis.

20. A method of treating a bromodomain-mediated disease or condition in a human in need thereof comprising administering a therapeutically effective amount to the human a combination comprising the compound according to claim 1, or a pharmaceutically acceptable salt thereof, and one or more therapeutically active agents.

* * * * *